(12) United States Patent
Armani et al.

(10) Patent No.: US 9,024,027 B2
(45) Date of Patent: May 5, 2015

(54) DERIVATIVES OF 1-PHENYL-2-PYRIDINYL ALKYL ALCOHOLS AS PHOSPHODIESTERASE INHIBITORS

(71) Applicant: Chiesi Farmaceutici S.p.A., Parma (IT)

(72) Inventors: Elisabetta Armani, Parma (IT); Gabriele Amari, Parma (IT); Carmelida Capaldi, Parma (IT); Laura Carzaniga, Parma (IT); Elena La Porta, Parma (IT); Matilde Guala, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 0 days.

(21) Appl. No.: 13/655,903

(22) Filed: Oct. 19, 2012

(65) Prior Publication Data

US 2013/0102576 A1    Apr. 25, 2013

(30) Foreign Application Priority Data

Oct. 21, 2011    (EP) ..................................... 11186056

(51) Int. Cl.
| | | |
|---|---|---|
| C07D 413/14 | (2006.01) | |
| C07D 413/12 | (2006.01) | |
| C07D 409/14 | (2006.01) | |
| C07D 401/14 | (2006.01) | |
| C07D 401/12 | (2006.01) | |
| A61K 31/44 | (2006.01) | |
| C07D 417/12 | (2006.01) | |
| C07D 417/14 | (2006.01) | |
| C07D 471/04 | (2006.01) | |
| C07D 473/04 | (2006.01) | |

(52) U.S. Cl.
CPC ............ *C07D 401/12* (2013.01); *C07D 401/14* (2013.01); *C07D 413/14* (2013.01); *C07D 409/14* (2013.01); *C07D 413/12* (2013.01); *C07D 417/12* (2013.01); *C07D 417/14* (2013.01); *C07D 471/04* (2013.01); *C07D 473/04* (2013.01)

(58) Field of Classification Search
None
See application file for complete search history.

(56) References Cited

U.S. PATENT DOCUMENTS 7,923,565 B2 *    4/2011    Delcanale et al. ............ 546/301

FOREIGN PATENT DOCUMENTS

| WO | 2009/018909 | 2/2009 |
|---|---|---|
| WO | 2010/089107 | 8/2010 |

OTHER PUBLICATIONS

U.S. Appl. No. 14/161,285, filed Jan. 22, 2014, Delcanale, et al.
U.S. Appl. No. 14/164,527, filed Jan. 27, 2014, Armani, et al.
U.S. Appl. No. 13/909,222, filed Jun. 4, 2013, Armani, et al.
U.S. Appl. No. 13/930,304, filed Jun. 28, 2013, Amari, et al.
U.S. Appl. No. 13/747,812, filed Jan. 23, 2013, Delcanale, et al.
European Search Report in Application 11186056.5 issued on Mar. 27, 2012.
Odingo, J O., Expert Opinion, vol. 15, No. 7, (2005) pp. 773-787.

* cited by examiner

*Primary Examiner* — Zinna Northington Davis
(74) *Attorney, Agent, or Firm* — Oblon, McClelland, Maier & Neustadt, L.L.P.

(57) ABSTRACT

Compounds, pyridine N-oxides, and pharmaceutically acceptable salts of formula (I) are useful as inhibitors of the phosphodiesterase 4 (PDE4) enzyme and for preventing and/or treating diseases of the respiratory tract characterized by airway obstruction, such as asthma or COPD.

27 Claims, No Drawings

DERIVATIVES OF 1-PHENYL-2-PYRIDINYL ALKYL ALCOHOLS AS PHOSPHODIESTERASE INHIBITORS

CROSS REFERENCES TO RELATED APPLICATIONS

This application claims priority to European Patent Application No. 11186056.5, filed on Oct. 21, 2011, which is incorporated herein by reference in its entirety.

BACKGROUND OF THE INVENTION

1. Field of the Invention

The present invention relates to inhibitors of the phosphodiesterase 4 (PDE4) enzyme. More particularly, the invention relates to derivatives of 1-phenyl-2-pyridinyl alkyl alcohols, methods of preparing such compounds, compositions containing them, and therapeutic use thereof.

2. Discussion of the Background

Airway obstruction characterizes a number of severe respiratory diseases including asthma and chronic obstructive pulmonary disease (COPD). Events leading to airway obstruction include oedema of airway walls, increased mucous production and inflammation.

Drugs for treating respiratory diseases such as asthma and COPD are currently administered through inhalation. One of the advantages of the inhalatory route over the systemic one is the possibility of delivering the drug directly at site of action, reducing systemic side-effects, thus resulting in a more rapid clinical response and a higher therapeutic ratio.

Inhaled corticosteroids are the current maintenance therapy of choice for asthma and together with bronchodilator beta$_2$-agonists for acute symptom relief, they form the mainstay of current therapy for the disease. The current management of COPD is largely symptomatic by means of bronchodilating therapy with inhaled anticholinergics and inhaled beta$_2$-adrenoceptor agonists. However, corticosteroids do not reduce the inflammatory response in COPD as they do in asthma.

Another class of therapeutic agents which has been widely investigated in view of its anti-inflammatory effects for the treatment of inflammatory respiratory diseases such as asthma and COPD is represented by the inhibitors of the enzymes phosphodiesterases (PDEs), in particular of the phosphodiesterase type 4 (hereinafter referred to as PDE4).

Various compounds acting as PDE4 inhibitors have been disclosed in the prior art. However, the usefulness of several PDE4 inhibitors of the first-generation such as rolipram and piclamilast has been limited due to their undesirable side effects. Said effects include nausea and emesis due to their action on PDE4 in the central nervous system and gastric acid secretion due to the action on PDE4 in parietal cells in the gut.

The cause of said side effects has been widely investigated. It has been found that PDE4 exists in two distinct forms representing different conformations, that were designated as high affinity rolipram binding site or HPDE4, especially present in the central nervous system and in parietal cells, and low affinity rolipram binding site or LPDE4 (Jacobitz, S et al., Mol. Pharmacol., 1996, 50, 891-899, which is incorporated herein by reference in its entirety), which is found in the immune and inflammatory cells. While both forms appear to exhibit catalytic activity, they differ with respect to their sensitivity to inhibitors. In particular compounds with higher affinity for LPDE4 appear less prone to induce side-effects such as nausea, emesis and increased gastric secretion.

The effort of targeting LPDE4 has resulted in a slight improvement in the selectivity for the second-generation PDE4 inhibitors such as roflumilast. Nonetheless, roflumilast is under dosed in order to achieve an acceptable side effect profile.

Other classes of compounds acting as PDE4 inhibitors have been disclosed in the prior art. For example, EP 1 634 606 discloses, inter alia, ketone derivatives like benzofuran or 1,3-benzodioxole derivatives.

WO 94/02465 discloses, inter alia, ketone derivatives of general formula

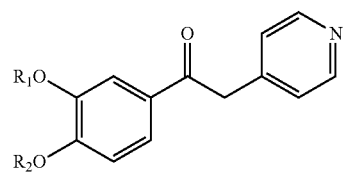

wherein $R_1$ is lower alkyl and $R_2$ may be alkyl, alkenyl, cycloalkyl, cycloalkyl, cycloalkenyl, cyclothioalkyl or cyclothioalkenyl.

WO 95/35281 in the name of Celltech Therapeutics concerns tri-substituted phenyl derivatives.

WO2009/018909 discloses derivatives of 1-phenyl-2-pyridinyl alkyl alcohols which have the following general formula

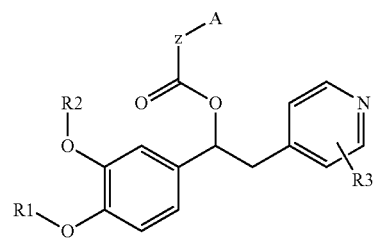

as inhibitors of phosphodiesterase 4 (PDE4) enzyme.

WO2009/077068 discloses further derivatives of 1-phenyl-2-pyridinyl alkyl alcohols which have the following general formula

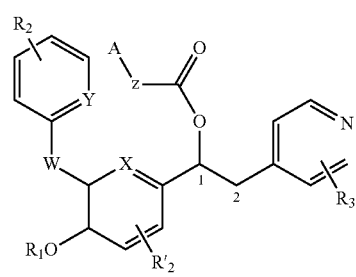

as inhibitors of phosphodiesterase 4 (PDE4) enzyme.

WO2010/089107 discloses further derivatives of 1-phenyl-2-pyridinyl alkyl alcohols which have the following general formula

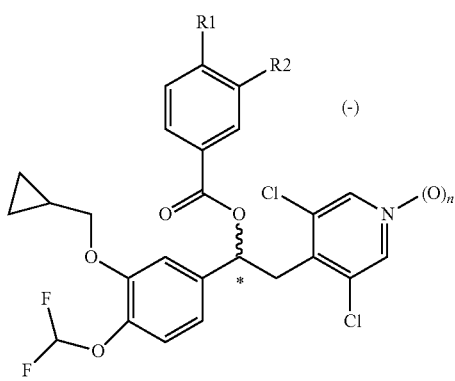

as inhibitors of phosphodiesterase 4 (PDE4) enzyme.

Although several PDE4 inhibitors have been disclosed so far as above reported, there is still a need for further PDE4 inhibitors. Particularly, there is still a need for further PDE4 inhibitors endowed with a high affinity for PDE4 enzyme and which show an appropriate developability profile as an inhalation treatment for example in terms of reduced side effects. Such reduction of side effects may be achieved, by way of example, through a low systemic exposure of the drug; an appropriate profile in terms of some pharmacokinetic characteristics, especially metabolic clearance, may be thus key to this goal. The present invention addresses the above mentioned need by providing the compounds of the invention.

SUMMARY OF THE INVENTION

Accordingly, it is one object of the present invention to provide novel compounds acting as inhibitors of the phosphodiesterase 4 (PDE4) enzyme.

It is another object of the present invention to provide novel methods of preparing such a compound.

It is another object of the present invention to provide novel compositions which contain such a compound.

It is another object of the present invention to provide novel methods of preventing and/or treating certain diseases and conditions by administering such a compound.

These and other objects, which will become apparent during the following detailed description, have been achieved by the inventors' discovery that compounds of formula (I) set out below are useful as phosphodiesterase 4 (PDE4) inhibitors.

In particular, the present invention is directed to derivatives of 1-phenyl-2-pyridinyl alkyl alcohols of general formula (I):

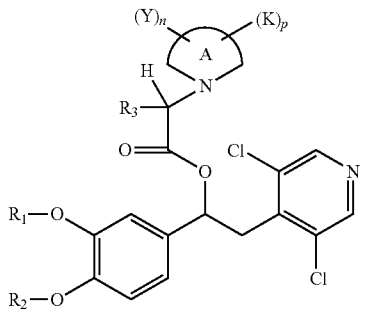

wherein:
$R_1$ and $R_2$, which can be the same or different, are independently selected from the group consisting of:
  $(C_1-C_6)$ alkyl, optionally substituted by $(C_3-C_7)$ cycloalkyl;
  $(C_1-C_6)$ haloalkyl;
  $(C_3-C_7)$ cycloalkyl; and
  $(C_3-C_7)$ heterocycloalkyl;
$R_3$ is hydrogen, $(C_1-C_6)$ alkyl or $(C_1-C_3)$ alkylthio$(C_1-C_6)$ alkyl;
A is a partially unsaturated or unsaturated bicyclic ring system consisting of two fused monocyclic ring systems B and C as below represented

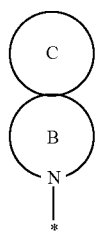

wherein ring B contains a nitrogen atom which represents the point of attachment for ring A to the rest of the molecule through a —(CHR$_3$)— group and wherein ring B and C may optionally contain further heteroatoms;
p is an integer from zero to 3;
Y is an oxo group;
n is an integer from zero to 3;
K is selected from the group consisting of:
  $(C_1-C_6)$ alkyl, optionally substituted by one or more $(C_3-C_7)$ cycloalkyl groups;
  $(C_3-C_7)$ heterocycloalkyl$(C_1-C_4)$ alkyl;
  $(C_3-C_7)$ heterocycloalkyl, optionally substituted by one or more $(C_1-C_6)$ alkyl groups;
  $(C_1-C_4)$ haloalkyl;
  a group —OR$_4$ wherein R$_4$ is selected from the group consisting of:
    H;
    $(C_1-C_{10})$ alkyl, optionally substituted by $(C_3-C_7)$ cycloalkyl or heteroaryl;
  halogen atoms;
  a group —CN;
  a group —NO$_2$;
  NR$_5$R$_6$ wherein R$_5$ and R$_6$, which can be the same or different, are independently selected from the group consisting of:
    H;
    a group —OH;
    NR$_7$R$_8$(C$_1$-C$_4$)alkyl wherein R$_7$ and R$_8$, which can be the same or different, are independently selected from the group consisting of: H; $(C_1-C_6)$ alkyl, optionally substituted with $(C_1-C_6)$ alkoxyl; and NR$_9$R$_{10}$(C$_1$-C$_6$) alkyl wherein R$_9$ and R$_{10}$, which can be the same or different, are H or $(C_1-C_6)$ alkyl; or they form with the nitrogen atom to which they are linked a $(C_3-C_7)$ heterocycloalkyl ring optionally substituted by $(C_1-C_6)$alkyl or $(C_1-C_6)$ alkylcarbonyl;
    $(C_1-C_6)$ alkyl, optionally substituted by $(C_1-C_6)$ alkoxyl or heteroaryl, $(C_3-C_7)$ heterocycloalkylcarbonyl, heteroarylcarbonyl, all of them being optionally further substituted by one or more $(C_1-C_6)$ alkyl, $(C_1-C_6)$ haloalkyl or $(C_1-C_6)$ alkoxyl groups, which may be the same or different and are independently selected;
    a group —SO$_2$R$_{11}$, wherein R$_{11}$ is $(C_1-C_6)$ alkyl;

a group —C(O)$R_{12}$, wherein $R_{12}$ is ($C_1$-$C_6$) alkyl optionally substituted by ($C_1$-$C_6$) alkoxyl;

$NR_{13}R_{14}$($C_1$-$C_4$)alkyl; wherein $R_{13}$ and $R_{14}$, which can be the same or different, are independently selected in the group consisting of: —$SO_2$($C_1$-$C_6$) alkyl, H, ($C_1$-$C_6$) alkyl, and ($C_3$-$C_7$)heterocycloalkyl($C_1$-$C_4$) alkyl; and —$SO_2NR_{15}R_{16}$: wherein $R_{15}$ and $R_{16}$, which can be the same or different, are independently H or ($C_1$-$C_6$) alkyl;

wherein groups $R_4$ to $R_{16}$ may have the same or different meanings at each occurrence, if present in more than one group;

and pyridine N-oxides, pharmaceutically acceptable salts, and solvates thereof;

and wherein the compound of formula (I) is not: 3,5-dichloro-4-(2-(3-(cyclopropylmethoxy)-4-(difluoromethoxy)phenyl)-2-(2-(1,3-dimethyl-2,6-dioxo-2,3-dihydro-1H-purin-7(6H)-yl)acetoxy)ethyl)pyridine.

The present invention also encompasses the pharmaceutically acceptable salts and/or solvates of the compounds of formula (I).

The present invention further provides the corresponding pyridine N-oxides.

Hereinafter, compounds of formula (I), pyridine N-oxides, and their pharmaceutically acceptable salts and solvates, defined in any aspect of the invention (except intermediate compounds described in the chemical processes) are referred to as "compounds of the invention".

The present invention further provides processes for the preparation of the compounds of the invention.

The present invention also provides pharmaceutical compositions of compounds of the invention either alone or in combination, in admixture with one or more pharmaceutically acceptable carriers.

In a further aspect, the present invention provides the use of the compounds of the invention as a medicament.

In another aspect, the present invention provides the use of the compounds of the invention for the manufacture of a medicament.

In particular, the present invention provides the use of the compounds of the invention for the prevention and/or treatment of any disease characterized by phosphodiesterase 4 (PDE4) overactivity and/or wherein an inhibition of PDE4 activity is desirable.

In particular, the compounds of the invention alone or combined with other active ingredients may be administered for the prevention and/or treatment of a disease of the respiratory tract characterized by airway obstruction such as asthma and COPD.

In a further aspect, the present invention provides the use of compounds of the invention for the preparation of a medicament for the prevention and/or treatment of any disease characterized by phosphodiesterase 4 (PDE4) overactivity and/or wherein an inhibition of PDE4 activity is desirable.

Moreover, the present invention provides a method of prevention and/or treatment of any disease wherein PDE4 inhibition is desirable, said method comprising administering to a patient in need of such treatment a therapeutically effective amount of a compound of the invention.

DETAILED DESCRIPTION OF THE PREFERRED EMBODIMENTS

The following definitions apply:

"Halogen atoms" includes fluorine, chlorine, bromine, and iodine, preferably chlorine.

"($C_1$-$C_x$) alkyl" where x is an integer greater than 1, means straight-chained and branched alkyl groups wherein the number of constituent carbon atoms is in the range 1 to x. Examples of alkyl groups are methyl, ethyl, n-propyl, isopropyl, and t-butyl.

"($C_1$-$C_x$) alkoxyl" where x is an integer greater than 1, means straight-chained and branched alkoxy groups wherein the number of carbon atoms is in the range 1 to x. Examples of alkyl groups are methoxyl, ethoxyl, n-propoxyl, isopropoxyl, and t-butoxyl.

"($C_1$-$C_x$)haloalkyl" refers to the above defined "($C_1$-$C_x$) alkyl" groups wherein one or more hydrogen atoms are replaced by one or more halogen atoms, which can be the same or different from each other. Examples of said ($C_1$-$C_x$) haloalkyl groups may include halogenated, poly-halogenated and fully halogenated alkyl groups wherein all of the hydrogen atoms are replaced by halogen atoms, e.g., trifluoromethyl or difluoro methyl groups.

"$NR_jR_w$($C_1$-$C_x$)alkyl" means the above defined "($C_1$-$C_x$) alkyl" groups wherein one hydrogen atom is replaced by one a group —$NR_jR_w$.

"($C_1$-$C_z$)alkylthio" where z is an integer greater than 1, means straight-chained and branched alkylthio groups wherein the number of constituent carbon atoms is in the range 1 to z and which are linked to other groups via the sulfur atom. Examples of alkylthio groups are methylthio, ethylthio, and so on.

"($C_1$-$C_z$)alkylthio($C_1$-$C_x$)alkyl" means the above "($C_1$-$C_x$) alkyl" group wherein one or more hydrogen atoms are replaced by one "($C_1$-$C_z$)alkylthio" group.

"($C_3$-$C_y$)cycloalkyl", where y is an integer greater than or equal to 3, means saturated cyclic hydrocarbon groups containing from 3 to y ring carbon atoms. Examples include cyclopropyl, cyclobutyl, cyclopentyl, cyclohexyl, and cycloheptyl.

The derived expression "($C_3$-$C_y$)heterocycloalkyl" refers to saturated monocyclic ($C_3$-$C_y$)cycloalkyl groups, in which at least one ring carbon atom is replaced by a heteroatom (e.g. N, NH, S, or O). Not limiting examples of ($C_3$-$C_y$)heterocycloalkyl are represented by: pyrrolidinyl, thiazolidinyl, piperazinyl, piperidinyl, morpholinyl, and thiomorpholinyl.

"($C_1$-$C_x$)alkylcarbonyl" means ($C_1$-$C_x$)alkylCO— groups wherein the group "($C_1$-$C_x$)alkyl" has the meaning above defined.

"($C_3$-$C_y$)heterocycloalkylcarbonyl" means "($C_3$-$C_y$)heterocycloalkylCO—" groups wherein the group "($C_3$-$C_y$)heterocycloalkyl" has the meaning above defined.

"($C_3$-$C_y$)heterocycloalkyl($C_1$-$C_x$) alkyl" means the above "($C_1$-$C_x$)alkyl" group wherein one or more hydrogen atoms are replaced by one or more "($C_3$-$C_y$)heterocycloalkyl" groups.

"Aryl" means mono or bi-cyclic ring systems which have 6 to 10 ring atoms, wherein at least one ring is aromatic.

"Heteroaryl" means mono- or bi-cyclic ring systems with 5 to 11 ring atoms, in which at least one ring is aromatic and in which at least one ring atom is a heteroatom (e.g. N, NH, S, or O).

Examples of suitable monocyclic aryl or heteroaryl systems include, for instance, phenyl, thiophene (thiophenyl), benzene (phenyl), pyrrole (pyrrolyl), pyrazole (pyrazolyl), imidazole (imidazolyl), isoxazole (isoxazolyl), oxazole (oxazolyl), isothiazole (isothiazolyl), thiazole (thiazolyl), pyridine (pyridinyl), imidazolidine (imidazolidinyl), furan (furanyl) radicals and the like.

Examples of suitable aryl or heteroaryl bicyclic systems include naphthalene (naphthyl), biphenylene (biphenylenyl), purine (purinyl), pteridine (pteridinyl), benzotriazole (benzotriazolyl), quinoline (quinolinyl), isoquinoline (isoquinolinyl), indole (indolyl), isoindole (isoindolyl), benzothiophene (benzothiophenyl), dihydrobenzo dioxin, dihydrobenzo dioxepin, benzo oxazine radicals and the like.

"Heteroarylcarbonyl" means heteroarylCO— groups wherein the group "heteroaryl" has the meaning above defined.

"Ring system" means mono- or bicyclic ring systems which may be saturated, partially unsaturated or unsaturated, such as aryl, $(C_3-C_8)$cycloalkyl, $(C_3-C_7)$-heterocycloalkyl or heteroaryl.

The present invention is directed to a class of compounds acting as inhibitors of the phosphodiesterase 4 (PDE4) enzyme. Said class of compounds inhibits the conversion of cyclic nucleotides, in particular cyclic adenosine monophosphate (cAMP), into their inactive 5'-mononucleotide forms.

In the airways, the physiological responses to elevated intracellular levels of cyclic nucleotides, in particular of cAMP, lead to the suppression of the activity of immune and pro-inflammatory cells such as mast cells, macrophages, T lymphocytes, eosinophils and neutrophils, resulting in a decrease of the release of inflammatory mediators which include cytokines such as IL-1, IL-3 and tumor necrosis factor-alpha (TNF-α). It also leads to an airway smooth muscle relaxation and a decrease in oedema.

The present invention relates to derivatives of 1-phenyl-2-pyridinyl alkyl alcohols of general formula (I), pharmaceutically acceptable salts and pyridine N-oxides thereof,

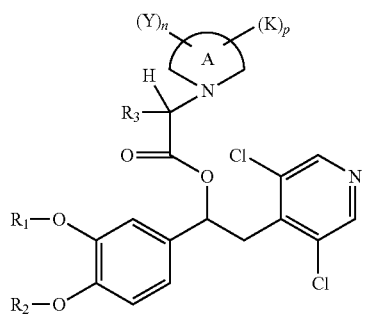

(I)

wherein $R_1$, $R_2$, $R_3$, Y, K, n, p. and A are as above defined.

The term "pharmaceutically acceptable salts", as used herein, refers to derivatives of compounds of formula (I) wherein the parent compound is suitably modified by converting any of the free acid or basic group, if present, into the corresponding addition salt with any base or acid conventionally intended as being pharmaceutically acceptable.

Suitable examples of said salts may include mineral or organic acid addition salts of basic residues such as amino groups, as well as mineral or organic basic residues such as carboxylic groups.

Suitable cations of inorganic bases for use in the preparation of said salts comprise ions of alkali or alkaline earth metals such as potassium, sodium, calcium or magnesium.

Those obtained by reacting the main compound, functioning as a base, with an inorganic or organic acid to form a salt comprise, for example, salts of hydrochloric acid, sulfuric acid, phosphoric acid, methane sulfonic acid, camphor sulfonic acid, oxalic acid, maleic acid, succinic acid and citric acid.

Compounds of general formula (I) contain at least one stereogenic center, namely represented by the carbon atom (1) with an asterisk below, and therefore exist as optical stereoisomers.

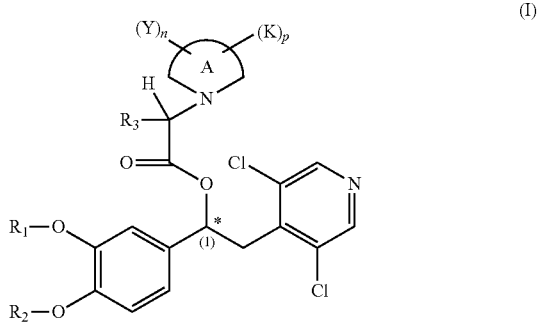

(I)

Where the compounds according to the invention have at least one stereogenic center, they may accordingly exist as enantiomers. Where the compounds according to the invention possess two or more stereogenic centers, they may additionally exist as diastereoisomers. It is to be understood that all such isomers and mixtures thereof in any proportion are encompassed within the scope of the present invention.

In a preferred embodiment, the present invention is directed to compounds of formula (I)', which are compounds of formula (I) as above defined where the absolute configuration of carbon (1) is that shown herebelow:

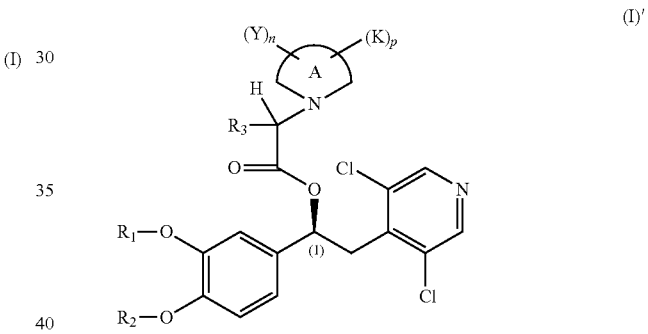

(I)'

The absolute configuration for carbon (1) is assigned on the basis of Cahn-Ingold-Prelog nomenclature based on groups' priorities.

In one preferred embodiment, for compounds of formula (I), the absolute configuration at carbon (1) is (S).

It is to be understood that all preferred groups or embodiments described herebelow for compounds of formula (I) may be combined among each other and apply to compounds of formula (I)' as well mutatis mutandis.

In a preferred embodiment, compounds of the invention are pyridine N-oxides.

Ring A consists of two fused monocyclic ring systems B and C as below represented

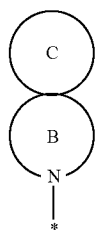

wherein ring B contains the nitrogen atom which represents the point of attachment for ring A to the rest of the molecule through a —(CHR$_3$)— group (hereabove indicated by an asterisk) and ring B and C may optionally contain further heteroatoms (e.g. N, NH, S or O).

Ring A, consisting of two fused monocyclic ring systems B and C, may be substituted by n groups Y and/or p groups K as above defined at any suitable position of rings B and C.

Not limiting examples of ring A are represented herebelow:

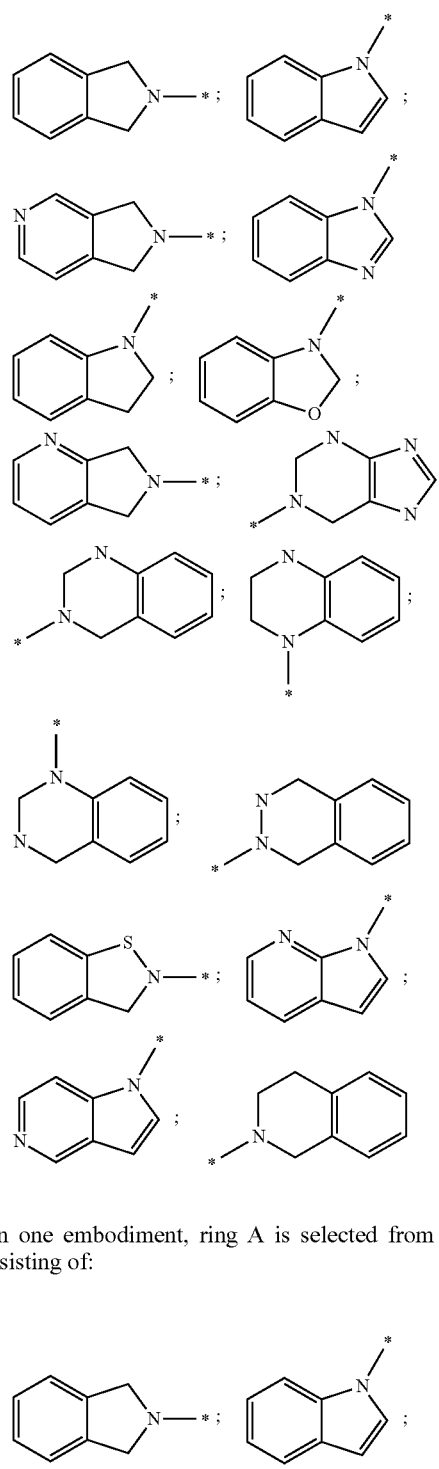
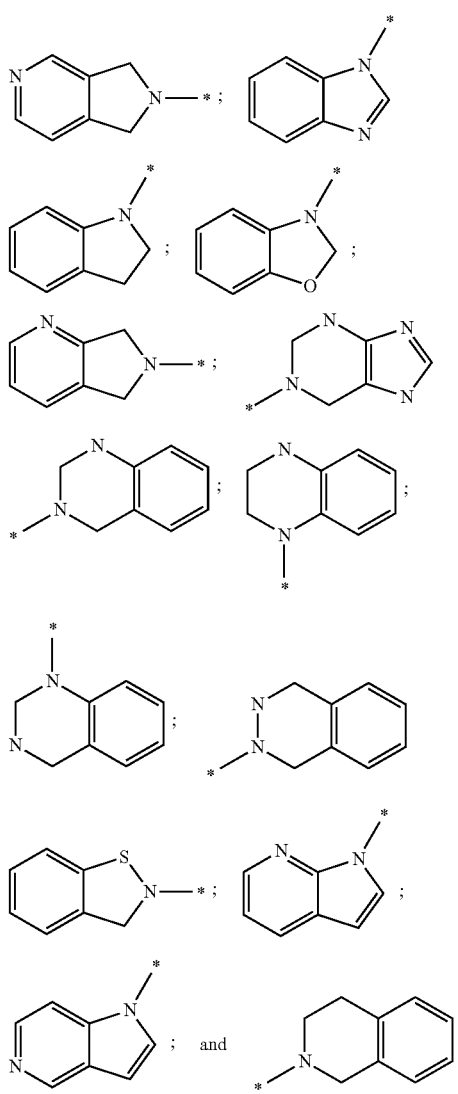

In one embodiment, ring A is selected from the group consisting of:

In one preferred embodiment, ring A is selected from the group consisting of:

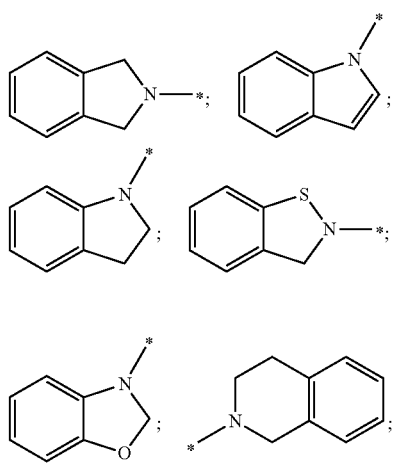

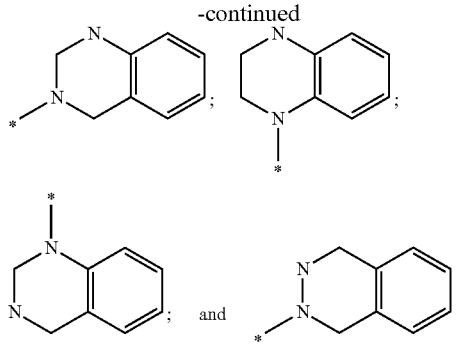

In one preferred embodiment, ring C is a monocyclic aryl or heteroaryl system.

In a further preferred embodiment, ring C is a phenyl group.

In a preferred embodiment, ring B contains only one nitrogen atom. In another preferred embodiment, ring B contains one further heteroatom which may be nitrogen or sulfur.

In one preferred embodiment, ring C is a monocyclic aryl or monocyclic heteroaryl ring system and ring B is a 5 or 6 membered heterocycloalkyl group.

In one preferred embodiment, zero Y groups are connected to ring C and n groups Y are connected to ring B.

In a further preferred embodiment, zero Y groups are connected to ring C, n groups Y are connected to ring B and n is an integer ranging from 0 to 3. In a still further preferred embodiment, zero Y groups are connected to ring C, n groups Y are connected to ring B and n is an integer ranging from 1 to 3.

In one preferred embodiment, ring A which is substituted by n groups Y is selected in the group consisting of:

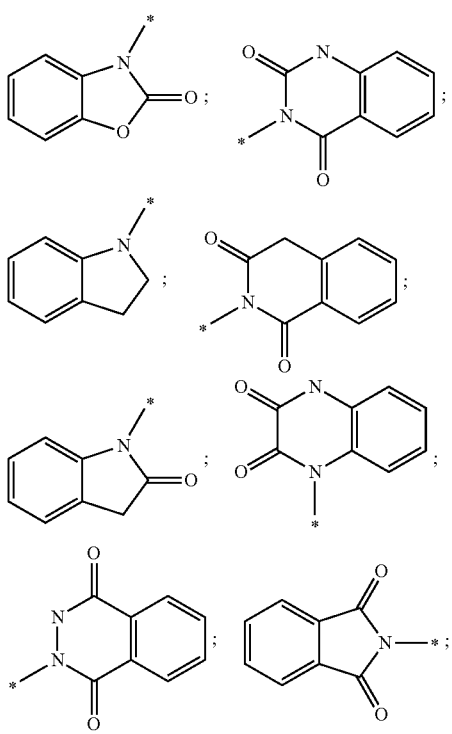

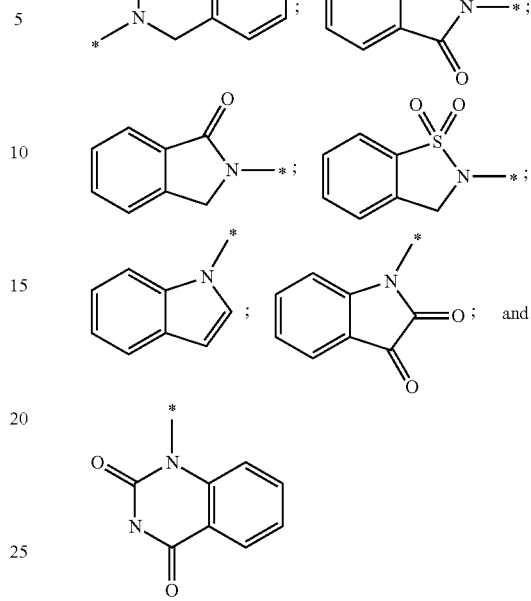

In one preferred embodiment, $R_2$ is $(C_1-C_6)$ haloalkyl or $(C_1-C_6)$ alkyl.

In another preferred embodiment, $R_1$ is $(C_1-C_6)$ alkyl which is optionally substituted by $(C_3-C_7)$ cycloalkyl.

In a further preferred embodiment, $R_2$ is $(C_1-C_6)$ haloalkyl and $R_1$ is $(C_1-C_6)$ alkyl which is substituted by $(C_3-C_7)$ cycloalkyl.

In one preferred embodiment, $R_3$ is hydrogen or methyl. In another preferred embodiment, $R_3$ is hydrogen.

In one preferred embodiment, n is zero. In another preferred embodiment, n is 1 or 2.

In one preferred embodiment, p is zero. In another preferred embodiment, p is 1 or 2.

In a preferred embodiment, K is selected from the group consisting of:
 a group —$OR_4$ wherein $R_4$ is $(C_1-C_{10})$ alkyl;
 $NR_5R_6$ wherein $R_5$ and $R_6$, which can be the same or different, are independently selected from the group consisting of:
  H;
  $NR_7R_8(C_1-C_4)$alkyl wherein $R_7$ and $R_8$, which can be the same or different, are independently selected from the group consisting of: H; $(C_1-C_6)$ alkyl, optionally substituted with $(C_1-C_6)$ alkoxyl; and $NR_9R_{10}(C_1-C_6)$alkyl wherein $R_9$ and $R_{10}$, which can be the same or different, are H or $(C_1-C_6)$ alkyl; or they form with the nitrogen atom to which they are linked a $(C_3-C_7)$ heterocycloalkyl ring optionally substituted by $(C_1-C_6)$alkyl or $(C_1-C_6)$ alkylcarbonyl;
  $(C_1-C_6)$ alkyl, optionally substituted by heteroaryl;
 a group —$SO_2R_{11}$, wherein $R_{11}$ is $(C_1-C_6)$ alkyl;
 a group —$C(O)R_{12}$, wherein $R_{12}$ is $(C_1-C_6)$ alkyl optionally substituted by $(C_1-C_6)$ alkoxyl.

In one embodiment, a compound of formula (I) is selected from the group consisting of:
(S)-3,5-dichloro-4-(2-(3-(cyclopropylmethoxy)-4-(difluoromethoxy)phenyl)-2-(2-(6,7-dimethoxy-3,4-dihydroisoquinolin-2(1H)-yl)acetoxy)ethyl)pyridine 1-oxide;

(S)-3,5-dichloro-4-(2-(3-(cyclopropylmethoxy)-4-(difluoromethoxy)phenyl)-2-(2-(1,1-dioxido-3-oxobenzo[d]isothiazol-2(3H)-yl)acetoxy)ethyl)pyridine 1-oxide;

(S)-3,5-dichloro-4-(2-(3-(cyclopropylmethoxy)-4-(difluoromethoxy)phenyl)-2-(2-(1,3-dioxoisoindolin-2-yl)acetoxy)ethyl)pyridine 1-oxide;

(S)-4-(2-(2-(4-amino-1,3-dioxoisoindolin-2-yl)acetoxy)-2-(3-(cyclopropylmethoxy)-4-(difluoromethoxy)phenyl)ethyl)-3,5-dichloropyridine 1-oxide;

(S)-4-(2-(2-(6-amino-1-oxoisoindolin-2-yl)acetoxy)-2-(3-(cyclopropylmethoxy)-4-(difluoromethoxy)phenyl)ethyl)-3,5-dichloropyridine 1-oxide;

(S)-3,5-dichloro-4-(2-(2-(6,7-dimethoxy-3,4-dihydroisoquinolin-2(1H)-yl)acetoxy)-2-(3,4-dimethoxyphenyl)ethyl)pyridine 1-oxide;

(S)-3,5-dichloro-4-(2-(3-(cyclopropylmethoxy)-4-(difluoromethoxy)phenyl)-2-(2-(6-(methylsulfonamido)-1-oxoisoindolin-2-yl)acetoxy)ethyl)pyridine 1-oxide;

(S)-3,5-dichloro-4-(2-(3-(cyclopropylmethoxy)-4-(difluoromethoxy)phenyl)-2-(2-(3,3-dimethyl-1,1-dioxidobenzo[d]isothiazol-2(3H)-yl)acetoxy)ethyl)pyridine 1-oxide;

(S)-3,5-dichloro-4-(2-(3-(cyclopropylmethoxy)-4-(difluoromethoxy)phenyl)-2-(2-(5-methoxy-1H-indol-1-yl)acetoxy)ethyl)pyridine 1-oxide;

(S)-3,5-dichloro-4-(2-(3-(cyclopropylmethoxy)-4-(difluoromethoxy)phenyl)-2-(2-(2,3-dioxoindolin-1-yl)acetoxy)ethyl)pyridine 1-oxide;

(S)-3,5-dichloro-4-(2-(3-(cyclopropylmethoxy)-4-(difluoromethoxy)phenyl)-2-(2-(5-(hydroxyamino)-1,3-dioxoisoindolin-2-yl)acetoxy)ethyl)pyridine 1-oxide;

(S)-3,5-dichloro-4-(2-(3-(cyclopropylmethoxy)-4-(difluoromethoxy)phenyl)-2-(2-(4-(hydroxyamino)-1,3-dioxoisoindolin-2-yl)acetoxy)ethyl)pyridine 1-oxide;

(S)-4-(2-(2-(5-amino-1,3-dioxoisoindolin-2-yl)acetoxy)-2-(3-(cyclopropylmethoxy)-4-(difluoromethoxy)phenyl)ethyl)-3,5-dichloropyridine 1-oxide;

3,5-dichloro-4-((2S)-2-(3-(cyclopropylmethoxy)-4-(difluoromethoxy)phenyl)-2-(2-(1,3-dioxoisoindolin-2-yl)propanoyloxy)ethyl)pyridine 1-oxide;

(S)-3,5-dichloro-4-(2-(3-(cyclopropylmethoxy)-4-(difluoromethoxy)phenyl)-2-(2-(5-(N-(2-morpholinoethyl)methylsulfonamido)-1,3-dioxoisoindolin-2-yl)acetoxy)ethyl)-pyridine 1-oxide;

(S)-3,5-dichloro-4-(2-(3-(cyclopropylmethoxy)-4-(difluoromethoxy)phenyl)-2-(2-(4-(methylsulfonamido)-1,3-dioxoisoindolin-2-yl)acetoxy)ethyl)pyridine 1-oxide;

(S)-3,5-dichloro-4-(2-(3-(cyclopropylmethoxy)-4-(difluoromethoxy)phenyl)-2-(2-(2,4-dioxo-1,2-dihydroquinazolin-3(4H)-yl)acetoxy)ethyl)pyridine 1-oxide;

(S)-3,5-dichloro-4-(2-(3-(cyclopropylmethoxy)-4-(difluoromethoxy)phenyl)-2-(2-(3,7-dimethyl-2,6-dioxo-2,3,6,7-tetrahydro-1H-purin-1-yl)acetoxy)ethyl)pyridine 1-oxide;

(S)-3,5-dichloro-4-(2-(3-(cyclopropylmethoxy)-4-(difluoromethoxy)phenyl)-2-(2-(5,6-dichloro-1,3-dioxoisoindolin-2-yl)acetoxy)ethyl)pyridine 1-oxide;

(S)-3,5-dichloro-4-(2-(3-(cyclopropylmethoxy)-4-(difluoromethoxy)phenyl)-2-(2-(5-(methylsulfonamido)-1,3-dioxoisoindolin-2-yl)acetoxy)ethyl)pyridine 1-oxide;

(S)-3,5-dichloro-4-(2-(3-(cyclopropylmethoxy)-4-(difluoromethoxy)phenyl)-2-(2-(1,3-dioxo-3,4-dihydroisoquinolin-2(1H)-yl)acetoxy)ethyl)pyridine 1-oxide;

(S)-3,5-dichloro-4-(2-(3-(cyclopropylmethoxy)-4-(difluoromethoxy)phenyl)-2-(2-(5,6-dimethoxy-1H-indol-1-yl)acetoxy)ethyl)pyridine 1-oxide;

(S)-3,5-dichloro-4-(2-(3-(cyclopropylmethoxy)-4-(difluoromethoxy)phenyl)-2-(2-(4-(methylsulfonamido)-1H-indol-1-yl)acetoxy)ethyl)pyridine 1-oxide;

(S)-3,5-dichloro-4-(2-(3-(cyclopropylmethoxy)-4-(difluoromethoxy)phenyl)-2-(2-(1,3-dioxo-1H-pyrrolo[3,4-c]pyridin-2(3H)-yl)acetoxy)ethyl)pyridine 1-oxide;

(S)-3,5-dichloro-4-(2-(3-(cyclopropylmethoxy)-4-(difluoromethoxy)phenyl)-2-(2-(5-hydroxy-1H-indol-1-yl)acetoxy)ethyl)pyridine 1-oxide;

(S)-3,5-dichloro-4-(2-(3-(cyclopropylmethoxy)-4-(difluoromethoxy)phenyl)-2-(2-(6-methoxy-2,3-dioxoindolin-1-yl)acetoxy)ethyl)pyridine 1-oxide;

(S)-3,5-dichloro-4-(2-(3-(cyclopropylmethoxy)-4-(difluoromethoxy)phenyl)-2-(2-(4-(2-methoxyacetamido)-1,3-dioxoisoindolin-2-yl)acetoxy)ethyl)pyridine 1-oxide;

(S)-3,5-dichloro-4-(2-(3-(cyclopropylmethoxy)-4-(difluoromethoxy)phenyl)-2-(2-(4-nitro-1,3-dioxoisoindolin-2-yl)acetoxy)ethyl)pyridine 1-oxide;

(S)-3,5-dichloro-4-(2-(3-(cyclopropylmethoxy)-4-(difluoromethoxy)phenyl)-2-(2-(5-nitro-1,3-dioxoisoindolin-2-yl)acetoxy)ethyl)pyridine 1-oxide;

(S)-3,5-dichloro-4-(2-(3-(cyclopropylmethoxy)-4-(difluoromethoxy)phenyl)-2-(2-(5-(methylsulfonamido)-1H-indol-1-yl)acetoxy)ethyl)pyridine 1-oxide;

(S)-3,5-dichloro-4-(2-(3-(cyclopropylmethoxy)-4-(difluoromethoxy)phenyl)-2-(2-(5-methoxy-2-oxoindolin-1-yl)acetoxy)ethyl)pyridine 1-oxide;

(S)-3,5-dichloro-4-(2-(3-(cyclopropylmethoxy)-4-(difluoromethoxy)phenyl)-2-(2-(4-(N-(2-morpholinoethyl)methylsulfonamido)-1,3-dioxoisoindolin-2-yl)acetoxy)ethyl)pyridine 1-oxide;

(S)-3,5-dichloro-4-(2-(3-(cyclopropylmethoxy)-4-(difluoromethoxy)phenyl)-2-(2-(5-methoxy-2,3-dioxoindolin-1-yl)acetoxy)ethyl)pyridine 1-oxide;

(S)-3,5-dichloro-4-(2-(3-(cyclopropylmethoxy)-4-(difluoromethoxy)phenyl)-2-(2-(5-(methylsulfonamido)-2-oxoindolin-1-yl)acetoxy)ethyl)pyridine 1-oxide;

(S)-3,5-dichloro-4-(2-(2-(4-(cyclopropylmethoxy)-1,3-dioxoisoindolin-2-yl)acetoxy)-2-(3-(cyclopropylmethoxy)-4-(difluoromethoxy)phenyl)ethyl)pyridine 1-oxide;

(S)-3,5-dichloro-4-(2-(3-(cyclopropylmethoxy)-4-(difluoromethoxy)phenyl)-2-(2-(2,3-dioxo-3,4-dihydroquinoxalin-1(2H)-yl)acetoxy)ethyl)pyridine 1-oxide;

(S)-3,5-dichloro-4-(2-(3-(cyclopropylmethoxy)-4-(difluoromethoxy)phenyl)-2-(2-(4-methoxy-1,3-dioxoisoindolin-2-yl)acetoxy)ethyl)pyridine 1-oxide;

(S)-3,5-dichloro-4-(2-(3-(cyclopropylmethoxy)-4-(difluoromethoxy)phenyl)-2-(2-(5-(methylsulfonamido)-2,3-dioxoindolin-1-yl)acetoxy)ethyl)pyridine 1-oxide;

(S)-3,5-dichloro-4-(2-(3-(cyclopropylmethoxy)-4-(difluoromethoxy)phenyl)-2-(2-(2,4-dioxo-3,4-dihydroquinazolin-1(2H)-yl)acetoxy)ethyl)pyridine 1-oxide;

(S)-4-(2-(2-(1H-benzo[d]imidazol-1-yl)acetoxy)-2-(3-(cyclopropylmethoxy)-4-(difluoromethoxy)phenyl)ethyl)-3,5-dichloropyridine 1-oxide;

(S)-3,5-dichloro-4-(2-(3-(cyclopropylmethoxy)-4-(difluoromethoxy)phenyl)-2-(2-(5-(N-(2-morpholinoethyl)methylsulfonamido)-1H-indol-1-yl)acetoxy)ethyl)-pyridine 1-oxide;

(S)-3,5-dichloro-4-(2-(3-(cyclopropylmethoxy)-4-(difluoromethoxy)phenyl)-2-(2-(3-(2-morpholinoethyl)-2,4-dioxo-3,4-dihydroquinazolin-1(2H)-yl)acetoxy)ethyl)pyridine 1-oxide;

(S)-3,5-dichloro-4-(2-(3-(cyclopropylmethoxy)-4-(difluoromethoxy)phenyl)-2-(2-(2-oxoindolin-1-yl)acetoxy)ethyl)pyridine 1-oxide;

(S)-3,5-dichloro-4-(2-(3-(cyclopropylmethoxy)-4-(difluoromethoxy)phenyl)-2-(2-(5,6-difluoro-2,3-dioxoindolin-1-yl)acetoxy)ethyl)pyridine 1-oxide;

(S)-3,5-dichloro-4-(2-(3-(cyclopropylmethoxy)-4-(difluoromethoxy)phenyl)-2-(2-(1-(2-morpholinoethyl)-2,4-dioxo-1,2-dihydroquinazolin-3(4H)-yl)a(S)-3,5-dichloro-4-(2-(3-(cyclopropylmethoxy)-4-(difluoromethoxy)phenyl)-2-(2-(4-(2-morpholinoethyl)-2,3-dioxo-3,4-dihydroquinoxalin-1(2H)-yl)acetoxy)ethyl)pyridine 1-oxide; cetoxy)ethyl)pyridine 1-oxide;

(S)-3,5-dichloro-4-(2-(3-(cyclopropylmethoxy)-4-(difluoromethoxy)phenyl)-2-(2-(5-nitro-2,3-dioxoindolin-1-yl)acetoxy)ethyl)pyridine 1-oxide;

(S)-3,5-dichloro-4-(2-(3-(cyclopropylmethoxy)-4-(difluoromethoxy)phenyl)-2-(2-(5,7-dioxo-5H-pyrrolo[3,4-b]pyridin-6(7H)-yl)acetoxy)ethyl)pyridine 1-oxide;

3,5-dichloro-4-((2S)-2-(3-(cyclopropylmethoxy)-4-(difluoromethoxy)phenyl)-2-(2-(1,3-dioxoisoindolin-2-yl)-4-(methylthio)butanoyloxy)ethyl)pyridine 1-oxide;

(S)-4-(2-(2-(1H-pyrrolo[2,3-b]pyridin-1-yl)acetoxy)-2-(3-(cyclopropylmethoxy)-4-(difluoromethoxy)phenyl)ethyl)-3,5-dichloropyridine 1-oxide;

(S)-3,5-dichloro-4-(2-(3-(cyclopropylmethoxy)-4-(difluoromethoxy)phenyl)-2-(2-(7-fluoro-2,3-dioxoindolin-1-yl)acetoxy)ethyl)pyridine 1-oxide;

(S)-3,5-dichloro-4-(2-(3-(cyclopropylmethoxy)-4-(difluoromethoxy)phenyl)-2-(2-(5-(N-(2-morpholinoethyl)methylsulfonamido)-2,3-dioxoindolin-1-yl)acetoxy)ethyl)pyridine 1-oxide;

(S)-3,5-dichloro-4-(2-(3-(cyclopropylmethoxy)-4-(difluoromethoxy)phenyl)-2-(2-(5-fluoro-2,3-dioxoindolin-1-yl)acetoxy)ethyl)pyridine 1-oxide;

(S)-3,5-dichloro-4-(2-(3-(cyclopropylmethoxy)-4-(difluoromethoxy)phenyl)-2-(2-(5-(N-(2-morpholinoethyl)methylsulfonamido)-2-oxoindolin-1-yl)acetoxy)ethyl)pyridine 1-oxide;

(S)-3,5-dichloro-4-(2-(3-(cyclopropylmethoxy)-4-(difluoromethoxy)phenyl)-2-(2-(7-nitro-1H-indol-1-yl)acetoxy)ethyl)pyridine 1-oxide;

(S)-3,5-dichloro-4-(2-(3-(cyclopropylmethoxy)-4-(difluoromethoxy)phenyl)-2-(2-(3-(2-morpholinoethyl)-1,4-dioxo-3,4-dihydrophthalazin-2(1H)-yl)acetoxy)ethyl)pyridine 1-oxide;

(S)-3,5-dichloro-4-(2-(3-(cyclopropylmethoxy)-4-(difluoromethoxy)phenyl)-2-(2-(1,4-dioxo-3,4-dihydrophthalazin-2(1H)-yl)acetoxy)ethyl)pyridine 1-oxide;

(S)-3,5-dichloro-4-(2-(3-(cyclopropylmethoxy)-4-(difluoromethoxy)phenyl)-2-(2-(3-(methylsulfonamido)-1H-indol-1-yl)acetoxy)ethyl)pyridine 1-oxide;

(S)-3,5-dichloro-4-(2-(3-(cyclopropylmethoxy)-4-(difluoromethoxy)phenyl)-2-(2-(6-morpholino-2,3-dioxoindolin-1-yl)acetoxy)ethyl)pyridine 1-oxide;

(S)-3,5-dichloro-4-(2-(3-(cyclopropylmethoxy)-4-(difluoromethoxy)phenyl)-2-(2-(6-fluoro-2,3-dioxoindolin-1-yl)acetoxy)ethyl)pyridine 1-oxide;

(S)-4-(2-(2-(1H-indol-1-yl)acetoxy)-2-(3-(cyclopropylmethoxy)-4-(difluoromethoxy)-phenyl)ethyl)-3,5-dichloropyridine 1-oxide;

(R)-3,5-dichloro-4-(2-(3-(cyclopropylmethoxy)-4-(difluoromethoxy)phenyl)-2-(2-(1,3-dioxoisoindolin-2-yl)acetoxy)ethyl)pyridine 1-oxide;

(S)-3,5-dichloro-4-(2-(3-(cyclopropylmethoxy)-4-(difluoromethoxy)phenyl)-2-(2-(6-(4-methylpiperazin-1-yl)-2,3-dioxoindolin-1-yl)acetoxy)ethyl)pyridine 1-oxide;

3,5-dichloro-4-((2S)-2-(4-(difluoromethoxy)-3-(tetrahydrofuran-3-yloxy)phenyl)-2-(2-(1,3-dioxoisoindolin-2-yl)acetoxy)ethyl)pyridine 1-oxide;

(S)-3,5-dichloro-4-(2-(3-(cyclopropylmethoxy)-4-(difluoromethoxy)phenyl)-2-(2-(2-oxobenzo[d]oxazol-3(2H)-yl)acetoxy)ethyl)pyridine 1-oxide;

(S)-3,5-dichloro-4-(2-(3-(cyclopropylmethoxy)-4-(difluoromethoxy)phenyl)-2-(2-(1,3-dioxo-5-(N-(pyridin-3-yl-methyl)methylsulfonamido)isoindolin-2-yl)acetoxy)ethyl)pyridine 1-oxide;

(S)-3,5-dichloro-4-(2-(2-(5-cyano-1H-indol-1-yl)acetoxy)-2-(3-(cyclopropylmethoxy)-4-(difluoromethoxy)phenyl)ethyl)pyridine 1-oxide;

(S)-3,5-dichloro-4-(2-(3-(cyclopropylmethoxy)-4-(difluoromethoxy)phenyl)-2-(2-(6-(trifluoromethyl)-1H-indol-1-yl)acetoxy)ethyl)pyridine 1-oxide;

(S)-3,5-dichloro-4-(2-(3-(cyclopropylmethoxy)-4-(difluoromethoxy)phenyl)-2-(2-(1,3-dioxo-5-(N-(2-(pyrrolidin-1-yl)ethyl)methylsulfonamido)isoindolin-2-yl)acetoxy)ethyl)pyridine 1-oxide;

(S)-3,5-dichloro-4-(2-(3-(cyclopropylmethoxy)-4-(difluoromethoxy)phenyl)-2-(2-(5,6-dimethoxy-1,3-dioxoisoindolin-2-yl)acetoxy)ethyl)pyridine 1-oxide;

(S)-3,5-dichloro-4-(2-(3-(cyclopropylmethoxy)-4-(difluoromethoxy)phenyl)-2-(2-(4-(N-(2-morpholinoethyl)methylsulfonamido)-1H-indol-1-yl)acetoxy)ethyl)pyridine 1-oxide;

(S)-3,5-dichloro-4-(2-(3-(cyclopropylmethoxy)-4-(difluoromethoxy)phenyl)-2-(2-(6-(methylsulfonamido)-1H-indol-1-yl)acetoxy)ethyl)pyridine 1-oxide;

(S)-3,5-dichloro-4-(2-(3-(cyclopropylmethoxy)-4-(difluoromethoxy)phenyl)-2-(2-(1,3-dioxo-5-(N-(2-(piperidin-1-yl)ethyl)methylsulfonamido)isoindolin-2-yl)acetoxy)ethyl)-pyridine 1-oxide;

(S)-3,5-dichloro-4-(2-(3-(cyclopropylmethoxy)-4-(difluoromethoxy)phenyl)-2-(2-(1,3-dioxo-5-(N-(pyridin-2-yl-methyl)methylsulfonamido)isoindolin-2-yl)acetoxy)ethyl)-pyridine 1-oxide;

(S)-4-(2-(2-(1H-pyrrolo[3,2-c]pyridin-1-yl)acetoxy)-2-(3-(cyclopropylmethoxy)-4-(difluoromethoxy)phenyl)ethyl)-3,5-dichloropyridine 1-oxide;

(S)-3,5-dichloro-4-(2-(3-(cyclopropylmethoxy)-4-(difluoromethoxy)phenyl)-2-(2-(5-(N-((3,5-dimethylisoxazol-4-yl)methyl)methylsulfonamido)-1,3-dioxoisoindolin-2-yl)acetoxy)ethyl)pyridine 1-oxide;

(S)-3,5-dichloro-4-(2-(3-(cyclopropylmethoxy)-4-(difluoromethoxy)phenyl)-2-(2-(6-(methylsulfonamido)-2-oxobenzo[d]oxazol-3(2H)-yl)acetoxy)ethyl)pyridine 1-oxide;

(S)-3,5-dichloro-4-(2-(2-(5-cyano-1,3-dioxoisoindolin-2-yl)acetoxy)-2-(3-(cyclopropylmethoxy)-4-(difluoromethoxy)phenyl)ethyl)pyridine 1-oxide;

(S)-4-(2-(2-(5-(N-(2-(4-acetylpiperazin-1-yl)ethyl)methylsulfonamido)-1,3-dioxoisoindolin-2-yl)acetoxy)-2-(3-(cyclopropylmethoxy)-4-(difluoromethoxy)-phenyl)ethyl)-3,5-dichloropyridine 1-oxide;

(S)-3,5-dichloro-4-(2-(3-(cyclopropylmethoxy)-4-(difluoromethoxy)phenyl)-2-(2-(5-(N,N-dimethylsulfamoyl)-2,3-dioxoindolin-1-yl)acetoxy)ethyl)pyridine 1-oxide;

(S)-3,5-dichloro-4-(2-(3-(cyclopropylmethoxy)-4-(difluoromethoxy)phenyl)-2-(2-(5-(N-(2-(4-methylpiperazin-1-yl)ethyl)methylsulfonamido)-1,3-dioxoisoindolin-2-yl)acetoxy)ethyl)pyridine 1-oxide;

(S)-3,5-dichloro-4-(2-(2-(3-cyano-1H-indol-1-yl)acetoxy)-2-(3-(cyclopropylmethoxy)-4-(difluoromethoxy)phenyl)ethyl)pyridine 1-oxide;

(S)-3,5-dichloro-4-(2-(3-(cyclopropylmethoxy)-4-(difluoromethoxy)phenyl)-2-(2-(1,3-dioxo-5-(N-(2-thiomorpholinoethyl)methylsulfonamido)isoindolin-2-yl)acetoxy)-ethyl)pyridine 1-oxide;

(S)-3,5-dichloro-4-(2-(3-(cyclopropylmethoxy)-4-(difluoromethoxy)phenyl)-2-(2-(5-(N-(2-morpholino-2-oxoethyl)methylsulfonamido)-1,3-dioxoisoindolin-2-yl)acetoxy)ethyl)pyridine 1-oxide;

(S)-3,5-dichloro-4-(2-(3-(cyclopropylmethoxy)-4-(difluoromethoxy)phenyl)-2-(2-(1,3-dioxo-5-(N-(2-oxo-2-(pyridin-2-yl)ethyl)methylsulfonamido)isoindolin-2-yl)acetoxy)ethyl)pyridine 1-oxide;

(S)-3,5-dichloro-4-(2-(3-(cyclopropylmethoxy)-4-(difluoromethoxy)phenyl)-2-(2-(5-(methylsulfonamido)indolin-1-yl)acetoxy)ethyl)pyridine 1-oxide;

(S)-3,5-dichloro-4-(2-(3-(cyclopropylmethoxy)-4-(difluoromethoxy)phenyl)-2-(2-(5-(N-(2-(dimethylamino)ethyl)methylsulfonamido)-1,3-dioxoisoindolin-2-yl)acetoxy)ethyl)pyridine 1-oxide;

(S)-4-(2-(2-(5-(N-(2-(1H-imidazol-1-yl)ethyl)methylsulfonamido)-1,3-dioxoisoindolin-2-yl)acetoxy)-2-(3-(cyclopropylmethoxy)-4-(difluoromethoxy)phenyl)ethyl)-3,5-dichloropyridine 1-oxide;

(S)-3,5-dichloro-4-(2-(3-(cyclopropylmethoxy)-4-(difluoromethoxy)phenyl)-2-(2-(5-methoxy-6-(methylsulfonamido)-1,3-dioxoisoindolin-2-yl)acetoxy)ethyl)pyridine 1-oxide;

(S)-3,5-dichloro-4-(2-(3-(cyclopropylmethoxy)-4-(difluoromethoxy)phenyl)-2-(2-(5-(methylsulfonamidomethyl)-1,3-dioxoisoindolin-2-yl)acetoxy)ethyl)pyridine 1-oxide;

(S)-3,5-dichloro-4-(2-(3-(cyclopropylmethoxy)-4-(difluoromethoxy)phenyl)-2-(2-(5-((N-(2-morpholinoethyl)methylsulfonamido)methyl)-1,3-dioxoisoindolin-2-yl)acetoxy)ethyl)pyridine 1-oxide;

(S)-3,5-dichloro-4-(2-(3-(cyclopropylmethoxy)-4-(difluoromethoxy)phenyl)-2-(2-(5-(N-(2-((2-(dimethylamino)ethyl)(methyl)amino)ethyl)methylsulfonamido)-1,3-dioxoisoindolin-2-yl)acetoxy)ethyl)pyridine 1-oxide;

(S)-3,5-dichloro-4-(2-(3-(cyclopropylmethoxy)-4-(difluoromethoxy)phenyl)-2-(2-(5-(N-(3-morpholinopropyl)methylsulfonamido)-1,3-dioxoisoindolin-2-yl)acetoxy)ethyl)pyridine 1-oxide;

(S)-3,5-dichloro-4-(2-(3-(cyclopropylmethoxy)-4-(difluoromethoxy)phenyl)-2-(2-(5-(N-((4-methoxypyridin-2-yl)methyl)methylsulfonamido)-1,3-dioxoisoindolin-2-yl)acetoxy)ethyl)pyridine 1-oxide;

(S)-3,5-dichloro-4-(2-(3-(cyclopropylmethoxy)-4-(difluoromethoxy)phenyl)-2-(2-(5-(N-(2-(2-methoxyethylamino)ethyl)methylsulfonamido)-1,3-dioxoisoindolin-2-yl)acetoxy)ethyl)pyridine 1-oxide;

(S)-3,5-dichloro-4-(2-(3-(cyclopropylmethoxy)-4-(difluoromethoxy)phenyl)-2-(2-(1,3-dioxo-5-(N-(quinolin-2-ylmethyl)methylsulfonamido)isoindolin-2-yl)acetoxy)ethyl)pyridine 1-oxide;

(S)-3,5-dichloro-4-(2-(3-(cyclopropylmethoxy)-4-(difluoromethoxy)phenyl)-2-(2-(5-(N-(2-methoxyethyl)methylsulfonamido)-1,3-dioxoisoindolin-2-yl)acetoxy)ethyl)pyridine 1-oxide;

(S)-3,5-dichloro-4-(2-(3-(cyclopropylmethoxy)-4-(difluoromethoxy)phenyl)-2-(2-(1,3-dioxo-5-(N-((6-(trifluoromethyl)pyridin-3-yl)methyl)methylsulfonamido)isoindolin-2-yl)acetoxy)ethyl)pyridine 1-oxide;

(S)-3,5-dichloro-4-(2-(3-(cyclopropylmethoxy)-4-(difluoromethoxy)phenyl)-2-(2-(1,3-dioxo-5-(N-(pyridin-4-ylmethyl)methylsulfonamido)isoindolin-2-yl)acetoxy)ethyl)pyridine 1-oxide;

(S)-3,5-dichloro-4-(2-(3-(cyclopropylmethoxy)-4-(difluoromethoxy)phenyl)-2-(2-(5-(N-((3-methylpyridin-2-yl)methyl)methylsulfonamido)-1,3-dioxoisoindolin-2-yl)acetoxy)ethyl)pyridine 1-oxide;

(S)-3,5-dichloro-4-(2-(3-(cyclopropylmethoxy)-4-(difluoromethoxy)phenyl)-2-(2-(6-(N-(2-morpholinoethyl)methylsulfonamido)-2-oxobenzo[d]oxazol-3(2H)-yl)acetoxy)ethyl)pyridine 1-oxide;

(S)-3,5-dichloro-4-(2-(3-(cyclopropylmethoxy)-4-(difluoromethoxy)phenyl)-2-(2-(2-oxo-6-(N-(pyridin-3-ylmethyl)methylsulfonamido)benzo[d]oxazol-3(2H)-yl)acetoxy)ethyl)pyridine 1-oxide;

(S)-3,5-dichloro-4-(2-(3-(cyclopropylmethoxy)-4-(difluoromethoxy)phenyl)-2-(2-(5-(N-((6-methylpyridin-2-yl)methyl)methylsulfonamido)-1,3-dioxoisoindolin-2-yl)acetoxy)ethyl)pyridine 1-oxide;

(S)-3,5-dichloro-4-(2-(3-(cyclopropylmethoxy)-4-(difluoromethoxy)phenyl)-2-(2-(1,3-dioxo-5-(N-(pyrimidin-2-ylmethyl)methylsulfonamido)isoindolin-2-yl)acetoxy)ethyl)pyridine 1-oxide;

(S)-3,5-dichloro-4-(2-(3-(cyclopropylmethoxy)-4-(difluoromethoxy)phenyl)-2-(2-(1,3-dioxo-5-(N-(thiophen-2-ylmethyl)methylsulfonamido)isoindolin-2-yl)acetoxy)ethyl)pyridine 1-oxide;

(S)-3,5-dichloro-4-(2-(3-(cyclopropylmethoxy)-4-(difluoromethoxy)phenyl)-2-(2-(1,3-dioxo-5-(pyridin-3-ylmethoxy)isoindolin-2-yl)acetoxy)ethyl)pyridine 1-oxide;

(S)-3,5-dichloro-4-(2-(3-(cyclopropylmethoxy)-4-(difluoromethoxy)phenyl)-2-(2-(1,3-dioxo-5-(N-(thiazol-2-ylmethyl)methylsulfonamido)isoindolin-2-yl)acetoxy)ethyl)pyridine 1-oxide;

(S)-3,5-dichloro-4-(2-(3-(cyclopropylmethoxy)-4-(difluoromethoxy)phenyl)-2-(2-(1,3-dioxo-5-(N-(pyrazin-2-ylmethyl)methylsulfonamido)isoindolin-2-yl)acetoxy)ethyl)pyridine 1-oxide;

and pharmaceutically acceptable salts or solvates thereof.

According to a preferred embodiment, a compound of formula (I) is selected from the group consisting of:

(S)-3,5-dichloro-4-(2-(3-(cyclopropylmethoxy)-4-(difluoromethoxy)phenyl)-2-(2-(6,7-dimethoxy-3,4-dihydroisoquinolin-2(1H)-yl)acetoxy)ethyl)pyridine 1-oxide;

(S)-3,5-dichloro-4-(2-(3-(cyclopropylmethoxy)-4-(difluoromethoxy)phenyl)-2-(2-(1,3-dioxoisoindolin-2-yl)acetoxy)ethyl)pyridine 1-oxide;

(S)-3,5-dichloro-4-(2-(3-(cyclopropylmethoxy)-4-(difluoromethoxy)phenyl)-2-(2-(5-(N-(2-morpholinoethyl)methylsulfonamido)-1,3-dioxoisoindolin-2-yl)acetoxy)ethyl) pyridine 1-oxide;

(S)-3,5-dichloro-4-(2-(3-(cyclopropylmethoxy)-4-(difluoromethoxy)phenyl)-2-(2-(2,4-dioxo-1,2-dihydroquinazolin-3(4H)-yl)acetoxy)ethyl)pyridine 1-oxide;

(S)-3,5-dichloro-4-(2-(3-(cyclopropylmethoxy)-4-(difluoromethoxy)phenyl)-2-(2-(5-(methylsulfonamido)-1,3-dioxoisoindolin-2-yl)acetoxy)ethyl)pyridine 1-oxide;

(S)-3,5-dichloro-4-(2-(3-(cyclopropylmethoxy)-4-(difluoromethoxy)phenyl)-2-(2-(4-(2-methoxyacetamido)-1,3-dioxoisoindolin-2-yl)acetoxy)ethyl)pyridine 1-oxide;

(S)-3,5-dichloro-4-(2-(3-(cyclopropylmethoxy)-4-(difluoromethoxy)phenyl)-2-(2-(5-(methylsulfonamido)-1H-indol-1-yl)acetoxy)ethyl)pyridine 1-oxide;

(S)-3,5-dichloro-4-(2-(3-(cyclopropylmethoxy)-4-(difluoromethoxy)phenyl)-2-(2-(5-(N-(2-morpholinoethyl)methylsulfonamido)-2,3-dioxoindolin-1-yl)acetoxy)ethyl) pyridine 1-oxide;

3,5-dichloro-4-((2S)-2-(4-(difluoromethoxy)-3-(tetrahydrofuran-3-yloxy)phenyl)-2-(2-(1,3-dioxoisoindolin-2-yl)acetoxy)ethyl)pyridine 1-oxide;-

(S)-3,5-dichloro-4-(2-(3-(cyclopropylmethoxy)-4-(difluoromethoxy)phenyl)-2-(2-(1,3-dioxo-5-(N-(pyridin-3-yl-methyl)methylsulfonamido)isoindolin-2-yl)acetoxy)ethyl)-pyridine 1-oxide;

(S)-3,5-dichloro-4-(2-(3-(cyclopropylmethoxy)-4-(difluoromethoxy)phenyl)-2-(2-(1,3-dioxo-5-(N-(2-(pyrrolidin-1-yl)ethyl)methylsulfonamido)isoindolin-2-yl)acetoxy)-ethyl)pyridine 1-oxide;

(S)-3,5-dichloro-4-(2-(3-(cyclopropylmethoxy)-4-(difluoromethoxy)phenyl)-2-(2-(5,6-dimethoxy-1,3-dioxoisoindolin-2-yl)acetoxy)ethyl)pyridine 1-oxide;

(S)-3,5-dichloro-4-(2-(3-(cyclopropylmethoxy)-4-(difluoromethoxy)phenyl)-2-(2-(1,3-dioxo-5-(N-(pyridin-2-yl-methyl)methylsulfonamido)isoindolin-2-yl)acetoxy)ethyl)-pyridine 1-oxide;

(S)-3,5-dichloro-4-(2-(3-(cyclopropylmethoxy)-4-(difluoromethoxy)phenyl)-2-(2-(1,1-dioxido-3-oxobenzo[d]isothiazol-2(3H)-yl)acetoxy)ethyl)pyridine 1-oxide;

and pharmaceutically acceptable salts or solvates thereof.

In one aspect of the present invention, a process for the preparation of compounds of the invention is provided, according to general synthetic routes a), b) or c) reported in General Scheme herebelow.

General Scheme.

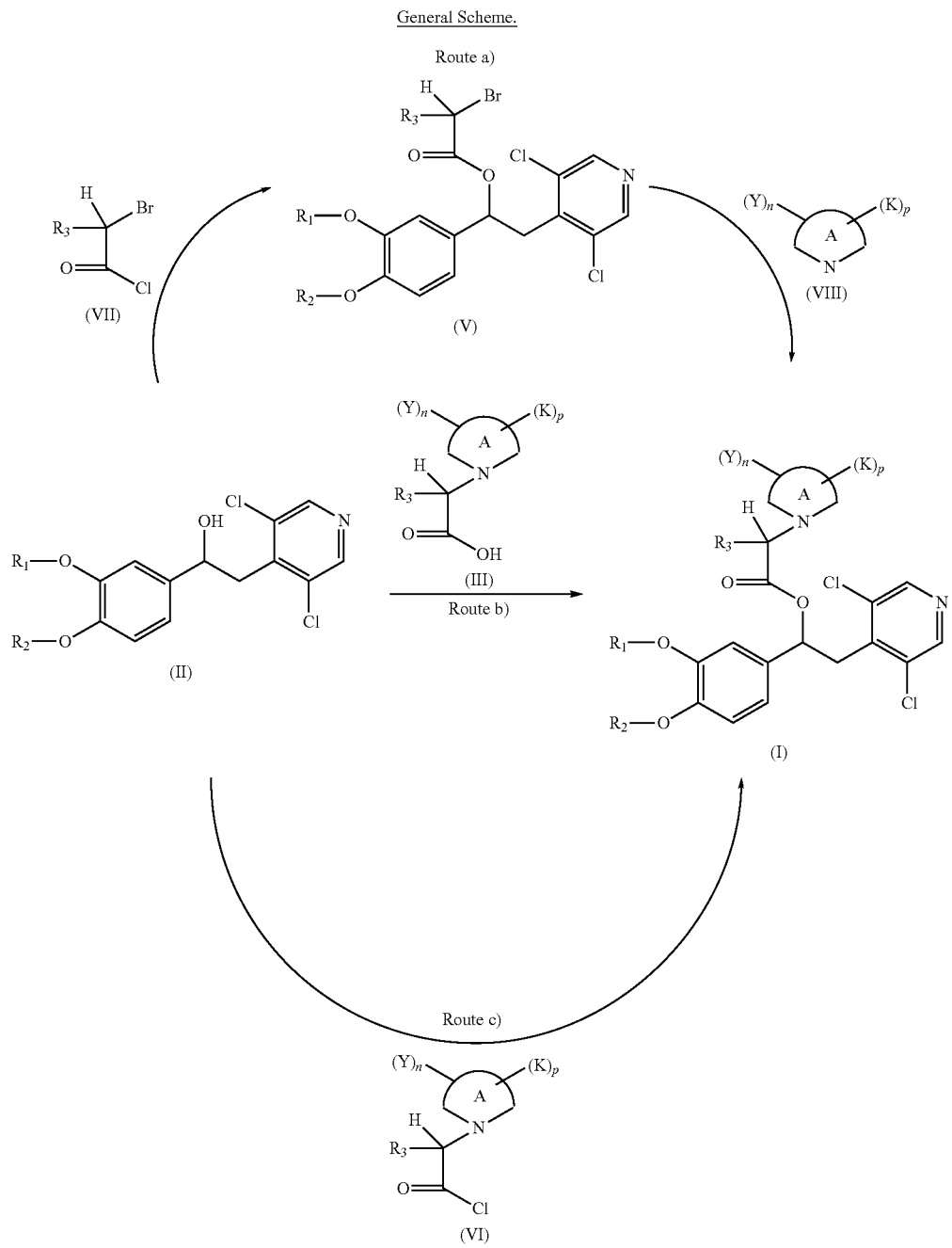

The skilled person may introduce, where appropriate, suitable variations to the conditions specifically described in the examples in order to adapt the synthetic routes to the provision of further compounds of the invention. Such variations may include, but are not limited to, use of appropriate starting materials to generate different compounds, changes in the solvent and temperature of reactions, replacements of reactants with analogous chemical role, introduction or removal of protection/deprotection stages of functional groups sensitive to reaction conditions and reagents.

Also, introduction or removal of specific synthetic steps oriented to further functionalization of the chemical scaffold may be contemplated and are included within the scope of the present invention.

In Table A herebelow, reference is made to specific synthetic Schemes where Routes a), b) and c) are better detailed and which are reported in the examples section:

TABLE A

| Example (Synthetic Scheme) | Route |
| --- | --- |
| 5 | a) |
| 4, 8, 9, 10, 11, 12, 13, 17, 18, 19, 20, 21, 22, 23, 25, 26, 27, 28, 29, 30, 33, 34, 35, 36, 37, 38, 40, 41, 42, 43, 44, 45, 46, 47 | b) |
| 2, 3, 6, 7, 14, 15, 16, 24, 31, 32, 39, 48 | Modified b) |
| 49 | c) |

Processes which can be used and are described and reported in the Examples and Schemes, should not be viewed as limiting the scope of the synthetic methods available for the preparation of the compounds of the invention.

The N-oxides on the 4-pyridinyl ring of the compounds of general formula (I) may be prepared according to methods available in the literature and well known to the skilled person. For instance they may be prepared by dissolving the compound of general formula (I) in $CH_2Cl_2$ or $CHCl_3$, then adding an oxidizing agent such as m-chloro perbenzoic acid (mCPBA) to the resulting solution. Other oxidizing agents which may be used are hydrogen peroxide, perbenzoic acid and peracetic acid.

Alternatively, in particular for those compounds where a functional group sensitive to oxidation is present, the corresponding N-oxides are prepared by carrying out the oxidation step before further functional groups are introduced, for example on compounds of formula (II), thus generating compounds of formula (IX).

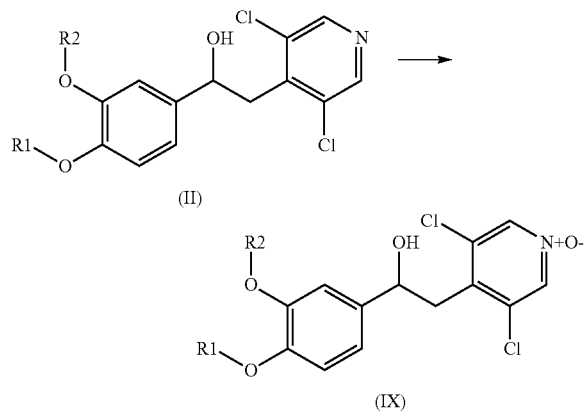

In a preferred embodiment, the process for preparation of compounds of formula (I) is performed starting from the pyridine N-oxide compound of formula (IX), thus allowing the preparation of compound of formula (I) in the form of pyridine N-oxides.

Compounds used as starting materials or intermediates may be commercially available, their preparation may be specifically described in the literature, or they may be prepared according to methods available in the literature and well known in the art. In some instances, procedures for the preparation of intermediates or starting materials may be also provided in the examples, for example, in Schemes 8, 9, 10, 11, 12, 13, 17, 18, 19, 20, 21, 22, 23, 25, 26, 27, 28, 29, 30, 33, 34, 35, 36, 37, 38, 40, 41, 42, 43, 44, 45, 46, 47, 49.

Compounds of formula (II) and (IX) may also be prepared as described in International Patent Application WO2009/018909, which is incorporated herein by reference in its entirety. Alternatively, certain compounds of formula (IX) may be prepared according to the procedure reported in Scheme 1 of the present application.

The process described is particularly advantageous as it is susceptible of being properly modulated, through any proper known variant, so as to obtain any of the desired compounds of the invention. Such variants are comprised within the scope of the present invention.

From all of the above, it should be clear to the skilled person that any of the described groups may be present as such or in any properly protected form.

In particular, functional groups present in the intermediate and compounds and which could generate unwanted side reaction and by-products, need to be properly protected before the alkylation, acylation, coupling or sulfonylation takes place. Likewise, subsequent deprotection of those same protected groups may follow upon completion of the said reactions.

In the present invention, unless otherwise indicated, the term "protecting group" designates a protective group adapted to preserve the function of the group it is bound to. Typically, protective groups are used to preserve amino, hydroxyl, or carboxyl functions. Appropriate protecting groups may thus include, for example, benzyl, benzyloxycarbonyl, t-butoxycarbonyl, alkyl or benzyl esters or the like, which are well known to those skilled in the art (see, for a general reference, T. W. Green; Protective Groups in Organic Synthesis (Wiley, N.Y. 1981) which is incorporated herein by reference in its entirety).

Likewise, selective protection and deprotection of any of the said groups, for instance including carbonyl, hydroxyl or amino groups, may be accomplished according to very well known methods commonly employed in organic synthetic chemistry.

Optional salification of the compounds of formula (I) or pyridine ring thereof may be carried out by properly converting any of the free acidic or amino groups into the corresponding pharmaceutically acceptable salts. In this case too, the operative conditions being employed for the optional salification of the compounds of the invention are all within the ordinary knowledge of the skilled person.

It is therefore evident that the above process, comprehensive of any variant thereof for the preparation of suitable compounds of the invention, may be conveniently modified so that to adapt the reaction conditions to the specific needs, for instance by choosing appropriate condensing agents, solvents and protective groups, as the case may be.

In the following Schemes, for compounds of formula (II) to (VIII), unless otherwise indicated, groups A, $R_1$ to $R_3$, Y, n, p and K have the same meanings as described for compounds of formula (I) above.

Route a).

Compounds of formula (I), may be prepared according to Scheme A1 shown below by reaction of a compound of formula (V), with an appropriate compound of formula (VIII):

Scheme A1.

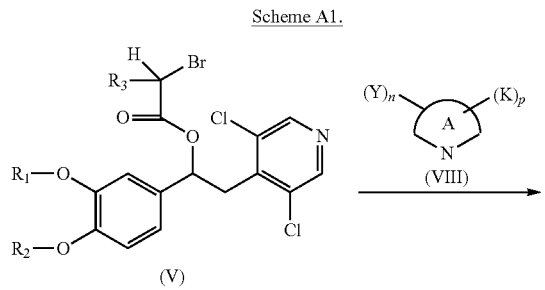

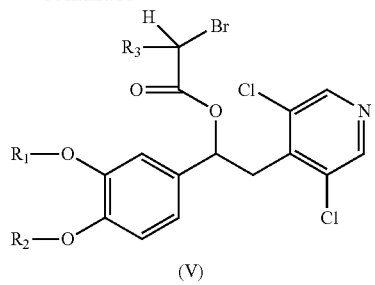

(V)

Typical reaction conditions comprise reacting a compound of formula (II) with a compound of formula (VII) in a suitable polar aprotic solvent, such as DCM or chloroform, in the presence an appropriate base, such as DMAP, TEA or DIPEA at an appropriate temperature such as, for example, RT.

Route b).

Compounds of formula (I), may be prepared according to Scheme B shown below by reaction of a compound of formula (II), with an appropriate compound of formula (III).

Scheme B.

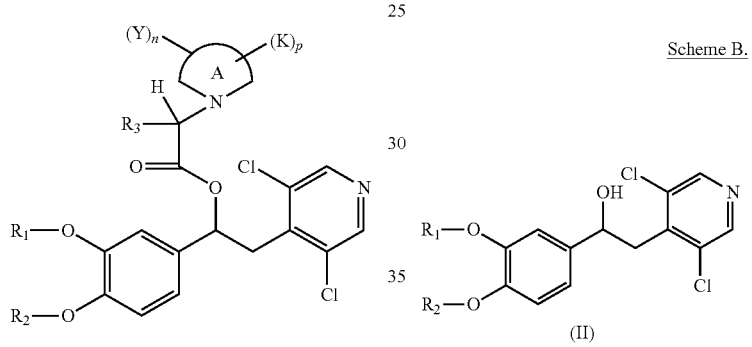

Typical reaction conditions comprise reacting a compound of formula (V) with a compound of formula (VIII) in a suitable polar solvent, such as DMF or acetonitrile, in the presence an appropriate base, such as $K_2CO_3$, alkaline bicarbonate, TEA or DIPEA at an appropriate temperature such as, for example, ranging from RT to 50° C.

Compounds of formula (V), as above defined may be prepared according to Scheme A2 shown below by reaction of a compound of formula (II), with an appropriate compound of formula (VII):

Scheme A2.

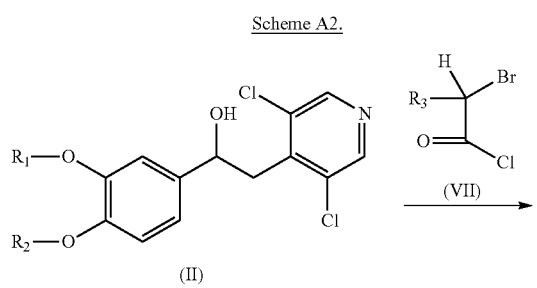

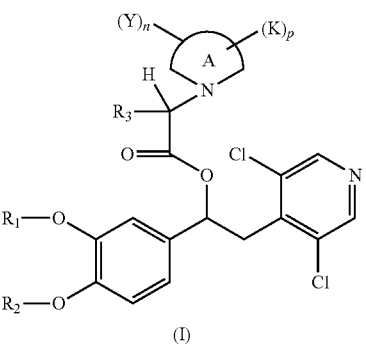

(I)

Typical reaction conditions comprise reacting a compound of formula (II) with a compound of formula (III) in a suitable polar aprotic solvent, such as DMF, THF, chloroform or DCM, in the presence of an appropriate condensing agent such as EDC, DCC or CDI and of an appropriate agent, such as DMAP, HOBT, 4-pyrrolidinopyridine (4-PPY) or other 4-alkylamino pyridine at room temperature.

Route c).

Compounds of formula (I), may be prepared according to Scheme C shown below by reaction of a compound of formula (II), with an appropriate compound of formula (VI).

Scheme C.

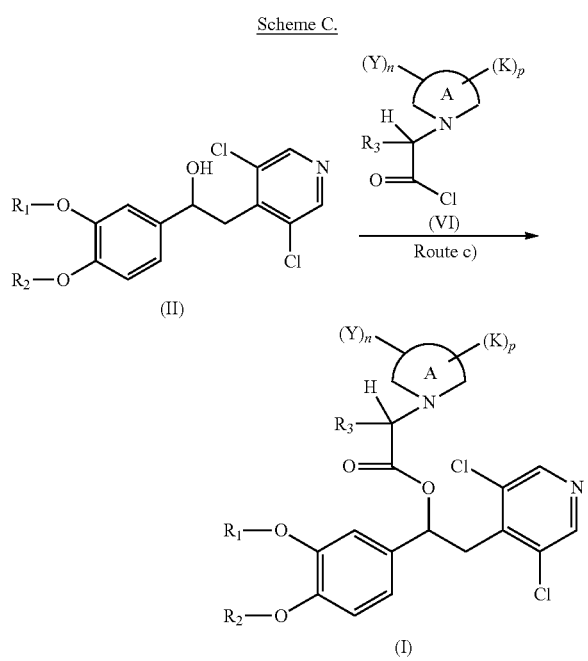

Typical reaction conditions comprise reacting a compound of formula (II) with a compound of formula (VIII) in a suitable polar aprotic solvent, such as DCM or chloroform, in the presence an appropriate base, such as DMAP, TEA or DIPEA at an appropriate temperature such as, for example, RT.

The present invention also provides pharmaceutical compositions of compounds of the invention in admixture with one or more pharmaceutically acceptable carriers, for example those described in Remington's Pharmaceutical Sciences Handbook, XVII Ed., Mack Pub., N.Y., U.S.A., which is incorporated herein by reference in it is entirety.

Administration of the compounds of the present invention may be accomplished according to patient needs, for example, orally, nasally, parenterally (subcutaneously, intravenously, intramuscularly, intrasternally and by infusion), by inhalation, rectally, vaginally, topically, locally, transdermally, and by ocular administration. Various solid oral dosage forms may be used for administering compounds of the invention including such solid forms as tablets, gelcaps, capsules, caplets, granules, lozenges and bulk powders. The compounds of the present invention may be administered alone or combined with various pharmaceutically acceptable carriers, diluents (such as sucrose, mannitol, lactose, starches) and excipients known in the art, including but not limited to suspending agents, solubilizers, buffering agents, binders, disintegrants, preservatives, colorants, flavorants, lubricants and the like. Time release capsules, tablets and gels are also advantageous in administering the compounds of the present invention.

Various liquid oral dosage forms may also be used for administering compounds of the invention, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention. The compounds of the present invention may be injected, for example, intravenously, in the form of an isotonic sterile solution. Other preparations are also possible.

Suppositories for rectal administration of the compounds of the present invention may be prepared by mixing the compound with a suitable excipient such as cocoa butter, salicylates and polyethylene glycols.

Formulations for vaginal administration may be in the form of cream, gel, paste, foam, or spray formula containing, in addition to the active ingredient, such suitable carriers as are known in the art.

For topical administration the pharmaceutical composition may be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

For the treatment of the diseases of the respiratory tract, the compounds according to the invention are preferably administered by inhalation.

Inhalable preparations include inhalable powders, propellant-containing metering aerosols or propellant-free inhalable formulations.

For administration as a dry powder, single- or multi-dose inhalers known from the prior art may be utilized. In that case, the powder may be filled in gelatine, plastic or other capsules, cartridges or blister packs or in a reservoir.

A diluent or carrier, generally non-toxic and chemically inert to the compounds of the invention, e.g. lactose or any other additive suitable for improving the respirable fraction may be added to the powdered compounds of the invention.

Inhalation aerosols containing propellant gas such as hydrofluoroalkanes may contain the compounds of the invention either in solution or in dispersed form. The propellant-driven formulations may also contain other ingredients such as co-solvents, stabilizers and optionally other excipients.

The propellant-free inhalable formulations comprising the compounds of the invention may be in form of solutions or suspensions in an aqueous, alcoholic or hydroalcoholic medium and they may be delivered by jet or ultrasonic nebulizers known from the prior art or by soft-mist nebulizers such as Respimat®.

The compounds of the invention may be administered as the sole active agent or in combination with other pharmaceutical active ingredients including those currently used in the treatment of respiratory disorders, e.g. beta2-agonists, antimuscarinic agents, corticosteroids, mitogen-activated protein kinases (P38 MAP kinase) inhibitors, nuclear factor kappa-B kinase subunit beta (IKK2) inhibitors, human neutrophil elastase (HNE) inhibitors, phosphodiesterase 4 (PDE4) inhibitors, leukotriene modulators, non-steroidal anti-inflammatory agents (NSAIDs), and mucus regulators.

The present invention also provides combinations of a compound of the invention with a β2-agonist selected from the group consisting of carmoterol, GSK-642444, indacaterol, milveterol, arformoterol, formoterol, salbutamol, levalbuterol, terbutaline, AZD-3199, BI-1744-CL, LAS-100977, bambuterol, isoproterenol, procaterol, clenbuterol, reproterol, fenoterol, and ASF-1020 and salts thereof.

The present invention also provides combinations of a compound of the invention with a corticosteroid selected from the group consisting of fluticasone propionate, fluticasone furoate, mometasone furoate, beclometasone dipropionate, ciclesonide, budesonide, GSK 685698, and GSK 870086.

The present invention also provides combinations of a compound of the invention with an antimuscarinic agent selected from the group consisting of aclidinium, tiotropium, ipratropium, trospium, glycopyrronium, and oxitropium salts.

The present invention also provides combinations of a compound of the invention with a PDE4 inhibitor selected from the group consisting of AN-2728, AN-2898, CBS-3595, apremilast, ELB-353, KF-66490, K-34, LAS-37779, IBFB-211913, AWD-12-281, cipamfylline, cilomilast, roflumilast, BAY19-8004 and SCH-351591, AN-6415, indus-82010, TPI-PD3, ELB-353, CC-11050, GSK-256066, oglemilast, OX-914, tetomilast, MEM-1414, and RPL-554.

The present invention also provides combinations of a compound of the invention with a P38 MAP kinase inhibitor selected from the group consisting of semapimod, talmapimod, pirfenidone, PH-797804, GSK-725, minokine and losmapimod, and salts thereof.

In a preferred embodiment, the present invention provides combinations of a compound of the invention with an IKK2 inhibitor.

The invention also provides combinations of a compound of the invention with a HNE inhibitor selected from the group consisting of AAT, ADC-7828, Aeriva, TAPI, AE-3763, KRP-109, AX-9657, POL-6014, AER-002, AGTC-0106, respriva, AZD-9668, zemaira, AAT IV, PGX-100, elafin, SPHD-400, prolastin C and prolastin inhaled.

The invention also provides combinations of a compound of the invention with a leukotriene modulator selected from the group consisting of montelukast, zafirlukast, and pranlukast.

The invention also provides combinations of a compound of the invention or of a compound of formula (II), with a NSAID selected from the group consisting of ibuprofen and ketoprofen.

The invention also provides combinations of a compound of the invention with a mucus regulator selected from the group consisting of INS-37217, diquafosol, sibenadet, CS-003, talnetant, DNK-333, MSI-1956, and gefitinib.

The dosages of the compounds of the present invention depend upon a variety of factors including the particular disease to be treated, the severity of the symptoms, the route of administration, the frequency of the dosage interval, the particular compound utilized, the efficacy, toxicology profile, and pharmacokinetic profile of the compound.

Advantageously, the compounds of the invention may be administered for example, at a dosage comprised between 0.001 and 1000 mg/day, preferably between 0.1 and 500 mg/day.

When they are administered by inhalation route, the dosage of the compounds of the invention is advantageously comprised between 0.01 and 20 mg/day, preferably between 0.1 and 10 mg/day.

Preferably, the compounds of the invention alone or combined with other active ingredients may be administered for the prevention and/or treatment of any obstructive respiratory disease such as asthma, chronic bronchitis, and chronic obstructive pulmonary disease (COPD).

However the compounds of the invention may be administered for the prevention and/or treatment of any disease wherein PDE4 inhibition is required. Said diseases include: allergic disease states such as atopic dermatitis, urticaria, allergic rhinitis, allergic conjunctivitis, vernal conjunctivitis, eosinophilic granuloma, psoriasis, inflammatory arthritis, rheumatoid arthritis, septic shock, ulcerative colitis, Crohn's disease, reperfusion injury of the myocardium and brain, chronic glomerulonephritis, endotoxic shock, cystic fibrosis, arterial restenosis, artherosclerosis, keratosis, rheumatoid spondylitis, osteoarthritis, pyresis, diabetes mellitus, pneumoconiosis, toxic and allergic contact eczema, atopic eczema, seborrheic eczema, lichen simplex, sunburn, pruritus in the anogenital area, alopecia greata, hypertrophic scars, discoid lupus erythematosus, systemic lupus erythematosus, follicular and wide-area pyodermias, endogenous and exogenous acne, acne rosacea, Beghet's disease, anaphylactoid purpura nephritis, inflammatory bowel disease, leukemia, multiple sclerosis, gastrointestinal diseases, autoimmune diseases and the like.

They also include neurological and psychiatric disorders such as Alzheimer's disease, multiple sclerosis, amylolaterosclerosis (ALS), multiple systems atrophy (MSA), schizophrenia, Parkinson's disease, Huntington's disease, Pick's disease, depression, stroke, and spinal cord injury.

Other features of the invention will become apparent in the course of the following descriptions of exemplary embodiments which are given for illustration of the invention and are not intended to be limiting thereof.

EXAMPLES

Chemical Names of the compounds were generated with Structure To Name Enterprise 10.0 Cambridge Software.

Abbreviations

EDC=1-ethyl-3-(3-dimethylaminopropyl) carbodiimide;
DMAP=4-dimethylaminopyridine;
DMF=dimethylformamide;
EtOAc=Ethyl acetate;
RT or Rt=room temperature;
THF=tetrahydrofuran;
DCM=dichloromethane;
Et2O=diethyl ether;
MeOH=methyl alcohol;
n-butOH=n-butyl alcohol;
EtOH=ethyl alcohol;
IprOH or IPA=isopropyl alcohol;
IprO2=diisopropylether;
TEA=Triethylamine;
Py=Pyridine;
MsCl=Methanesulfonyl chloride;
TFA=trifluoroacetic acid;
$CH_3CN$=acetonitrile;
$(Boc)_2O$=ditertbutyl dicarbonate;
AcOH=acetic acid;
CDI=carbonyldiimidazole;
DIPEA=di-isopropyl ethyl amine;
HBTU=2-(1H-benzotriazol-1-yl)-1,1,3,3-tetramethyluronium hexafluorophosphate;
HOBT=Hydroxybenzotriazole.
Procedures for Salt Formation.

Unless otherwise stated, trifluoroacetate salts described in the examples section were obtained according to the following procedure: Compounds containing one or more basic centres and purified by preparative HPLC were obtained as trifluoroacetate salts, once clean fractions collected from chromatography were evaporated under reduced pressure without any further basic treatment.

If not otherwise indicated, any other salt was obtained by treating the base with a solution of the corresponding acid under conditions know to the skilled person. The salt stoichiometry was determined, if required, by NMR.
NMR Characterization.

NMR spectra were recorder either with:
$^1$H-NMR spectra were recorded on a 400 MHz Varian AS400 spectrometer. Chemical shift are reported as δ values in ppm relative to trimethyl silane (TMS) as an internal standard. Coupling constants (J values) are given in hertz (Hz) and multiplicities are reported using the following abbreviation (s=singlet, d=doublet, t=triplet, q=quartet, m=multiplet, br=broad, nd=not determined).
or $^1$H-NMR spectra were recorded on a Bruker ARX300 Spectrometer at 300.13 MHz (1H) using deuterated solvents, such as deuterated dimethylsulfoxide (DMSO-d6) or deuterated chloroform (CDCl$_3$). The instrument was equipped with a multinuclear inverse probe and temperature controller. Chemical shifts are expressed in parts per million (ppm) downfield of tetramethylsilane (d units). Multiplicity is indicated as follow: (s) singlet, (d) doublet, (dd) double doublet, (ddd) triple doublet, (t) triplet, (dt) double triplet, (q) quartet, (m) multiplet, (br s) broad signal. Coupling constants J are expressed in units of hertz (Hz).

Preparative HPLC—Method 1.
Column: Waters Symmetry Prep C18 17 um 19×300
Flow: 20 ml/min
Mobile phase: 90% H$_2$O, 10% acetonitrile, 0.05% TFA (A), 10% H$_2$O, 90% acetonitrile, 0.05% TFA (B)
Gradient:

| Time (min) | % A | % B |
|---|---|---|
| 0.00 | 95 | 5 |
| 5 | 95 | 5 |
| 28 | 0 | 100 |
| 30 | 0 | 100 |

The same gradient without TFA in mobile phase was used for preparative HPLC under neutral conditions.

Preparative HPLC—Method 2.
Waters Micromass ZQ; Sample manager 2767; Photodiode array detector 2996;
Column XTerra Prep MS C18 Column (5 μm, 19×150 mm, Waters); flow rate of 20 ml/min with MS detection or UV set at 254 nm.
Gradient:

| Time (min) | % A | % B |
|---|---|---|
| 0.00 | 100.0 | 0.00 |
| 1.00 | 100 | 0.00 |
| 10.00 | 0.00 | 100.00 |
| 11.00 | 0.00 | 100.00 |
| 12.00 | 100.0 | 0.00 |

Eluent
Solvent A (water:MeCN:HCOOH 95:5:0.05)
Solvent B (water:MeCN:HCOOH 5:95:0.05)
Preparative HPLC (Method 3).
Waters Micromass ZQ/sample manager 2767
Photodiode array detector: 2996
Column: XTERRA Prep MS C18 10 um 19×300
Flow: 20 ml/min
Mobile phases: H$_2$O, 0.1% TFA (A); acetonitrile, 0.1% TFA (B)
Gradient:

| Time (min) | % A | % B |
|---|---|---|
| 0.00 | 90 | 10 |
| 2 | 90 | 10 |
| 23 | 0 | 100 |
| 30 | 0 | 100 |

Conditioning:

| Time (min) | % A | % B |
|---|---|---|
| 30.5 | 90 | 10 |
| 32 | 90 | 10 |

Chiral HPLC:
The enantiomeric purity was determined on Hewlett Packard 1050 HPLC system using Chiracel OD column (5 μl, 4.6×250 mm), eluting using isocratic mixture of hexane and isopropanol in different ratios as indicated in each specific example.
Flow=0.8 ml/min
UV detection=230 nm.
Optical Rotation (Activity) Determination.
Specific rotations of compounds were measured with a Polarimeter Perkin Elmer model 241 or 341.
Temperature (° C.) 25
Path Length (dm) 1
Wavelength Sodium D-line (589 nm)
The MS/ESI$^+$ [MH]$^+$ values reported in the text below may be obtained or by MS instrument Waters ZQ (or equivalent) or by UPLC Waters instrument:
MS instrument: Waters ZQ (or equivalent).
Polarity ES+
Capillary (kV) 3.00
Cone (V) 20.00
Extractor (V) 3.00
RF Lens (V) 1.0
Polarity ES−
Capillary (kV) 3.00
Cone (V) 20.00
Extractor (V) 3.00
RF Lens (V) 1.0
Source Temperature (° C.) 110
Desolvation Temperature (° C.) 210
Cone Gas Flow (L/Hr) 150
Desolvation Gas Flow (L/Hr) 650
Mass range: 100 to 950
Scan time (sec): 0.32
Inter-Scan delay (sec): 0.03
LC instrument: Acquity Waters UPLC.
Instrument: UPLC Waters coupled with ZQ micromass and interfaced with 2996 PDA detector
Column: Acquity UPLC BEH C18 1.7 um 50×2.1 mm
Method: TFA long
Conditions: ESI+, 3.2 KV, 25V, 350° C.
Wavelength: PBI

| Time (sec) | % B | Flow (mL/min) | A | B |
|---|---|---|---|---|
| 0.00 | 5.0 | 0.6 | 95:5 H2O:ACN (0.1% TFA) | 5:95 H2O:ACN (0.1% TFA) |
| 0.50 | 5.0 | 0.6 | | |
| 6.00 | 100.0 | 0.6 | | |
| 7.00 | 100.0 | 0.6 | | |
| 7.10 | 5.0 | 0.6 | | |
| 8.50 | 5.0 | 0.6 | | |

Detailed synthetic pathways and procedures for specific examples are outlined in Examples 1-49. The synthesis of compound 7 was described in WO2010/089107, which is incorporated herein by reference in its entirety, (compound 7). The synthesis of compound (R)-3,5-dichloro-4-(2-(3-(cyclopropylmethoxy)-4-(difluoromethoxy)phenyl)-2-hydroxyethyl)pyridine 1-oxide (starting material of compound 29) was described in WO2010/089107, which is incorporated herein by reference in its entirety, (compound 9).

In the procedures that follow, after each starting material, reference to a compound number is sometimes provided. This is provided merely for assistance to the skilled chemist. The starting material may not necessarily have been prepared from the batch referred to.

When reference is made to the use of a "similar" or "analogous" procedure, as will be appreciated by those skilled in the art, such a procedure may involve minor variations, for example reaction temperature, reagent/solvent amount, reaction time, work-up conditions or chromatographic purification conditions.

Example 1

S)-3,5-Dichloro-4-(2-(3,4-dimethoxyphenyl)-2-hydroxyethyl)pyridine 1-oxide (Compound 5

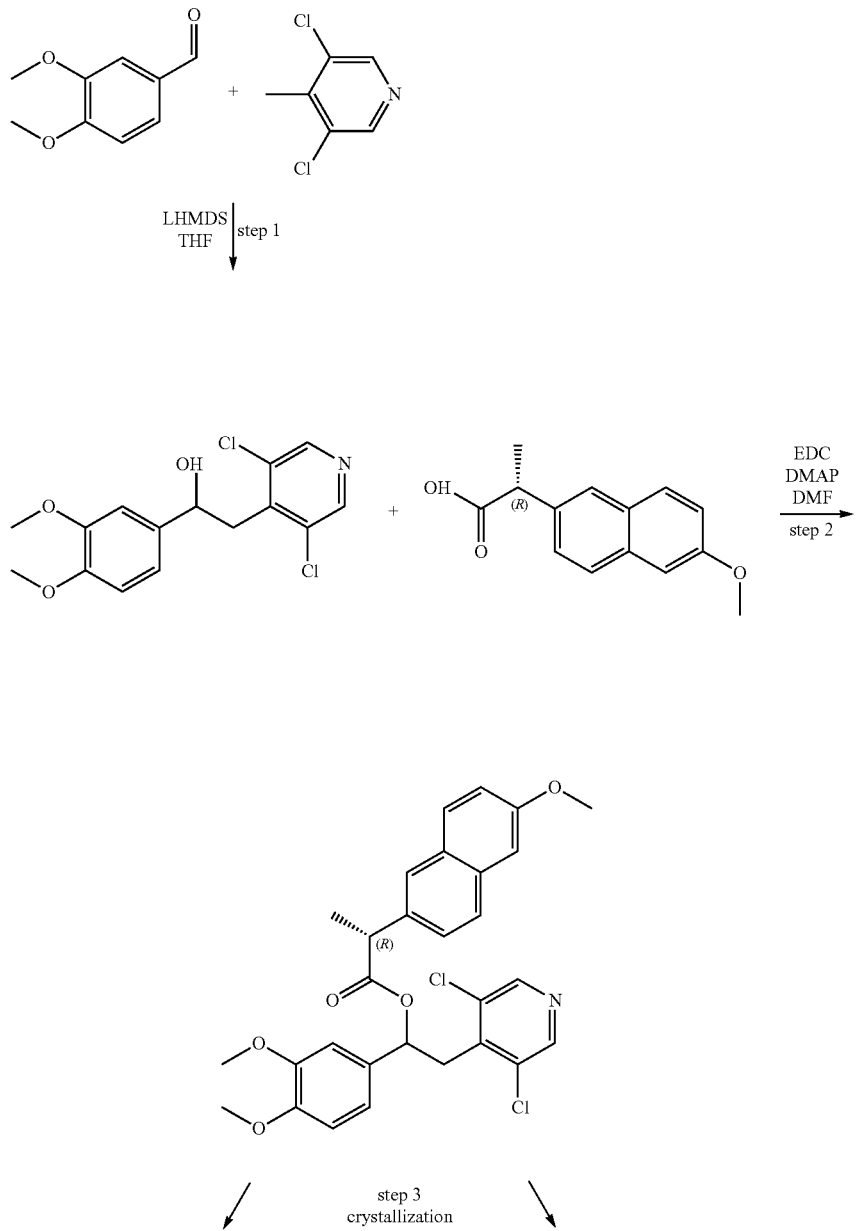

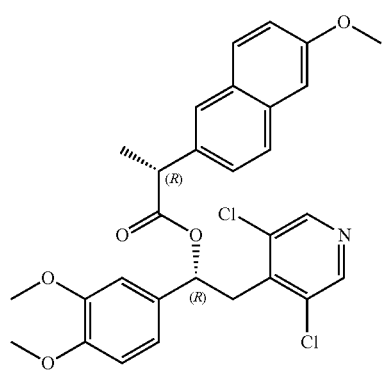
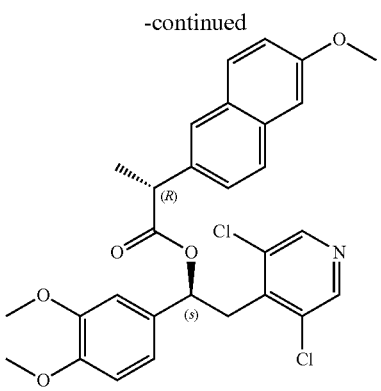

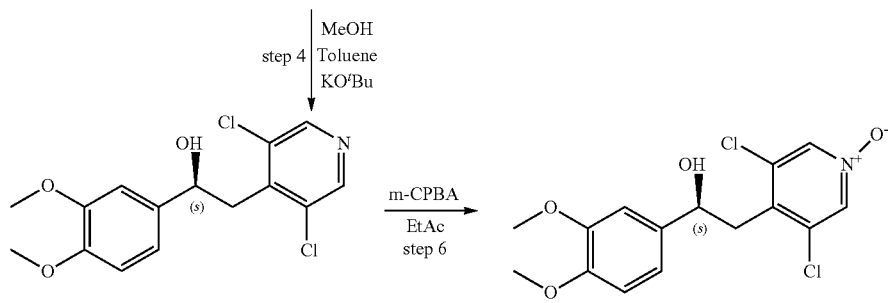

Step 1: Preparation of 2-(3,5-dichloropyridin-4-yl)-1-(3,4-dimethoxyphenyl)ethanol (1)

3,5-dichloro-4-methylpyridine (54 g, 331 mmol) was dissolved in dry THF (480 mL) under argon atmosphere and cooled at −78° C. in dry-ice/acetone bath. LHMDS 1N THF solution (331 ml, 331 mmol) was added drop-wise keeping the temperature at −78°. The mixture was stirred at −78° for 1 hour. Thereafter, a solution of 3,4-dimethoxybenzaldehyde (50 g, 301 mmol) in dry THF (120 ml) was added drop-wise keeping the temperature at −78° C. When the addition was completed, the mixture was allowed to warm at RT.

The reaction was poured into ice and water (1 L) and the mixture was stirred until a copious precipitate formed. The solid was filtered, and dissolved in ethyl acetate (500 ml), dried over Na$_2$SO$_4$ and the solvent evaporated under vacuum. The crude was crystallized in CHCl$_3$/hexane. The precipitate was filtered, washed with hexane and dried under vacuum at 40° C. for 8 hours to give 55 g of the title compound (45% yield). The mother liquor solution was evaporated under vacuum at 40° C., dissolved in ethyl acetate (200 ml) and extracted with 200 ml of water. The organic solution was dried over Na$_2$SO$_4$ and the solvent evaporated under vacuum at 40° C. The crude was crystallized in CHCl$_3$/hexane, and additional 15 g of the title product were obtained (70% overall yield).

Step 2: Preparation of ((R)-2-(3,5-dichloropyridin-4-yl)-1-(3,4-dimethoxyphenyl)ethyl) 2-(6-methoxynaphthalen-2-yl)propanoate (2)

2-(3,5-dichloropyridin-4-yl)-1-(3,4-dimethoxyphenyl)ethanol (50 g, 152 mmol), (R)-2-(6-methoxynaphthalen-2-yl)propanoic acid (38.6 g, 168 mmol), DMAP (20.5 g, 168 mmol), and EDC (43.8 g, 229 mmol) were dissolved in DMF (300 ml), and the reaction mixture was stirred at RT for 2 hours. Thereafter, water (500 ml) was added, and the solution stirred till complete precipitation occurs. The solid was filtered and dissolved in DCM (500 ml). The organic solution was washed with aqueous HCl 1N (2×500 ml), saturated aqueous NaHCO$_3$ solution (500 ml) and dried over Na$_2$SO$_4$. The solvent was evaporated under vacuum and the solid residue sonicated in EtOH (300 ml) and triturated for 1 hour. The resulting precipitate was collected by filtration and dried under vacuum at 40° C. for 4 h to give 79 g (99% yield) of the title compound, as diastereoisomeric mixture.

Step 3: Preparation of (R)—((S)-2-(3,5-dichloropyridin-4-yl)-1-(3,4-dimethoxyphenyl)ethyl) 2-(6-methoxynaphthalen-2-yl)propanoate (3)

((S)-2-(3,5-dichloropyridin-4-yl)-1-(3,4-dimethoxyphenyl)ethyl) 2-(6-methoxynaphthalen-2-yl)propanoate (diastereoisomeric mixture prepared as described in Ex 1, Step 1, 79 g, 146 mmol) was dissolved in CHCl$_3$ (100 ml), and MeOH (30 ml) was slowly added up to persistent opalescence and the mixture left at RT for 2 hours. The solid formed was collected by filtration and re-crystallized by CHCl$_3$/MeOH (70 ml/20 ml) solvent system to obtain 35 g of the desired compound (yield 88%, ee 98%). Chiral HPLC analysis R$_t$=42.33 min; eluent:hexane:isopropanol 97:3; $^1$H NMR (600 MHz, CHLOROFORM-d) δ ppm 8.04 (s, 2H), 7.67 (d, J=8.79 Hz, 1H), 7.58 (d, J=8.52 Hz, 1H), 7.53 (m, 1H), 7.12-7.20 (m, 3H), 6.95 (dd, J=8.24, 1.92 Hz, 1H), 6.78-6.88 (m, 2H), 6.14 (dd, J=10.44, 4.12 Hz, 1H), 3.95 (s, 3H), 3.88 (s, 3H), 3.78-3.81 (m, 4H), 3.55 (dd, J=13.73, 10.44 Hz, 1H), 3.14 (dd, J=13.60, 4.26 Hz, 1H), 1.44 (d, J=7.14 Hz, 3H).

Step 4: Preparation of (S)-2-(3,5-dichloropyridin-4-yl)-1-(3,4-dimethoxyphenyl)ethanol, (4)

(R)—((S)-2-(3,5-dichloropyridin-4-yl)-1-(3,4-dimethoxyphenyl)ethyl) 2-(6-methoxynaphthalen-2-yl)propanoate (30 g, 56 mmol) was dissolved in MeOH, and toluene was slowly added. Potassium terbutoxide was slowly added to the suspension. The mixture was stirred for 24 hours at RT. The reaction was diluted with water (500 ml), and the aqueous mixture was extracted with CHCl$_3$ (500 ml). The organic layer was dried over Na$_2$SO$_4$ and the solvent was evaporated under vacuum. The residue was crystallized from CHCl$_3$ (100 ml) and hexane (20 ml). The mother liquor was concentrated and recrystallized with an analogous procedure giving a second crop of desired compound. In total, 16 g of the title compound (87% yield) were obtained. Chiral HPLC analysis R$_t$=58.03 min; eluent:hexane:isopropanol=95:5; [α]$_D^{20}$=+ 10.21 (c=0.506, Methanol); $^1$H NMR (400 MHz, acetone) δ ppm 8.47 (s, 2H), 6.96-7.15 (m, 1H), 6.87 (m, 2H), 4.93-5.21 (m, 1H), 4.50 (d, J=3.97 Hz, 1H), 3.78 (s, 6H), 3.44 (dd, J=12.79, 8.38 Hz, 1H), 3.22 (dd, J=13.01, 5.51 Hz, 1H). MS/ESI$^+$ [MH]$^+$: 328.19

Step 5: Preparation of (S)-3,5-dichloro-4-(2-(3,4-dimethoxyphenyl)-2-hydroxyethyl)pyridine 1-oxide (5)

(S)-2-(3,5-dichloropyridin-4-yl)-1-(3,4-dimethoxyphenyl)ethanol (4 g, 12 mmol) was dissolved in ethyl acetate, and m-CPB acid was added to the solution. The mixture was stirred at RT for 5 hours. The formed solid was collected by filtration, washed with ethyl acetate and dried under vacuum to give 1.72 g of (−) (41% yield). Chiral HPLC analysis R$_t$=22.16 min; eluent:hexane:isopropanol=6:4; [α]$_D^{20}$=+ 68.91 (c=0.253, Methanol/CHCl$_3$ 1:1); $^1$H NMR (400 MHz, CHLOROFORM-d) δ ppm 8.15 (s, 2H), 6.99 (m, 1H), 6.79-6.88 (m, 2H), 5.03 (dd, J=8.50, 5.32 Hz, 1H), 3.75-3.98 (m, 6H), 3.42 (dd, J=13.57, 8.56 Hz, 1H), 3.19 (dd, J=13.51, 5.32 Hz, 1H), 2.06-2.15 (m, 1H); MS/ESI$^+$ [MH]$^+$: 344.19

Example 2

(S)-4-(2-(2-(6-Amino-1-oxoisoindolin-2-yl)acetoxy)-2-(3-(cyclopropylmethoxy)-4-(difluoromethoxy)phenyl)ethyl)-3,5-dichloropyridine 1-oxide (Compound 9) and (S)-3,5-Dichloro-4-(2-(3-(cyclopropylmethoxy)-4-(difluoromethoxy)phenyl)-2-(2-(6-(methylsulfonamido)-1-oxoisoindolin-2-yl)acetoxy)ethyl)pyridine 1-oxide (Compound 10)

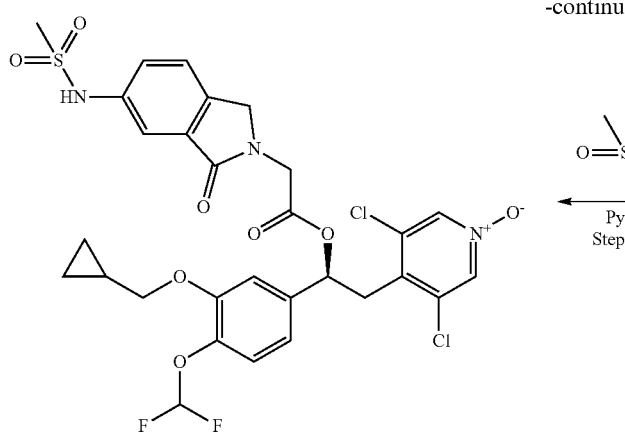 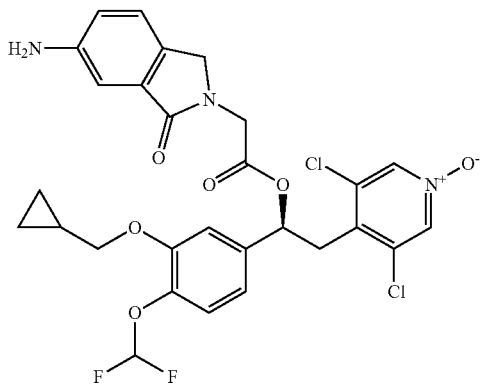

Step 1: Preparation of 2-(6-(tert-butoxycarbonylamino)-1-oxoisoindolin-2-yl)acetic acid (6)

2-(6-amino-1-oxoisoindolin-2-yl)acetic acid (200 mg, 0.970 mmol) was dissolved in THF (5 ml), then di-tert-butyl dicarbonate (0.676 ml, 2.91 mmol), sodium bicarbonate (122 mg, 1.455 mmol) and water (5 ml, 278 mmol) were added, and the reaction was stirred at RT overnight. The solvent was removed under vacuum, and the mixture was diluted with HCl 1M and extracted with EtOAc. The organic phase was dried over $Na_2SO_4$ and concentrated under vacuum to give 2-(6-(tert-butoxycarbonylamino)-1-oxoisoindolin-2-yl)acetic acid (200 mg, 0.653 mmol, 67/0 yield). MS/ESI$^+$ 296.07 [MH]$^+$

Step 2: Preparation of (S)-4-(2-(2-(6-(tert-butoxycarbonylamino)-1-oxoisoindolin-2-yl)acetoxy)-2-(3-(cyclopropylmethoxy)-4-(difluoromethoxy)-phenyl)ethyl)-3,5-dichloropyridine 1-oxide (8)

(S)-3,5-dichloro-4-(2-(3-(cyclopropylmethoxy)-4-(difluoromethoxy)phenyl)-2-hydroxyethyl)pyridine 1-oxide (Compound 7, 60 mg, 0.143 mmol), 2-(6-(tert-butoxycarbonylamino)-1-oxoisoindolin-2-yl)acetic acid (65.6 mg, 0.214 mmol), DMAP (20.93 mg, 0.171 mmol), and EDC (82 mg, 0.428 mmol) were dissolved in DMF (5 ml). The reaction was stirred at RT overnight. The reaction mixture was diluted with water, and the precipitate was washed with water, dissolved in EtOAc and extracted with HCl 1N, $Na_2CO_3$ sat. sol. and brine. The organic phase was dried over $Na_2SO_4$ and concentrated under vacuum to give (S)-4-(2-(2-(6-(tert-butoxycarbonylamino)-1-oxoisoindolin-2-yl)acetoxy)-2-(3-(cyclopropylmethoxy)-4-(difluoromethoxy)phenyl)ethyl)-3,5-dichloropyridine 1-oxide (70 mg, 0.099 mmol, 69% yield). MS/ESI$^+$ 306.12 [MH]$^+$

Step 3: Preparation of (S)-4-(2-(2-(6-amino-1-oxoisoindolin-2-yl)acetoxy)-2-(3-(cyclopropylmethoxy)-4-(difluoromethoxy)phenyl)ethyl)-3,5-dichloropyridine 1-oxide (9)

(S)-4-(2-(2-(6-(tert-butoxycarbonylamino)-1-oxoisoindolin-2-yl)acetoxy)-2-(3-(cyclopropylmethoxy)-4-(difluoromethoxy)phenyl)ethyl)-3,5-dichloropyridine 1-oxide (70 mg, 0.099 mmol) was dissolved in HCl 4M in ethyl acetate (1.5 ml, 49.4 mmol). The reaction was stirred at RT for 2 hours. The reaction mixture was concentrated under vacuum, the crude product was triturated with $Et_2O$ and filtered to give (S)-4-(2-(2-(6-amino-1-oxoisoindolin-2-yl)acetoxy)-2-(3-(cyclopropylmethoxy)-4-(difluoromethoxy)phenyl)ethyl)-3,5-dichloropyridine 1-oxide (60 mg, 0.099 mmol, quantitative yield). $^1$H NMR (400 MHz, acetone) δ ppm 8.33 (s, 2H), 7.68-7.94 (m, 3H), 7.16-7.32 (m, 2H), 7.06 (dd, J=8.19, 1.83 Hz, 1H), 6.93 (t, 1H, CHF2), 6.12-6.23 (m, 1H), 4.61 (s, 2H), 4.46 (d, J=3.18 Hz, 2H), 3.99 (dd, J=6.85, 1.22 Hz, 2H), 3.57 (d, J=9.78 Hz, 1H), 3.37 (d, J=4.65 Hz, 1H), 1.22-1.37 (m, 1H), 0.54-0.68 (m, 2H), 0.40 (d, J=4.65 Hz, 2H); MS/ESI$^+$ 608.42 [MH]$^+$.

Step 4: Preparation of (S)-3,5-dichloro-4-(2-(3-(cyclopropylmethoxy)-4-(difluoromethoxy)phenyl)-2-(2-(6-(methylsulfonamido)-1-oxoisoindolin-2-yl)acetoxy)ethyl)pyridine 1-oxide (10)

(S)-4-(2-(2-(6-amino-1-oxoisoindolin-2-yl)acetoxy)-2-(3-(cyclopropylmethoxy)-4-(difluoromethoxy)phenyl)ethyl)-3,5-dichloropyridine 1-oxide (50 mg, 0.08 mmol) was dissolved in $CH_2Cl_2$ (2 ml) and pyridine (50 µl), then methanesulfonyl chloride was added (11 mg, 0.1 mmol) at 0° C. The mixture was stirred at RT for 2 hours, then diluted with $CH_2Cl_2$ (20 ml) and quenched with HCl 1N aqueous solution (30 ml). The two phases were separated, and the organic phase washed with HCl 1N aqueous solution (2×20 ml), dried over $Na_2SO_4$ and evaporated under vacuum. The crude was purified by preparative HPLC (Method 2) to yield 41 mg of the title compound. (Yield 75%). $^1$H NMR (400 MHz, acetone) δ ppm 8.71-8.92 (m, 1H), 8.22 (s, 2H), 7.73 (m, 1H), 7.59 (m, 2H), 7.15-7.30 (m, 2H), 7.05 (dd, J=8.38, 1.76 Hz, 1H), 6.93 (t, 1H, CHF$_2$), 6.15 (dd, J=9.70, 4.85 Hz, 1H), 4.49 (s, 2H), 4.44 (d, J=3.53 Hz, 2H), 3.98 (d, J=7.06 Hz, 2H), 3.55 (dd, J=14.11, 9.26 Hz, 1H), 3.32 (dd, J=14.11, 4.85 Hz, 1H), 3.05 (s, 3H), 1.29 (m, 1H), 0.55-0.69 (m, 2H), 0.27-0.47 (m, 2H); MS/ESI$^+$ 686.51 [MH]$^+$.

Example 3

(S)-3,5-Dichloro-4-(2-(3-(cyclopropylmethoxy)-4-(difluoromethoxy)-phenyl)-2-(2-(4-nitro-1,3-dioxoisoindolin-2-yl)acetoxy)ethyl)-pyridine 1-oxide (Compound 11) and (S)-4-(2-(2-(4-amino-1,3-dioxoisoindolin-2-yl)acetoxy)-2-(3-(cyclopropyl methoxy)-4-(difluoromethoxy)phenyl)ethyl)-3,5-dichloropyridine 1-oxide (Compound 12)

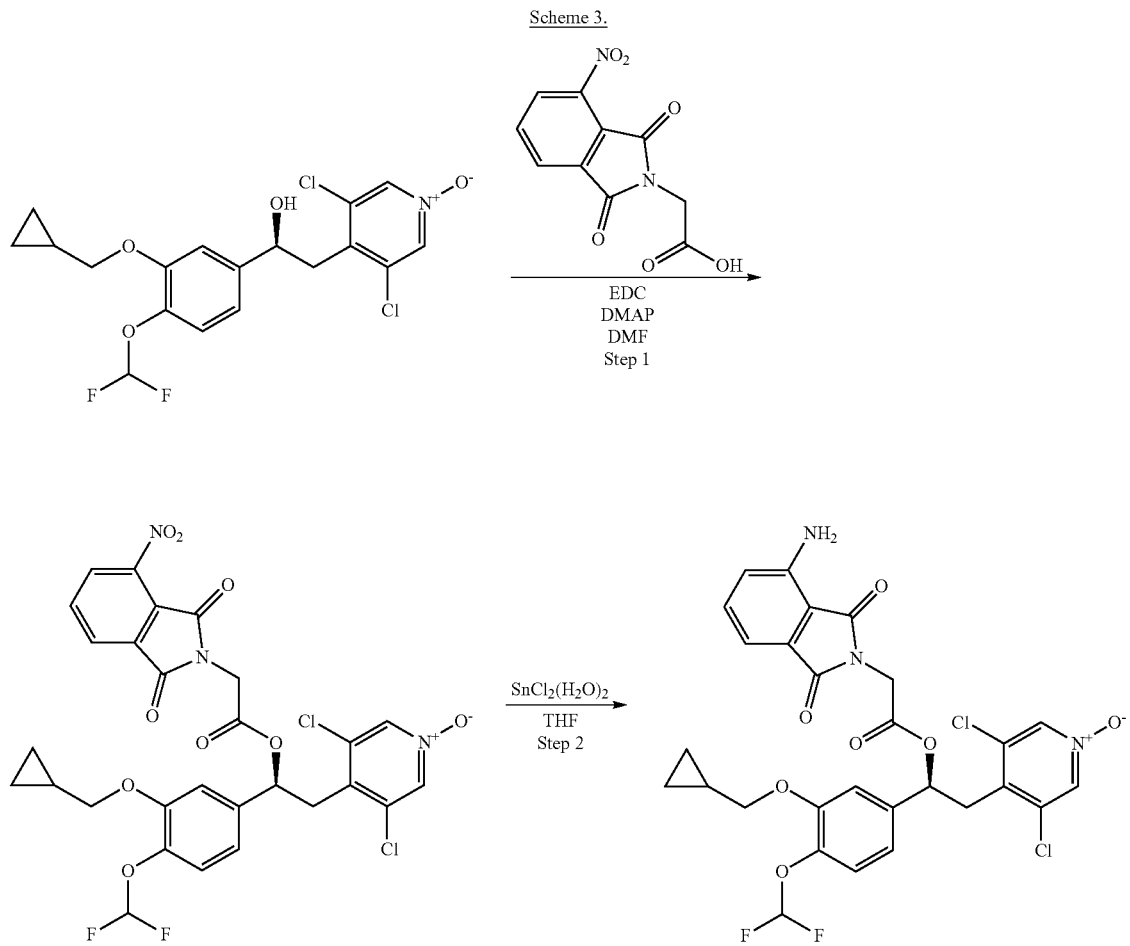

Scheme 3.

Step 1: Preparation of (S)-3,5-dichloro-4-(2-(3-(cyclopropylmethoxy)-4-(difluoromethoxy)phenyl)-2-(2-(4-nitro-1,3-dioxoisoindolin-2-yl)acetoxy)-ethyl)pyridine 1-oxide (11)

(S)-3,5-dichloro-4-(2-(3-(cyclopropylmethoxy)-4-(difluoromethoxy)phenyl)-2-hydroxyethyl)pyridine 1-oxide (100 mg, 0.238 mmol) was placed in a 50 ml round bottom flask and dissolved in DMF (3 ml); EDC (45.6 mg, 0.238 mmol) was added to it followed by DMAP (29.1 mg, 0.238 mmol) and 2-(4-nitro-1,3-dioxoisoindolin-2-yl)acetic acid (90 mg, 0.357 mmol). The reaction was stirred at RT for 6 hours. The reaction was quenched by adding 30 ml of HCl/H2O (1M) and extracted with EtOAc (30 ml). The organic phase (EtOAc) was extracted with HCl/H2O 1M (30 ml; ×3) and subsequently with K2CO3/H2O (20 ml; ×3). The resulting organic extract was dried over Na2SO4, filtered and the solvent removed under reduced pressure to yield 120 mg of title compound (77% yield). $^1$H NMR (400 MHz, acetone) δ ppm 8.35 (d, J=7.50 Hz, 1H), 8.24-8.30 (m, 1H), 8.16-8.24 (m, 3H), 7.16-7.25 (m, 2H), 7.05 (dd, J=8.16, 1.98 Hz, 1H), 6.94 (t, 1H, CHF2), 6.14 (dd, J=9.48, 4.63 Hz, 1H), 4.52 (s, 2H), 4.01 (dd, J=6.62, 3.97 Hz, 2H), 3.54 (dd, J=14.33, 9.48 Hz, 1H), 3.26-3.40 (m, 1H), 1.25-1.38 (m, 1H), 0.56-0.73 (m, 2H), 0.36-0.48 (m, 2H); MS/ESI$^+$ 652.1 [MH]$^+$ Step 2: Preparation of (S)-4-(2-(2-(4-amino-1,3-dioxoisoindolin-2-yl)acetoxy)-2-(3-(cyclopropylmethoxy)-4-(difluoromethoxy)phenyl)ethyl)-3,5-dichloropyridine 1-oxide (12)

(S)-3,5-dichloro-4-(2-(3-(cyclopropylmethoxy)-4-(difluoromethoxy)phenyl)-2-(2-(5-nitro-1,3-dioxoisoindolin-2-yl)acetoxy)ethyl)pyridine 1-oxide (80 mg, 0.123 mmol) was dissolved in THF (10 ml), and added with tin(II) chloride dihydrate (80 mg, 0.355 mmol). The reaction was stirred at RT for 3 days. The reaction was quenched by addition of K₂CO₃/H₂O. The solid precipitated was filtered and the solution extracted with EtOAc (50 ml). The organic phase was washed with K₂CO₃/H₂O conc. (×3), dried over Na₂SO₄ and the solvent removed under reduced pressure to yield the title compound (50.0 mg, 66% yield).). ¹H NMR (400 MHz, acetone) ppm 8.20 (s, 2H), 7.50 (d, J=7.50 Hz, 1H), 7.14-7.24 (m, 2H), 7.01-7.13 (m, 3H), 6.92 (t, J=75.00 Hz, 1H), 6.17 (dd, J=9.48, 5.07 Hz, 3H), 4.37 (d, J=7.50 Hz, 2H), 4.00 (dd, J=7.06, 3.09 Hz, 2H), 3.53 (m, 1H), 3.34 (d, J=4.41 Hz, 1H), 1.30 (br. s., 2H), 0.56-0.68 (m, 2H), 0.41 (d, J=4.41 Hz, 2H); MS/ESI⁺ 608.39 [MH]⁺

The compound listed in Table 1 was prepared with analogous synthetic steps and procedures to that described in Example 3, by reacting the appropriate precursors (commercially available or synthesized by a person skilled in the art) with suitable reagents. Specific variations in the experimentals or purification methods are indicated in the table.

A mixture of (S)-3,5-dichloro-4-(2-(3-(cyclopropylmethoxy)-4-(difluoromethoxy)phenyl)-2-hydroxyethyl)pyridine 1-oxide (0.615 g, 1.463 mmol), 2-(1H-indol-1-yl)acetic acid (0.282 g, 1.610 mmol), EDC (0.842 g, 4.39 mmol), and DMAP (0.268 g, 2.195 mmol) in DCM (20 ml) was

TABLE 1

| Entry | Structure | NMR characterization | MS/ESI⁺ [MH]⁺ | Purification and yield | Starting material (precursor) |
|---|---|---|---|---|---|
| 13 | 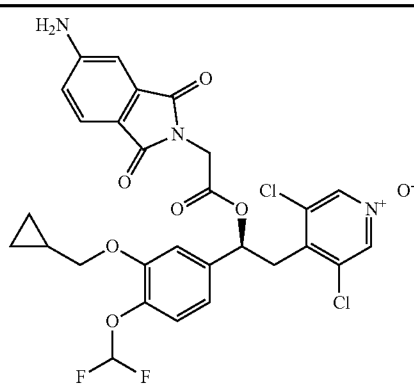 | ¹H NMR (400 MHz, acetone) ppm 8.19 (s, 2 H), 7.56 (d, J = 8.38 Hz, 1 H), 7.15-7.24 (m, 2 H), 7.07-7.13 (m, 1 H), 7.01 (ddd, J = 13.78, 8.27, 2.21 Hz, 2 H), 6.92 (t, J = 75.00 Hz, 1 H), 6.13 (dd, J = 9.48, 4.63 Hz, 2 H), 6.00 (br. s., 2 H), 4.35 (s, 2 H), 3.99 (dd, J = 6.84, 2.43 Hz, 2 H), 3.42-3.57 (m, 1 H), 3.32 (d, J =4.85 Hz, 1 H), 1.17-1.36 (m, 1 H), 0.55-0.70 (m, 2 H), 0.33-0.48 (m, 2 H). | 608.39 | Crystallization from hexane/EtOAc (3:1). Yield 72%. | |

Example 4

S)-4-(2-(2-(1H-Indol-1-yl)acetoxy)-2-(3-(cyclopropylmethoxy)-4-(difluoromethoxy)phenyl)ethyl)-3,5-dichloropyridine 1-oxide (Compound 14

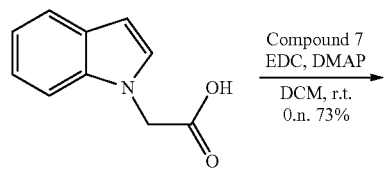

Scheme 4.

Compound 7
EDC, DMAP
DCM, r.t.
O.n. 73% stirred at room temperature overnight. The reaction was washed with 1N HCl, aqueous NaHCO₃ and brine; the organic phase was dried over Na₂SO₄ and evaporated to dryness. The crude was purified by flash chromatography on silica gel column (DCM/MeOH from 99/1 to 98/2) to afford (S)-4-(2-(2-(1H-indol-1-yl)acetoxy)-2-(3-(cyclopropylmethoxy)-4-(difluoromethoxy)phenyl)ethyl)-3,5-dichloropyridine 1-oxide (0.615 g, 1.065 mmol, 72.8% yield). MS/ESI⁺ 577.2 [MH]⁺; [α_D]=+5.500, c=0.44, DCM; ¹H NMR (300 MHz, DMSO-d₆) d ppm 8.52 (s, 2H), 7.48-7.63 (m, 1H), 7.27 (d, 1H), 7.13-7.19 (m, 2H), 7.10 (td, 1H), 7.00-7.05 (m, 1H), 6.99 (d, 1H), 6.92 (dd, 1H), 7.06 (t, 1H), 6.45 (dd, 1H), 6.02 (dd, 1H), 5.23 (d, 1H), 5.05 (d, 1H), 3.84 (d, 2H), 3.42 (dd, 1H), 3.20 (dd, 1H), 1.13-1.34 (m, 1H), 0.49-0.67 (m, 2H), 0.29-0.46 (m, 2H).

The compounds listed in Table 2 were prepared with analogous synthetic steps and procedures to that described in Example 4, by reacting the appropriate precursors (commercially available or synthesized by a person skilled in the art) with suitable reagents. Specific variations in the experimentals or purification methods are indicated in the table.

TABLE 2

| Entry | Structure | NMR characterization | MS/ESI+ [MH]+ | [α_D] | Experimental procedure | Purification and yield | Starting material (precursor) |
|---|---|---|---|---|---|---|---|
| 15 | 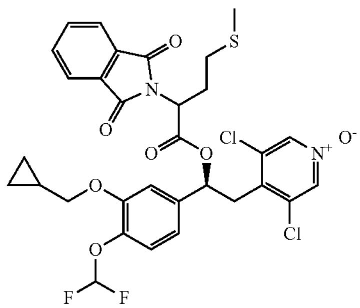 | $^1$H NMR (400 MHz, DMSO-$d_6$) δ ppm 8.48 (s) 8.19 (s) 7.84-7.95 (m) 7.18-7.29 (m) 7.05-7.15 (m) 6.87-6.98 (m) 6.86 (d, J = 1.96 Hz) 5.90-6.00 (m) 4.98-5.08 (m) 3.92 (dd, J = 7.04, 2.35 Hz) 3.81 (dd, J = 7.04, 3.52 Hz) 3.11 (dd, J = 14.28, 4.11 Hz) 2.35-2.48 (m) 2.29 (dd, J = 12.33, 5.67 Hz) 2.11-2.25 (m) 1.94-2.00 (m) 1.14-1.30 (m) 0.57-0.64 (m) 0.34-0.41 (m) 0.33 (d, J = 4.70 Hz) | 681.0 | | Solvent: DMF | Crystallization from EtOH. Yield 25% | |
| 16 | 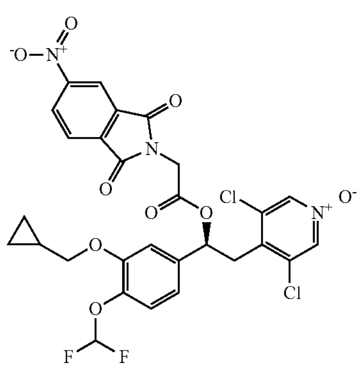 | $^1$H NMR (400 MHz, acetone) δ ppm 8.77 (dd, J = 8.16, 1.98 Hz, 1 H), 8.62 (d, J = 2.20 Hz, 1 H), 8.30 (s, 2 H), 8.24 (d, J = 7.94 Hz, 1 H), 7.16-7.24 (m, 2 H), 7.04 (dd, J = 8.16, 1.98 Hz, 1 H), 6.99 (t, J = 75.00 Hz, 1H), 6.13 (dd, J = 9.70, 4.41 Hz, 1 H), 4.54 (s, 2 H), 4.00 (dd, J = 7.06, 2.65 Hz, 2 H), 3.50 (dd, J = 14.11, 9.70 Hz, 1 H), 3.31 (dd, J = 14.11, 4.85 Hz, 1 H), 1.30 (m, 1 H), 0.55-0.68 (m, 2 H), 0.35-0.45 (m, 2 H). | 652.1 | | Solvent: DMF | No purification. Yield 39% | |

TABLE 2-continued

| Entry | Structure | NMR characterization | MS/ ESI+ [MH]+ | [α_D] | Experimental procedure | Purification and yield | Starting material (precursor) |
|---|---|---|---|---|---|---|---|
| 17 | 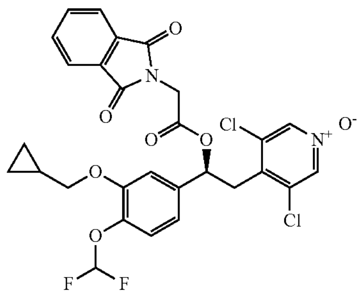 | 1H NMR (400 MHz, acetone) δ ppm 8.18 (s, 2 H), 7.92 (s, 4 H), 7.15-7.25 (m, 2 H), 7.04 (d, J = 8.38 Hz, 1 H), 6.83 (t, J = 75.00 Hz, 1 H), 6.15 (dd, J = 9.70, 4.41 Hz, 1 H), 4.46 (s, 2 H), 4.00 (d, J = 6.62 Hz, 2 H), 3.52 (dd, J = 14.11, 9.70 Hz, 1 H), 3.32 (dd, J = 14.11, 4.41 Hz, 1 H), 1.22-1.37 (m, 1 H), 0.57-0.68 (m, 2 H), 0.41 (d, J = 4.85 Hz, 2 H). | 607.39 | | Solvent: DMF | Crystallization from EtOAc. Yield 73% | |
| 18 | 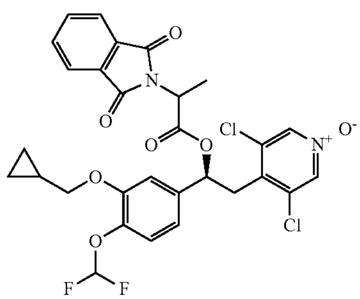 | 1H NMR (400 MHz, acetone) δ ppm 8.20 (s, 2 H), 7.80-8.02 (m, 5 H), 7.17-7.26 (m, 1 H), 7.06-7.12 (m, 1 H), 6.93 (t, 1 H, CHF2), 6.01-6.13 (m, 1 H), 4.87-5.08 (m, 1 H), 3.95-4.06 (d, 2 H), 3.92 (d, J = 7.06 Hz, 1 H), 3.41-3.52 (m, 1 H), 1.52-1.54 (d, 3 H), 1.19-1.40 (m, 1 H), 0.63 (dd, J = 7.94, 1.32 Hz, 2 H), 0.40 (d, J = 5.29 Hz, 2 H). | 621.41 | | Solvent: DMF | Crystallization from EtOH. Yield 40% | |
| 19 | 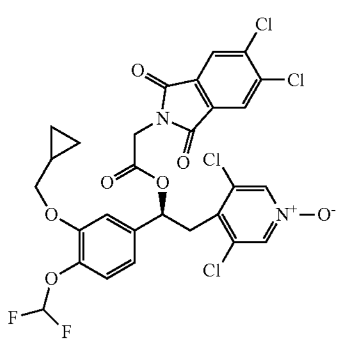 [SMILES: O=C(CN1C(=O)c2cc(Cl)c(Cl)cc2C1=O)O[C@@H](Cc1c(Cl)c[n+]([O-])cc1Cl)c1ccc(OC(F)F)c(OCC2CC2)c1] | ¹H NMR (400 MHz, acetone) δ ppm 8.22 (s, 2 H), 8.12 (s, 2 H), 7.16-7.24 (m, 2 H), 7.05 (dd, J = 8.38, 1.76 Hz, 1 H), 6.93 (t, J = 75.00 Hz, 1 H), 6.15 (dd, J = 9.70, 4.41 Hz, 1 H), 4.48 (s, 2 H), 4.00 (dd, J = 6.84, 1.98 Hz, 2 H), 3.53 (dd, J = 14.11, 9.70 Hz, 1 H), 3.32 (dd, J = 14.11, 4.41 Hz, 1 H), 1.21-1.41 (m, 1 H), 0.54-0.75 (m, 2 H), 0.31-0.51 (m, 2 H). | 675.1 | | Solvent: DMF | Crystallization from EtOH. Yield 37% | |

TABLE 2-continued

| Entry | Structure | NMR characterization | MS/ESI+ [MH]+ | [α$_D$] | Experimental procedure | Purification and yield | Starting material (precursor) |
|---|---|---|---|---|---|---|---|
| 20 | 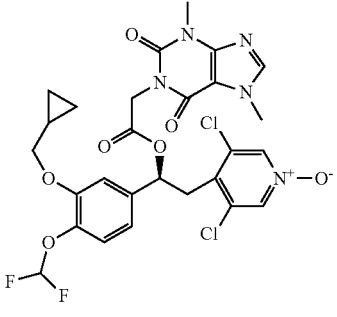 [SMILES: Cn1cnc2c1c(=O)n(CC(=O)O[C@@H](Cc1c(Cl)c[n+]([O-])cc1Cl)c1ccc(OC(F)F)c(OCC3CC3)c1)c(=O)n2C] | $^1$H NMR (400 MHz, acetone) δ ppm 8.15 (s, 2 H), 7.91 (s, 1 H), 7.16-7.27 (m, 2 H), 7.06 (dd, J = 7.94, 1.76 Hz, 1 H), 6.93 (t, J = 75.00 Hz, 1 H), 6.14 (dd, J = 10.36, 4.19 Hz, 1 H), 4.65 (s, 2 H), 4.02-4.10 (m, 2 H), 4.00 (s, 3 H), 3.55 (s, 3 H), 3.50-3.55 (m, 1 H), 3.47 (d, J = 10.14 Hz, 1 H), 3.30 (dd, J = 14.55, 4.41 Hz, 1 H), 1.32 (ddd, J = 11.80, 6.95, 4.63 Hz, 2 H), 0.55-0.70 (m, 2 H), 0.38-0.50 (m, 2 H). | 640.2 | | Solvent: DMF | Crystallization from EtOH. Yield 39% | 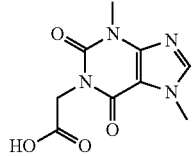 [SMILES: Cn1cnc2c1c(=O)n(CC(=O)O)c(=O)n2C] |
| 21 | 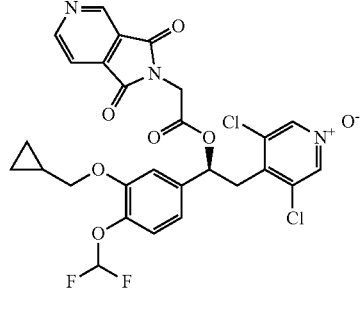 | $^1$H NMR (400 MHz, CHLOROFORM-d) δ ppm 9.20 (s, 1 H), 9.12 (d, J = 4.40 Hz, 1 H), 8.16 (s, 2 H), 7.80 (d, J = 4.40 Hz, 1 H), 7.19 (d, J = 8.54 Hz, 1 H), 6.94 (m, 2 H), 6.65 (t, J = 75.00 Hz, 1 H), 5.99-6.22 (m, 1 H), 4.30-4.59 (m, 2 H), 3.93 (d, J = 6.82 Hz, 2 H), 3.54 (dd, J = 13.90, 10.01 Hz, 1 H), 3.25 (dd, J = 14.07, 3.88 Hz, 1 H), 1.31 (m, 1 H), 0.69 (d, J = 7.42 Hz, 2 H), 0.41 (d, J = 4.49 Hz, 2 H). | 608.2 | | Solvent: DMF | Crystallization from EtOH. Yield 60% | 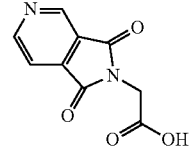 [SMILES: O=C(O)CN1C(=O)c2ccncc2C1=O] |

TABLE 2-continued

| Entry | Structure | NMR characterization | MS/ESI+ [MH]+ | [α_D] | Experimental procedure | Purification and yield | Starting material (precursor) |
|---|---|---|---|---|---|---|---|
| 22 | 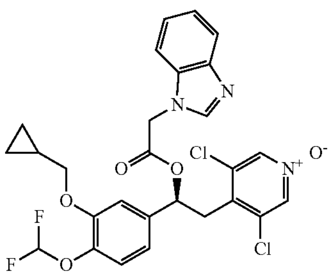 | ¹H NMR (300 MHz, DMSO-d₆) δ ppm 8.70 (s, 1 H), 8.51 (s, 2 H), 7.69-7.83 (m, 1 H), 7.48-7.58 (m, 1 H), 7.34-7.46 (m, 2 H), 7.17 (d, 1 H), 7.01 (d, 1 H), 6.93 (dd, 1 H), 7.07 (t, 1 H), 6.02 (dd, 1 H), 5.47 (d, 1 H), 5.34 (d, 1 H), 3.86 (d, 2 H), 3.42 (dd, 1 H), 3.21 (dd, 1 H), 1.13-1.31 (m, 1 H), 0.52-0.65 (m, 2 H), 0.31-0.42 (m, 2 H) | 578.28 | −7.156 c = 0.9, DCM | | Preparative HPLC (Method 1) under neutral conditions; 22% yield | |
| 23 | 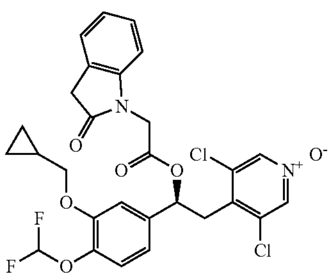 | ¹H NMR (300 MHz, DMSO-d₆) δ ppm 8.46 (s, 2 H), 7.29 (d, 1 H), 7.14-7.24 (m, 2 H), 6.99-7.07 (m, 2 H), 6.95 (dd, 1 H), 7.07 (t, 1 H), 6.74 (d, 1 H), 6.02 (dd, 1 H), 4.58 (d, 1 H), 4.50 (d, 1 H), 3.91 (d, 2 H), 3.62 (s, 2 H), 3.40 (dd, 1 H), 3.21 (dd, 1 H), 1.14-1.26 (m, 1 H), 0.47-0.66 (m, 2 H), 0.31-0.46 (m, 2 H) | 593.32 | +17.68 c = 1.0 MeOH | | Preparative HPLC (Method 1) 27% yield | |
| 24 | 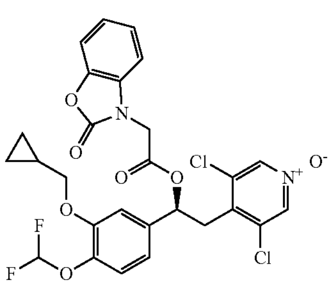 | ¹H NMR (300 MHz, DMSO-d₆) δ ppm 8.42 (s, 2 H), 7.35-7.45 (m, 1 H), 7.12-7.26 (m, 4 H), 7.03-7.10 (m, 1 H), 6.96 (dd, 1 H), 7.07 (t, 1 H), 6.04 (dd, 1 H), 4.84 (d, 1 H), 4.73 (d, 1 H), 3.90 (d, 2 H), 3.40 (dd, 1 H), 3.22 (dd, 1 H), 1.13-1.29 (m, 1 H), 0.50-0.69 (m, 2 H), 0.27-0.46 (m, 2 H) | 595.14 | +8.44, c = 0.505, DCM | | Flash chromatography on silica gel (DCM/EtOAc 7/3) 86% yield | |

TABLE 2-continued

| Entry | Structure | NMR characterization | MS/ESI+ [MH]+ | [α_D] | Experimental procedure | Purification and yield | Starting material (precursor) |
|---|---|---|---|---|---|---|---|
| 25 | 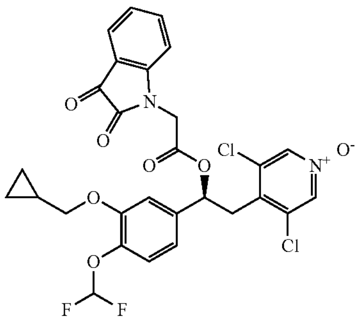 | 1H NMR (300 MHz, DMSO-d_6) δ ppm 8.41 (s, 2 H) 7.57-7.67 (m, 2 H) 7.12-7.27 (m, 2 H) 7.06 (d, 1 H) 6.97-7.02 (m, 1 H) 6.95 (dd, 1 H) 7.07 (t, 1 H) 6.03 (dd, 1 H) 4.65 (d, 1 H) 4.58 (d, 1 H) 3.89 (d, 2 H) 3.35-3.46 (m, 1 H) 3.14-3.25 (m, 1 H) 1.12-1.24 (m, 1 H) 0.55-0.64 (m, 2 H) 0.32-0.41 (m, 2 H) | 607.16 | +42.61 c = 0.635 DCM | | Flash chromatography on silica gel (DCM/MEOH 97/3) 47% yield | |
| 26 | 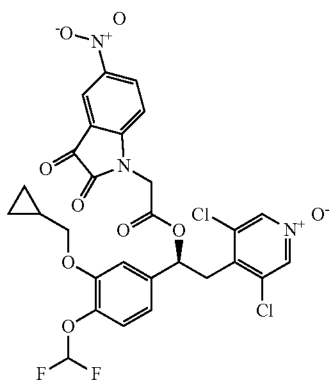 | 1H NMR (300 MHz, DMSO-d_6) δ ppm 8.51 (dd, 1 H), 8.42 (s, 2 H), 8.35 (d, 1 H), 7.27 (d, 1 H), 7.19 (d, 1 H), 7.07 (d, 1 H), 6.95 (dd, 1 H), 7.07 (t, 1 H), 6.02 (dd, 1 H), 4.72 (s, 2 H), 3.89 (d, 2 H), 3.40 (dd, 1 H), 3.22 (dd, 1 H), 1.07-1.35 (m, 1 H), 0.50-0.70 (m, 2 H), 0.25-0.46 (m, 2 H) | 652.23 | −33.56 c = 0.32, MeOH | | Flash chromatography on silica gel (DCM/MEOH 99/1 to 97/3) 48% yield | |
| 27 | 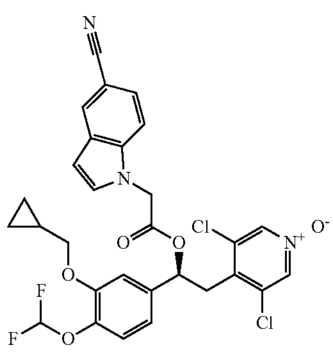 | 1H NMR (300 MHz, DMSO-d_6) δ ppm 8.52 (s, 2 H), 8.10 (dd, 1 H), 7.49 (d, 1 H), 7.47 (dd, 1 H), 7.41 (d, 1 H), 7.16 (d, 1 H), 6.98 (d, 1 H), 6.91 (dd, 1 H), 7.06 (t, 1 H), 6.63 (dd, 1 H), 6.02 (dd, 1 H), 5.33 (d, 1 H), 5.18 (d, 1 H), 3.84 (d, 2 H), 3.40 (dd, 1 H), 3.20 (dd, 1 H), 1.15-1.23 (m, 1 H), 0.50-0.69 (m, 2 H), 0.25-0.45 (m, 2 H) | 602.17 | −20.31 c = 0.510; MeOH | | Flash Chromatography on silica gel (DCM/MEOH 98/2) 45% yield | |

TABLE 2-continued

| Entry | Structure | NMR characterization | MS/ESI+ [MH]+ | [α_D] | Experimental procedure | Purification and yield | Starting material (precursor) |
|---|---|---|---|---|---|---|---|
| 28 | 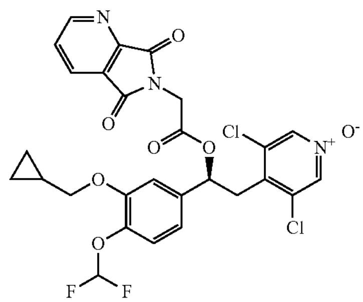 | $^1$H NMR (400 MHz, DMSO-d$_6$) δ ppm 9.05 (dd, J = 4.89, 1.47 Hz) 8.47 (s) 8.37 (dd, J = 7.34, 1.47 Hz) 7.86 (dd, J = 7.34, 4.89 Hz) 7.27 (s) 7.19 (d, J = 8.31 Hz) 7.05-7.12 (m) 6.96 (dd, J = 8.31, 1.96 Hz) 6.90 (s) 5.96-6.06 (m) 4.48 (q, J = 17.61 Hz) 3.86-3.99 (m) 3.39 (dd, J = 14.43, 9.54 Hz) 3.22 (dd, J = 14.18, 4.89 Hz) 1.14-1.33 (m) 0.51-0.67 (m) 0.37 (q, J = 4.73 Hz) | 608.0 | | Solvent: DMF | Crystallization from EtOH. Yield 28% | |
| 29 | 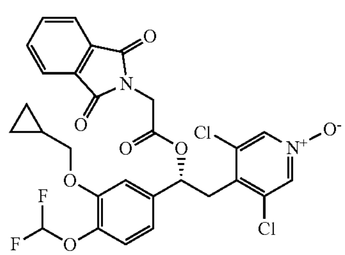 [SMILES: O=C(CN1C(=O)c2ccccc2C1=O)O[C@H](Cc1c(Cl)c[n+]([O-])cc1Cl)c1ccc(OC(F)F)c(OCC2CC2)c1] | $^1$H NMR (400 MHz, DMSO-d$_6$) δ ppm 8.46 (s, 2 H), 7.92 (d, J = 1.32 Hz, 4 H), 6.81-7.37 (m, 4 H), 6.01 (dd, J = 9.04, 4.19 Hz, 1 H), 4.43 (d, J = 4.85 Hz, 2 H), 3.92 (d, J = 6.62 Hz, 2 H), 3.33-3.49 (m, 1 H), 3.21 (dd, J = 14.11, 3.97 Hz, 1 H), 1.23 (m, 1 H), 0.59 (d, J = 7.06 Hz, 2 H), 0.36 (d, J = 3.53 Hz, 2 H). | 606.7 | | Solvent: DMF | Crystallization from AcOEt. Yield 74% | |

TABLE 2-continued

| Entry | Structure | NMR characterization | MS/ESI+ [MH]+ | [α_D] | Experimental procedure | Purification and yield | Starting material (precursor) |
|---|---|---|---|---|---|---|---|
| 30 | 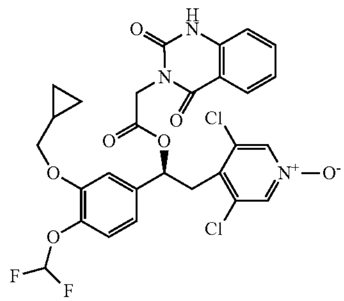 [SMILES: O=C(Cn1c(=O)[nH]c2ccccc2c1=O)O[C@@H](Cc1c(Cl)c[n+]([O-])cc1Cl)c1ccc(OC(F)F)c(OCC2CC2)c1] | $^1$H NMR (400 MHz, acetone) δ ppm 10.48 (bs, 1 H), 8.16 (s, 2 H), 8.04 (d, J = 7.94 Hz, 1 H), 7.70-7.79 (m, 1 H), 7.37 (d, J = 7.94 Hz, 1 H), 7.30 (t, J = 7.50 Hz, 1 H), 7.16-7.22 (m, 2 H), 7.01-7.08 (m, 1 H), 6.93 (t, J = 75.00 Hz, 1 H), 6.15 (dd, J = 9.70, 4.41 Hz, 1 H), 4.59-4.84 (m, 2 H), 4.02 (t, J = 6.62 Hz, 2 H), 3.49 (dd, J = 14.11, 10.14 Hz, 1 H), 3.30 (dd, J = 14.11, 4.41 Hz, 1 H), 1.31 (m, 1 H), 0.57-0.73 (m, 2 H), 0.36-0.49 (m, 2 H). | 622.2 | | Solvent: DMF | Crystallization from EtOH. Yield 54% | |
| 31 | 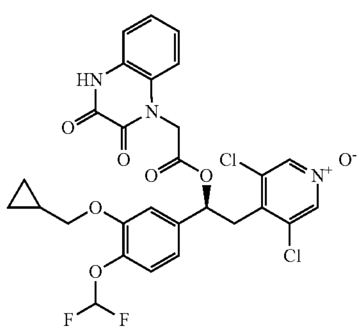 | $^1$H NMR (400 MHz, acetone) δ ppm 10.90-11.07 (m, 1 H), 8.05 (s, 2 H), 7.34-7.48 (m, 1 H), 7.23-7.30 (m, 1 H), 7.16-7.22 (m, 2 H), 7.08-7.15 (m, 1 H), 6.99-7.06 (m, 2 H), 6.94 (t, J = 75.00 Hz, 1 H), 6.07-6.21 (m, 1 H), 4.82-5.18 (m, 2 H), 3.92-4.11 (m, 2 H), 3.42-3.53 (m, 1 H), 3.20-3.30 (m, 1 H), 1.26-1.38 (m, 1 H), 0.58-0.68 (m, 2 H), 0.40-0.51 (m, 2 H). | 622.2 | | | Yield 89% | |

TABLE 2-continued

| Entry | Structure | NMR characterization | MS/ESI+ [MH]+ | [α_D] | Experimental procedure | Purification and yield | Starting material (precursor) |
|---|---|---|---|---|---|---|---|
| 32 | 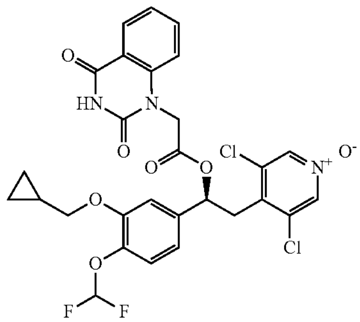 | ¹H NMR (400 MHz, acetone) δ ppm 10.35-10.56 (bs, 1 H), 8.13-8.20 (m, 1 H), 8.11 (s, 2 H), 7.58-7.70 (m, 1 H), 7.30-7.39 (m, 1 H), 7.19 (m, 2 H), 7.01-7.10 (m, 2 H), 6.94 (t, J = 75.00 Hz, 1 H), 6.11-6.22 (m, 1 H), 4.82-5.10 (m, 2 H), 3.98 (d, J = 6.62 Hz, 2 H), 3.46-3.57 (m, 1 H), 3.23-3.33 (m, 1 H), 1.23-1.40 (m, 1 H), 0.59-0.70 (m, 2 H), 0.37-0.45 (m, 2 H). | 622.2 | | | Yield 97% | |
| 33 | 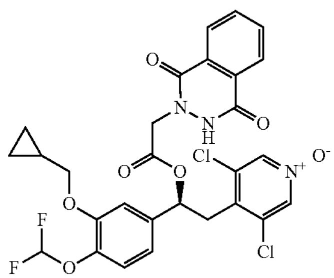 | ¹H NMR (400 MHz, DMSO-d₆) δ ppm 11.61-12.09 (m, 1 H), 8.53 (s, 2 H), 8.16-8.34 (m, 1 H), 7.78-8.05 (m, 3 H), 7.09-7.19 (m, 1 H), 6.98-7.08 (m, 2 H), 6.83-6.96 (m, 1 H), 5.94-6.12 (m, 1 H), 4.89-5.06 (m, 2 H), 3.74-3.89 (m, 2 H), 3.39-3.55 (m, 1 H), 3.22 (m, 1 H), 1.20-1.37 (m, 1 H), 0.48-0.63 (m, 2 H), 0.20-0.41 (m, 2 H). | 621.73 | | | Yield 92% | |

Example 5

(S)-3,5-Dichloro-4-(2-(3-(cyclopropylmethoxy)-4-(difluoromethoxy)-phenyl)-2-(2-(3,3-dimethyl-1,1-dioxidobenzo[d]isothiazol-2(3H)-yl)acetoxy)-ethyl)pyridine 1-oxide (Compound 35)

Scheme 5.

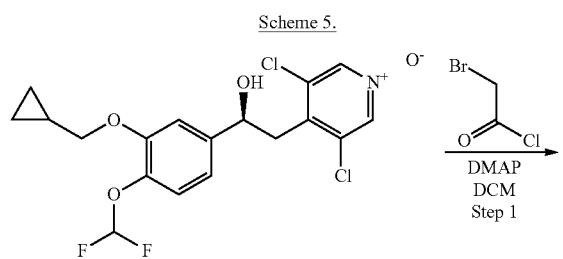

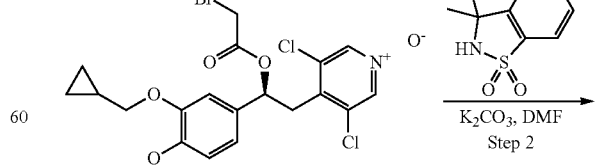

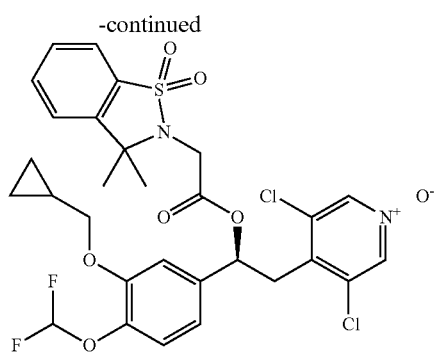

Step 1: Preparation of (S)-4-(2-(2-bromoacetoxy)-2-(3-(cyclopropylmethoxy)-4-(difluoromethoxy)phenyl)ethyl)-3,5-dichloropyridine 1-oxide (34)

(S)-3,5-dichloro-4-(2-(3-(cyclopropylmethoxy)-4-(difluoromethoxy)phenyl)-2-hydroxyethyl)pyridine 1-oxide (500 mg, 1.2 mmol) is dissolved in CH$_2$Cl$_2$ (15 ml), DMAP (180 mg, 1.8 mmol) and 2-bromoacetyl chloride (243 mg, 1.55 mmol) are added. The mixture is stirred at RT for 2 hours, then is diluted with CH$_2$Cl$_2$ (50 ml) and quenched with HCl 1N aqueous solution (50 ml). The two phases are separated, and the organic phase is washed with HCl 1N aqueous solution (2×50 ml), dried over Na$_2$SO$_4$ and evaporated under vacuum. The crude contains a mixture of the title compound (bromoacetoxy-derivative) and an undesired compound (chloroacetoxy-derivative), in a cumulative amount of 550 mg. The compound undergoes the next step without any further purification. MS/ESI$^+$ 541.17 [MH]$^+$.

Step 2: Preparation of, (S)-3,5-dichloro-4-(2-(3-(cyclopropylmethoxy)-4-(difluoromethoxy)phenyl)-2-(2-(3,3-dimethyl-1,1-dioxidobenzo[d]isothiazol-2(3H)-yl)acetoxy)ethyl)pyridine 1-oxide (35)

(S)-4-(2-(2-bromoacetoxy)-2-(3-(cyclopropylmethoxy)-4-(difluoromethoxy)-phenyl)ethyl)-3,5-dichloropyridine (mixture obtained as described in Example 5, Step 1, 100 mg, 0.18 mmol) is dissolved in DMF (2 ml), then K$_2$CO$_3$ (30 mg, 0.22 mmol) and 2,3-dihydro-3,3-dimethyl-1,2-benzisothiazole 1,1-dioxide (71 mg, 0.36 mmol) are added. The mixture is stirred at RT for 5 hours. The reaction is quenched with water (10 ml), and the product extracted with Ethyl Acetate. The organic layer is washed with H2O (3×15 ml), dried over Na$_2$SO$_4$ and evaporated under vacuum. The crude is purified by preparative HPLC (Method 2), to yield 100 mg of the title compound (85% yield). MS/ESI$^+$ 657.51 [MH]$^+$; $^1$H NMR (400 MHz, acetone) ppm 8.40 (s, 2H), 7.38 (m, 2H), 7.36 (m, 3H), 7.03 (m, 1H), 6.81 (m, 2H), 5.63 (m, 1H), 4.14 (s, 2H), 3.90 (d, 2H), 3.54-3.29 (2H), 3.25-3.00 (2m, 2H), 1.27 (s, 6H), 0.72 (m, 1H), 0.30-0.05 (2 m, 4H).

Example 6

(S)-3,5-Dichloro-4-(2-(3-(cyclopropylmethoxy)-4-(difluoromethoxy)-phenyl)-2-(2-(4-(2-morpholinoethyl)-2,3-dioxo-3,4-dihydroquinoxalin-1(2H)-yl)acetoxy)ethyl)pyridine 1-oxide (Compound 37)

Scheme 6.

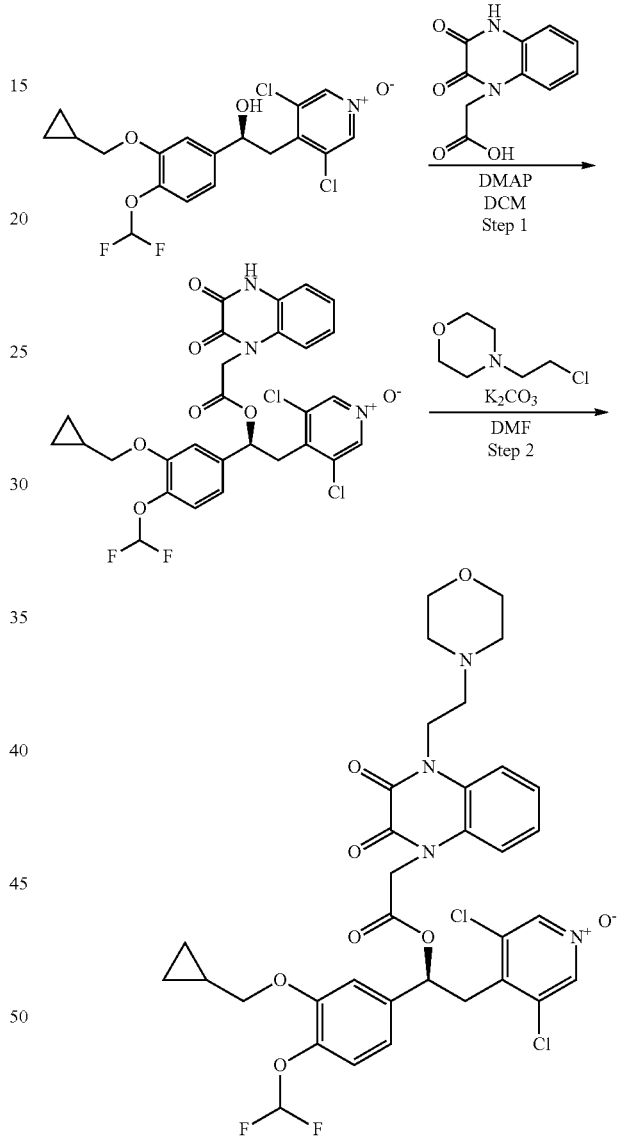

Step 1: Preparation of (S)-3,5-dichloro-4-(2-(3-(cyclopropylmethoxy)-4-(difluoromethoxy)phenyl)-2-(2-(2,3-dioxo-3,4-dihydroquinoxalin-1(2H)-yl)acetoxy)ethyl)pyridine 1-oxide (36)

1-Ethyl-3-[3-dimethylaminopropyl]carbodiimide hydrochloride (EDC HCl) (59 mg, 0.309 mmol) was added to a solution of compounds (S)-3,5-dichloro-4-(2-(3-(cyclopropylmethoxy)-4-(difluoromethoxy)phenyl)-2-hydroxyethyl) pyridine 1-oxide (100 mg, 0.238 mmol), 2-(2,3-dioxo-3,4-dihydroquinoxalin-1(2H)-yl)acetic acid (63 mg, 0.286 mmol) and 4-dimethylaminopyridine (6 mg, 0.048 mmol) in CH$_2$Cl$_2$ (1 mL) at room temperature under nitrogen atmosphere. The mixture was stirred at room temperature overnight. The mixture was then diluted with CH$_2$Cl$_2$ (5 mL) and washed with NaHCO$_3$ saturated solution (5 mL), HCL 0.1 N (5 mL) and brine (5 ml). The organic phase was dried over Na$_2$SO$_4$ and the solvent was evaporated, to yield 70 mg of the title compound (80% yield). MS/ESI$^+$ 621.09 [MH]$^+$ Step 2: Preparation of (S)-3,5-dichloro-4-(2-(3-(cyclopropylmethoxy)-4-(difluoromethoxy)phenyl)-2-(2-(4-(2-morpholinoethyl)-2,3-dioxo-3,4-dihydroquinoxalin-1(2H)-yl)acetoxy)ethyl)pyridine 1-oxide (37)

To a solution of (S)-3,5-dichloro-4-(2-(3-(cyclopropylmethoxy)-4-(difluoromethoxy)phenyl)-2-(2-(2,3-dioxo-3,4-dihydroquinoxalin-1(2H)-yl)acetoxy)-ethyl)pyridine 1-oxide (70 mg, 0.112 mmol) dissolved in DMF (1 mL), 4-(2-chloroethyl)morpholine (34 mg, 0.225 mmol) and potassium carbonate (23 mg, 0.169 mmol) were added. The mixture was stirred at 40 degrees for 5 hours. The mixture was then diluted with H$_2$O (10 mL) and the aqueous phase extracted with AcOEt (2×3 mL). The organic phase was washed with brine (10 ml), dried over Na$_2$SO$_4$ and the solvent was evaporated, to yield 22 mg of the title compound (yield 37%). MS/ESI$^+$ 735.4 [MH]$^+$; $^1$H NMR (400 MHz, acetone) δ ppm 8.01 (s, 2H), 7.53-7.62 (m, 1H), 7.28-7.39 (m, 1H), 7.09-7.24 (m, 3H), 6.99-7.07 (m, 2H), 6.93 (t, J=75.00 Hz, 1H), 5.97-6.21 (m, 1H), 5.10-5.21 (m, 1H), 4.76-4.84 (m, 1H), 4.36-4.56 (m, 2H), 3.89-4.12 (m, 2H), 3.61 (m, 4H), 3.35-3.51 (m, 1H), 3.15-3.27 (m, 1H), 2.76-2.80 (m, 2H), 2.52-2.65 (m, 4H), 1.25-1.39 (m, 1H), 0.55-0.68 (m, 2H), 0.37-0.52 (m, 2H).

The compounds listed in Table 3 were prepared with analogous synthetic steps and procedures to that described in Example 9, by reacting the appropriate precursors (commercially available or synthesized by a person skilled in the art) with suitable reagents. Specific variations in the experimentals or purification methods are indicated in the table.

TABLE 3

| Entry | Structure | NMR characterization | MS/ESI$^+$ Experimental [MH]$^+$ | Purification procedure and yield | Starting material (precursor) |
|---|---|---|---|---|---|
| 38 | 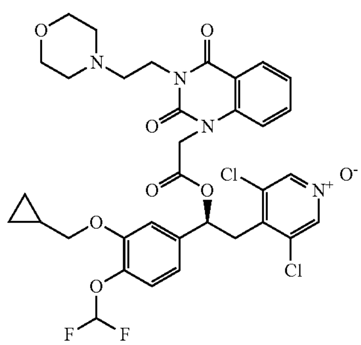 | $^1$H NMR (400 MHz, acetone) δ ppm 8.18-8.24 (m, 1 H), 8.03 (s, 2 H), 7.57-7.69 (m, 1 H), 7.31-7.41 (m, 1 H), 7.17-7.28 (m, 2 H), 7.03-7.11 (m, 2 H), 6.94 (t, J = 75.00 Hz, 1 H), 6.12-6.23 (m, 1H), 4.79-5.18 (m, 2 H), 4.13-4.33 (m, 2 H), 3.95-4.07 (m, 2 H), 3.55-3.62 (m, 4 H), 3.44-3.53 (m, 1 H), 3.22-3.31 (m, 1 H), 2.58-2.71 (m, 4 H), 2.39-2.57 (m, 4 H), 1.25-1.41 (m, 1 H), 0.59-0.72 (m, 2 H), 0.38-0.50 (m, 2 H). | 735.4 | Preparative HPLC. Yield 37% | |
| 39 | 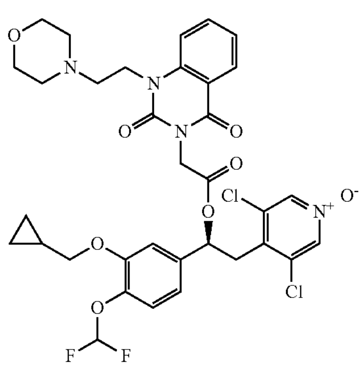 | $^1$H NMR (400 MHz, acetone) δ ppm 8.14 (m, 3 H), 7.79-7.88 (m, 1 H), 7.51-7.61 (m, 1 H), 7.32-7.41 (m, 1 H), 7.16-7.25 (m, 2 H), 7.02-7.10 (m, 1 H), 6.92 (t, J = 75.00 Hz, 1 H), 6.11-6.21 (m, 1H), 4.77 (s, 2 H), 4.26-4.42 (m, 2 H), 3.92-4.10 (m, 2 H), 3.56 (m, 5 H), 3.18-3.36 (m, 1 H), 2.62-2.70 (m, 2 H), 2.43-2.57 (m, 4 H), 1.23-1.47 (m, 1 H), 0.58-0.67 (m, 2 H), 0.38-0.50 (m, 2 H). | 735.4 | Salification of the crude with HCl in Et2O 4 M. The salt is dissolved with H2O, NaHCO3 is added till precipitation and the precipitate extracted with EtOAc, which is evaporate under reduced pressure to give the desired compound. Yield 53% | |

TABLE 3-continued

| Entry | Structure | NMR characterization | MS/ESI+ [MH]+ | Experimental procedure | Purification and yield | Starting material (precursor) |
|---|---|---|---|---|---|---|
| 40 | 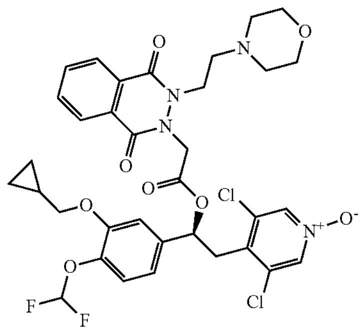 [SMILES: O=C(Cn1c(=O)c2ccccc2c(=O)n1CCN1CCOCC1)O[C@@H](Cc1c(Cl)c[n+]([O-])cc1Cl)c1ccc(OC(F)F)c(OCC2CC2)c1] | ¹H NMR (400 MHz, acetone) δ ppm 8.33 (d, J = 7.50 Hz, 1 H), 8.24 (s, 2 H), 7.87-8.08 (m, 3 H), 7.09-7.22 (m, 2 H), 7.00 (d, J = 7.94 Hz, 1 H), 6.92 (t, J = 75.00 Hz, 1 H), 6.18 (d, J = 4.41 Hz, 1 H), 4.99 (d, J = 3.53 Hz, 2 H), 3.75-4.07 (m, 4 H), 3.44-3.66 (m, 5 H), 3.33 (m, 1 H), 2.48 (m, 2 H), 2.36 (m, 4 H), 1.17-1.35 (m, 1 H), 0.60 (d, J = 7.06 Hz, 2 H), 0.35 (d, J = 4.41 Hz, 2 H). | 735.4 | The reaction was stirred at 50 degrees for 2 hrs, then kept at 0 deg on and stirred at 50 deg for 1 hr. | Yield 21% | |

Example 7

S)-3,5-Dichloro-4-(2-(3-(cyclopropylmethoxy)-4-(difluoromethoxy)-phenyl)-2-(2-(5-hydroxy-1H-indol-1-yl)acetoxy)ethyl)pyridine 1-oxide (Compound 42)

Scheme 7.

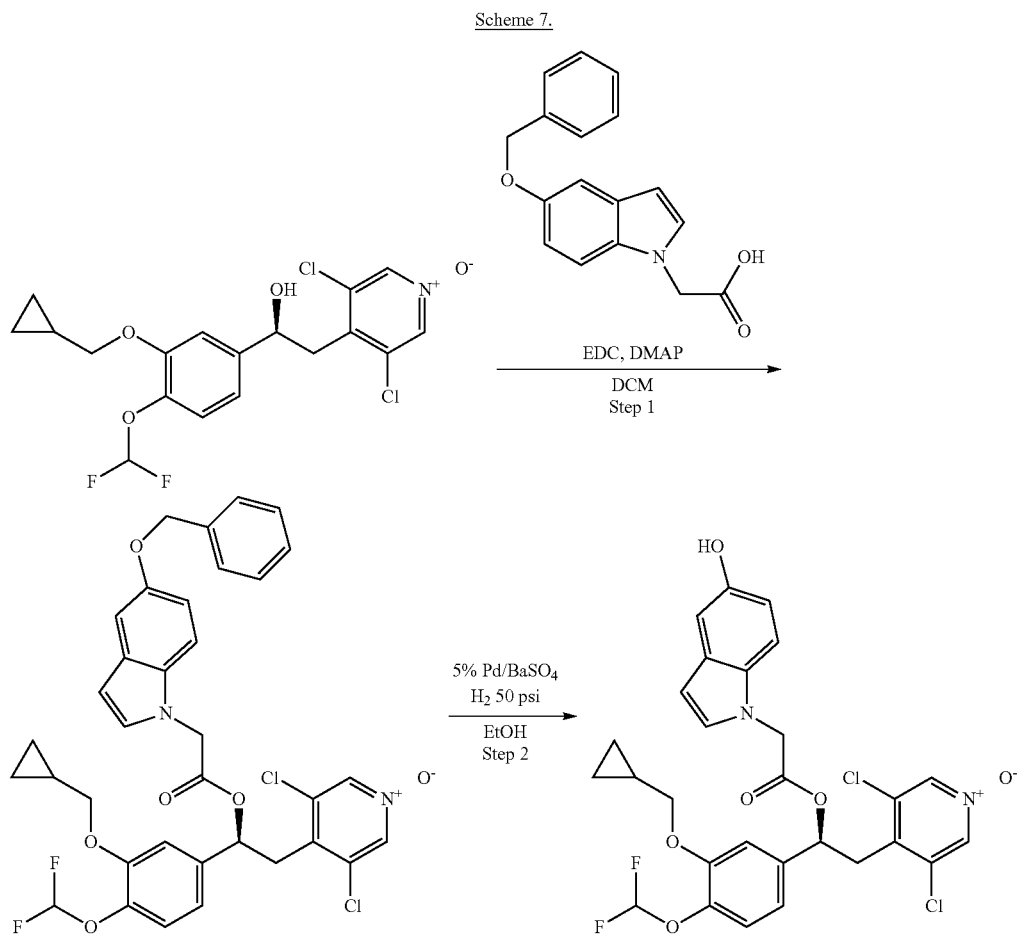

Step 1: Preparation of (S)-4-(2-(2-(5-(benzyloxy)-1H-indol-1-yl)acetoxy)-2-(3-(cyclopropylmethoxy)-4-(difluoromethoxy)phenyl)ethyl)-3,5-dichloropyridine 1-oxide (41)

To a mixture of 2-(5-(benzyloxy)-1H-indol-1-yl)acetic acid (164 mg, 0.583 mmol) in DCM (20 ml), (S)-3,5-dichloro-4-(2-(3-(cyclopropylmethoxy)-4-(difluoromethoxy)phenyl)-2-hydroxyethyl)pyridine 1-oxide (245 mg, 0.583 mmol), EDC (335 mg, 1.749 mmol) and DMAP (35.6 mg, 0.291 mmol) were added, and the reaction was stirred at room temperature for 5 hours. The organic solution was washed with NaHCO$_3$ sat. sol. and 1N HCl, dried over Na$_2$SO$_4$, filtered and evaporated. The crude was purified by flash chromatography on silica gel (DCM/MeOH from 99.5:0.5 to 98.5:1.5) affording (S)-4-(2-(2-(5-(benzyloxy)-1H-indol-1-yl)acetoxy)-2-(3-(cyclopropylmethoxy)-4-(difluoromethoxy)phenyl)ethyl)-3,5-dichloropyridine 1-oxide (319 mg, 0.467 mmol, 80% yield). MS/ESI$^+$ 683.0 [MH]$^+$.

Step 2: Preparation of (S)-3,5-dichloro-4-(2-(3-(cyclopropylmethoxy)-4-(difluoromethoxy)phenyl)-2-(2-(5-hydroxy-1H-indol-1-yl)acetoxy)ethyl)pyridine 1-oxide (42)

A mixture of (S)-4-(2-(2-(5-(benzyloxy)-1H-indol-1-yl)acetoxy)-2-(3-(cyclopropylmethoxy)-4-(difluoromethoxy)phenyl)ethyl)-3,5-dichloropyridine 1-oxide (155 mg, 0.227 mmol) and 5% Pd/BaSO$_4$ dry powder (type D1863 Chimet spa) (290 mg, 0.136 mmol) in 20 ml of EtOH was hydrogenated for 5 hours at 50 psi. The catalyst was filtered off, solvent was evaporated and the crude was purified by flash chromatography on silica gel (DCM/MeOH from 99.5:0.5 to 99:1) affording (S)-3,5-dichloro-4-(2-(3-(cyclopropylmethoxy)-4-(difluoromethoxy)phenyl)-2-(2-(5-hydroxy-1H-indol-1-yl)acetoxy)ethyl)pyridine 1-oxide (41.8 mg, 0.070 mmol, 31% yield). MS/ESI$^+$ 593.18 [MH]$^+$, [α$_D$]=+30.50, c=0.6 in DCM; $^1$H NMR (300 MHz, DMSO-d$_6$) δ ppm 8.67 (s, 1H) 8.54 (s, 2H) 7.12-7.19 (m, 2H) 6.99 (d, 1H) 6.93 (d, 1H) 6.91 (dd, 1H) 6.85 (d, 1H) 7.05 (t, 1H) 6.61 (dd, 1H) 6.24 (dd, 1H) 6.01 (dd, 1H) 5.13 (d, 1H) 4.94 (d, 1H) 3.84 (d, 2H) 3.42 (dd, 1H) 3.20 (dd, 1H) 1.11-1.31 (m, 1H) 0.51-0.66 (m, 2H) 0.27-0.44 (m, 2H)

Example 8

S)-3,5-Dichloro-4-(2-(3-(cyclopropylmethoxy)-4-(difluoromethoxy)-phenyl)-2-(2-(5-methoxy-1H-indol-1-yl)acetoxy)ethyl)pyridine 1-oxide (Compound 45

Scheme 8.

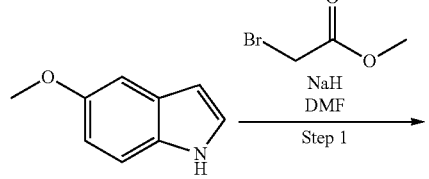

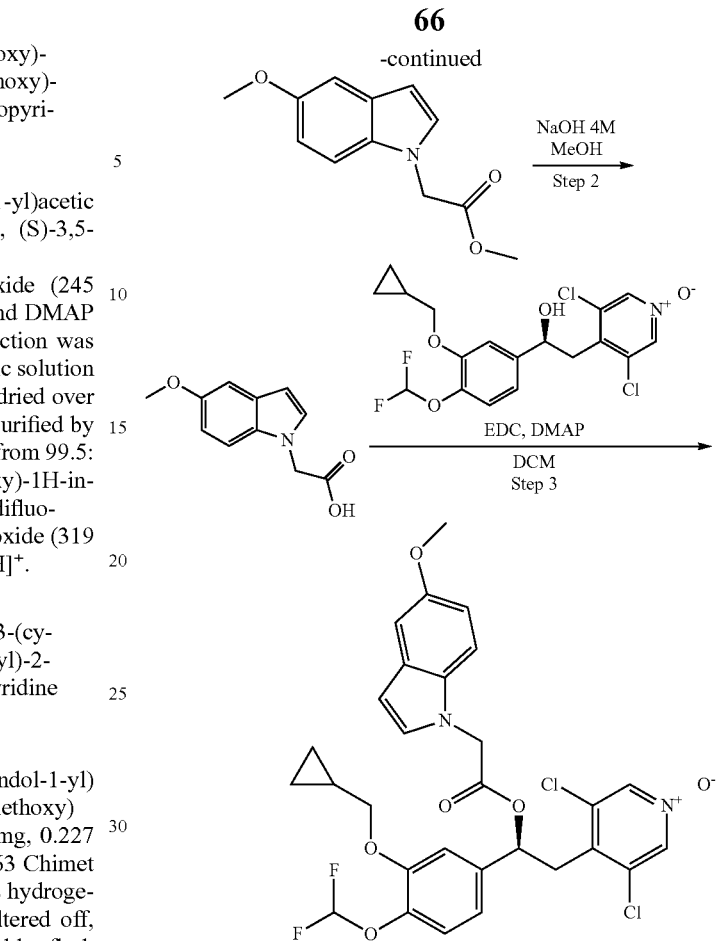

Step 1: Preparation of methyl 2-(5-methoxy-1H-indol-1-yl)acetate (43)

To a solution of 5-methoxy-1H-indole (500 mg, 3.40 mmol) in dry DMF (8 ml), cooled at 0° C., sodium hydride (60% w/w dispersion in mineral oil, 136 mg, 3.40 mmol) was slowly added portionwise and the reaction was stirred at 0° C. for 45 minutes; then methyl 2-bromoacetate (315 μl, 3.40 mmol) was added dropwise, and the reaction was stirred at room temperature for 15 hours. Water was slowly added, and the product was extracted with Et$_2$O and then with ethyl acetate. The combined organic layers were washed with water, dried over Na$_2$SO$_4$ and evaporated to dryness. The title compound was obtained and used for the next step without further purification (745 mg, 3.40 mmol, quantitative yield). MS/ESI$^+$ 220.1 [MH]$^+$.

Step 2: Preparation of 2-(5-methoxy-1H-indol-1-yl)acetic acid (44)

To a solution of methyl 2-(5-methoxy-1H-indol-1-yl)acetate (745 mg, 3.40 mmol) in MeOH (20 ml), aqueous 4N sodium hydroxide (935 μl, 3.74 mmol) was slowly added and the reaction was stirred at room temperature for 1 hour. The solvent was removed and the residue was partitioned between ethyl acetate and water. The aqueous phase was acidified with 2.5M HCl and extracted with ethyl acetate. This organic phase was washed with brine, dried over Na$_2$SO$_4$ and evaporated to dryness to give the title compound (510 mg, 2.485 mmol, 73% yield). MS/ESI$^+$ 206.1 [MH]$^+$.

Step 3: Preparation of (S)-3,5-dichloro-4-(2-(3-(cyclopropylmethoxy)-4-(difluoromethoxy)phenyl)-2-(2-(5-methoxy-1H-indol-1-yl)acetoxy)ethyl)pyridine 1-oxide (45)

A mixture of (S)-3,5-dichloro-4-(2-(3-(cyclopropylmethoxy)-4-(difluoromethoxy)phenyl)-2-hydroxyethyl)pyridine 1-oxide (279 mg, 0.665 mmol), 2-(5-methoxy-1H-indol-1-yl)acetic (150 mg, 0.731 mmol), EDC (382 mg, 1.994 mmol) and DMAP (162 mg, 1.329 mmol) was dissolved in DCM (20 ml) and the reaction was stirred at room temperature for 15 hours. The mixture was washed with 1M HCl, NaHCO$_3$ sat. sol. and brine, dried over Na$_2$SO$_4$ and evaporated. The resulting oil was purified by silica gel flash chromatography (DCM/MeOH 98/2). The title compound was obtained (296.4 mg, 0.488 mmol, 73.4% yield). MS/ESI$^+$ 607.17 [MH]$^+$; [α$_D$]=−3.66, c=0.53 in DCM; $^1$H NMR (300 MHz, DMSO-d$_6$) δ ppm 8.53 (s, 2H) 7.21 (d, 1H) 7.15 (d, 1H) 7.02-7.07 (m, 2H) 6.99 (d, 1H) 6.91 (dd, 1H) 7.05 (t, 1H) 6.75 (dd, 1H) 6.35 (dd, 1H) 6.02 (dd, 1H) 5.17 (d, 1H) 4.99 (d, 1H) 3.84 (d, 2H) 3.76 (s, 3H) 3.42 (dd, 1H) 3.20 (dd, 1H) 1.12-1.28 (m, 1H) 0.54-0.65 (m, 2H) 0.30-0.40 (m, 2H)

Example 9

Synthesis of (S)-3,5-dichloro-4-(2-(3-(cyclopropylmethoxy)-4-(difluoromethoxy)phenyl)-2-(2-(6-(trifluoromethyl)-1H-indol-1-yl)acetoxy)ethyl)-pyridine 1-oxide (Compound 48)

Scheme 9.

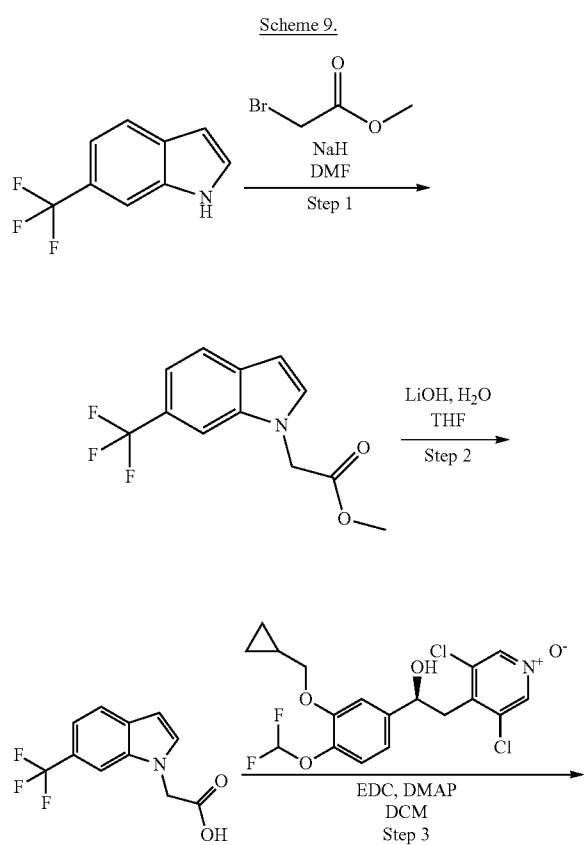

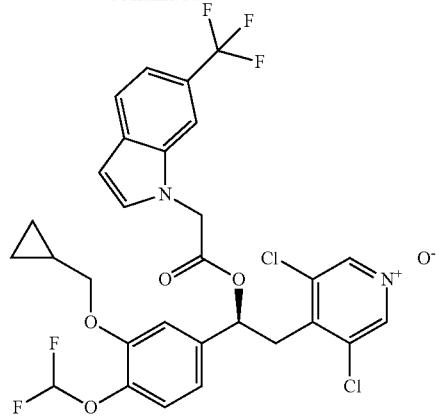

Step 1: Preparation of methyl 2-(6-(trifluoromethyl)-1H-indol-1-yl)acetate (46)

To a solution of 6-(trifluoromethyl)-1H-indole (250 mg, 1.350 mmol) in dry DMF (3 ml), sodium hydride (60% w/w dispersion in mineral oil, 64.8 mg, 1.620 mmol) was added at room temperature. After 10 minutes, methyl 2-bromoacetate (150 μl, 1.620 mmol) was added and the mixture was stirred at room temperature for 1 hour. The solvent was removed under reduced pressure and the crude was purified by flash chromatography on silica gel column (hexane/ethyl acetate 90/10) to afford methyl 2-(6-(trifluoromethyl)-1H-indol-1-yl)acetate (120 mg, 0.467 mmol, 34.6% yield). MS/ESI$^+$ 258.1 [MH]$^+$.

Step 2: Preparation of 2-(6-(trifluoromethyl)-1H-indol-1-yl)acetic acid (47)

Methyl 2-(6-(trifluoromethyl)-1H-indol-1-yl)acetate (120 mg, 0.467 mmol) was dissolved in a mixture (1/1) of THF/H$_2$O (4 ml), and lithium hydroxide (112 mg, 4.67 mmol) was added. The mixture was stirred at room temperature for 2 hours. The organic solvent was evaporated and 2N HCl was added to the resulting mixture (pH=5). The precipitate was collected by filtration affording 2-(6-(trifluoromethyl)-1H-indol-1-yl)acetic acid (90 mg, 0.370 mmol, 79% yield). MS/ESI$^+$ 244.0 [MH]$^+$.

Step 3: Preparation of (S)-3,5-dichloro-4-(2-(3-(cyclopropylmethoxy)-4-(difluoromethoxy)phenyl)-2-(2-(6-(trifluoromethyl)-1H-indol-1-yl)acetoxy)ethyl)pyridine 1-oxide (48)

A mixture of 2-(6-(trifluoromethyl)-1H-indol-1-yl)acetic acid (90 mg, 0.370 mmol), (S)-3,5-dichloro-4-(2-(3-(cyclopropylmethoxy)-4-(difluoromethoxy)phenyl)-2-hydroxyethyl)pyridine 1-oxide (130 mg, 0.308 mmol), EDC (83 mg, 0.432 mmol) and DMAP (75 mg, 0.617 mmol) in dry DCM (5 ml) was stirred at room temperature overnight. Aqueous 1N HCl was added to the reaction mixture and the organic phase was separated, washed with brine and dried over sodium sulfate. The solvent was removed under vacuum, and the crude was purified by flash chromatography on silica gel column (DCM/MeOH 96/4) to give (S)-3,5-dichloro-4-(2-(3-(cyclopropylmethoxy)-4-(difluoromethoxy)phenyl)-2-(2-(6-(trifluoromethyl)-1H-indol-1-yl)acetoxy)ethyl)pyridine 1-oxide (95 mg, 0.147 mmol, 48% yield). MS/ESI$^+$ 645.03 [MH]$^+$; [α$_D$]=−2.157, c=0.510; DCM; $^1$H NMR (300 MHz, DMSO-d$_6$) δ ppm 8.45 (s, 2H), 7.67-7.85 (m, 2H), 7.51 (d, 1H), 7.32 (dd, 1H), 7.12 (d, 1H), 6.97 (d, 1H), 6.87 (dd, 1H), 7.03 (t, 1H), 6.61 (dd, 1H), 5.98 (dd, 1H), 5.38 (d, 1H), 5.25 (d, 1H), 3.82 (d, 2H), 3.39 (dd, 1H), 3.19 (dd, 1H), 1.10-1.22 (m, 1H), 0.46-0.70 (m, 2H), 0.15-0.46 (m, 2H)

The compound listed in Table 4 was prepared with analogous synthetic steps and procedures to that described in Example 9, by reacting the appropriate precursors (commercially available or synthesized by a person skilled in the art) with suitable reagents. Specific variations in the experimentals or purification methods are indicated in the table.

TABLE 4

| Entry | Structure | NMR characterization | MS/ESI$^+$ [MH]$^+$ | [α$_D$] | Purification and yield | Starting material (precursor) |
|---|---|---|---|---|---|---|
| 49 | 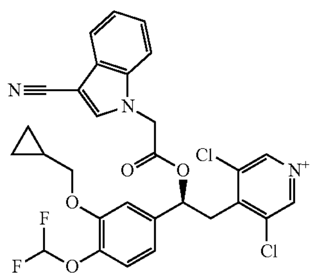 | $^1$H NMR (300 MHz, DMSO-d$_6$) d ppm 8.49 (s, 2 H), 8.19 (s, 1 H), 7.58-7.74 (m, 1 H), 7.35-7.45 (m, 1 H), 7.30-7.35 (m, 2 H), 7.16 (d, 1 H), 6.99 (d, 1 H), 6.91 (dd, 1 H), 7.06 (t, 1 H), 6.02 (dd, 1 H), 5.37 (d, 1 H), 5.23 (d, 1 H), 3.85 (d, 2 H), 3.41 (dd, 1 H), 3.19 (dd, 1 H), 1.00-1.34 (m, 1 H), 0.49-0.73 (m, 2 H), 0.13-0.49 (m, 2 H) | 602.12 | −2.36 c = 0.500, DCM | Flash chromatography on silica gel DCM/MeOH 97:3) 36% yield |  |

Example 10

S)-3,5-Dichloro-4-(2-(3-(cyclopropylmethoxy)-4-(difluoromethoxy)phenyl)-2-(2-(7-nitro-1H-indol-1-yl)acetoxy)ethyl)pyridine 1-oxide (Compound 52

Scheme 10.

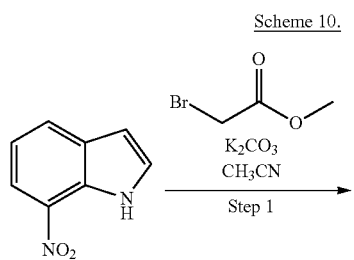

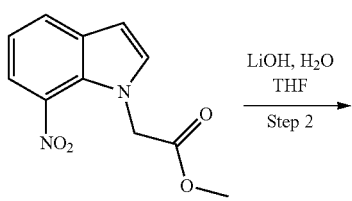

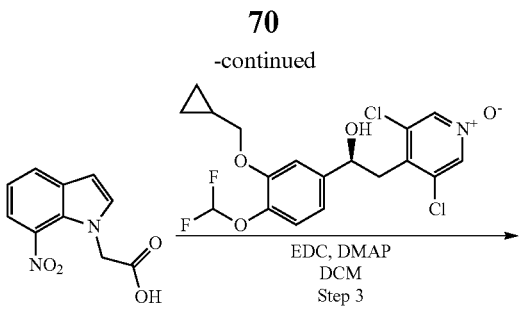

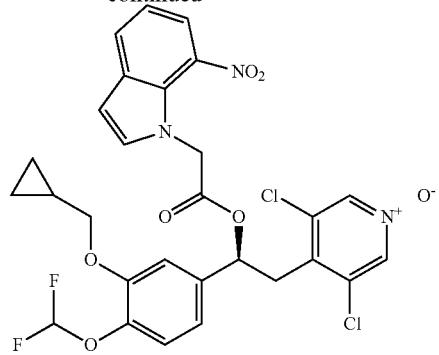

Step 1: Preparation of methyl 2-(7-nitro-1H-indol-1-yl)acetate (50)

To a solution of 7-nitro-1H-indole (0.5 g, 3.08 mmol) in dry CH$_3$CN (20 ml), K$_2$CO$_3$ (0.511 g, 3.70 mmol) was added at room temperature. After 10 minutes, methyl 2-bromoacetate (0.343 ml, 3.70 mmol) was added dropwise, and the reaction was refluxed for 24 hours. Additional K$_2$CO$_3$ (0.511 g, 3.70 mmol) and methyl 2-bromoacetate (0.343 ml, 3.70 mmol) were added, and the stirring was prolonged for further 16 hours. The reaction was cooled at room temperature and the solvent was evaporated under vacuum. The resulting crude was partitioned between water and DCM; the organic phase was dried over sodium sulfate and evaporated under vacuum. The crude was purified by flash column chromatography on silica gel (hexane:ethyl acetate=9:1) affording methyl 2-(7-nitro-1H-indol-1-yl)acetate that crystallizes on standing (0.37 g, 1.580 mmol, 51% yield). MS/ESI$^+$ 234.9 [MH]$^+$.

Step 2: Preparation of 2-(7-nitro-1H-indol-1-yl)acetic acid (51)

To a solution of methyl 2-(7-nitro-1H-indol-1-yl)acetate (0.37 g, 1.580 mmol) in THF (20 ml), LiOH 1N (3.16 ml, 3.16 mmol) was added at room temperature. The reaction was stirred at the same temperature for 16 hours. Aqueous 2N HCl was added and the solvent was partially removed under vacuum. The remaining aqueous phase was extracted with ethyl acetate; the organic phase was dried over sodium sulfate and the solvent was evaporated under vacuum affording 2-(7-nitro-1H-indol-1-yl)acetic acid (0.33 g, 1.499 mmol, 95% yield). MS/ESI$^+$ 220.9 [MH]$^+$. This compound was used without any additional purification.

Step 3: Preparation of (S)-3,5-dichloro-4-(2-(3-(cyclopropylmethoxy)-4-(difluoromethoxy)phenyl)-2-(2-(7-nitro-1H-indol-1-yl)acetoxy)ethyl)pyridine 1-oxide (52)

A mixture of 2-(7-nitro-1H-indol-1-yl)acetic acid (0.15 g, 0.681 mmol), EDC (0.131 g, 0.681 mmol), DMAP (0.128 g, 1.048 mmol) and (S)-3,5-dichloro-4-(2-(3-(cyclopropylmethoxy)-4-(difluoromethoxy)phenyl)-2-hydroxyethyl)pyridine 1-oxide (0.220 g, 0.524 mmol) in dry DCM (15 ml) was stirred at room temperature for 16 hours. Aqueous 2N HCl was added, and the organic phase was separated and dried over sodium sulfate; the solvent was removed and the crude was triturated with MeOH. The precipitate was filtered, washed with MeOH and dried affording (S)-3,5-dichloro-4-(2-(3-(cyclopropylmethoxy)-4-(difluoromethoxy)phenyl)-2-(2-(7-nitro-1H-indol-1-yl)acetoxy)ethyl)pyridine 1-oxide (0.066 g, 0.106 mmol, 20% yield). MS/ESI$^+$ 622.1 [MH]$^+$; [$\alpha_D$]=−112.6, c=0.22, MeOH; $^1$H NMR (300 MHz, DMSO-d6) δ ppm 8.44 (s, 2H), 8.00 (dd, 1H), 7.82 (dd, 1H), 7.52 (d, 1H), 7.22 (t, 1H), 7.16 (d, 1H), 7.05 (d, 1H), 6.92 (dd, 1H), 7.06 (t, 1H), 6.76 (d, 1H), 5.95 (dd, 1H), 5.30 (d, 1H), 5.17 (d, 1H), 3.90 (d, 2H), 3.33-3.54 (m, 1H), 3.18 (dd, 1H), 0.99-1.39 (m, 1H), 0.48-0.72 (m, 2H), 0.36 (q, 2H).

The compounds listed in Table 5 were prepared with analogous synthetic steps and procedures to that described in Example 10, by reacting the appropriate precursors (commercially available or synthesized by a person skilled in the art) with suitable reagents. Specific variations in the experimentals or purification methods are indicated in the table.

TABLE 5

| Entry | Structure | NMR characterization | MS/ESI$^+$ [MH]$^+$ | [$\alpha_D$] | Experimental procedure | Purification and yield | Starting material (precursor) |
|---|---|---|---|---|---|---|---|
| 53 | 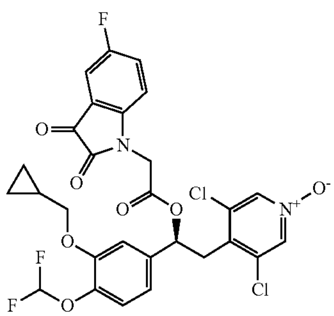 [SMILES: O=C(CN1C(=O)C(=O)c2cc(F)ccc21)O[C@@H](Cc1c(Cl)c[n+]([O-])cc1Cl)c1ccc(OC(F)F)c(OCC2CC2)c1] | $^1$H NMR (300 MHz, DMSO-d$_6$) d ppm 8.44 (s, 2 H), 7.45-7.60 (m, 2 H), 7.18 (d, 1 H), 7.02-7.11 (m, 2 H), 6.95 (dd, 1 H), 7.07 (t, 1 H), 6.03 (dd, 1 H), 4.66 (d, 1 H), 4.58 (d, 1 H), 3.89 (d, 2 H), 3.40 (dd, 1 H), 3.21 (dd, 1 H), 1.09-1.36 (m, 1 H), .49-0.70 (m, 2 H), 0.26-0.49 (m, 2 H) | 625.28 | −8.194 c = 31, MeOH | Step 1 was performed at 100° C. for 1 h under MW irradiation in DMF (partial degradation observed) | Chromatography on silica gel (DCM/MeOH 99/1 to 98/2) followed by trituration with etroleum ether/ethyl acetate 3/1). 49% yield | |
| 54 | 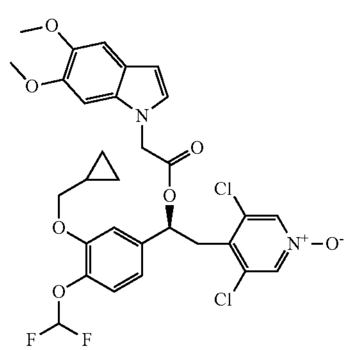 [SMILES: COc1cc2ccn(CC(=O)O[C@@H](Cc3c(Cl)c[n+]([O-])cc3Cl)c3ccc(OC(F)F)c(OCC4CC4)c3)c2cc1OC] | 1H NMR (300 MHz, DMSO-d6) δ ppm 8.49 (s, 2 H), 7.13 (d, 1 H), 7.07 (d, 1 H), 7.05 (s, 1 H), 6.97 (d, 1 H), 6.90 (dd, 1 H), 6.84 (s, 1 H), 7.04 (t, 1 H), 6.30 (dd, 1 H), 5.99 (dd, 1 H), 5.15 (d, 1 H), 5.02 (d, 1 H), 3.82 (d, 2 H), 3.75 (s, 3 H), 3.68 (s, 3 H), 3.39 (dd, 1 H), 3.19 (dd, 1 H), 0.98-1.35 (m, 1 H), 0.45-0.73 (m, 2 H), 0.20-0.45 (m, 2 H) | 637.17 | +0.36 c = 0.5, DCM | Step 1 was performed at 80° C. for 30 min under MW irradiation in DMF (partial degradation observed) Step 2 was performed using 2M NaOH (10 eq) instead of LiOH | Trituration with EtOH/MeOH 8/2 Yield 43% | |

Example 11

(S)-3,5-Dichloro-4-(2-(3-(cyclopropylmethoxy)-4-(difluoromethoxy)-phenyl)-2-(2-(5-methoxy-2,3-dioxoindolin-1-yl)acetoxy)ethyl)-pyridine 1-oxide (Compound 57)

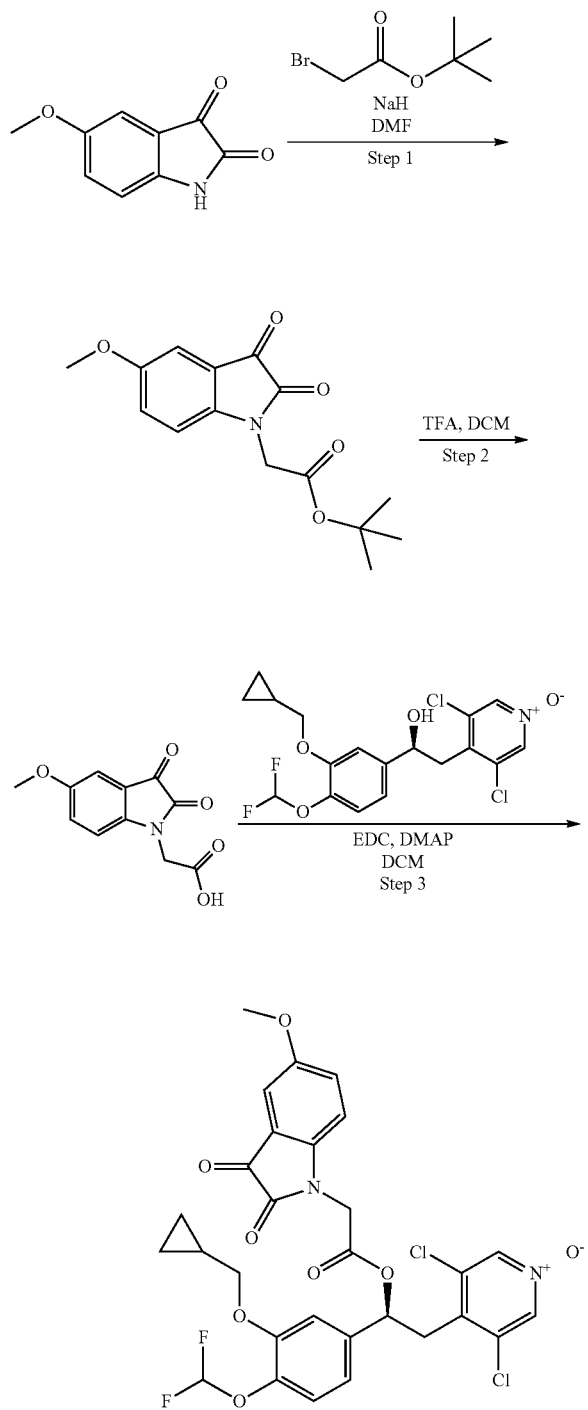

Scheme 11.

Step 1a: Preparation of tert-butyl 2-(5-methoxy-2,3-dioxoindolin-1-yl)acetate (55)

A solution of 5-methoxyindoline-2,3-dione (0.5 g, 2.82 mmol) in dry DMF (7 ml), under nitrogen atmosphere, was cooled to 0° C., and sodium hydride (60% w/w dispersion in mineral oil, 0.135 g, 3.39 mmol) was added portionwise. The mixture was stirred at 0° C. for 1 hour, and tert-butyl 2-bromoacetate (0.458 ml, 3.10 mmol) was added dropwise. The reaction was then stirred at room temperature overnight. The solvent was evaporated, ethyl acetate was added, and the mixture was washed with brine. The organic layer was dried over $Na_2SO_4$, filtered and evaporated. The crude was purified by flash chromatography on silica gel (ethyl acetate:petroleum ether=8:2) to afford tert-butyl 2-(5-methoxy-2,3-dioxoindolin-1-yl)acetate (0.650 g, 2.231 mmol, 79% yield). MS/ESI$^+$ 235.8 [MH-tert-Bu]$^+$.

Step 2: Preparation of 2-(5-methoxy-2,3-dioxoindolin-1-yl)acetic acid (56)

To a solution of tert-butyl 2-(5-methoxy-2,3-dioxoindolin-1-yl)acetate (0.65 g, 2.231 mmol) in DCM (20 ml), TFA (2.58 ml, 33.5 mmol) was added. The reaction was stirred at room temperature for 72 hours, then the solvent was evaporated to dryness affording 2-(5-methoxy-2,3-dioxoindolin-1-yl)acetic acid that was used in the next step without further purification (0.48 g, 2.041 mmol, 91% yield). MS/ESI$^+$ 235.9 [MH]$^+$

Step 3: Preparation of (S)-3,5-dichloro-4-(2-(3-(cyclopropylmethoxy)phenyl)-2-(2-(5-methoxy-2,3-dioxoindolin-1-yl)acetoxy)ethyl)-pyridine 1-oxide (57)

A mixture of (S)-3,5-dichloro-4-(2-(3-(cyclopropylmethoxy)-4-(difluoromethoxy)phenyl)-2-hydroxyethyl)pyridine 1-oxide (0.2 g, 0.476 mmol), 2-(5-methoxy-2,3-dioxoindolin-1-yl)acetic acid (0.112 g, 0.476 mmol), DMAP (0.029 g, 0.238 mmol) and EDC (0.274 g, 1.428 mmol) in DCM (10 ml) was stirred at room temperature overnight. The reaction was washed with 1N HCl, aqueous 5% $NaHCO_3$ and brine. The organic layer was dried over $Na_2SO_4$ and evaporated to dryness. The crude was purified by flash chromatography on silica gel (ethyl acetate:DCM=7:3) to give (S)-3,5-dichloro-4-(2-(3-(cyclopropylmethoxy)-4-(difluoromethoxy)phenyl)-2-(2-(5-methoxy-2,3-dioxoindolin-1-yl)acetoxy)ethyl)pyridine 1-oxide (0.18635 g, 0.292 mmol, 61% yield). MS/ESI$^+$ 637.19 [MH]$^+$; $[\alpha_D]$=+60.39 c=0.155 in DCM; $^1$H NMR (300 MHz, DMSO-d$_6$) δ ppm 8.41 (s, 2H), 7.22 (dd, 1H), 7.19-7.21 (m, 1H), 7.18 (d, 1H), 7.06 (d, 1H), 6.89-6.98 (m, 2H), 7.07 (t, 1H), 6.03 (dd, 1H), 4.62 (d, 1H), 4.54 (d, 1H), 3.89 (d, 2H), 3.81 (s, 3H), 3.40 (dd, 1H), 3.21 (dd, 1H), 1.09-1.37 (m, 1H), 0.51-0.67 (m, 2H), 0.28-0.47 (m, 2H)

The compounds listed in Table 6 were prepared with analogous synthetic steps and procedures to that described in Example 11, by reacting the appropriate precursors (commercially available or synthesized by a person skilled in the art) with suitable reagents. Specific variations in the experimentals or purification methods are indicated in the table.

TABLE 6

| Entry | Structure | NMR characterization | MS/ESI+ [MH]+ | [α_D] | Purification and yield | Starting material (precursor) |
|---|---|---|---|---|---|---|
| 58 | 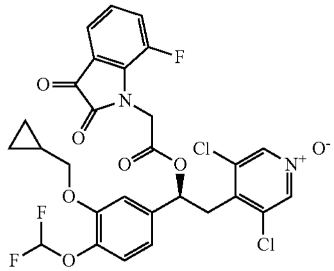 | ¹H NMR (300 MHz, DMSO-d₆) δ ppm 8.45 (s, 2 H), 7.51 (dd, 1 H), 7.42-7.51 (m, 1 H), 7.15-7.24 (m, 2 H), 7.09 (d, 1 H), 6.94 (dd, 1 H), 7.08 (t, 1 H), 6.05 (dd, 1 H), 4.66 (dd, 1 H), 4.59 (dd, 1 H), 3.91 (dd, 1 H), 3.86 (dd, 1 H), 3.43 (dd, 1 H), 3.22 (dd, 1 H), 1.13-1.33 (m, 1 H), 0.51-0.67 (m, 2 H), 0.28-0.42 (m, 2 H) | 625.48 | -3.96 c = 0.5, DCM | Trituration with MeOH 21% yield | |
| 59 | 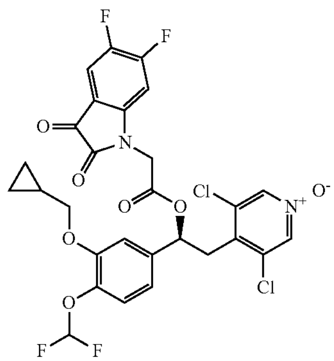 | ¹H NMR (300 MHz, DMSO-d₆) δ ppm 8.43 (s, 2 H), 7.86 (t, 1 H), 7.40 (dd, 1 H), 7.18 (d, 1 H), 7.06 (d, 1 H), 6.94 (dd, 1 H), 7.07 (t, 1 H), 6.01 (dd, 1 H), 4.60 (s, 2 H), 3.74-4.04 (m, 2 H), 3.40 (dd, 1 H), 3.21 (dd, 1 H), 1.09-1.29 (m, 1 H), 0.47-0.70 (m, 2 H), 0.21-0.47 (m, 2 H) | 643.19 | -10.29 c = 0.44, MeOH | Flash chromatography on silica gel (DCM/MeOH 99/1) 36% yield | |
| 60 | 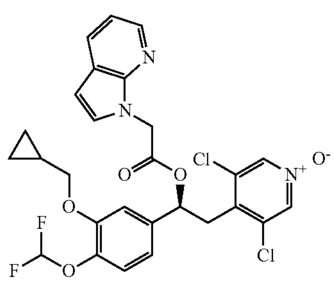 | ¹H NMR (300 MHz, DMSO-d6) δ ppm 8.50 (s, 2 H), 8.20 (dd, 1 H), 7.97 (dd, 1 H), 7.47 (d, 1 H), 7.17 (d, 1 H), 7.10 (dd, 1 H), 7.04 (d, 1 H), 6.93 (dd, 1 H), 7.07 (t, 1 H), 6.49 (d, 1 H), 6.04 (dd, 1 H), 5.18 (d, 1 H), 5.09 (d, 1 H), 3.89 (d, 2 H), 3.40 (dd, 1 H), 3.21 (dd, 1 H), 1.14-1.27 (m, 1 H), 0.51-0.65 (m, 2 H), 0.31-0.42 (m, 2 H) | 578.22 | -5.08 c = 0.5 DCM | Flash chromatography on silica gel (DCM/MeOH 98/2) followed by preparative HPLC (Method 1). 13% yield | |
| 61 | 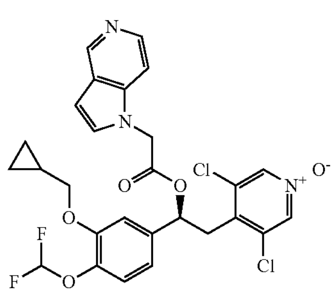 | ¹H NMR (300 MHz, DMSO-d₆) δ ppm 9.31 (s, 1 H), 8.50 (s, 2 H), 8.50 (dd, 1 H), 8.02 (d, 1 H), 7.88 (d, 1 H), 7.18 (d, 1 H), 7.10 (d, 1 H), 7.03 (d, 1 H), 6.92 (dd, 1 H), 7.07 (t, 1 H), 6.02 (dd, 1 H), 5.53 (d, 1 H), 5.41 (d, 1 H), 3.89 (d, 2 H), 3.39 (dd, 1 H), 3.21 (dd, 1 H), 0.51-0.65 (m, 2 H), 0.22-0.43 (m, 2 H) | 578.1 | -34.96 c =0.520; DCM | Flash chromatography on silica gel (DCM/MeOH 96/4) followed by preparative HPLC (Method 1). 22% yield | |

Example 12

(S)-3,5-Dichloro-4-(2-(3-(cyclopropylmethoxy)-4-(difluoromethoxy)-phenyl)-2-(2-(6-methoxy-2,3-dioxoindolin-1-yl)acetoxy)ethyl)-pyridine 1-oxide (Compound 64)

Scheme 12.

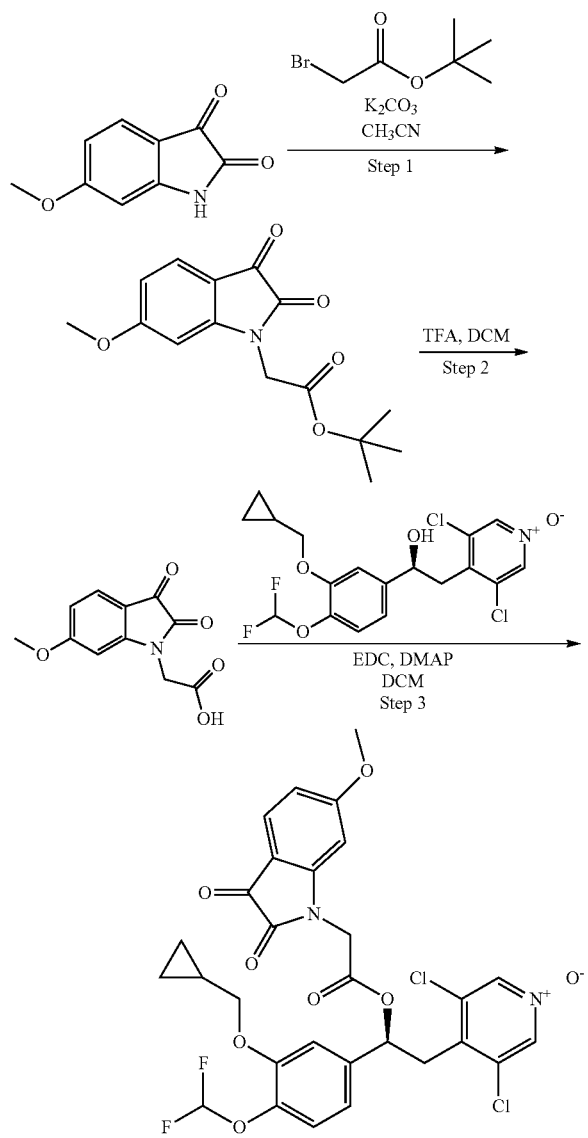

Step 1: Preparation of tert-butyl 2-(6-methoxy-2,3-dioxoindolin-1-yl)acetate (62)

To a solution of 6-methoxyindoline-2,3-dione (350 mg, 1.976 mmol) in acetonitrile (10 ml), K$_2$CO$_3$ (328 mg, 2.371 mmol) and tert-butyl 2-bromoacetate (350 µl, 2.371 mmol) were added, and the mixture was reacted at room temperature overnight. The insoluble inorganic salts were filtered off and the solvent was evaporated obtaining the crude title compound (550 mg, 1.888 mmol, 96% yield). MS/ESI$^+$ 292.1 [MH]$^+$. The crude was used in the next step without further purification.

Step 2: Preparation of 2-(6-methoxy-2,3-dioxoindolin-1-yl)acetic acid (63)

To a solution of tert-butyl 2-(6-methoxy-2,3-dioxoindolin-1-yl)acetate (0.245 g, 0.841 mmol) in DCM (10 ml), TFA (0.648 ml, 8.41 mmol) was added. The reaction was stirred at room temperature overnight. Another two additions of TFA (0.648 ml, 8.41 mmol and 0.324 ml, 4.21 mmol) were performed. The solvent was evaporated to dryness to afford crude 2-(6-methoxy-2,3-ioxoindolin-1-yl)acetic acid that was used in the next step without further purification (0.198 g, 0.842 mmol, quantitative yield). MS/ESI$^+$ 235.8 [MH]$^+$.

Preparation of (S)-3,5-dichloro-4-(2-(3-(cyclopropylmethoxy)-4-(difluoromethoxy)phenyl)-2-(2-(6-methoxy-2,3-dioxoindolin-1-yl)acetoxy)ethyl)-pyridine 1-oxide (64)

A mixture of (S)-3,5-dichloro-4-(2-(3-(cyclopropylmethoxy)-4-(difluoromethoxy)phenyl)-2-hydroxyethyl)pyridine 1-oxide (0.200 g, 0.476 mmol), 2-(6-methoxy-2,3-dioxoindolin-1-yl)acetic acid (0.112 g, 0.476 mmol), DMAP (0.029 g, 0.238 mmol) and EDC (0.274 g, 1.428 mmol) in DCM (10 ml) was stirred at room temperature for 4 hours; then the reaction mixture was washed with 1N HCl, aqueous 5% NaHCO$_3$ and brine. The organic layer was dried over Na$_2$SO$_4$ and evaporated to dryness. The crude was purified by flash chromatography on silica gel (ethyl acetate:DCM=7:3) to give (S)-3,5-dichloro-4-(2-(3-(cyclopropylmethoxy)-4-(difluoromethoxy)phenyl)-2-(2-(6-methoxy-2,3-dioxoindolin-1-yl)acetoxy)ethyl)pyridine 1-oxide (0.166 g, 0.260 mmol, 55% yield). MS/ESI$^+$ 637.19 [MH]$^+$; [α$_D$]=+67.91 c=0.22 in DCM; $^1$H NMR (300 MHz, DMSO-d$_6$) δ ppm 8.37 (s, 2H), 7.61 (d, 1H), 7.17 (d, 1H), 7.05 (d, 1H), 6.94 (dd, 1H), 7.07 (t, 1H), 6.69 (dd, 1H), 6.66 (d, 1H), 6.02 (dd, 1H), 4.60 (s, 2H), 3.89 (d, 2H), 3.86 (s, 3H), 3.38 (dd, 1H), 3.19 (dd, 1H), 1.07-1.33 (m, 1H), 0.48-0.67 (m, 2H), 0.18-0.48 (m, 2H)

Example 13

(S)-3,5-Dichloro-4-(2-(3-(cyclopropylmethoxy)-4-(difluoromethoxy)-phenyl)-2-(2-(4-methoxy-1,3-dioxoisoindolin-2-yl)acetoxy)-ethyl)pyridine 1-oxide (Compound 68)

Scheme 13.

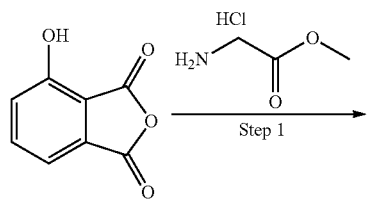

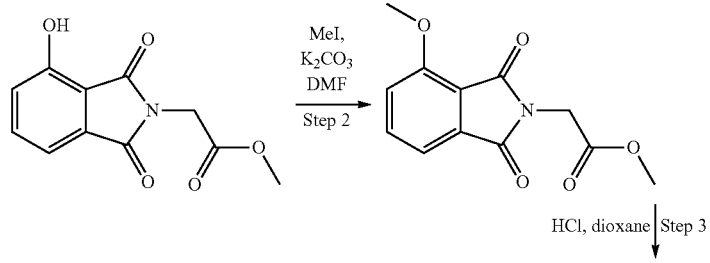

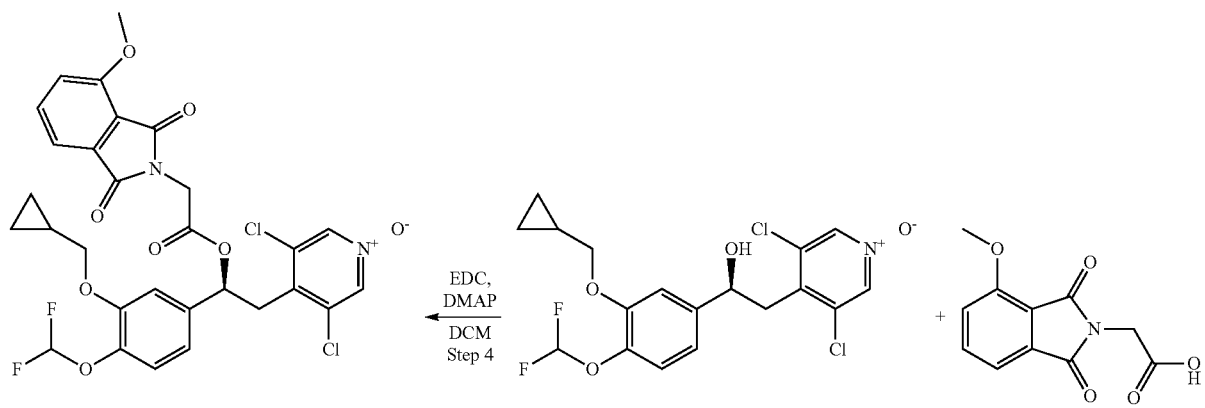

Step 1: Preparation of methyl 2-(4-hydroxy-1,3-dioxoisoindolin-2-yl)acetate (65)

4-Hydroxyisobenzofuran-1,3-dione (600 mg, 3.66 mmol) and methyl 2-aminoacetate hydrochloride (505 mg, 4.02 mmol) were finely dispersed on Montmorillonite K10 (powder, Sigma-Aldrich) (1.2 g) and the solid mixture was reacted under microwave irradiation at 150° C. for 30 minutes. Montmorillonite was washed with MeOH and the solvent was evaporated under vacuum. The crude was purified by preparative HPLC (Method 1) recovering the title compound (160 mg, 0.680 mmol, 19% yield). MS/ESI⁺ 236.1 [MH]⁺.

Step 2: Preparation of methyl 2-(4-methoxy-1,3-dioxoisoindolin-2-yl)acetate (66)

To a solution of methyl 2-(4-hydroxy-1,3-dioxoisoindolin-2-yl)acetate (160 mg, 0.680 mmol) in DMF (5 ml), $K_2CO_3$ (94 mg, 0.680 mmol) and iodomethane (88 µl, 1.361 mmol) were added, and the mixture was stirred under microwave irradiation at 100° C. for 1 hour. The insoluble inorganic salts were filtered off, the solvent was removed and the resulting crude product (130 mg, 0.522 mmol, 77% yield) was used in the following step without further purification. MS/ESI⁺ 250.1 [MH]⁺.

Step 3. Preparation of 2-(4-methoxy-1,3-dioxoisoindolin-2-yl)acetic acid (67)

To a solution of methyl 2-(4-methoxy-1,3-dioxoisoindolin-2-yl)acetate (130 mg, 0.522 mmol) in dioxane (15 ml) a 12 N aqueous solution of HCl (15 ml) was added and the mixture was reacted overnight at room temperature. The organic layer was evaporated and the desired compound was extracted with EtOAc (2×20 ml) obtaining the title compound that was used in the next step without further purification (57 mg, 0.242 mmol, 47% yield). MS/ESI⁺ 236.1 [MH]⁺.

Step 4. Preparation of, (S)-3,5-dichloro-4-(2-(3-(cyclopropylmethoxy)-4-(difluoromethoxy)phenyl)-2-(2-(4-methoxy-1,3-dioxoisoindolin-2-yl)acetoxy)-ethyl)pyridine 1-oxide (68)

To a solution of 2-(4-methoxy-1,3-dioxoisoindolin-2-yl) acetic acid (30 mg, 0.128 mmol) in DCM (3 ml), (S)-3,5-dichloro-4-(2-(3-(cyclopropylmethoxy)-4-(difluoromethoxy)phenyl)-2-hydroxyethyl)pyridine 1-oxide (53.6 mg, 0.128 mmol), EDC (73.4 mg, 0.383 mmol) and DMAP (15.58 mg, 0.128 mmol) were added, and the mixture was reacted overnight at room temperature. The solvent was removed, and the resulting crude was purified by flash chromatography on silica gel (DCM:MeOH=98:2) recovering the title compound (33.7 mg, 0.053 mmol, 41% yield). MS/ESI⁺ 637.34 [MH]⁺; $[\alpha_D]$=−12.96, c=0.25 in DCM; ¹H NMR (300 MHz, DMSO-d₆) δ ppm 8.43 (s, 2H), 7.85 (dd, 1H), 7.54 (d, 1H), 7.46 (dd, 1H), 7.18 (d, 1H), 7.06 (d, 1H), 6.95 (dd, 1H), 7.08 (t, 1H), 5.99 (dd, 1H), 4.36 (s, 2H), 3.99 (s, 3H), 3.94 (dd, 1H), 3.90 (dd, 1H), 3.38 (dd, 1H), 3.22 (dd, 1H), 1.07-1.36 (m, 1H), 0.50-0.68 (m, 2H), 0.24-0.45 (m, 2H).

The compound listed in Table 7 was prepared with analogous synthetic steps and procedures to that described in Example 13, by reacting the appropriate precursors (commercially available or synthesized by a person skilled in the art) with suitable reagents. Specific variations in the experimentals or purification methods are indicated in the table.

TABLE 7

| Entry | Structure | NMR characterization | MS/ESI+ [MH]+ | [α_D] | Experimental procedure | Purification and yield | Starting material (precursor) |
|---|---|---|---|---|---|---|---|
| 69 | 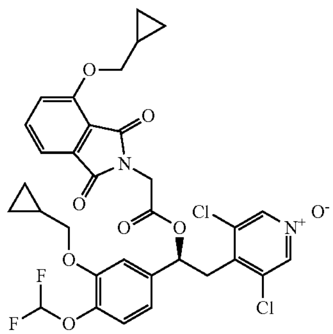 | ¹H NMR (300 MHz, DMSO-d₆) δ ppm 8.43 (s, 2 H), 7.80 (dd, 1 H), 7.50 (d, 1 H), 7.43 (d, 1 H), 7.18 (d, 1 H), 7.07 (d, 1 H), 6.95 (dd, 1 H), 7.08 (t, 1 H), 6.00 (dd, 1 H), 4.36 (s, 2 H), 4.11 (d, 2 H), 3.92 (d, 2 H), 3.40 (dd, 1 H), 3.23 (dd, 1 H), 1.18-1.34 (m, 2 H), 0.48-0.70 (m, 4 H), 0.23-0.48 (m, 4 H) | 677.17 | −29.50 c = 0.4 DCM | Step 2 was performed heating termically in CH₃CN at 80° C. overnight | Preparative HPLC (Method 1). 24% yield | |

Example 14

(S)-3,5-Dichloro-4-(2-(3-(cyclopropylmethoxy)-4-(difluoromethoxy)phenyl)-2-(2-(5-(methylsulfonamido)-1H-indol-1-yl)acetoxy)-ethyl)pyridine 1-oxide (Compound 76)

Scheme 14.
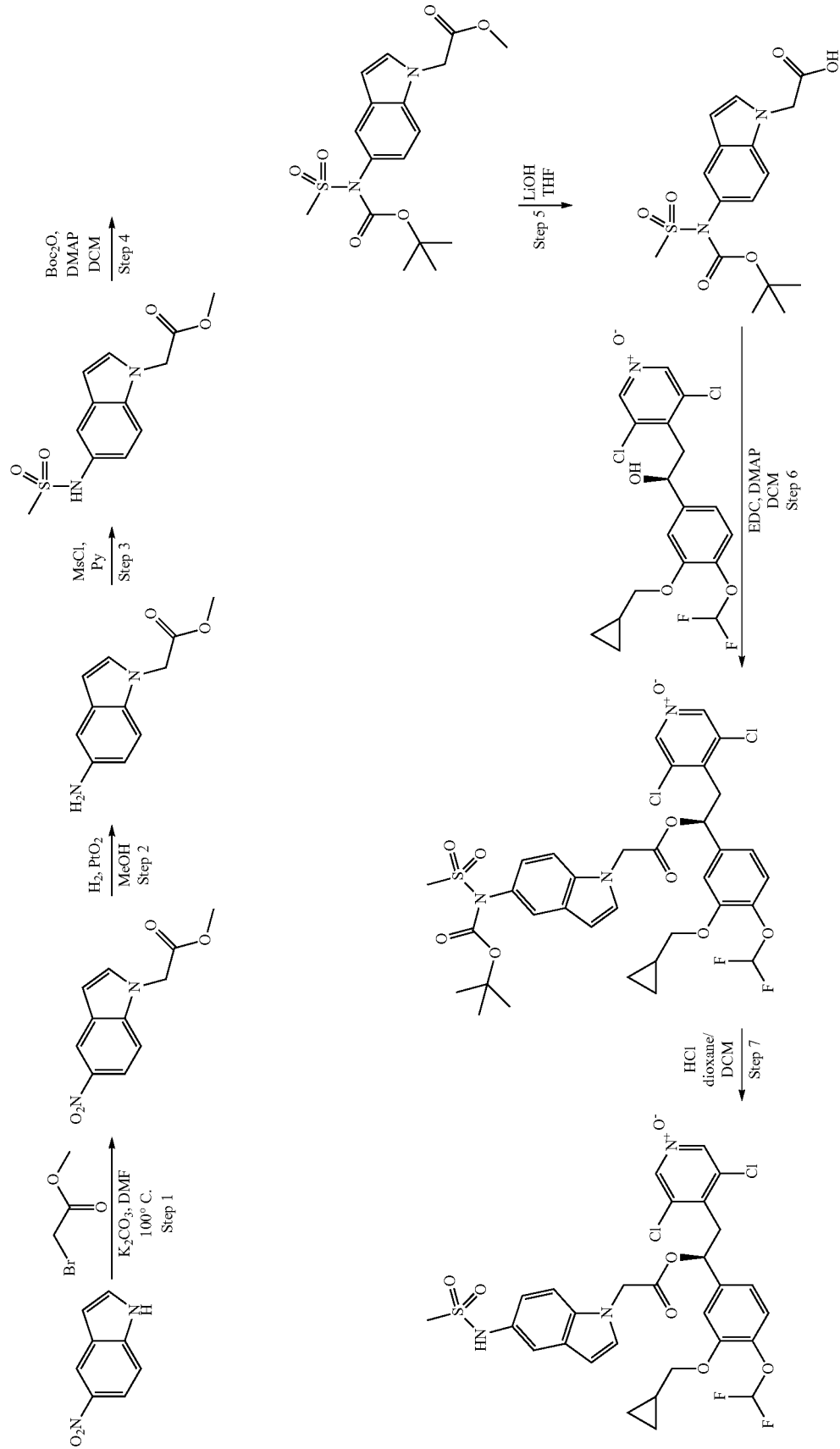

Step 1: Preparation of methyl 2-(5-nitro-1H-indol-1-yl)acetate (70)

To a solution of 5-nitro-1H-indole (1 g, 6.17 mmol) in DMF (15 ml), $K_2CO_3$ (1.023 g, 7.40 mmol) and methyl 2-bromoacetate (0.686 ml, 7.40 mmol) were added, and the mixture was reacted under MW irradiation for 1 hour at 100° C. The insoluble inorganic salts were filtered off, the solvent was removed and the resulting crude was purified by flash chromatography on silica gel column (petroleum ether:ethyl acetate=8:2) to afford methyl 2-(5-nitro-1H-indol-1-yl)acetate (830 mg, 3.54 mmol, 58% yield). MS/ESI$^+$ 234.2[MH]$^+$.

Step 2: Preparation of methyl 2-(5-amino-1H-indol-1-yl)acetate (71)

To a solution of methyl 2-(5-nitro-1H-indol-1-yl)acetate (830 mg, 3.54 mmol) in MeOH (50 ml), a catalytic amount of $PtO_2$ was added, and the mixture was reacted under $H_2$ atmosphere in a Parr apparatus at 30 psi for 15 minutes. The catalyst was filtered off, the solvent was removed and crude methyl 2-(5-amino-1H-indol-1-yl)acetate was obtained and was used in the next step without any additional purification (730 mg, 3.54 mmol, quantitative yield). MS/ESI$^+$ 205.2 [MH]$^+$.

Step 3: Preparation of methyl 2-(5-(methylsulfonamido)-1H-indol-1-yl)acetate (72)

To a solution of methyl 2-(5-amino-1H-indol-1-yl)acetate (730 mg, 3.54 mmol) in pyridine (15 ml), methanesulfonyl chloride (418 μl, 5.36 mmol) was added, and the mixture was reacted for 2 hours at room temperature. The solvent was evaporated and the resulting crude was partitioned between 1N HCl and ethyl acetate; the aqueous phase was extracted with ethyl acetate (3×30 ml) and dried over sodium sulfate. The solvent was removed obtaining crude methyl 2-(5-(methylsulfonamido)-1H-indol-1-yl)acetate that was used in the next step without any additional purification (1 g, 3.54 mmol, quantitative yield). MS/ESI$^+$ 283.3 [MH]$^+$.

Step 4: Preparation of methyl 2-(5-(N-(tert-butoxycarbonyl)methylsulfonamido)-1H-indol-1-yl)acetate (73)

To a solution of methyl 2-(5-(methylsulfonamido)-1H-indol-1-yl)acetate (1 g, 3.54 mmol) in DCM, di-tert-butyl dicarbonate (1.160 g, 5.31 mmol) and DMAP (0.649 g, 5.31 mmol) were added, and the mixture was reacted overnight at room temperature. The solvent was evaporated and the resulting crude was purified by flash chromatography on silica gel column (petroleum ether:ethyl acetate=2/8) obtaining methyl 2-(5-(N-(tert-butoxycarbonyl)methylsulfonamido)-1H-indol-1-yl)acetate (1.0 g, 2.61 mmol, 74% yield over 2 steps) MS/ESI$^+$ 383.0[MH]$^+$.

Step 5: Preparation of 2-(5-(N-(tert-butoxycarbonyl)methylsulfonamido)-1H-indol-1-yl)acetic acid (74)

To a solution of methyl 2-(5-(N-(tert-butoxycarbonyl)methylsulfonamido)-1H-indol-1-yl)acetate (520 mg, 1.360 mmol) in a 1:1 mixture of THF and water (20 ml), lithium hydroxide (326 mg, 13.60 mmol) was added, and the mixture was reacted for 2 hours at room temperature. The organic layer was evaporated and 1N HCl was added to the reaction mixture (pH 5); the resulting solid was filtered off affording 2-(5-(N-(tert-butoxycarbonyl)methylsulfonamido)-1H-indol-1-yl)acetic acid that was used in the next step without any additional purification (450 mg, 1.221 mmol, 90% yield). MS/ESI$^+$ 369.2 [MH]$^+$.

Step 6: Preparation of (S)-4-(2-(2-(5-(N-(tert-butoxycarbonyl)-methylsulfonamido)-1H-indol-1-yl)acetoxy)-2-(3-(cyclopropylmethoxy)-4-(difluoromethoxy)phenyl)ethyl)-3,5-dichloropyridine 1-oxide (75)

To a solution of 2-(5-(N-(tert-butoxycarbonyl)methylsulfonamido)-1H-indol-1-yl)acetic acid (120 mg, 0.326 mmol) in DCM (10 ml), (S)-3,5-dichloro-4-(2-(3-(cyclopropylmethoxy)-4-(difluoromethoxy)phenyl)-2-hydroxyethyl)pyridine 1-oxide (137 mg, 0.326 mmol), EDC (187 mg, 0.977 mmol) and DMAP (19.90 mg, 0.163 mmol) were added, and the mixture was reacted at room temperature for 6 hours. The mixture was portioned between DCM and 1N HCl (50 ml) and the desired compound was extracted with DCM (3×50 ml). Crude (S)-4-(2-(2-(5-(N-(tert-butoxycarbonyl)-methylsulfonamido)-1H-indol-1-yl)acetoxy)-2-(3-(cyclopropylmethoxy)-4-(difluoromethoxy)phenyl)ethyl)-3,5-dichloropyridine 1-oxide was obtained and used in the next step without any additional purification (170 mg, 0.221 mmol, 68% yield). MS/ESI$^+$ 770.1 [MH]$^+$.

Step 7: Preparation of (S)-3,5-dichloro-4-(2-(3-(cyclopropylmethoxy)-4-(difluoromethoxy)phenyl)-2-(2-(5-(methylsulfonamido)-1H-indol-1-yl)acetoxy)-ethyl)pyridine 1-oxide (76)

To a solution of (S)-4-(2-(2-(5-(N-(tert-butoxycarbonyl)methylsulfonamido)-1H-indol-1-yl)acetoxy)-2-(3-(cyclopropylmethoxy)-4-(difluoromethoxy)phenyl)ethyl)-3,5-dichloropyridine 1-oxide (170 mg, 0.221 mmol) in DCM (10 ml), 4M HCl in dioxane (552 μl, 2.206 mmol) was added, and the mixture was reacted overnight at room temperature. The solvent was evaporated and the resulting crude was purified by preparative HPLC (Method 1) affording (S)-3,5-dichloro-4-(2-(3-(cyclopropylmethoxy)-4-(difluoromethoxy)phenyl)-2-(2-(5-(methylsulfonamido)-1H-indol-1-yl)acetoxy)ethyl)pyridine 1-oxide (63 mg, 0.094 mmol, 43% yield). MS/ESI$^+$ 670.09 [MH]$^+$, $[\alpha_D]$=7.68, c=0.5 in DCM. $^1$H NMR (300 MHz, DMSO-d$_6$) δ ppm 9.27 (s, 1H) 8.51 (s, 2H) 7.42 (d, 1H) 7.29 (d, 1H) 7.13-7.22 (m, 2H) 7.02 (d, 1H) 7.02 (dd, 1H) 6.91 (dd, 1H) 7.05 (t, 1H) 6.44 (dd, 1H) 6.01 (dd, 1H) 5.21 (d, 1H) 5.06 (d, 1H) 3.87 (d, 2H) 3.41 (dd, 1H) 3.21 (dd, 1H) 2.87 (s, 3H) 1.13-1.32 (m, 1H) 0.50-0.71 (m, 2H) 0.22-0.48 (m, 2H)

The compound listed in Table 8 was prepared with analogous synthetic steps (with the exclusion of steps 4 and 7) and procedures to that described in Example 14, by reacting the appropriate precursors (commercially available or synthesized by a person skilled in the art) with suitable reagents. Specific variations in the experimentals or purification methods are indicated in the table.

TABLE 8

| Entry | Structure | NMR characterization | MS/ESI+ [MH]+ | [α_D] | Purification and yield | Starting material (precursor) |
|---|---|---|---|---|---|---|
| 77 | 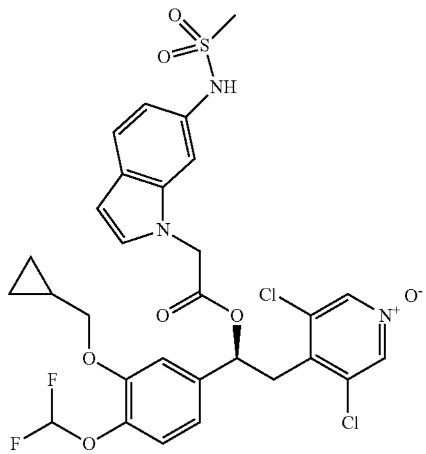 | ¹H NMR (300 MHz, DMSO-d₆) δ ppm 9.41 (s, 1H), 8.50 (s, 2H), 7.50 (d, 1H), 7.25 (d, 1H), 7.10-7.16 (m, 2H), 6.91-6.98 (m, 2H), 6.87 (dd, 1H), 7.03 (t, 1H), 6.43 (dd, 1H), 5.99 (dd, 1H), 5.16 (d, 1H), 5.03 (d, 1H), 3.81 (d, 2H), 3.41 (dd, 1H), 3.21 (dd, 1H), 2.86 (s, 3H), 1.01-1.31 (m, 1H), 0.48-0.70 (m, 2H), 0.25-0.45 (m, 2H) | 670.18 | −45.76 c = 0.25 DCM | Preparative HPLC (Method 3) 29% yield | |

Example 15

(S)-3,5-Dichloro-4-(2-(3-(cyclopropylmethoxy)-4-(difluoromethoxy)-phenyl)-2-(2-(4-(methylsulfonamido)-1H-indol-1-yl)acetoxy)ethyl)pyridine 1-oxide (Compound 84)

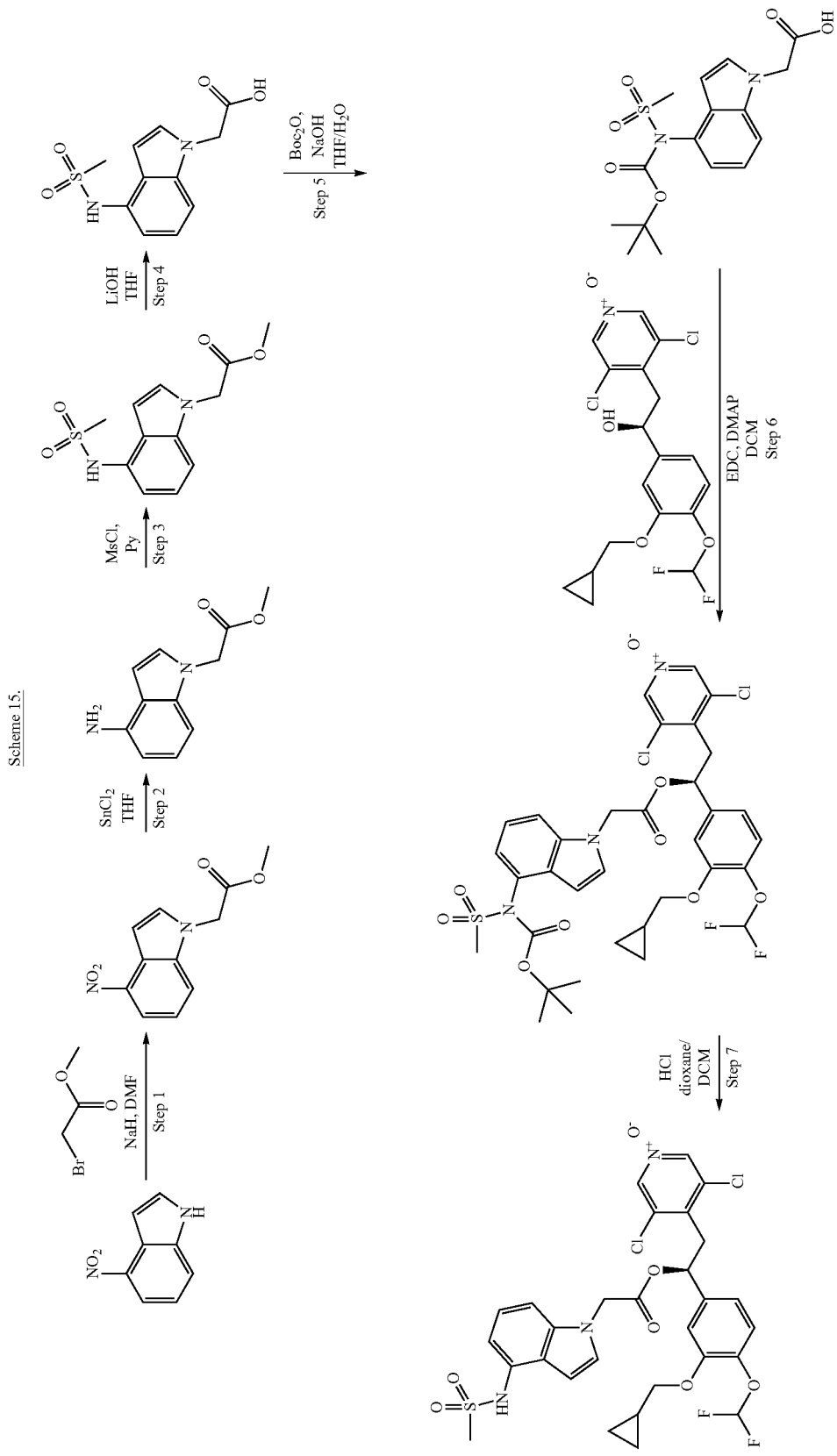

Step 1: Preparation of methyl 2-(4-nitro-1H-indol-1-yl)acetate (78)

To a solution of 4-nitro-1H-indole (500 mg, 3.08 mmol) in DMF (10 ml), $K_2CO_3$ (511 mg, 3.70 mmol) and methyl 2-bromoacetate (343 µl, 3.70 mmol) were added, and the mixture was stirred at 100° C. under MW irradiation for 30 minutes. The insoluble inorganic salts was filtered off, and the solvent was evaporated, recovering crude desired methyl 2-(4-nitro-1H-indol-1-yl)acetate which was used in the next step without further purification (810 mg). MS/ESI$^+$ 235.1 [MH]$^+$.

Step 2: Preparation of methyl 2-(4-amino-1H-indol-1-yl)acetate (79)

To a solution of crude methyl 2-(4-nitro-1H-indol-1-yl)acetate (obtained as reported in Example 15, Step 1, theoretical amount 3.08 mmol) in THF (15 ml), tin(II) chloride dihydrate (6.243 g, 27.7 mmol) was added, and the mixture was reacted at 50° C. for 5 hours and at room temperature overnight. A saturated solution of $NaHCO_3$ (120 ml) was added to the cooled reaction mixture, and the resulting precipitate was filtered off on a celite pad. The filtrate was extracted with ethyl acetate (3×20 ml) and the combined organic layers were dried over sodium sulfate. After evaporation of the solvent, crude methyl 2-(4-amino-1H-indol-1-yl)acetate was obtained and used in the next step without any additional purification (810 mg). MS/ESI$^+$ 205.0 [MH]$^+$.

Step 3: Preparation of methyl 2-(4-(methylsulfonamido)-1H-indol-1-yl)acetate (80)

To a solution of crude methyl 2-(4-amino-1H-indol-1-yl)acetate (obtained as reported in Example 15, Step 2, theoretical amount 3.08 mmol) in pyridine (10 ml), methanesulfonyl chloride (464 µl, 5.95 mmol) was added, and the mixture was reacted overnight at room temperature. The solvent was evaporated, and the residue was partitioned between 1N HCl (10 ml) and ethyl acetate (20 ml); the aqueous phase was extracted with ethyl acetate (3×20 ml) and the combined organic layers were dried over sodium sulfate. After evaporation of the solvent, crude methyl 2-(4-(methylsulfonamido)-1H-indol-1-yl)acetate was obtained and used in the next step without any additional purification (620 mg, 2.196 mmol, 71% yield over 3 steps). MS/ESI$^+$ 283.1 [MH]$^+$.

Step 4: Preparation of 2-(4-(methylsulfonamido)-1H-indol-1-yl)acetic acid (81)

To a solution of methyl 2-(4-(methylsulfonamido)-1H-indol-1-yl)acetate (620 mg, 2.196 mmol) in a 1:1 mixture of $H_2O$ and THF (10 ml), lithium hydroxide (526 mg, 21.96 mmol) was added, and the mixture was reacted for 1 hour at room temperature. The organic solvent was evaporated and 1N HCl was added to the aqueous residue (pH=2); the aqueous phase was extracted with ethyl acetate (3×20 ml), and the combined organic layers were dried over sodium sulfate. The crude was purified by flash chromatography on silica gel column (DCM:MeOH=95:5) affording 2-(4-(methylsulfonamido)-1H-indol-1-yl)acetic acid (530 mg, 1.975 mmol, 90% yield). MS/ESI$^+$ 269.1 [MH]$^+$.

Step 5: Preparation of 2-(4-(N-(tert-butoxycarbonyl)methylsulfonamido)-1H-indol-1-yl)acetic acid (82)

To a solution of 2-(4-(methylsulfonamido)-1H-indol-1-yl)acetic acid (230 mg, 0.857 mmol) in a mixture of THF/$H_2O$ 1/1 (10 ml), sodium hydroxide (51.4 mg, 1.286 mmol) and di-tert-butyl dicarbonate (281 mg, 1.286 mmol) were added, and the mixture was reacted for 3 hours at room temperature. The organic solvent was evaporated and 1N HCl was added (pH=4) to the aqueous residue; the desired compound was extracted with EtOAc (3×20 ml), the organic phase was dried over sodium sulfate and the solvent was removed affording 2-(4-(N-(tert-butoxycarbonyl)methylsulfonamido)-1H-indol-1-yl)acetic acid (250 mg, 0.679 mmol, 79% yield). MS/ESI$^+$ 368.1 [MH]$^+$. This product was used in the next step without any additional purification.

Step 6: Preparation of (S)-4-(2-(2-(4-(N-(tert-butoxycarbonyl)-methylsulfonamido)-1H-indol-1-yl)acetoxy)-2-(3-(cyclopropylmethoxy)-4-(difluoromethoxy)phenyl)ethyl)-3,5-dichloropyridine 1-oxide (83)

To a solution of 2-(4-(N-(tert-butoxycarbonyl)methylsulfonamido)-1H-indol-1-yl)acetic acid (250 mg, 0.679 mmol) in DCM (10 ml), (S)-3,5-dichloro-4-(2-(3-(cyclopropylmethoxy)-4-(difluoromethoxy)phenyl)-2-hydroxyethyl)pyridine 1-oxide (285 mg, 0.679 mmol), EDC (390 mg, 2.036 mmol) and DMAP (41.5 mg, 0.339 mmol) were added, and the mixture was reacted at room temperature overnight. The mixture was partitioned between DCM and 1N HCl and the aqueous phase was extracted with DCM (3×20 ml); the solvent was removed to give (S)-4-(2-(2-(4-(N-(tert-butoxycarbonyl)-methylsulfonamido)-1H-indol-1-yl)acetoxy)-2-(3-(cyclopropylmethoxy)-4-(difluoromethoxy)phenyl)ethyl)-3,5-dichloropyridine 1-oxide (420 mg, 0.545 mmol, 80% yield). MS/ESI$^+$ 770.9 [MH]$^+$. This intermediate was used in the following steps without purification.

Step 7: Preparation of (S)-3,5-dichloro-4-(2-(3-(cyclopropylmethoxy)-4-(difluoromethoxy)phenyl)-2-(2-(4-(methylsulfonamido)-1H-indol-1-yl)acetoxy)ethyl)pyridine 1-oxide (84)

To a solution of (S)-4-(2-(2-(4-(N-(tert-butoxycarbonyl)methylsulfonamido)-1H-indol-1-yl)acetoxy)-2-(3-(cyclopropylmethoxy)-4-(difluoromethoxy)phenyl)ethyl)-3,5-dichloropyridine 1-oxide (420 mg, 0.545 mmol) in DCM (10 ml), 4M HCl in dioxane (1.363 ml, 5.45 mmol) was added, and the mixture was stirred at room temperature overnight. The solvent was evaporated and the resulting crude was purified by HPLC preparative (Method 3) recovering (S)-3,5-dichloro-4-(2-(3-(cyclopropylmethoxy)-4-(difluoromethoxy)phenyl)-2-(2-(4-(methylsulfonamido)-1H-indol-1-yl)acetoxy)ethyl)pyridine 1-oxide (180 mg, 0.268 mmol, 49% yield). MS/ESI$^+$ 670.09 [MH]$^+$; $[\alpha_D]=-14.56$, c=0.5 in DCM; $^1$H NMR (300 MHz, DMSO-$d_6$) δ ppm 9.51 (s, 1H) 8.52 (s, 2H) 7.24 (d, 1H) 7.16 (d, 1H) 6.96-7.12 (m, 4H) 6.92 (dd, 1H) 7.06 (t, 1H) 6.76 (d, 1H) 6.02 (dd, 1H) 5.22 (d, 1H) 5.05 (d, 1H) 3.89 (d, 2H) 3.41 (dd, 1H) 3.21 (dd, 1H) 2.95 (s, 3H) 1.10-1.33 (m, 1H) 0.51-0.69 (m, 2H) 0.27-0.44 (m, 2H).

Example 16

(S)-3,5-Dichloro-4-(2-(3-(cyclopropylmethoxy)-4-(difluoromethoxy)-phenyl)-2-(2-(3-(methylsulfonamido)-1H-indol-1-yl)acetoxy)ethyl)pyridine 1-oxide (Compound 93)

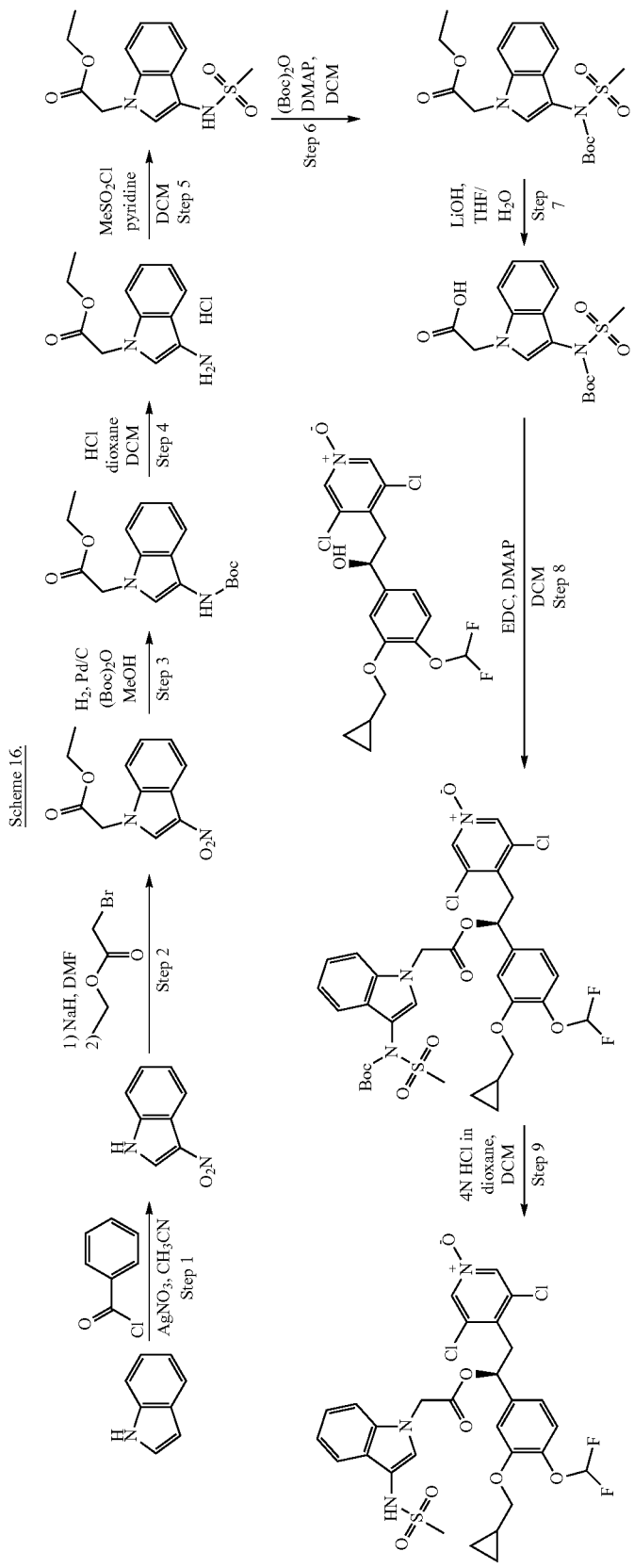

Step 1: Preparation of 3-nitro-1H-indole (85)

To a solution of 1H-indole (2 g, 17.07 mmol) and silver(I) nitrate (3.1 g, 18.25 mmol) in acetonitrile (16 ml), cooled at 0° C. under nitrogen, benzoyl chloride (2.066 ml, 17.79 mmol) was added dropwise. The reaction was stirred at 0° C. for 1 hour and 30 minutes. The mixture was partitioned between Et$_2$O and water; the aqueous layer was extracted several times with Et$_2$O, and the combined organic layers were washed with brine and then dried over Na$_2$SO$_4$. The solvent was removed and the residue was purified by flash chromatography on silica gel (petroleum ether:Et$_2$O form 1:1 to 4:6) to afford 3-nitro-1H-indole (1.651 g, 10.18 mmol, 60% yield). MS/ESI$^+$ 163.1 [MH]$^+$.

Step 2: Preparation of ethyl 2-(3-nitro-1H-indol-1-yl)acetate (86)

To a solution of 3-nitro-1H-indole (1 g, 6.17 mmol) in dry DMF (10 ml), under nitrogen, sodium hydride (60% w/w dispersion in mineral oil, 0.259 g, 6.48 mmol) was added. The mixture was stirred at room temperature for 15 minutes, and then ethyl 2-bromoacetate (0.723 ml, 6.17 mmol) was added. After stirring at the same temperature for 45 minutes, the mixture was partitioned between aqueous sat. NaHCO$_3$ and Et$_2$O; the aqueous layer was extracted with Et$_2$O and the combined organic layers were washed with brine and dried over Na$_2$SO$_4$. The solvent was removed and the resulting crude solid was purified by flash chromatography on silica gel (petroleum ether:Et$_2$O from 6:4 to 1:1) to give ethyl 2-(3-nitro-1H-indol-1-yl)acetate (983 mg, 3.96 mmol, 64% yield). MS/ESI$^+$ 249.1 [MH]$^+$.

Step 3: Preparation of 2-(3-(tert-butoxycarbonylamino)-1H-indol-1-yl)acetate (87)

A mixture of ethyl 2-(3-nitro-1H-indol-1-yl)acetate (578 mg, 2.328 mmol), di-tert-butyl dicarbonate (1525 mg, 6.99 mmol) and a catalytic amount of 10% w/w Pd/C in dry MeOH (20 ml) was hydrogenated in a Parr apparatus at 40 psi overnight. The catalyst was filtered off, and the filtrate was evaporated (30° C., 100 mBar) to give a crude that was purified by flash chromatography on silica gel (petroleum ether:ethyl acetate from 90:10 to 85:15) to afford ethyl 2-(3-(tert-butoxycarbonylamino)-1H-indol-1-yl)acetate (452 mg, 1.420 mmol, 61% yield). MS/ESI$^+$ 341.1 [MNa]$^+$.

Step 4: Preparation of ethyl 2-(3-amino-1H-indol-1-yl)acetate hydrochloride (88)

To a solution of ethyl 2-(3-(tert-butoxycarbonylamino)-1H-indol-1-yl)acetate (275 mg, 0.864 mmol) in dry DCM (8 ml), cooled at 0° C. and under nitrogen, 4N HCl in dioxane (2.159 ml, 8.64 mmol) was added, and the mixture was stirred at room temperature for 36 hours. The solvent was removed under reduced pressure without heating to give ethyl 2-(3-amino-1H-indol-1-yl)acetate hydrochloride (220 mg, 0.864 mmol, quantitative yield). MS/ESI$^+$ 219.1 [MH]$^+$.

Step 5: Preparation of ethyl 2-(3-(methylsulfonamido)-1H-indol-1-yl)acetate (89)

To a suspension of ethyl 2-(3-amino-1H-indol-1-yl)acetate hydrochloride (220 mg, 0.864 mmol) in dry DCM (4 ml), cooled at 0° C. under nitrogen, methanesulfonyl chloride (67.3 µl, 0.864 mmol) and dry pyridine (559 µl, 6.91 mmol) were added. After stirring at 0° C. for 4 hours, the mixture was partitioned between 5% aqueous citric acid and DCM; the organic phase was washed with water, dried over Na$_2$SO$_4$ and evaporated to give ethyl 2-(3-(methylsulfonamido)-1H-indol-1-yl)acetate (221 mg, 0.746 mmol, 86% yield). MS/ESI$^+$ 319.0 [MNa]$^+$. This product was used in the next step without any additional purification.

Step 6: Preparation of ethyl 2-(3-(N-(tert-butoxycarbonyl)-methylsulfonamido)-1H-indol-1-yl)acetate (90)

A solution of ethyl 2-(3-(methylsulfonamido)-1H-indol-1-yl)acetate (256 mg, 0.864 mmol), di-tert-butyl dicarbonate (283 mg, 1.296 mmol) and DMAP (158 mg, 1.296 mmol) in dry DCM (20 ml) was stirred at room temperature for 2 hours and 30 minutes. The solvent was removed and the crude was purified by flash chromatography on silica gel (petroleum ether:ethyl acetate=7:3) to provide ethyl 2-(3-(N-(tert-butoxycarbonyl)-methylsulfonamido)-1H-indol-1-yl)acetate (248 mg, 0.626 mmol, 72% yield). MS/ESI$^+$ 318.9 [MNa]$^+$.

Step 7: Preparation of 2-(3-(N-(tert-butoxycarbonyl) methylsulfonamido)-1H-indol-1-yl)acetic acid (91)

A suspension of ethyl 2-(3-(N-(tert-butoxycarbonyl)methylsulfonamido)-1H-indol-1-yl)acetate (248 mg, 0.626 mmol) and LiOH (74.9 mg, 3.13 mmol) in THF/water 1/1 (10 ml) was stirred at room temperature for 30 minutes. The mixture was diluted with ethyl acetate and carefully acidified by slow addition of 1N HCl (pH=1). The phases were separated and the aqueous layer was extracted with ethyl acetate; the combined organic layers were dried over Na$_2$SO$_4$ and evaporated to dryness to give 2-(3-(N-(tert-butoxycarbonyl)methylsulfonamido)-1H-indol-1-yl)acetic acid as a yellow solid (220 mg, 0.597 mmol, 95% yield). MS/ESI$^+$ 369.1 [MH]$^+$.

Step 8: Preparation of (S)-4-(2-(2-(3-(N-(tert-butoxycarbonyl)-methylsulfonamido)-1H-indol-1-yl)acetoxy)-2-(3-(cyclopropylmethoxy)-4-(difluoromethoxy)phenyl)ethyl)-3,5-dichloropyridine 1-oxide (92)

A solution of 2-(3-(N-(tert-butoxycarbonyl)methylsulfonamido)-1H-indol-1-yl)acetic acid (220 mg, 0.597 mmol), (S)-3,5-dichloro-4-(2-(3-(cyclopropylmethoxy)-4-(difluoromethoxy)phenyl)-2-hydroxyethyl)pyridine 1-oxide (228 mg, 0.543 mmol), EDC (312 mg, 1.629 mmol) and DMAP (66.3 mg, 0.543 mmol) in dry DCM (10 ml), under nitrogen, was stirred at room temperature for 24 hours. The mixture was washed with aqueous 5% citric acid, with water and then with brine; the organic phase was dried over Na$_2$SO$_4$ and evaporated to dryness. The crude was purified by flash chromatography on silica gel (DCM:ethyl acetate=6:4) to give (S)-4-(2-(2-(3-(N-(tert-butoxycarbonyl)-methylsulfonamido)-1H-indol-1-yl)acetoxy)-2-(3-(cyclopropylmethoxy)-4-(difluoromethoxy)phenyl)ethyl)-3,5-dichloropyridine 1-oxide (297 mg, 0.385 mmol, 71% yield). MS/ESI$^+$ 770.0 [MH]$^+$.

Step 9: Preparation of (S)-3,5-dichloro-4-(2-(3-(cyclopropylmethoxy)-4-(difluoromethoxy)phenyl)-2-(2-(3-(methylsulfonamido)-1H-indol-1-yl)acetoxy)ethyl)pyridine 1-oxide (93)

A solution of (S)-4-(2-(2-(3-(N-(tert-butoxycarbonyl)methylsulfonamido)-1H-indol-1-yl)acetoxy)-2-(3-(cyclopropylmethoxy)-4- (difluoromethoxy)phenyl)ethyl)-3,5-dichloropyridine 1-oxide (297 mg, 0.385 mmol) and 4N HCl in dioxane (2 ml, 8.00 mmol) in DCM (4 ml) was stirred at room temperature for 18 hours. The volatiles were removed under vacuum and the crude was purified by flash chromatography on silica gel (DCM:EtOAc=6:4) to give (S)-3,5-dichloro-4-(2-(3-(cyclopropylmethoxy)-4-(difluoromethoxy)phenyl)-2-(2-(3-(methylsulfonamido)-1H-indol-1-yl)acetoxy)ethyl) pyridine 1-oxide (210 mg, 0.313 mmol, 81% yield). MS/ESI$^+$ 670.36 [MH]$^+$; [$\alpha_D$]=+7.7, c=0.6, MeOH; $^1$H NMR (300 MHz, DMSO-d$_6$) δ ppm 9.18 (br. s., 1H), 8.51 (s, 2H), 7.67 (d, 1H), 7.29 (s, 1H), 7.04-7.20 (m, 4H), 7.02 (d, 1H), 6.91 (dd, 1H), 7.06 (t, 1H), 6.01 (dd, 1H), 5.23 (d, 1H), 5.06 (d, 1H), 3.85 (d, 2H), 3.42 (dd, 1H), 3.20 (dd, 1H), 2.86 (s, 3H), 1.08-1.31 (m, 1H), 0.54-0.68 (m, 2H), 0.30-0.48 (m, 2H))

Example 17

(S)-3,5-Dichloro-4-(2-(3-(cyclopropylmethoxy)-4-(difluoromethoxy)-phenyl)-2-(2-(5-(methylsulfonamido)-2,3-dioxoindolin-1-yl)acetoxy)ethyl)-pyridine 1-oxide (Compound 99)

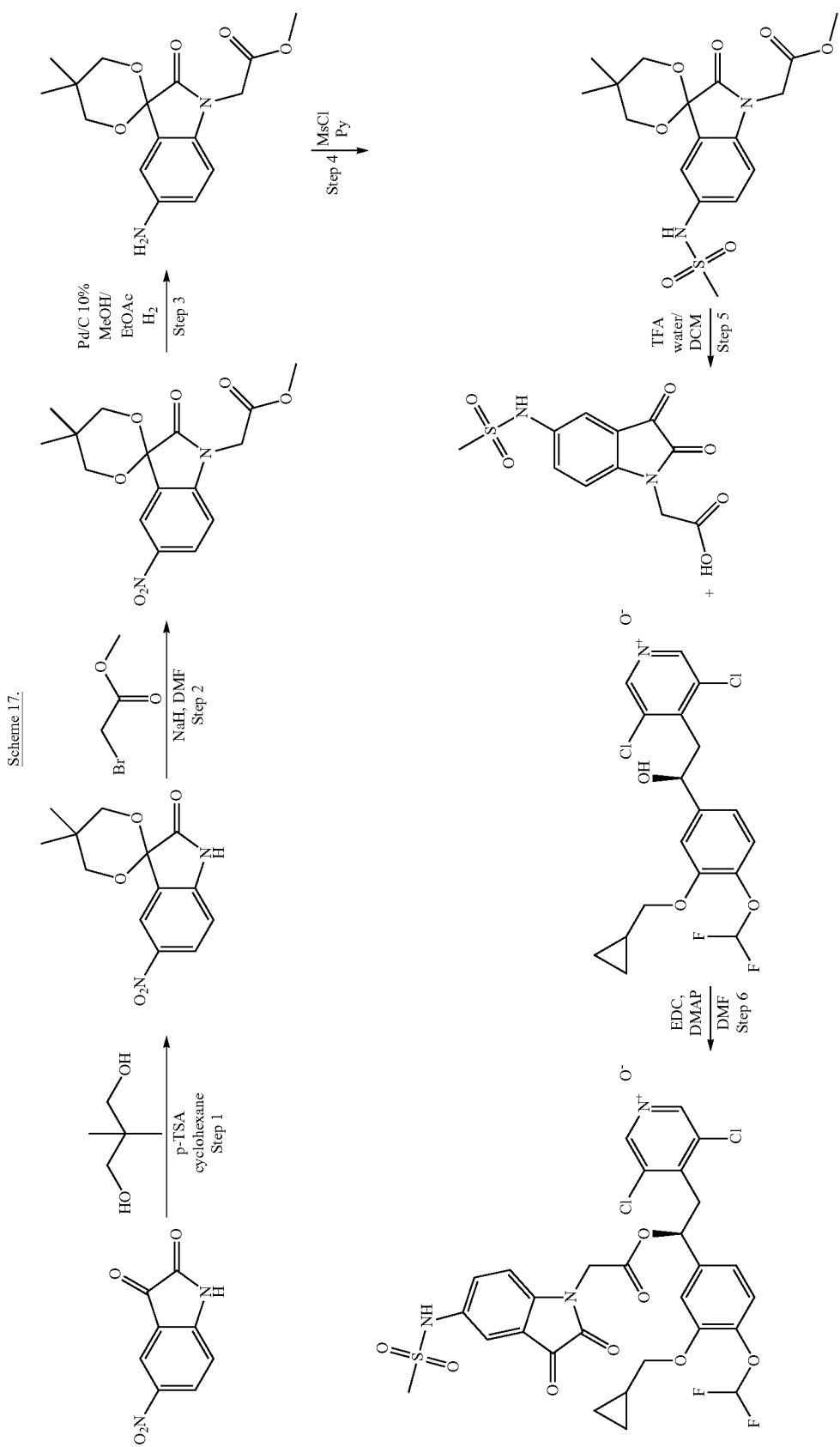

Step 1: Preparation of 5,5-dimethyl-5'-nitrospiro[[1,3]dioxane-2,3'-indolin]-2'-one (94)

A mixture of 5-nitroindoline-2,3-dione (305 mg, 1.587 mmol), 2,2-dimethylpropane-1,3-diol (165 mg, 1.587 mmol) and p-toluenesulfonic acid monohydrate (catalytic amount) in cyclohexane (9 ml) was stirred at reflux temperature (removing water by a Dean-Stark apparatus) for 6 hours. The reaction was cooled to room temperature and the solid was recovered by filtration and washed with petroleum ether, affording 5,5-dimethyl-5'-nitrospiro[[1,3]dioxane-2,3'-indolin]-2'-one (481 mg). that was used as such in the following step. MS/ESI$^+$ 279.0 [MH]$^+$.

Step 2: Preparation of methyl 2-(5,5-dimethyl-5'-nitro-2'-oxospiro[[1,3]dioxane-2,3'-indoline]-1'-yl)acetate (95)

Crude 5,5-dimethyl-5'-nitrospiro[[1,3]dioxane-2,3'-indolin]-2'-one (obtained as described in Example 17, Step 1) (361 mg) was dissolved in dry DMF (11 ml) and cooled to 0° C.; NaH (60% w/w dispersion in mineral oil, 83 mg, 2.076 mmol) was added; and the mixture was stirred at 0° C. for 10 minutes (the reaction turned dark orange). Methyl 2-bromoacetate (0.144 ml, 1.557 mmol) was then added, the reaction was warmed to room temperature and stirred for 3 hours. The solvent was evaporated, water was added and extracted with EtOAc; the combined organic layers were dried over Na$_2$SO$_4$, filtered and evaporated. The crude was purified by flash chromatography on silica gel cartridge (petroleum ether:EtOAc from 95:5 to 85:15) affording methyl 2-(5,5-dimethyl-5'-nitro-2'-oxospiro[[1,3]dioxane-2,3'-indoline]-1'-yl)acetate (344 mg, 0.982 mmol, 84% yield). MS/ESI$^+$ 351.0 [MH]$^+$.

Step 3: Preparation of methyl 2-(5'-amino-5,5-dimethyl-2'-oxospiro[[1,3]dioxane-2,3'-indoline]-1'-yl)acetate (96)

A mixture of methyl 2-(5,5-dimethyl-5'-nitro-2'-oxospiro[[1,3]dioxane-2,3'-indoline]-1'-yl)acetate (344 mg, 0.982 mmol) and 10% w/w Pd/C (cat. amount) in MeOH/EtOAc 1:1 (50 ml) was hydrogenated at 15 psi in a Parr apparatus for 2 hours. The catalyst was removed by filtration, and the residue was evaporated affording crude methyl 2-(5'-amino-5,5-dimethyl-2'-oxospiro[[1,3]dioxane-2,3'-indoline]-1'-yl)acetate (307 mg, 0.958 mmol, 98% yield) that was used in the following step without further purification. MS/ESI$^+$ 321.0 [MH]$^+$

Step 4: Preparation of methyl 2-(5,5-dimethyl-5'-(methylsulfonamido)-2'-oxospiro[[1,3]dioxane-2,3'-indoline]-1'-yl)acetate (97)

A solution of methyl 2-(5'-amino-5,5-dimethyl-2'-oxospiro[[1,3]dioxane-2,3'-indoline]-1'-yl)acetate (307 mg, 0.958 mmol) in pyridine (15 ml) was cooled to 0° C. and methanesulfonyl chloride (0.090 ml, 1.150 mmol) was added; the reaction was warmed to room temperature and stirred for 25 minutes. The solvent was evaporated, and the residue was partitioned between ethyl acetate and 1N HCl; the organic phase was dried over Na$_2$SO$_4$, filtered and evaporated. The crude was purified by flash chromatography on silica gel (DCM:MeOH from 99.5:0.5 to 98.75:1.25) affording methyl 2-(5,5-dimethyl-5'-(methylsulfonamido)-2'-oxospiro[[1,3]dioxane-2,3'-indoline]-1'-yl)acetate (351 mg, 0.881 mmol, 92% yield). MS/ESI$^+$ 398.9 [MH]$^+$.

Step 5: Preparation of 2-(5-(methylsulfonamido)-2,3-dioxoindolin-1-yl)acetic acid (98)

A solution of methyl 2-(5,5-dimethyl-5'-(methylsulfonamido)-2'-oxospiro[[1,3]dioxane-2,3'-indoline]-1'-yl)acetate (200 mg, 0.502 mmol) in dioxane/water 1:1 (7 ml) and TFA (0.193 ml, 2.510 mmol) was stirred at 80° C. overnight. TFA (0.271 ml, 3.51 mmol) was freshly added and stirring at 80° C. was continued for 24 hours. Then TFA (0.155 ml, 2.008 mmol) was freshly added and stirring at 80° C. was continued for additional 48 hours. The volatiles were removed under vacuum and the crude was purified by flash chromatography on silica gel (DCM:MeOH from 99.5:0.5 to 7:3+0.5% AcOH), affording 2-(5-(methylsulfonamido)-2,3-dioxoindolin-1-yl)acetic acid (143 mg, 0.479 mmol, 96% yield). MS/ESI$^+$ 298.9 [MH]$^+$.

Step 6. Preparation of (S)-3,5-dichloro-4-(2-(3-(cyclopropylmethoxy)-4-(difluoromethoxy)phenyl)-2-(2-(5-(methylsulfonamido)-2,3-dioxoindolin-1-yl)acetoxy)ethyl)pyridine 1-oxide (99)

A mixture of 2-(5-(methylsulfonamido)-2,3-dioxoindolin-1-yl)acetic acid (141 mg, 0.473 mmol), (S)-3,5-dichloro-4-(2-(3-(cyclopropylmethoxy)-4-(difluoromethoxy)phenyl)-2-hydroxyethyl)pyridine 1-oxide (166 mg, 0.394 mmol), EDC (227 mg, 1.182 mmol) and DMAP (24.06 mg, 0.197 mmol) in DCM (25 ml) was stirred at room temperature overnight. The solvent was evaporated, DMF (10 ml) was added, and the resulting solution was stirred at 80° C. for 6 hours. DMAP (48.1 mg, 0.394 mmol) was added, and stirring at 80° C. was continued for 2 days. The solvent was evaporated, DCM was added, and the mixture was washed with NaHCO$_3$ 5% and 1N HCl; the organic layer was dried over Na$_2$SO$_4$, filtered and evaporated affording a crude that was purified by flash chromatography on silica gel (DCM:Ethyl acetate from 50:50 to 30:70; then 100% DCM and then DCM:MeOH from 99:1 to 97:3). The product was further purified by Preparative HPLC (Method 3) affording (S)-3,5-dichloro-4-(2-(3-(cyclopropylmethoxy)-4-(difluoromethoxy)-phenyl)-2-(2-(5-(methylsulfonamido)-2,3-dioxoindolin-1-yl)acetoxy)ethyl)pyridine 1-oxide (0.012 g, 0.017 mmol, 4% yield). MS/ESI$^+$ 700.16 [MH]$^+$; [α$_D$]=+63.50, c=0.12 in DCM; $^1$H NMR (300 MHz, DMSO-d$_6$) δ ppm 9.75 (br. s., 1H), 8.43 (s, 2H), 7.45 (dd, 1H), 7.41 (d, 1H), 7.18 (d, 1H), 7.07 (d, 1H), 7.05 (d, 1H), 6.95 (dd, 1H), 7.07 (t, 1H), 6.03 (dd, 1H), 4.64 (d, 1H), 4.56 (d, 1H), 3.91 (d, 2H), 3.40 (dd, 1H), 3.22 (dd, 1H), 3.02 (s, 3H), 1.12-1.31 (m, 1H), 0.54-0.63 (m, 2H), 0.31-0.44 (m, 2H).

Example 18

(S)-3,5-Dichloro-4-(2-(3-(cyclopropylmethoxy)-4-(difluoromethoxy)-phenyl)-2-(2-(1,1-dioxido-3-oxobenzo[d]isothiazol-2(3H)-yl)acetoxy)-ethyl)pyridine 1-oxide (Compound 102)

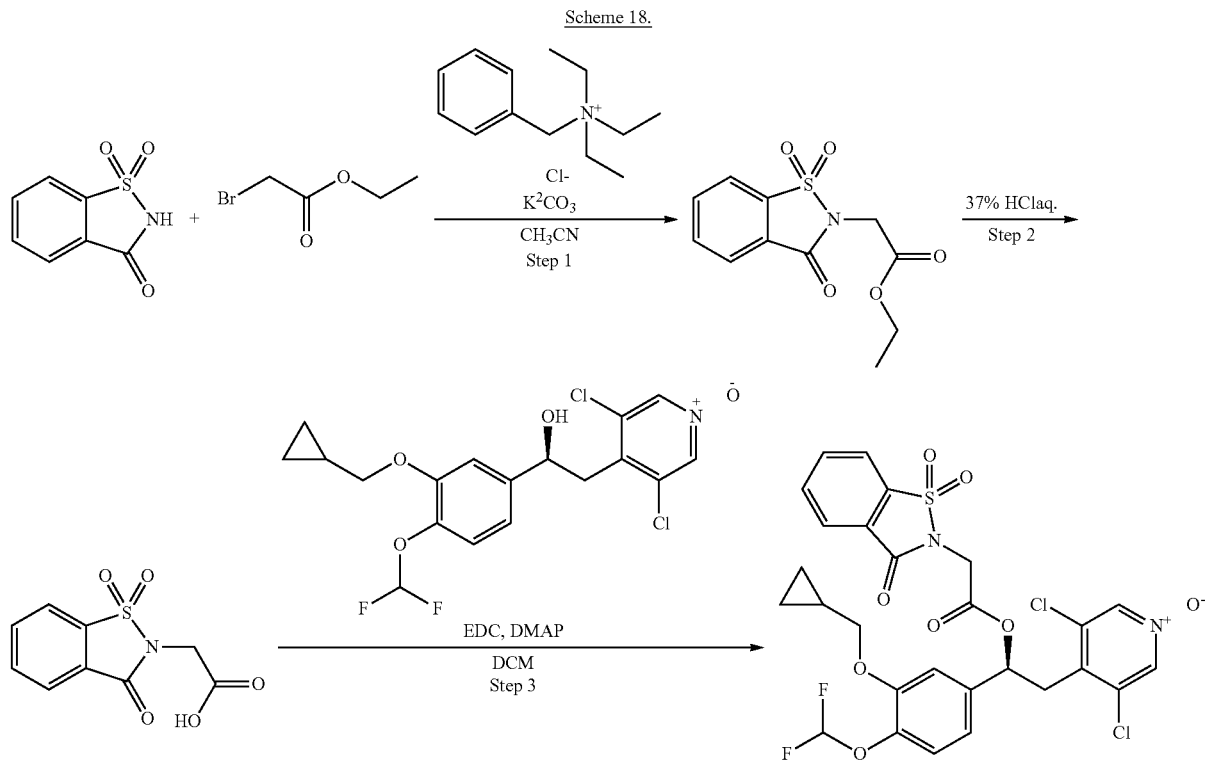

Scheme 18.

Step 1: Preparation of 1,2-Benzoisothiazol-1,1-dioxide-3(2H)-on-2-yl-alkanoic acid ethyl ester (100)

To a stirred suspension of 1,1-dioxo-1,2-benzothiazol-3-one (2.5 g, 13.65 mmol) in acetonitrile (50 ml), potassium carbonate (2.263 g, 16.38 mmol) was added.

Precipitation started to take place, and ethyl 2-bromoacetate (2.266 ml, 20.47 mmol) was added followed by N-benzyl-N,N-diethylethanaminium chloride (0.200 g, 0.878 mmol). The resulting mixture was stirred under reflux. After 3 hours, the solvent was removed in vacuo, the crude was partitioned between water and ethyl acetate, and the organic layer was washed with water, brine and finally dried over $Na_2SO_4$. The organic solution was evaporated and the resulting crude was crystallized from ethanol affording the desired compound as a white solid (2.9 g, 10.77 mmol, 79% yield). MS/ESI$^+$ 292.0 [MNa]$^+$.

Step 2: Preparation of 1,2-Benzoisothiazol-1,1-dioxide-3(2H)-on-2-yl-alkanoic acid (101)

1,2-Benzoisothiazol-1,1-dioxide-3(2H)-on-2-yl-alkanoic acid ethyl ester (2.9 g, 10.77 mmol) was suspended HCl$_{aq}$ 37% (7 ml, 84 mmol). The mixture was stirred at 100° C. for 2 hours. After additional 30 minutes, a white solid started to precipitate. The mixture was kept at 100° C. for additional 90 minutes. The mixture was then cooled to room temperature, diluted with water and the solid was recovered by filtration. Recrystallization from EtOH afforded the title compound as a white solid (1.9 g, 0.79 mmol, 73% yield). MS/ESI$^+$ 263.9 [MNa]$^+$.

Step 3: Preparation of (S)-3,5-dichloro-4-(2-(3-(cyclopropylmethoxy)-4-(difluoromethoxy)phenyl)-2-(2-(1,1-dioxido-3-oxobenzo[d]isothiazol-2(3H)-yl) acetoxy)ethyl)pyridine 1-oxide (102)

1,2-Benzoisothiazol-1,1-dioxide-3(2H)-on-2-yl-alkanoic acid (965 mg, 3.998 mmol) was suspended in anhydrous DCM (20 ml); EDC (767 mg, 3.998 mmol) and DMAP (545 mg, 4.462 mmol) were added, and the mixture was stirred at room temperature for 30 minutes, then (S)-3,5-dichloro-4-(2-(3-(cyclopropylmethoxy)-4-(difluoromethoxy)phenyl)-2-hydroxyethyl)pyridine 1-oxide (1.250 g, 2.975 mmol) was added in one portion. After 48 hours stirring at room temperature, the solvent was removed in vacuo and the crude was purified by silica gel flash chromatography (DCM:MeOH 10:0.2). The obtained amorphous was crystallized from iPrOH; the solid was collected by filtration and washed with cold iPrOH, with petroleum ether and dried under vacuum. (S)-3,5-dichloro-4-(2-(3-(cyclopropylmethoxy)-4-(difluoromethoxy)-phenyl)-2-((1,1-Dioxo-1,2-benzothiazol-3-one-2-ethoxy) carbonyloxy)ethyl)pyridine 1-oxide was obtained (1.038 g, 1.613 mmol, 54% yield). MS/ESI$^+$ 642.96 [MH]$^+$;

[α_D]=−12.46, c=0.560 in DCM; $^1$H NMR (300 MHz, DMSO-d$_6$) δ ppm 8.43 (s, 2H), 8.30-8.38 (m, 1H), 8.12-8.18 (m, 1H), 8.10 (dd, 1H), 8.05 (td, 1H), 7.18 (d, 1H), 7.11 (d, 1H), 6.98 (dd, 1H), 7.07 (t, 1H), 6.04 (dd, 1H), 4.63 (s, 2H), 3.90 (d, 2H), 3.40 (dd, 1H), 3.21 (dd, 1H), 1.01-1.33 (m, 1H), 0.49-0.67 (m, 2H), 0.22-0.45 (m, 2H).

Example 19

(S)-3,5-Dichloro-4-(2-(3-(cyclopropylmethoxy)-4-(difluoromethoxy)-phenyl)-2-(2-(6,7-dimethoxy-3,4-dihydroisoquinolin-2(1H)-yl)acetoxy)-ethyl)pyridine 1-oxide (Compound 105)

TEA 100:1:1) affording the title compound (2.6 g, 9.81 mmol, 75% yield). MS/ESI$^+$ 266.1 [MH]$^+$.

Step 2: Preparation of 2-(6,7-dimethoxy-3,4-dihydroisoquinolin-2(1H)-yl)acetic acid hydrochloride (104)

Methyl 2-(6,7-dimethoxy-3,4-dihydroisoquinolin-2(1H)-yl)acetate (2.5 g, 9.42 mmol) was dissolved in dioxane (20 ml), and aqueous 12M HCl (6 ml, 72.0 mmol) was added. The mixture was stirred under reflux for 8 hours, then the volatiles were removed under vacuum and the resulting solid was

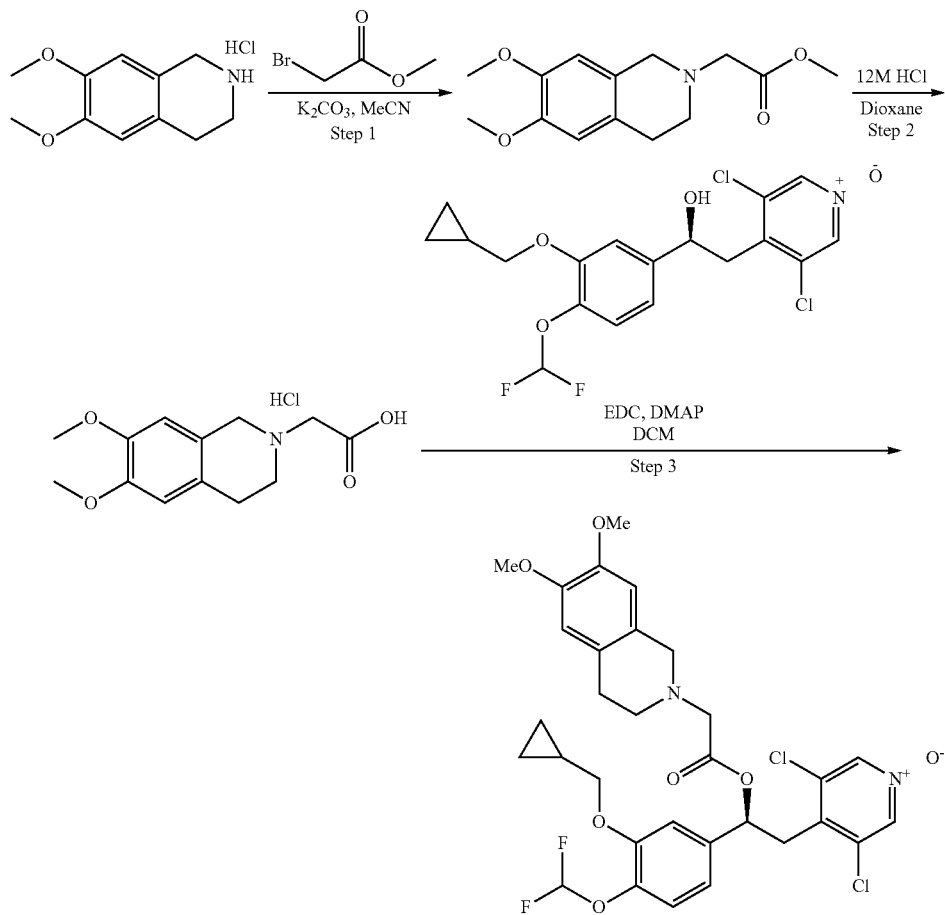

Scheme 19.

Step 1: Preparation of methyl 2-(6,7-dimethoxy-3,4-dihydroisoquinolin-2(1H)-yl)acetate (103)

6,7-Dimethoxy-1,2,3,4-tetrahydroisoquinoline hydrochloride (3 g, 13.06 mmol) was suspended in acetonitrile (40 ml); potassium carbonate (3.61 g, 26.1 mmol) and methyl 2-bromoacetate (3.00 g, 19.59 mmol) were added; and the reaction mixture was stirred under microwave irradiation at 100° C. for 1 hour. Then the mixture was diluted with ethyl acetate and washed with water, brine and dried over Na$_2$SO$_4$. The organic layer was evaporated and the resulting crude was purified by flash chromatography on silica gel (DCM:MeOH:

suspended in CH$_3$CN and recovered by filtration affording the title compound (2.2 g, 7.65 mmol, 81% yield). MS/ESI$^+$ 252.1 [MH]$^+$.

Step 3: Preparation of (S)-3,5-dichloro-4-(2-(3-(cyclopropylmethoxy)-4-(difluoromethoxy)phenyl)-2-(2-(6,7-dimethoxy-3,4-dihydroisoquinolin-2(1H)-yl) acetoxy)ethyl)pyridine 1-oxide (105)

To a stirred suspension of 2-(6,7-dimethoxy-3,4-dihydroisoquinolin-2(1H)-yl)acetic acid hydrochloride (822 mg, 2.86 mmol) in anhydrous DCM (30 ml), DMAP (523 mg, 4.28 mmol) and EDC (712 mg, 3.71 mmol) were added. The mixture was stirred at room temperature for 1 hour and then (S)-3,5-dichloro-4-(2-(3-(cyclopropylmethoxy)-4-(difluoromethoxy)phenyl)-2-hydroxyethyl)pyridine 1-oxide (1.200 g, 2.86 mmol) was added. The mixture was stirred at room temperature for 48 hours, then diluted with DCM and washed with 1N HCl, dried over Na$_2$SO$_4$ and evaporated. The desired product was first purified by flash chromatography on silica gel (DCM:MeOH 10:0.2) followed by preparative HPLC (Method 2). The title compound was obtained (1.354 g, 73% yield). MS/ESI$^+$ 653.18 [MH]$^+$; [α$_D$]=−43.91, c=0.69 in MeOH); $^1$H NMR (300 MHz, DMSO-d$_6$) δ ppm 8.60 (s, 2H) 7.20 (d, 1H) 7.13 (d, 1H) 7.01 (dd, 1H) 7.07 (t, 1H) 6.64 (s, 1H) 6.58 (s, 1H) 6.10 (dd, 1H) 3.81-3.99 (m, 2H) 3.70 (s, 3H) 3.71 (s, 3H) 3.35-3.56 (m, 4H) 3.19-3.28 (m, 2H) 2.57-2.81 (m, 4H) 1.11-1.34 (m, 1H) 0.49-0.67 (m, 2H) 0.16-0.44 (m, 2H).

The compound listed in Table 9 was prepared with analogous synthetic steps and procedures to that described in Example 19, by reacting the appropriate precursors (commercially available or synthesized by a person skilled in the art) with suitable reagents. Specific variations in the experimentals or purification methods are indicated in the table.

TABLE 9

| Entry | Structure | NMR characterization | MS/ESI$^+$ [MH]$^+$ | [α$_D$] | Experimental procedure |
|---|---|---|---|---|---|
| 106 | 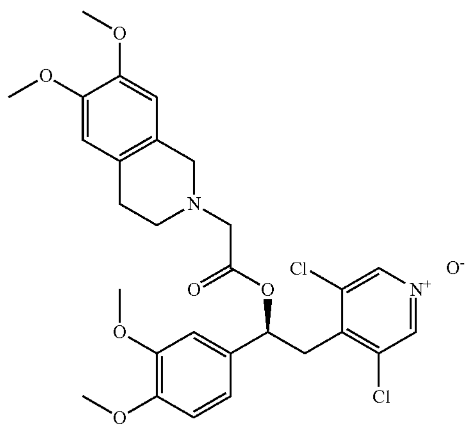 | $^1$H NMR (300 MHz, DMSO-d6) δ ppm 8.61 (s, 2 H), 6.86-7.03 (m, 3 H), 6.64 (s, 1 H), 6.58 (s, 1 H), 6.11 (dd, 1 H), 3.76 (s, 6 H), 3.71 (s, 3 H), 3.70 (s, 3 H), 3.34-3.56 (m, 5 H), 3.20-3.27 (m, 1 H), 2.57-2.72 (m, 4 H) | 577.09 | −60.67 c = 0.54, MeOH | |

| Entry | Purification and yield | Starting material (precursor) | Alcohol used as reagent in step 3 |
|---|---|---|---|
| 106 | Flash chromatography on silicagel (DCM/MeOH from 99/1 to 98/2) 44% yield | | |

Example 20

(S)-3,5-Dichloro-4-(2-(3-(cyclopropylmethoxy)-4-(difluoromethoxy)phenyl)-2-(2-(5-(methylsulfonamido)-2-oxoindolin-1-yl)acetoxy)ethyl)pyridine 1-oxide (Compound 112)

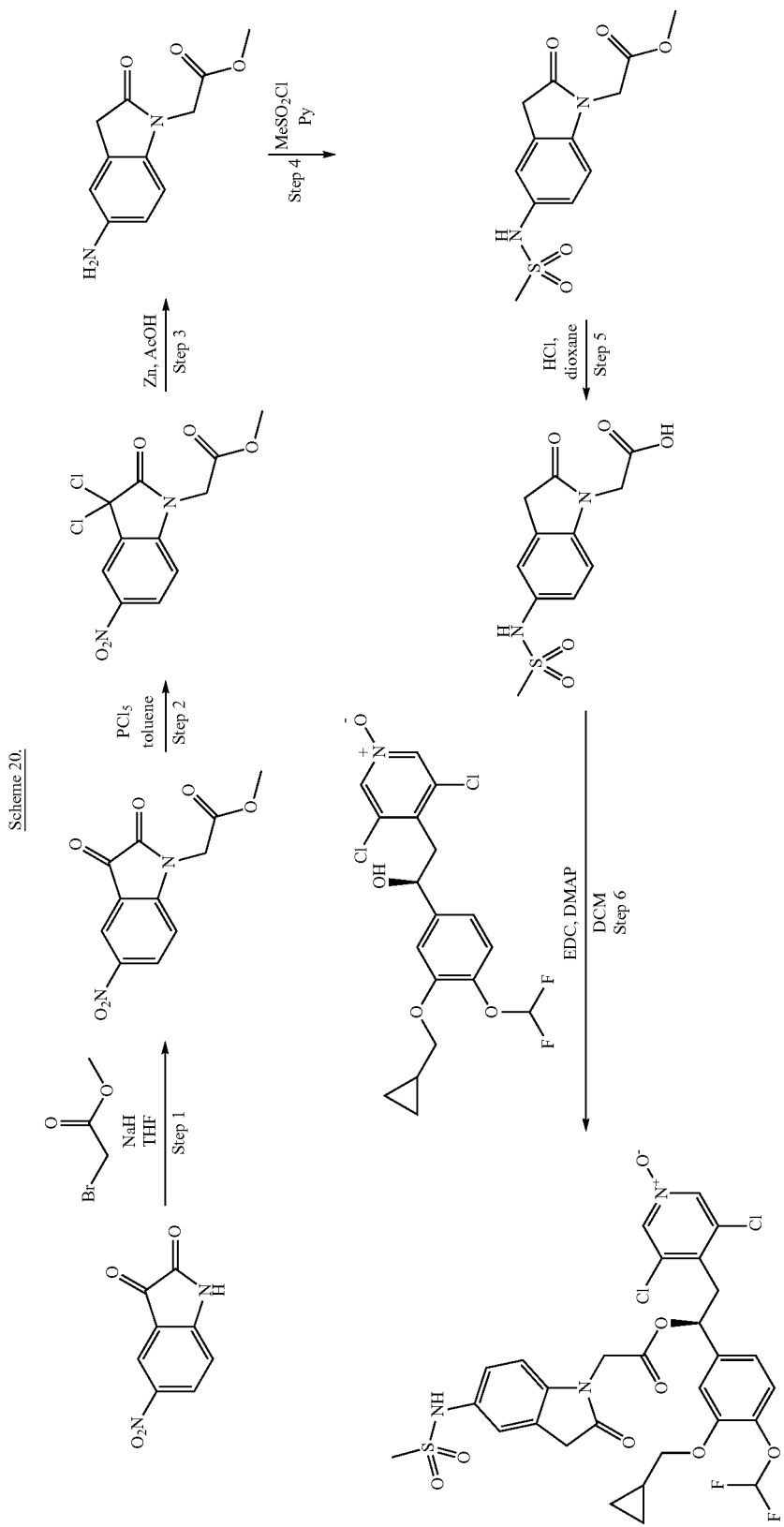

Step 1: Preparation of methyl 2-(5-nitro-2,3-dioxoindolin-1-yl)acetate (107)

A solution of 5-nitroindoline-2,3-dione (1 g, 5.20 mmol) in DMF (20 ml) was cooled to 0° C., and NaH (60% w/w dispersion in mineral oil, 0.208 g, 5.20 mmol) was added portion wise. The mixture was stirred at 0° C. for 1 hour, and methyl 2-bromoacetate (0.483 ml, 5.20 mmol) was added. The mixture was stirred at room temperature for 4 hours, then it was portioned between ethyl acetate and 1N HCl. The organic phase was washed twice with brine and dried over sodium sulfate. The solvent was removed and the crude was purified by flash chromatography on silica gel (DCM:EtOAc=95:5) affording methyl 2-(5-nitro-2,3-dioxoindolin-1-yl)acetate (0.976 g, 3.69 mmol, 71% yield) MS/ESI$^+$ 264.9 [MH]$^+$.

Step 2: Preparation of methyl 2-(3,3-dichloro-5-nitro-2-oxoindolin-1-yl)acetate (108)

A mixture of methyl 2-(5-nitro-2,3-dioxoindolin-1-yl)acetate (0.676 g, 2.56 mmol) and PCl$_5$ (1.226 g, 5.89 mmol) in toluene (60 ml) was heated at 55° C. for 48 hours. PCl$_5$ (0.533 g, 2.56 mmol) was freshly added, and the mixture was heated at 60° C. for 5 hours. Then the solvent was removed and the crude was purified by flash chromatography on silica gel. Methyl 2-(3,3-dichloro-5-nitro-2-oxoindolin-1-yl)acetate was obtained (0.340 g, 1.066 mmol, 42% yield). MS/ESI$^+$ 318.9 [MH]$^+$.

Step 3: Preparation of methyl 2-(5-amino-2-oxoindolin-1-yl)acetate (109)

To a suspension of methyl 2-(3,3-dichloro-5-nitro-2-oxoindolin-1-yl)acetate (0.314 g, 0.984 mmol) in acetic acid (10 ml), zinc powder (0.901 g, 13.78 mmol) was added potion wise at room temperature, and the mixture was stirred for 2 hours. Then the mixture was diluted with ethyl acetate, the solid was filtered off and washed with ethyl acetate and water. The filtrate was basified with solid K$_2$CO$_3$ (pH=8), and the phases were separated. The aqueous phase was extracted with DCM, and the combined organic layers were dried over sodium sulfate. The solvent was removed, and the crude was purified by filtration on silica gel cartridge (DCM:EtOAc from 80:20 to 50:50) affording methyl 2-(5-amino-2-oxoindolin-1-yl)acetate (0.120 g, 0.545 mmol, 55% yield). MS/ESI$^+$ 220.9 [MH]$^+$.

Step 4: Preparation of methyl 2-(5-(methylsulfonamido)-2-oxoindolin-1-yl)acetate (110)

To a solution of methyl 2-(5-amino-2-oxoindolin-1-yl)acetate (0.120 g, 0.545 mmol) in pyridine (8 ml) cooled to 0° C., methanesulfonyl chloride (0.047 ml, 0.599 mmol) was added, and the mixture was allowed to warm to room temperature and stirred for 1.5 hours. The solvent was removed and the crude was portioned between DCM and 1N HCl. The organic phase was dried over sodium sulfate, and the solvent was removed. The crude was purified by filtration on silica gel cartridge (DCM:MeOH from 99:1 to 97:3) affording methyl 2-(5-(methylsulfonamido)-2-oxoindolin-1-yl)acetate (0.133 g, 0.446 mmol, 82% yield). MS/ESI$^+$ 298.9 [MH]$^+$.

Step 5: Preparation of 2-(5-(methylsulfonamido)-2-oxoindolin-1-yl)acetic acid (111)

To a solution of methyl 2-(5-(methylsulfonamido)-2-oxoindolin-1-yl)acetate (0.133 g, 0.446 mmol) in dioxane (5 ml), 12M HCl (4 ml, 48.0 mmol) was added, and the mixture was stirred at room temperature for 24 hours. The volatiles fractions were evaporated and the residue was dried under vacuum. Crude of 2-(5-(methylsulfonamido)-2-oxoindolin-1-yl)acetic acid (0.130 g, 0.446 mmol, 100% yield) was used for the next step without any further purification. MS/ESI$^+$ 284.9 [MH]$^+$.

Step 6: Preparation of (S)-3,5-dichloro-4-(2-(3-(cyclopropylmethoxy)-4-(difluoromethoxy)phenyl)-2-(2-(5-(methylsulfonamido)-2-oxoindolin-1-yl)acetoxy)ethyl)pyridine 1-oxide (112)

A mixture of 2-(5-(methylsulfonamido)-2-oxoindolin-1-yl)acetic acid (0.130 g, 0.457 mmol), (S)-3,5-dichloro-4-(2-(3-(cyclopropylmethoxy)-4-(difluoromethoxy)-phenyl)-2-hydroxyethyl)pyridine 1-oxide (0.192 g, 0.457 mmol), EDC (0.263 g, 1.372 mmol) and DMAP (0.028 g, 0.229 mmol) in DCM (15 ml) was stirred at room temperature overnight. The mixture was diluted with DCM and washed with 1N HCl and brine. The organic phase was dried over sodium sulfate, and the solvent was removed. The crude was purified by filtration on silica gel cartridge (DCM:EtOAc from 80:20 to 60:40, then DCM, then DCM:MeOH from 99:1 to 98:2) affording 0.080 g of product, that was further purified by trituration with a little amount of EtOAc, affording (S)-3,5-dichloro-4-(2-(3-(cyclopropylmethoxy)-4-(difluoromethoxy)phenyl)-2-(2-(5-(methylsulfonamido)-2-oxoindolin-1-yl)acetoxy)ethyl)pyridine 1-oxide (0.054 g, 0.079 mmol, 17% yield). MS/ESI$^+$ 686.18 [MH]$^+$; [α$_D$]=−11.10 c=0.49 in MeOH; $^1$H NMR (300 MHz, DMSO-d$_6$) δ ppm 9.43 (br. s., 1H), 8.46 (s, 2H), 7.12-7.26 (m, 2H), 7.01-7.12 (m, 2H), 6.95 (dd, 1H), 7.07 (t, 1H), 6.78 (d, 1H), 6.01 (dd, 1H), 4.57 (d, 1H), 4.49 (d, 1H), 3.92 (d, 2H), 3.64 (s, 2H), 3.40 (dd, 1H), 3.22 (dd, 1H), 2.93 (s, 3H), 1.13-1.38 (m, 1H), 0.51-0.70 (m, 2H), 0.29-0.45 (m, 2H).

Example 21

(S)-3,5-Dichloro-4-(2-(3-(cyclopropylmethoxy)-4-(difluoromethoxy)phenyl)-2-(2-(5-methoxy-2-oxoindolin-1-yl)acetoxy)ethyl)pyridine 1-oxide (Compound 117)

Scheme 21.
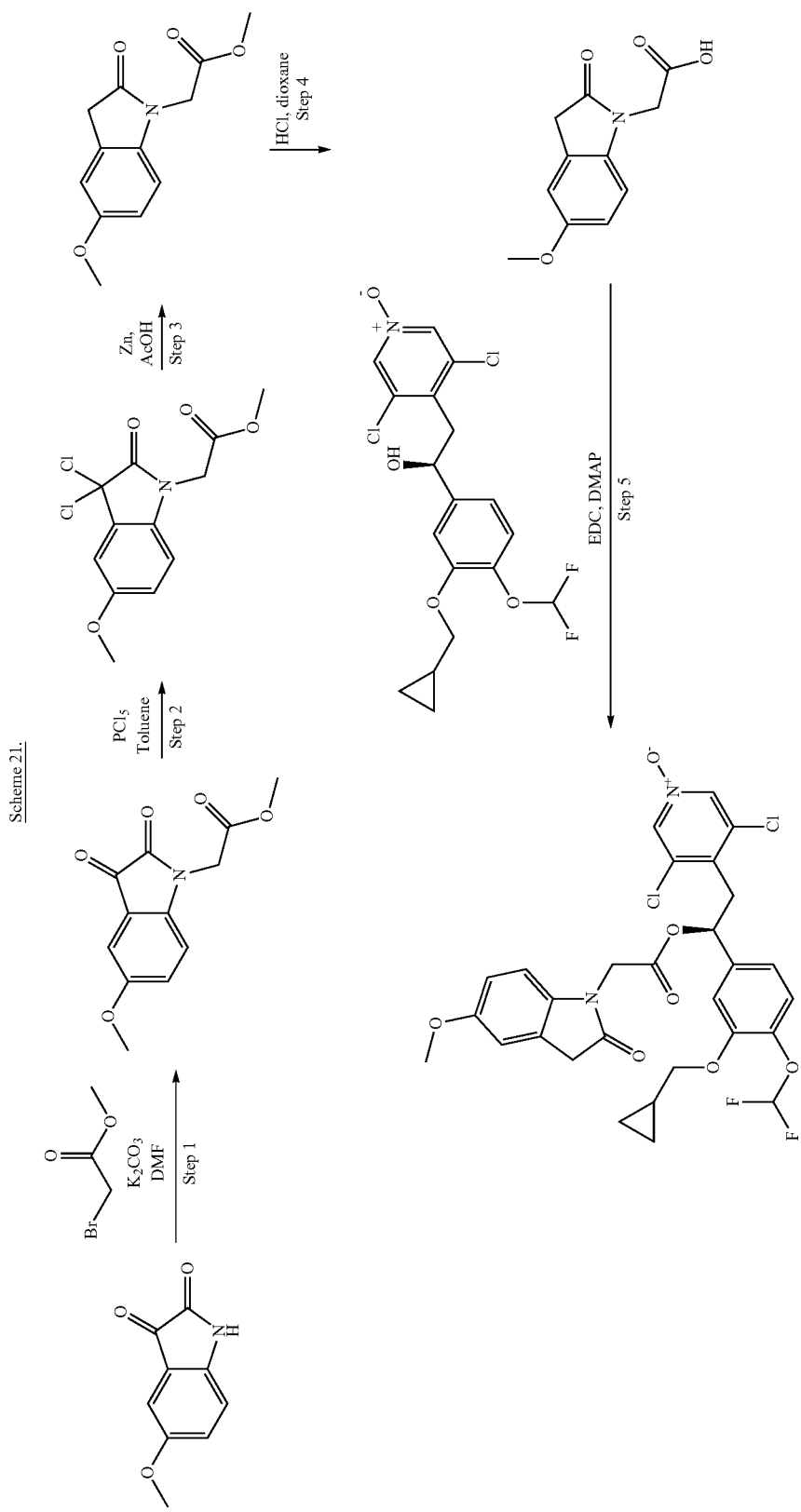

Step 1: Preparation of methyl 2-(5-methoxy-2,3-dioxoindolin-1-yl)acetate (113)

To a solution of 5-methoxyindoline-2,3-dione (1 g, 5.64 mmol) in DMF (15 ml), $K_2CO_3$ (0.936 g, 6.77 mmol) and methyl 2-bromoacetate (0.628 ml, 6.77 mmol) were added, and the mixture was reacted under microwave irradiation for 1 hour at 100° C. Then the insoluble inorganic salts were filtered off, and the resulting crude title compound was obtained (1.6 g) and used in the next step without further purification. MS/ESI$^+$ 250.1 [MH]$^+$.

Step 2: Preparation of methyl 2-(3,3-dichloro-5-methoxy-2-oxoindolin-1-yl)acetate (114)

To a solution of crude methyl 2-(5-methoxy-2,3-dioxoindolin-1-yl)acetate (obtained as described in Example 21, step 1, (1.6 g, theoretical amount 5.64 mmol) in toluene (50 ml), $PCl_5$ (3.07 g, 14.77 mmol) was added, and the mixture was reacted at 70° C. for 2 hours. The solvent was evaporated, and the resulting crude was suspended in DCM; the insoluble salts were filtered off and the crude desired product (−) was used in the next step without any further purification (1.3 g, 4.27 mmol, 76% yield over 2 steps). MS/ESI$^+$ 304.8 [MH]$^+$.

Step 3: Preparation of methyl 2-(5-methoxy-2-oxoindolin-1-yl)acetate (115)

To a solution of methyl 2-(3,3-dichloro-5-methoxy-2-oxoindolin-1-yl)acetate (1.3 g, 4.27 mmol) in acetic acid (30 ml), zinc powder (1.118 g, 17.10 mmol) was added, and the mixture was reacted at room temperature for 15 minutes; then the insoluble inorganics were filtered off and washed with MeOH. The crude title compound was obtained after evaporation under reduced pressure and used in the next step without further purification (760 mg, 3.23 mmol, 76% yield). MS/ESI$^+$ 236.0 [MH]$^+$.

Step 4: Preparation of 2-(5-methoxy-2-oxoindolin-1-yl)acetic acid (116)

To a solution of methyl 2-(5-methoxy-2-oxoindolin-1-yl) acetate (350 mg, 1.488 mmol) in dioxane (10 ml), 12N HCl (10 ml) was added, and the mixture was stirred at room temperature for 24 hours. Then the solvent was evaporated and the resulting crude was dissolved in MeOH (5 ml); by addition of iPrO$_2$ (50 ml) the title compound precipitated, was filtered and used in the next step without further purification (200 mg, 0.904 mmol, 61% yield). MS/ESI$^+$ 222.2 [MH]$^+$.

Step 5: Preparation of (S)-3,5-dichloro-4-(2-(3-(cyclopropylmethoxy)-4-(difluoromethoxy)phenyl)-2-(2-(5-methoxy-2-oxoindolin-1-yl)acetoxy)-ethyl) pyridine 1-oxide (117)

To a solution of 2-(5-methoxy-2-oxoindolin-1-yl)acetic acid (200 mg, 0.904 mmol) in DCM (30 ml), (S)-3,5-dichloro-4-(2-(3-(cyclopropylmethoxy)-4-(difluoromethoxy)phenyl)-2-hydroxyethyl)pyridine 1-oxide (380 mg, 0.904 mmol), EDC (520 mg, 2.71 mmol) and DMAP (55.2 mg, 0.452 mmol) were added, and the mixture was reacted at room temperature overnight. The solvent was evaporated, and the resulting crude was partitioned between DCM (20 ml) and a 1N HCl (20 ml), and the desired compound was extracted with ethyl acetate (3×20 ml). The combined organic layers were dried over sodium sulfate and the solvent was removed. The crude was purified by flash chromatography on silica gel (DCM:MeOH 98:2) recovering the title compound (149.2 mg, 0.239 mmol, 27% yield). MS/ESI$^+$ 623.12 [MH]$^+$; [α$_D$]=+19.12 c=0.5 in DCM; $^1$H NMR (300 MHz, DMSO-d$_6$) δ ppm 8.45 (s, 2H), 7.18 (d, 1H), 7.06 (d, 1H), 6.92-6.98 (m, 2H), 7.07 (t, 1H), 6.76 (dd, 1H), 6.64 (d, 1H), 6.02 (dd, 1H), 4.54 (d, 1H), 4.46 (d, 1H), 3.91 (d, 2H), 3.74 (s, 3H), 3.59 (s, 2H), 3.40 (dd, 1H), 3.21 (dd, 1H), 1.03-1.41 (m, 1H), 0.50-0.70 (m, 2H), 0.21-0.50 (m, 2H).

Example 22

(S)-3,5-Dichloro-4-(2-(3-(cyclopropylmethoxy)-4-(difluoromethoxy)phenyl)-2-(2-(5-methoxy-6-(methylsulfonamido)-1,3-dioxoisoindolin-2-yl)acetoxy) ethyl)pyridine 1-oxide (Compound 126)

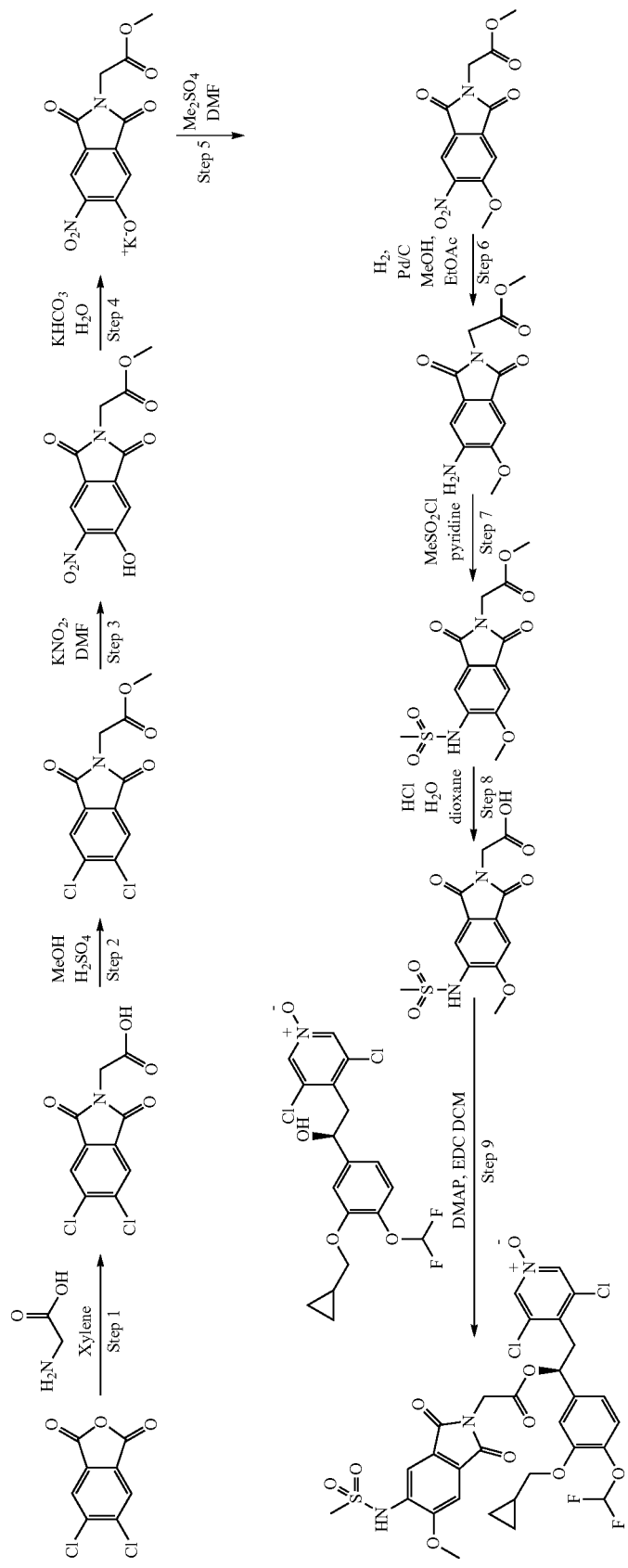

Step 1: Preparation of 2-(5,6-dichloro-1,3-dioxoisoindolin-2-yl)acetic acid (118)

To a solution of 5,6-dichloroisobenzofuran-1,3-dione (2 g, 9.22 mmol) in xylene (10 ml), 2-aminoacetic acid (0.761 g, 10.14 mmol) was added, and the reaction was heated at 160° C. for 40 hours. The precipitate that formed during the reaction was filtered, washed with water and hexanes and dried affording 2-(5,6-dichloro-1,3-dioxoisoindolin-2-yl)acetic acid (2.33 g, 8.50 mmol, 92% yield).

Step 2: Preparation of methyl 2-(5,6-dichloro-1,3-dioxoisoindolin-2-yl)acetate (119)

To a solution of 2-(5,6-dichloro-1,3-dioxoisoindolin-2-yl) acetic acid (2.33 g, 8.50 mmol) in MeOH (35 ml), conc. $H_2SO_4$ (3 ml) was added at 0° C. The reaction was warmed at room temperature and stirred for 16 hours. The mixture was poured into an ice/water mixture and neutralized with aqueous $NaHCO_3$. The resulting precipitate was recovered by filtration, washed with water and dried affording methyl 2-(5,6-dichloro-1,3-dioxoisoindolin-2-yl)acetate (2.42 g, 8.40 mmol, 99% yield). MS/ESI$^+$ 288.0 [MH]$^+$.

Step 3: Preparation of methyl 2-(5-hydroxy-6-nitro-1,3-dioxoisoindolin-2-yl)acetate (120)

A mixture of methyl 2-(5,6-dichloro-1,3-dioxoisoindolin-2-yl)acetate (1.420 g, 4.927 mmol) and potassium nitrite (1.678 g, 19.72 mmol) in dry DMF (23 ml) was heated to reflux for 5 hours. The reaction was cooled to room temperature, poured into 0.5N HCl (100 ml) and extracted twice with diethyl ether (2×100 ml). The combined organic layers were washed with 0.5N HCl (120 ml), with brine (100 ml) and dried over sodium sulfate. The solvent was removed, and the crude was purified by chromatography on silica gel cartridge (petroleum ether:ethyl acetate from 90:10 to 100% ethyl acetate). Two different impure fractions of desired compound were isolated. The first fraction was purified by trituration with MeOH affording 0.250 g of title compound. The second fraction was purified by flash chromatography on silica gel cartridge (petroleum ether:ethyl acetate:TFA from 80:20:0.2 to ethyl acetate:TFA=100:0.2) to obtain 0.160 g of title compound. The two clean portions of desired compound were mixed affording methyl 2-(5-hydroxy-6-nitro-1,3-dioxoisoindolin-2-yl)acetate (0.410 g, 1.463 mmol, 30% yield). MS/ESI$^+$ 281.1 [MH]$^+$.

Step 4: Preparation of potassium 2-(2-methoxy-2-oxoethyl)-6-nitro-1,3-dioxoisoindolin-5-olate (121)

To a stirred solution of potassium bicarbonate (0.324 g, 3.23 mmol) in water (7 ml) methyl 2-(5-hydroxy-6-nitro-1,3-dioxoisoindolin-2-yl)acetate (0.410 g, 1.463 mmol) was added, and the mixture was stirred at room temperature. When foaming ceased, the precipitate was filtered and washed with cold water (2 ml) affording potassium 2-(2-methoxy-2-oxoethyl)-6-nitro-1,3-dioxoisoindolin-5-olate (0.380 g, 1.194 mmol, 82% yield) MS/ESI$^+$ 281.1 [MH]$^+$.

Step 5: Preparation of methyl 2-(5-methoxy-6-nitro-1,3-dioxoisoindolin-2-yl)acetate (122)

To a solution of potassium 2-(2-methoxy-2-oxoethyl)-6-nitro-1,3-dioxoisoindolin-5-olate (0.380 g, 1.194 mmol) in DMF (10 ml), dimethyl sulfate (0.324 ml, 3.34 mmol) was added, and the mixture was heated at 60° C. for 6 hours and then stirred at 40° C. overnight. Additional dimethyl sulfate (0.116 ml, 1.194 mmol) was added, and the reaction mixture was heated at 60° C. for 4 hours. The mixture was partitioned between 1N $NaHCO_3$ (150 ml) and diethyl ether (100 ml). The organic phase was washed with 1N $NaHCO_3$ (100 ml), and the combined aqueous layers were extracted with diethyl ether (2×100 ml). The organic layers were mixed, washed twice with brine (2×100 ml) and dried over sodium sulfate; the solvent was removed under vacuum affording methyl 2-(5-methoxy-6-nitro-1,3-dioxoisoindolin-2-yl)acetate (0.225 g, 0.765 mmol, 64% yield). MS/ESI$^+$ 294.9 [MH]$^+$). This product was used without any further purification.

Step 6: Preparation of methyl 2-(5-amino-6-methoxy-1,3-dioxoisoindolin-2-yl)acetate (123)

A mixture of methyl 2-(5-methoxy-6-nitro-1,3-dioxoisoindolin-2-yl)acetate (0.225 g, 0.765 mmol) and 10% w/w Pd/C (a catalytic amount) in MeOH (20 ml) and ethyl acetate (10 ml) was hydrogenated in a Parr apparatus at 15 psi for 1 hour. The mixture was diluted with DCM till complete dissolution of the yellow precipitate, the catalyst was filtered off and the filtrate was evaporate to dryness affording methyl 2-(5-amino-6-methoxy-1,3-dioxoisoindolin-2-yl)acetate (0.202 g, 0.764 mmol, 100% yield). MS/ESI$^+$ 265.0 [MH]$^+$.

Step 7: Preparation of methyl 2-(5-methoxy-6-(methylsulfonamido)-1,3-dioxoisoindolin-2-yl)acetate (124)

A solution of methyl 2-(5-amino-6-methoxy-1,3-dioxoisoindolin-2-yl)acetate (0.202 g, 0.764 mmol) in pyridine (10 ml) was cooled to 0° C., and methanesulfonyl chloride (0.071 ml, 0.917 mmol) was added. The mixture was warmed to room temperature and stirred for 1 hour. Additional methanesulfonyl chloride (0.090 ml, 1.146 mmol) was added over 30 hour, cooling to 0° C. and stirring at room temperature. The solvent was removed under vacuum, and the crude was partitioned between ethyl acetate and 1N HCl. The organic phase was washed with brine and dried over sodium sulfate. The solvent was removed and the crude was purified by chromatography on silica gel cartridge (petroleum ether:ethyl acetate from 6:4 to 100% ethyl acetate) affording methyl 2-(5-methoxy-6-(methylsulfonamido)-1,3-dioxoisoindolin-2-yl)acetate (0.200 g, 0.584 mmol, 76% yield). MS/ESI$^+$ 342.9 [MH]$^+$.

Step 8: Preparation of 2-(5-methoxy-6-(methylsulfonamido)-1,3-dioxoisoindolin-2-yl)acetic acid (125)

To a solution of methyl 2-(5-methoxy-6-(methylsulfonamido)-1,3-dioxoisoindolin-2-yl)acetate (0.200 g, 0.584 mmol) in dioxane (10 ml), aqueous 37% HCl (3.5 ml) was added, and the mixture was stirred at room temperature overnight. Additional aqueous 37% HCl (4 ml) was added over 30 hours with stirring the reaction at room temperature. The volatiles were removed under vacuum affording 2-(5-methoxy-6-(methylsulfonamido)-1,3-dioxoisoindolin-2-yl)acetic acid (0.183 g, 0.557 mmol, 95% yield). MS/ESI$^+$ 328.9 [MH]$^+$. This product was used without purification.

Step 9: Preparation of (S)-3,5-dichloro-4-(2-(3-(cyclopropylmethoxy)-4-(difluoromethoxy)phenyl)-2-(2-(5-methoxy-6-(methylsulfonamido)-1,3-dioxoisoindolin-2-yl)acetoxy)ethyl)pyridine 1-oxide (126)

A mixture of 2-(5-methoxy-6-(methylsulfonamido)-1,3-dioxoisoindolin-2-yl)acetic acid (0.183 g, 0.557 mmol), (S)-

3,5-dichloro-4-(2-(3-(cyclopropylmethoxy)-4-(difluoromethoxy)phenyl)-2-hydroxyethyl)pyridine 1-oxide (0.234 g, 0.557 mmol), EDC (0.321 g, 1.672 mmol) and DMAP (0.034 g, 0.279 mmol) in DCM (20 ml) was stirred at room temperature for 2 hours. The mixture was diluted with DCM and washed with 1N HCl, 5% NaHCO$_3$ and brine. The organic phase was dried over sodium sulfate, the solvent was removed, and the crude was purified by flash chromatography on silica gel cartridge (DCM:ethyl acetate from 1:1 to 4:1) affording (S)-3,5-dichloro-4-(2-(3-(cyclopropylmethoxy)-4-(difluoromethoxy)phenyl)-2-(2-(5-methoxy-6-(methylsulfonamido)-1,3-dioxoisoindolin-2-yl)acetoxy)ethyl)pyridine 1-oxide as a pale orange solid (0.097 g, 0.133 mmol, 24% yield). MS/ESI$^+$ 730.13 [MH]$^+$; [$\alpha_D$]=−33.40, c=0.43, DCM; $^1$H NMR (300 MHz, DMSO-d$_6$) δ ppm 9.54 (br. s., 1H), 8.44 (s, 2H), 7.77 (s, 1H), 7.55 (s, 1H), 7.19 (d, 1H), 7.08 (d, 1H), 6.96 (dd, 1H), 7.08 (t, 1H), 6.01 (dd, 1H), 4.39 (s, 2H), 4.04 (s, 3H), 3.93 (d, 2H), 3.39 (dd, 1H), 3.23 (dd, 1H), 3.15 (s, 3H), 1.01-1.37 (m, 1H), 0.50-0.72 (m, 2H), 0.25-0.45 (m, 2H)

Example 23

(S)-3,5-Dichloro-4-(2-(3-(cyclopropylmethoxy)-4-(difluoromethoxy)-phenyl)-2-(2-(5-(methylsulfonamido)indolin-1-yl)acetoxy)ethyl)pyridine-1-oxide (Compound 131)

Scheme 23.
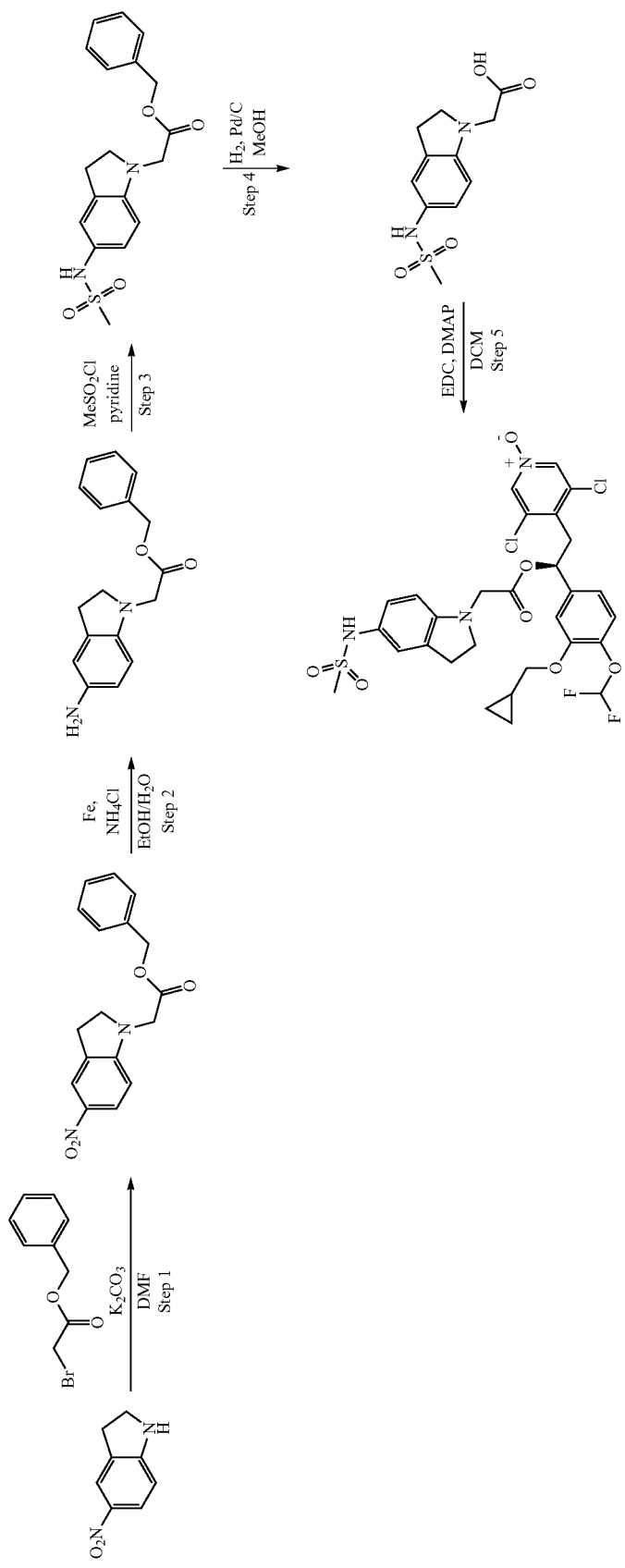

Step 1: Preparation of benzyl 2-(5-nitroindolin-1-yl)acetate (127)/

To a solution of 5-nitroindoline (1 g, 6.09 mmol) in dry DMF (20 ml), $K_2CO_3$ (1.094 g, 7.92 mmol) and benzyl 2-bromoacetate (1.242 ml, 7.92 mmol) were added, and the resulting suspension was heated at 65° C. for 2 hours. The mixture was cooled to room temperature, diluted with ethyl acetate and washed with water and brine. The organic layer was dried over sodium sulfate and the solvent was removed. The residue was purified by flash chromatography on silica gel column (DCM:petroleum ether=60:40) affording benzyl 2-(5-nitroindolin-1-yl)acetate (0.782 g, 2.504 mmol, 41% yield). MS/ESI$^+$ 312.9 [MH]$^+$.

Step 2: Preparation of benzyl 2-(5-aminoindolin-1-yl)acetate (128)

To a suspension of benzyl 2-(5-nitroindolin-1-yl)acetate (0.700 g, 2.241 mmol) in a mixture of ethanol (20 ml) and water (10 ml), iron powder (0.751 g, 13.45 mmol) and ammonium chloride (0.084 g, 1.569 mmol) were added, and the resulting mixture was heated to reflux for 1 hour and 15 minutes. The insoluble was filtered off, and the filtrate was concentrated under vacuum. The residue was dissolved in ethyl acetate and washed with water and brine. The organic layer was dried over sodium sulfate and evaporated to dryness to give benzyl 2-(5-aminoindolin-1-yl)acetate (0.626 g, 2.217 mmol, 99% yield). MS/ESI$^+$ 283.0 [MH]$^+$.

Step 3: Preparation of benzyl 2-(5-(methylsulfonamido)indolin-1-yl)acetate (129)

To a solution of benzyl 2-(5-aminoindolin-1-yl)acetate (0.610 g, 2.161 mmol) in pyridine (15 ml), methanesulfonyl chloride (0.251 ml, 3.24 mmol) was added at 0° C. The mixture was allowed to warm to room temperature and stirred for 1 hour. The solvent was removed under vacuum and the residue was partitioned between DCM and water; the organic phase was washed with brine, dried over sodium sulfate and evaporated to dryness. The crude was purified by flash chromatography on silica gel column (petroleum ether:ethyl acetate=70:30 to 60:40) affording benzyl 2-(5-(methylsulfonamido)indolin-1-yl)acetate (0.565 g, 1.568 mmol, 73% yield). MS/ESI$^+$ 361.0 [MH]$^+$.

Step 4: Preparation of 2-(5-(methylsulfonamido)indolin-1-yl)acetic acid (130)

A solution of benzyl 2-(5-(methylsulfonamido)indolin-1-yl)acetate (0.565 g, 1.568 mmol) in methanol was added to a suspension of 10% w/w Pd/C (a catalytic amount) in water and the mixture was hydrogenated in a Parr apparatus at 30 psi overnight. The catalyst was filtered off and the filtrate was evaporated to dryness affording 2-(5-(methylsulfonamido)indolin-1-yl)acetic acid (0.351 g, 1.299 mmol, 83% yield). MS/ESI$^+$ 271.0 [MH]$^+$.

Step 5: Preparation of (S)-3,5-dichloro-4-(2-(3-(cyclopropylmethoxy)-4-(difluoromethoxy)phenyl)-2-(2-(5-(methylsulfonamido)indolin-1-yl)acetoxy)-ethyl)pyridine 1-oxide (131)

A mixture of 2-(5-(methylsulfonamido)indolin-1-yl)acetic acid (0.154 g, 0.571 mmol), (S)-3,5-dichloro-4-(2-(3-(cyclopropylmethoxy)-4-(difluoromethoxy)-phenyl)-2-hydroxy-ethyl)pyridine 1-oxide (0.200 g, 0.476 mmol), EDC (0.128 g, 0.666 mmol) and DMAP (0.116 g, 0.952 mmol) in dry DCM (10 ml) was stirred at room temperature for 2.5 hours. Additional 2-(5-(methylsulfonamido)indolin-1-yl)acetic acid (0.072 g, 0.267 mmol) was added, and the mixture was stirred overnight at room temperature. The solvent was removed and the crude was purified by flash chromatography on silica gel column (DCM:MeOH=98:2). A further purification by preparative HPLC (Method 1) under neutral conditions was required to afford (S)-3,5-dichloro-4-(2-(3-(cyclopropylmethoxy)-4-(difluoromethoxy)phenyl)-2-(2-(5-(methylsulfonamido)indolin-1-yl)acetoxy)ethyl)-pyridine 1-oxide (0.0817 g, 0.121 mmol, 26% yield). MS/ESI$^+$ 672.05 [MH]$^+$; [$\alpha_D$]=+10.81, c=0.518; DCM; $^1$H NMR (300 MHz, DMSO-d$_6$) δ ppm 8.84 (br. s., 1H), 8.55 (s, 2H), 7.17 (d, 1H), 7.08 (d, 1H), 6.94 (dd, 1H), 6.92 (d, 1H), 7.06 (t, 1H), 6.81 (dd, 1H), 6.22 (d, 1H), 6.03 (dd, 1H), 4.10 (d, 1H), 3.90 (d, 2H), 3.92 (d, 1H), 3.43 (dd, 1H), 3.32-3.39 (m, 2H), 3.22 (dd, 1H), 2.89 (t, 2H), 2.83 (s, 3H), 1.08-1.31 (m, 1H), 0.49-0.68 (m, 2H), 0.18-0.46 (m, 2H).

Example 24

(S)-3,5-Dichloro-4-(2-(3-(cyclopropylmethoxy)-4-(difluoromethoxy)phenyl)-2-(2-(6-(methylsulfonamido)-2-oxobenzo[d]oxazol-3(2H)-yl)acetoxy)-ethyl)pyridine 1-oxide (Compound 138)

Scheme 24.
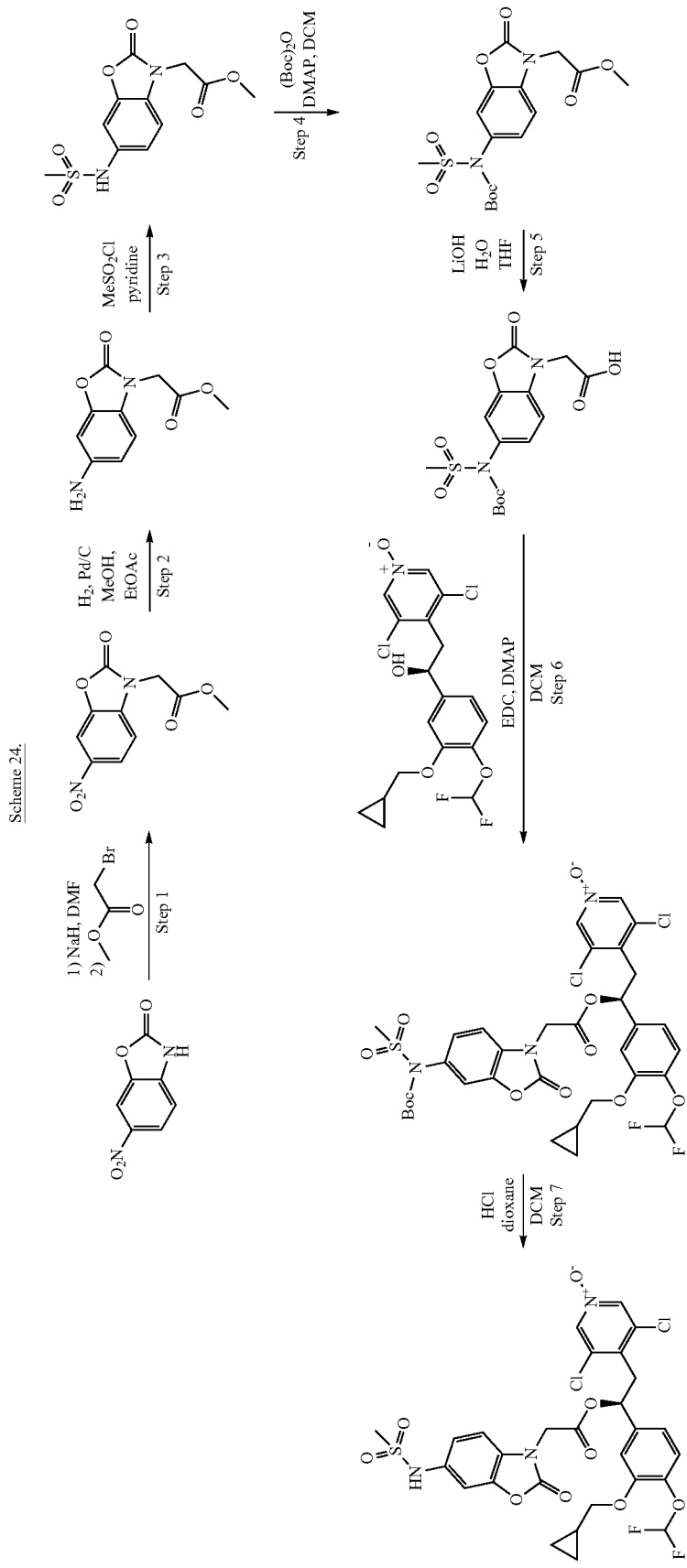

Step 1: Preparation of methyl 2-(6-nitro-2-oxobenzo[d]oxazol-3(2H)-yl)acetate (132)

A solution of 6-nitrobenzo[d]oxazol-2(3H)-one (0.500 g, 2.78 mmol) in DMF (10 ml) was cooled to 0° C. NaH (60% w/w dispersion in mineral oil, 0.133 g, 3.33 mmol) was added, and the reaction was allowed to warm to room temperature and stirred for 15 minutes. The mixture was cooled to 0° C., methyl 2-bromoacetate (0.309 ml, 3.33 mmol) was added, and the reaction was warmed to room temperature and stirred for 4 hours. The mixture was partitioned between ethyl acetate and 1N HCl. The organic phase was washed several times with brine and dried over sodium sulfate. The solvent was removed, and the crude was purified by trituration with diethyl ether (50 ml) affording methyl 2-(6-nitro-2-oxobenzo[d]oxazol-3(2H)-yl)acetate (0.570 g, 2.260 mmol, 81% yield). MS/ESI$^+$ 252.9 [MH]$^+$.

Step 2: Preparation of methyl 2-(6-amino-2-oxobenzo[d]oxazol-3(2H)-yl)acetate (133)

A mixture of methyl 2-(6-nitro-2-oxobenzo[d]oxazol-3(2H)-yl)acetate (0.570 g, 2.260 mmol) and 10% w/w Pd/C (a catalytic amount) in MeOH (30 ml) and ethyl acetate (30 ml) was hydrogenated in a Parr apparatus at 20 psi for 1 hour. The catalyst was filtered off and the solvent was removed affording methyl 2-(6-amino-2-oxobenzo[d]oxazol-3(2H)-yl)acetate (0.497 g, 2.237 mmol, 99% yield). MS/ESI$^+$ 222.9 [MH]$^+$.

Step 3: Preparation of methyl 2-(6-(methylsulfonamido)-2-oxobenzo[d]oxazol-3(2H)-yl)acetate (134)

A solution of methyl 2-(6-amino-2-oxobenzo[d]oxazol-3(2H)-yl)acetate (0.497 g, 2.237 mmol) in pyridine (15 ml) was cooled to 0° C., and methanesulfonyl chloride (0.209 ml, 2.68 mmol) was added. The mixture was warmed to room temperature and stirred for 1 hour. The solvent was removed and the residue was portioned between ethyl acetate and 1N HCl. The organic phase was washed with brine and dried over sodium sulfate; the solvent was removed and the crude was purified by trituration with diethyl ether affording methyl 2-(6-(methylsulfonamido)-2-oxobenzo[d]oxazol-3(2H)-yl)acetate (0.523 g, 1.742 mmol, 78% yield). MS/ESI$^+$ 300.9 [MH]$^+$.

Step 4: Preparation of methyl 2-(6-(N-(tert-butoxycarbonyl)-methylsulfonamido)-2-oxobenzo[d]oxazol-3(2H)-yl)acetate (135)

A mixture of methyl 2-(6-(methylsulfonamido)-2-oxobenzo[d]oxazol-3(2H)-yl)acetate (0.523 g, 1.742 mmol), di-tert-butyl dicarbonate (0.494 g, 2.264 mmol) and DMAP (0.277 g, 2.264 mmol) in DCM (50 ml) was stirred at room temperature for 2 hours. The mixture was diluted with DCM and washed twice with aqueous 5% NaHCO$_3$ and twice with 1N HCl. The organic phase was dried over sodium sulfate and the solvent was removed affording methyl 2-(6-(N-(tert-butoxycarbonyl)-methylsulfonamido)-2-oxobenzo[d]oxazol-3(2H)-yl)acetate (0.660 g, 1.648 mmol, 95% yield). MS/ESI$^+$ 422.8 [MNa]$^+$. This product was used without purification.

Step 5: Preparation of 2-(6-(N-(tert-butoxycarbonyl)methylsulfonamido)-2-oxobenzo[d]oxazol-3(2H)-yl)acetic acid (136)

To a solution of methyl 2-(6-(N-(tert-butoxycarbonyl)methylsulfonamido)-2-oxobenzo[d]oxazol-3(2H)-yl)acetate (0.300 g, 0.749 mmol) in THF (5 ml), aqueous 1N LiOH (1.124 ml, 1.124 mmol) was added, and the mixture was stirred at room temperature for 30 minutes. The mixture was acidified with 1N HCl and extracted with ethyl acetate; the organic phase was washed several times with 1N HCl, dried over sodium sulfate and evaporated to dryness affording 2-(6-(N-(tert-butoxycarbonyl)-methylsulfonamido)-2-oxobenzo[d]oxazol-3(2H)-yl)acetic acid (0.234 g, 0.606 mmol, 81% yield). MS/ESI$^+$ 386.9 [MH]$^+$. This product was used without any further purification.

Step 6: Preparation of (S)-4-(2-(2-(6-(N-(tert-butoxycarbonyl)-methylsulfonamido)-2-oxobenzo[d]oxazol-3(2H)-yl)acetoxy)-2-(3-(cyclopropylmethoxy)-4-(difluoromethoxy)phenyl)ethyl)-3,5-dichloropyridine 1-oxide (137)

A mixture of 2-(6-(N-(tert-butoxycarbonyl)methylsulfonamido)-2-oxobenzo[d]oxazol-3(2H)-yl)acetic acid (0.234 g, 0.606 mmol), (S)-3,5-dichloro-4-(2-(3-(cyclopropylmethoxy)-4-(difluoromethoxy)phenyl)-2-hydroxyethyl)pyridine 1-oxide (0.212 g, 0.505 mmol), EDC (0.290 g, 1.514 mmol) and DMAP (0.031 g, 0.252 mmol) in DCM (15 ml) was stirred at room temperature for 2 hours. The mixture was diluted with DCM and washed with 1N HCl, 1N NaHCO$_3$ and brine. The organic phase was dried over sodium sulfate and the solvent was removed. The crude was purified by flash chromatography on silica gel cartridge (DCM:MeOH=99:1) affording (S)-4-(2-(2-(6-(N-(tert-butoxycarbonyl)methylsulfonamido)-2-oxobenzo[d]oxazol-3(2H)-yl)acetoxy)-2-(3-(cyclopropylmethoxy)-4-(difluoromethoxy)phenyl)ethyl)-3,5-dichloropyridine 1-oxide (0.200 g, 0.254 mmol, 50% yield). MS/ESI$^+$ 787.8 [MH]$^+$.

Step 7: Preparation of ((S)-3,5-dichloro-4-(2-(3-(cyclopropylmethoxy)-4-(difluoromethoxy)phenyl)-2-(2-(6-(methylsulfonamido)-2-oxobenzo[d]oxazol-3(2H)-yl)acetoxy)ethyl)pyridine 1-oxide (138)

To a solution of (S)-4-(2-(2-(6-(N-(tert-butoxycarbonyl)methylsulfonamido)-2-oxobenzo[d]oxazol-3(2H)-yl)acetoxy)-2-(3-(cyclopropylmethoxy)-4-(difluoromethoxy)phenyl)ethyl)-3,5-dichloropyridine 1-oxide (0.200 g, 0.254 mmol) in DCM (10 ml) cooled to 0° C., HCl 4M in THF (0.634 ml, 2.54 mmol) was added, and the mixture was warmed to room temperature and stirred for 48 hours. A white solid precipitated. The precipitate was collected by filtration and washed with DCM affording (S)-3,5-dichloro-4-(2-(3-(cyclopropylmethoxy)-4-(difluoromethoxy)phenyl)-2-(2-(6-(methylsulfonamido)-2-oxobenzo[d]oxazol-3(2H)-yl)acetoxy)ethyl)pyridine 1-oxide (0.140 g, 0.203 mmol, 80% yield). MS/ESI$^+$ 688.1 [MH]$^+$; [$\alpha_D$]=−31.04, c=0.46, MeOH; $^1$H NMR (300 MHz, DMSO-d$_6$) δ ppm 9.66 (br. s., 1H), 8.43 (s, 2H), 7.25 (d, 1H), 7.19 (d, 1H), 7.15 (d, 1H), 7.08 (d, 1H), 7.05 (dd, 1H), 6.96 (dd, 1H), 7.07 (t, 1H), 6.04 (dd, 1H), 4.82 (d, 1H), 4.70 (d, 1H), 3.92 (d, 2H), 3.40 (dd, 1H), 3.22 (dd, 1H), 2.99 (s, 3H), 1.07-1.41 (m, 1H), 0.48-0.70 (m, 2H), 0.25-0.44 (m, 2H).

Example 25

(S)-3,5-Dichloro-4-(2-(3-(cyclopropylmethoxy)-4-(difluoromethoxy)phenyl)-2-(2-(6-morpholino-2,3-dioxoindolin-1-yl)acetoxy)ethyl)pyridine 1-oxide (Compound 142)

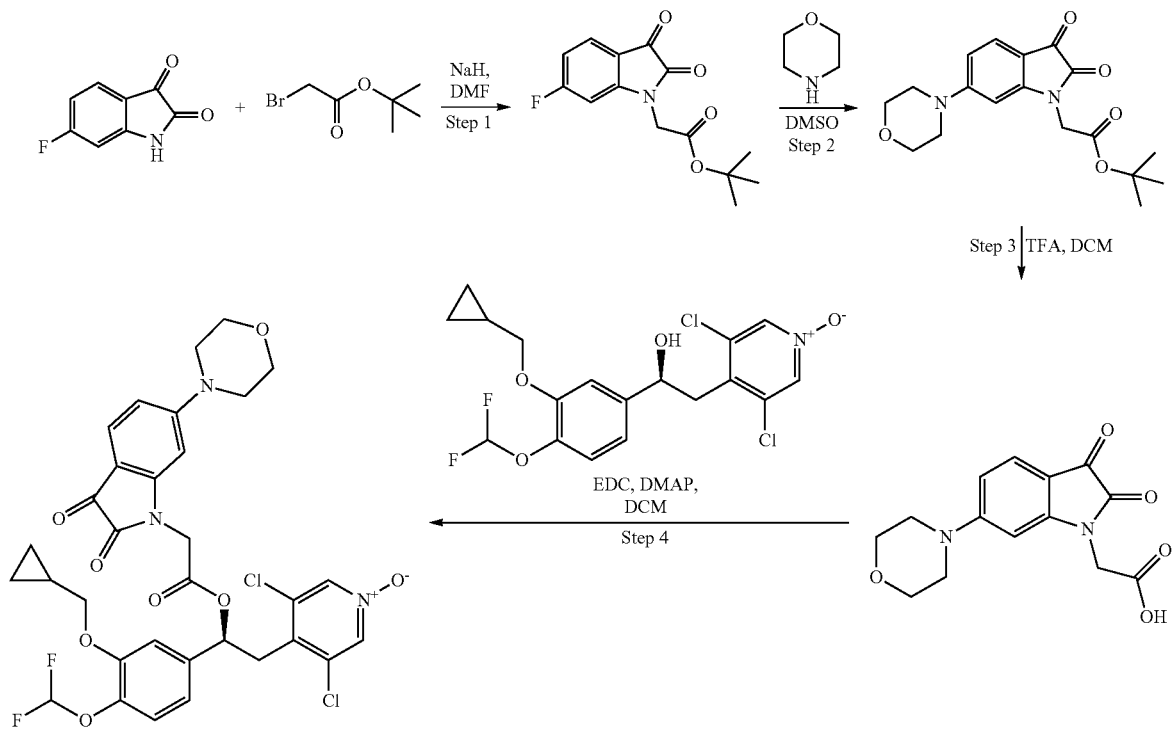

Scheme 25.

Step 1: Preparation of tert-butyl 2-(6-fluoro-2,3-dioxoindolin-1-yl)acetate (139)

A solution of 6-fluoroindoline-2,3-dione (2 g, 12.11 mmol) in dry DMF (100 ml) was cooled to 0° C., and NaH (60% w/w dispersion in mineral oil; 0.484 g, 12.11 mmol) was added portion wise over 10 minutes. The mixture was stirred at the same temperature for 10 minutes, then tert-butyl 2-bromoacetate (1.788 ml, 12.11 mmol) was added drop wise. The mixture was left warm to room temperature and stirred for 2 hours. DMF was evaporated under vacuum, and the crude was portioned between ethyl acetate (50 ml) and aqueous 1N HCl (40 ml). The aqueous phase was extracted with ethyl acetate (2×50 ml), and the combined organic layers were dried over sodium sulfate, filtered and concentrate under vacuum. The crude was purified by flash chromatography on silica gel cartridge (petroleum ether:ethyl acetate=80:20) affording tert-butyl 2-(6-fluoro-2,3-dioxoindolin-1-yl)acetate (2.21 g, 7.91 mmol, 65% yield).

Step 2: Preparation of tert-butyl 2-(6-morpholino-2,3-dioxoindolin-1-yl)acetate (140)

To a solution of tert-butyl 2-(6-fluoro-2,3-dioxoindolin-1-yl)acetate (0.400 g, 1.432 mmol) in DMSO (10 ml), morpholine (1.248 ml, 14.32 mmol) was added drop wise at room temperature. The resulting orange mixture was stirred at room temperature for 24 hours. Ethyl acetate (50 ml) was added and the solution was washed with brine (3×30 ml); the organic phase was dried over sodium sulfate, filtered and concentrated under vacuum. The crude was purified by silica gel flash chromatography (DCM:MeOH=98:2) affording tert-butyl 2-(6-morpholino-2,3-dioxoindolin-1-yl)acetate (0.400 g, 1.155 mmol, 81% yield 0. MS/ESI⁺ 347.1 [MH]⁺.

Step 3: Preparation of 2-(6-morpholino-2,3-dioxoindolin-1-yl)acetic acid (141)

To a solution of tert-butyl 2-(6-morpholino-2,3-dioxoindolin-1-yl)acetate (0.400 g, 1.155 mmol) in DCM (10 ml), TFA (1.716 ml, 23.10 mmol) was added drop wise. The resulting red solution was stirred at room temperature overnight. The volatiles were evaporated under vacuum to afford 2-(6-morpholino-2,3-dioxoindolin-1-yl)acetic acid (0.330 g, 1.137 mmol, 98% yield). MS/ESI⁺ 291.1 [MH]⁺.

Step 4: Preparation of (S)-3,5-dichloro-4-(2-(3-(cyclopropylmethoxy)-4-(difluoromethoxy)phenyl)-2-(2-(6-morpholino-2,3-dioxoindolin-1-yl)acetoxy)ethyl)pyridine 1-oxide (142)

To a solution of (S)-3,5-dichloro-4-(2-(3-(cyclopropylmethoxy)-4-(difluoromethoxy)phenyl)-2-hydroxyethyl)pyridine 1-oxide (0.200 g, 0.476 mmol) in DCM (15 ml), DMAP (0.070 g, 0.571 mmol), EDC (0.274 g, 1.428 mmol) and 2-(6-morpholino-2,3-dioxoindolin-1-yl)acetic acid (0.166 g, 0.571 mmol) were added in one portion at room temperature, and the resulting solution was stirred overnight. The solvent was removed under vacuum and the crude was purified by silica gel flash chromatography (DCM: MeOH=98:2) to afford a red solid. After trituration with diethyl ether (S)-3,5-dichloro-4-(2-(3-(cyclopropylmethoxy)-4-(difluoromethoxy)-phenyl)-2-(2-(6-morpholino-2,3-dioxoindolin-1-yl)acetoxy)ethyl)pyridine 1-oxide was obtained (0.145 mg, 0.209 mmol, 44% yield). MS/ESI⁺ 692.31 [MH]⁺; [α$_D$]=+227.4, c=0.25, MeOH; ¹H NMR (300 MHz, DMSO-d₆) δ ppm 8.33 (s, 2H), 7.44 (d, 1H), 7.17 (d, 1H), 7.04 (d, 1H), 6.94 (dd, 1H), 7.08 (t, 1H), 6.59 (dd, 1H), 6.48 (d, 1H), 6.01 (dd, 1H), 4.56 (s, 2H), 3.90 (d, 2H), 3.63-3.80 (m, 4H), 3.43-3.55 (m, 4H), 3.37 (dd, 1H), 3.18 (dd, 1H), 1.13-1.35 (m, 1H), 0.50-0.66 (m, 2H), 0.23-0.48 (m, 2H)

The compound listed in Table 10 was prepared with analogous synthetic steps and procedures to that described in Example 25, by reacting the appropriate precursors (commercially available or synthesized by a person skilled in the art) with suitable reagents. Specific variations in the experimentals or purification methods are indicated in the table.

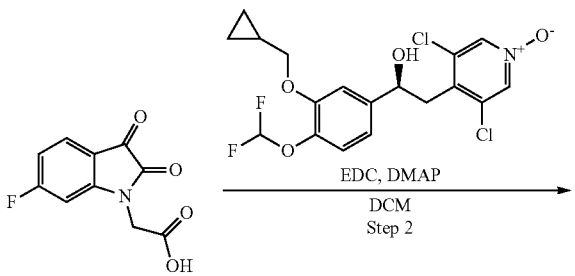

TABLE 10

| Entry | Structure | NMR characterization | MS/ESI⁺ [MH]⁺ | [αD] | Purification and yield | Starting material (precursor) | Nucleophilic agent |
|---|---|---|---|---|---|---|---|
| 143 | 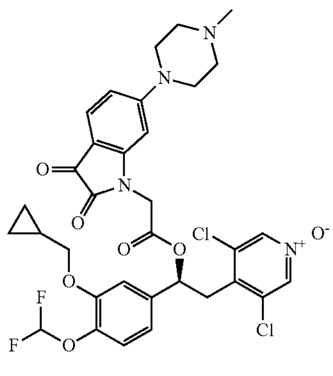 | ¹H NMR (300 MHz, DMSO-d₆) δ ppm 8.34 (s, 2 H), 7.40 (d, 1 H), 7.16 (d, 1 H), 7.03 (d, 1 H), 6.93 (dd, 1 H), 7.07 (t, 1 H), 6.58 (dd, 1 H), 6.48 (d, 1 H), 6.01 (dd, 1 H), 4.60 (d, 1 H), 4.54 (d, 1 H), 3.89 (d, 2 H), 3.44-3.61 (m, 4 H), 3.36 (dd, 1 H), 3.18 (dd, 1 H), 2.40 (t, 4 H), 2.23 (s, 3 H), 1.13-1.32 (m, 1 H), 0.59 (m, 2 H), 0.37 (m, 2 H) | 705.28 | +220.8 c = 0.5, MeOH | Flash chromatography on silica gel (DCM to DCM/MeOH 99:1 33% yield | | |

Example 26

(S)-3,5-Dichloro-4-(2-(3-(cyclopropylmethoxy)-4-(difluoromethoxy)phenyl)-2-(2-(6-fluoro-2,3-dioxoindolin-1-yl)acetoxy)ethyl)pyridine 1-oxide (145) and (S)-3,5-dichloro-4-(2-(3-(cyclopropylmethoxy)-4-(difluoromethoxy)phenyl)-2-(2-(6-(4-(dimethylamino)pyridinium-1-yl)-2,3-dioxoindolin-1-yl)acetoxy)ethyl)pyridine 1-oxide 2,2,2-trifluoroacetate (146)

Scheme 26.

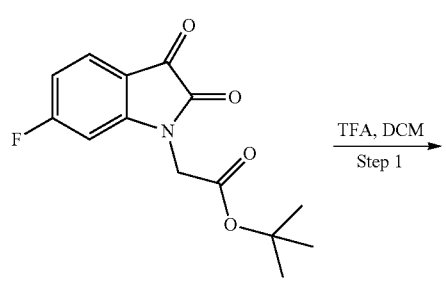

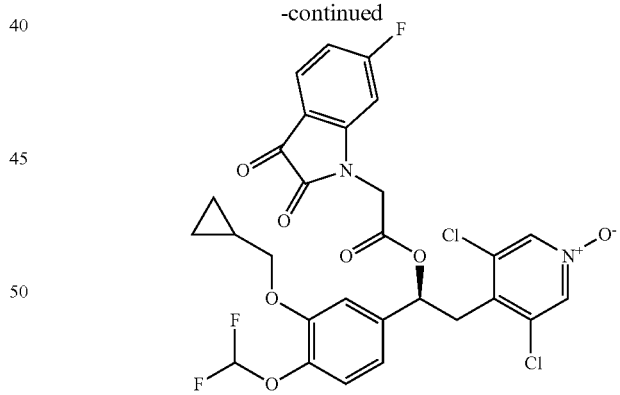

Step 1: Preparation of benzyl 2-(6-fluoro-2,3-dioxoindolin-1-yl)acetic acid (144)

To a solution of tert-butyl 2-(6-fluoro-2,3-dioxoindolin-1-yl)acetate (0.300 g, 1.074 mmol), obtained as described in Example 25, Scheme 25, Step 1, in DCM (10 ml), TFA (1.655 ml, 21.49 mmol) was added, and the mixture was stirred at room temperature overnight. The volatiles were removed and the crude 2-(6-fluoro-2,3-dioxoindolin-1-yl)acetic acid obtained was used for the next step without further purification (0.240 g, 1.075 mmol, 100% yield).

Step 2: Preparation of (S)-3,5-dichloro-4-(2-(3-(cyclopropylmethoxy)-4-(difluoromethoxy)phenyl)-2-(2-(6-fluoro-2,3-dioxoindolin-1-yl)acetoxy)-ethyl)pyridine 1-oxide (145)

To a solution of (S)-3,5-dichloro-4-(2-(3-(cyclopropylmethoxy)-4-(difluoromethoxy)phenyl)-2-hydroxyethyl)pyridine 1-oxide (0.200 g, 0.476 mmol) in DCM (15 ml), DMAP (0.058. g, 0.476 mmol), EDC (0.274 g, 1.428 mmol) and 2-(6-fluoro-2,3-dioxoindolin-1-yl)acetic acid (0.127 g, 0.571 mmol) were added in one portion at room temperature. The resulting solution was stirred at room temperature for 24 hours; the solvent was removed under vacuum and the residue was dissolved in ethyl acetate (40 ml), washed with a saturated solution of $NaHCO_3$ (20 ml), with 1N HCl (20 ml) and finally with brine (20 ml). The organic layer was dried over sodium sulfate and the solvent was evaporated under vacuum. The crude was purified by preparative HPLC (Method 1) and two pure fractions were isolated:

(S)-3,5-dichloro-4-(2-(3-(cyclopropylmethoxy)-4-(difluoromethoxy)phenyl)-2-(2-(6-fluoro-2,3-dioxoindolin-1-yl)acetoxy)ethyl)pyridine 1-oxide (145) (0.020 g, 0.032 mmol, 7% yield). MS/ESI$^+$ 625.22 [MH]$^+$; $[\alpha_D]$=−15.60, c=0.05, MeOH; $^1$H NMR (300 MHz, DMSO-d$_6$) δ ppm 8.41 (s, 2H), 7.73 (dd, 1H), 7.17 (d, 1H), 7.12 (dd, 1H), 7.06 (d, 1H), 6.89-7.03 (m, 2H), 7.07 (t, 1H), 6.01 (dd, 1H), 4.61 (s, 2H), 3.89 (dd, 2H), 3.40 (dd, 1H), 3.21 (dd, 1H), 1.05-1.34 (m, 1H), 0.49-0.70 (m, 2H), 0.26-0.46 (m, 2H);

(S)-3,5-dichloro-4-(2-(3-(cyclopropylmethoxy)-4-(difluoromethoxy)phenyl)-2-(2-(6-(4-(dimethylamino)pyridinium-1-yl)-2,3-dioxoindolin-1-yl)acetoxy)ethyl)pyridine 1-oxide 2,2,2-trifluoroacetate (146) (0.030 g, 0.035 mmol, 8% yield). MS/ESI$^+$ 727.25 [MH]$^+$; $[\alpha_D]$=+54.20, c=0.1, DCM; $^1$H NMR (300 MHz, DMSO-d$_6$) δ ppm 8.48-8.59 (m, 2H), 8.28 (s, 2H), 7.91 (d, 1H), 7.44-7.55 (m, 2H), 7.18-7.27 (m, 2H), 7.15 (d, 1H), 7.08 (d, 1H), 6.95 (dd, 1H), 7.06 (t, 1H), 5.99 (dd, 1H), 4.68 (d, 1H), 4.60 (d, 1H), 3.91 (d, 2H), 3.43-3.56 (m, 1H), 3.20 (dd, 1H), 1.13-1.50 (m, 1H), 0.46-0.67 (m, 2H), 0.25-0.47 (m, 2H)

Example 27

(S)-3,5-Dichloro-4-(2-(3-(cyclopropylmethoxy)-4-(difluoromethoxy)phenyl)-2-(2-(5-(N,N-dimethylsulfamoyl)-2,3-dioxoindolin-1-yl)acetoxy)-ethyl)pyridine 1-oxide (compound 151)

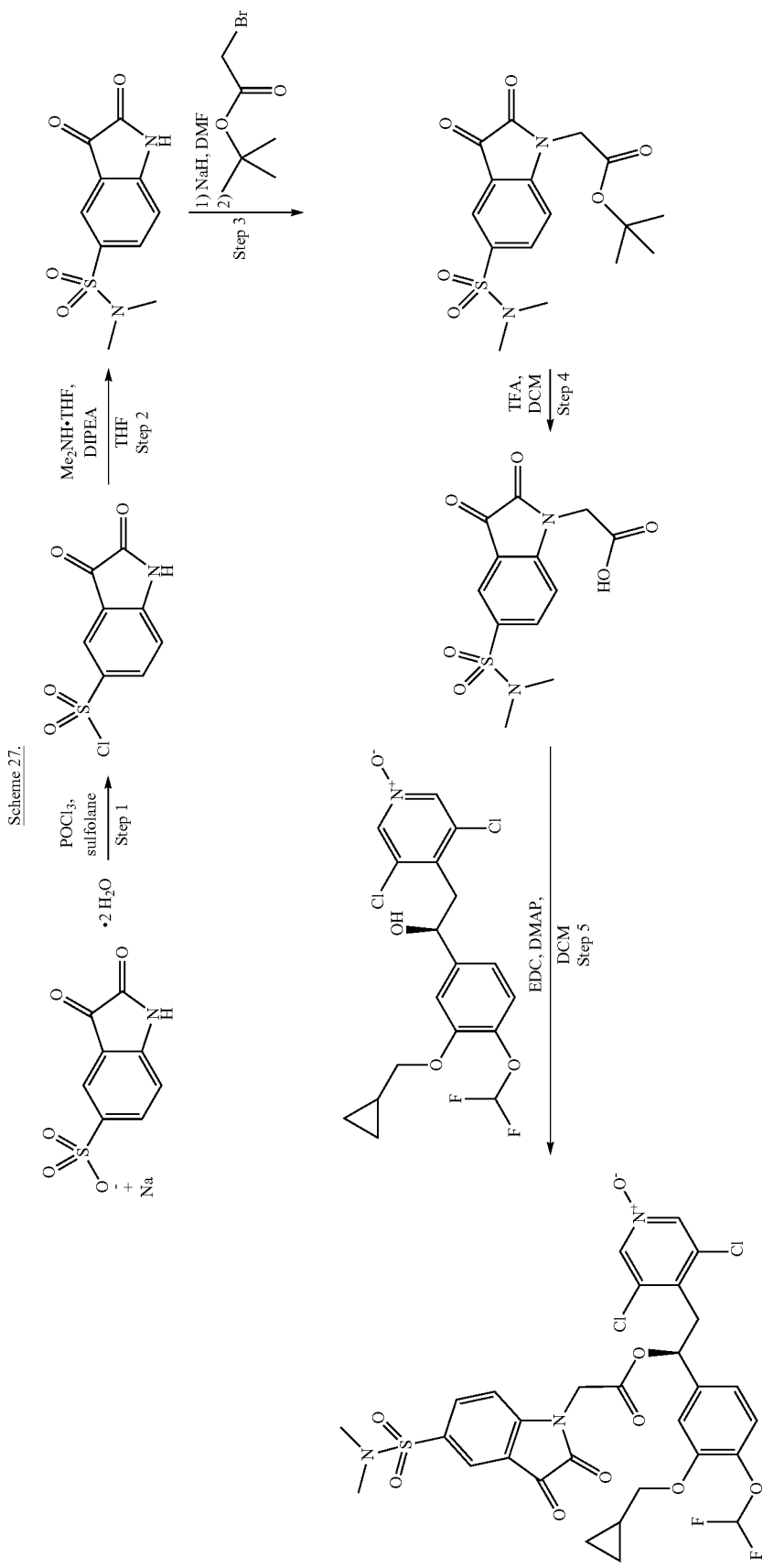

Step 1: Preparation of 2,3-dioxoindoline-5-sulfonyl chloride (147)

A suspension of sodium 2,3-dioxoindoline-5-sulfonate dihydrate (5.0 g, 17.53 mmol) and $POCl_3$ (8.17 ml, 88 mmol) in sulfolane (25 ml, 264 mmol) was heated at 60° C. for 3 hours. The solution was cooled to 0° C. and water (60 ml) was added drop wise; the green precipitate was filtered and washed with a small amount of water. The solid was dissolved in ethyl acetate and washed three times with water; the organic phase was then dried over sodium sulfate and evaporated to give a crude solid that was purified by crystallization from hexane/ethyl acetate 1:1 to give 2,3-dioxoindoline-5-sulfonyl chloride (3.52 g, 14.33 mmol, 82% yield).

Step 2: Preparation of N,N-dimethyl-2,3-dioxoindoline-5-sulfonamide (148)

To a mixture of 2,3-dioxoindoline-5-sulfonyl chloride (0.800 g, 3.26 mmol) in dry THF (10 ml), cooled at 0° C. under nitrogen, DIPEA (1.138 ml, 6.51 mmol) and dimethylamine 2M in THF (2.117 ml, 4.23 mmol) were added, and the mixture was allowed to stir at room temperature for 2.5 hours. The mixture was partitioned between ethyl acetate and water, and the aqueous layer was extracted three times with ethyl acetate. The combined organic layers were dried over sodium sulfate and evaporated to dryness to give N,N-dimethyl-2,3-dioxoindoline-5-sulfonamide (0.639 g, 2.51 mmol, 77% yield). MS/ESI$^+$ 254.9 [MH]$^+$.

Step 3: Preparation of tert-butyl 2-(5-(N,N-dimethylsulfamoyl)-2,3-dioxoindolin-1-yl)acetate (149)

To a solution of N,N-dimethyl-2,3-dioxoindoline-5-sulfonamide (0.639 g, 2.51 mmol) in dry DMF (10 ml), cooled at 0° C. under nitrogen, NaH (60% dispersion in mineral oil, 0.111 g, 2.76 mmol) was added. The mixture turned dark blue. After stirring at 0° C. for 30 minutes, tert-butyl bromoacetate (0.446 ml, 3.02 mmol) was added, and the mixture was stirred at room temperature for 36 hours. The mixture was partitioned between ethyl acetate and brine and the aqueous phase was extracted three times with ethyl acetate. The combined organic layers were dried over sodium sulfate and evaporated to dryness affording tert-butyl 2-(5-(N,N-dimethylsulfamoyl)-2,3-dioxoindolin-1-yl)acetate (0.926 g, 2.51 mmol). MS/ESI$^+$ 368.9 [MH]$^+$.

Step 4: Preparation of 2-(5-(N,N-dimethylsulfamoyl)-2,3-dioxoindolin-1-yl)acetic acid (150)

A solution of tert-butyl 2-(5-(N,N-dimethylsulfamoyl)-2,3-dioxoindolin-1-yl)acetate (0.926 g, 2.51 mmol) and TFA (3 ml, 38.9 mmol) in DCM (10 ml) was stirred at room temperature for 4 hours. The volatiles were removed under vacuum affording 2-(5-(N,N-dimethylsulfamoyl)-2,3-dioxoindolin-1-yl)acetic acid which was used as such in the next step (1.29 g, 4.13 mmol). MS/ESI$^+$ 312.9 [MH]$^+$.

Step 5: Preparation of (S)-3,5-dichloro-4-(2-(3-(cyclopropylmethoxy)-4-(difluoromethoxy)phenyl)-2-(2-(5-(N,N-dimethylsulfamoyl)-2,3-dioxoindolin-1-yl)acetoxy)ethyl)pyridine 1-oxide (151)

A mixture of crude 2-(5-(N,N-dimethylsulfamoyl)-2,3-dioxoindolin-1-yl)acetic acid (0.178 g, 0.57 mmol), (S)-3,5-dichloro-4-(2-(3-(cyclopropylmethoxy)-4-(difluoromethoxy)phenyl)-2-hydroxyethyl)pyridine 1-oxide (0.200 g, 0.476 mmol), EDC (0.274 g, 1.428 mmol) and DMAP (0.029 g, 0.238 mmol) in dry DCM (10 ml) was stirred at room temperature overnight. The mixture was washed with 1N HCl, aqueous 5% $NaHCO_3$ and brine. The organic layer was dried over sodium sulfate and concentrated under vacuum. The crude was purified by silica gel flash chromatography (DCM:MeOH from 99.5:0.5 to 98:2) to give (S)-3,5-dichloro-4-(2-(3-(cyclopropylmethoxy)-4-(difluoromethoxy)phenyl)-2-(2-(5-(N,N-dimethylsulfamoyl)-2,3-dioxoindolin-1-yl)acetoxy)ethyl)pyridine 1-oxide (0.128 g, 0.179 mmol, 37% yield). This product was further purified by crystallization from ethyl acetate/hexane 1/1 to afford (S)-3,5-dichloro-4-(2-(3-(cyclopropylmethoxy)-4-(difluoromethoxy)phenyl)-2-(2-(5-(N,N-dimethyl sulfamoyl)-2,3-dioxoindolin-1-yl)acetoxy)ethyl)pyridine 1-oxide (0.052 g, 0.179 mmol, 15% yield). MS/ESI$^+$ 714.11 [MH]$^+$; $[\alpha_D]=-37.09$, c=0.488; MeOH; $^1$H NMR (300 MHz, CHLOROFORM-d) δ ppm 8.15 (s, 2H), 8.06 (d, 1H), 8.00 (dd, 1H), 7.19 (d, 1H), 6.83-7.01 (m, 2H), 6.74 (d, 1H), 6.67 (t, 1H), 6.13 (dd, 1H), 4.53 (d, 2H), 3.91 (d, 2H), 3.58 (dd, 1H), 3.28 (dd, 1H), 2.79 (s, 6H), 1.09-1.43 (m, 1H), 0.55-0.84 (m, 2H), 0.18-0.52 (m, 2H)

Example 28

(S)-3,5-Dichloro-4-(2-(3-(cyclopropylmethoxy)-4-(difluoromethoxy)-phenyl)-2-(2-(5,6-dimethoxy-1,3-dioxoisoindolin-2-yl)acetoxy)ethyl)pyridine 1-oxide (Compound 156)

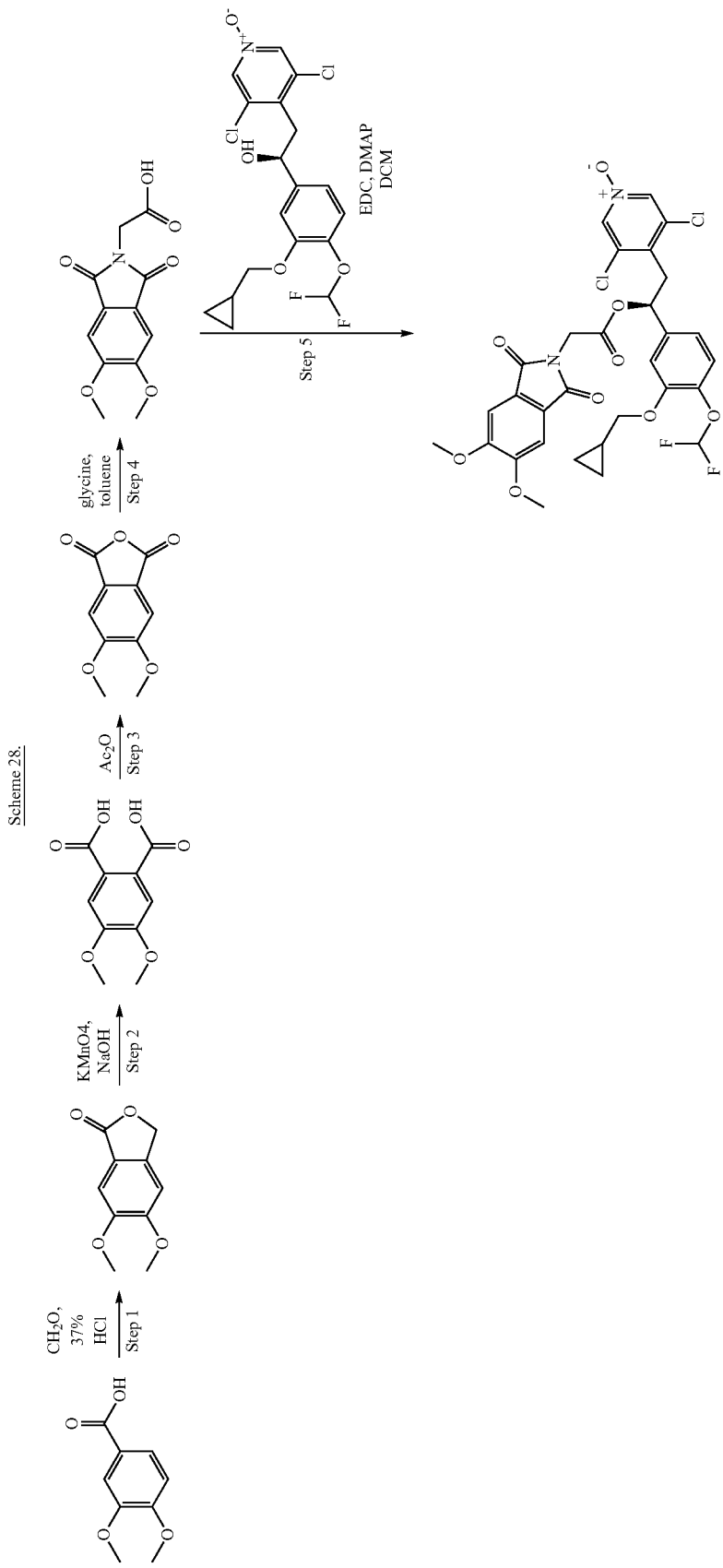

Step 1: Preparation of 5,6-dimethoxyisobenzofuran-1(3H)-one (152)

A suspension of 3,4-dimethoxybenzoic acid (10 g, 54.9 mmol) in aqueous 37% HCl (126 ml, 1522 mmol) and a 37% solution in water of formaldehyde (25 ml, 54.9 mmol) were heated to 90 to 100° C. for 6 hours. Stirring was prolonged overnight at room temperature, and then the obtained insoluble material was removed by filtration. The filtrate was quenched with water (200 ml) and extracted with ethyl acetate (200 ml×3). The combined organic layers were washed with aqueous 1N NaOH (100 ml) and then with brine (2×100 ml). The organic phase was dried over $Na_2SO_4$, filtered and evaporated to dryness. The obtained yellow solid was triturated with ethyl acetate to afford 5,6-dimethoxyisobenzofuran-1(3H)-one as a white solid (3.171 g, 16.33 mmol, 30% yield). MS/ESI$^+$ 195.0 [MH]$^+$.

Step 2: Preparation of 4,5-dimethoxyphthalic acid (153)

5,6-Dimethoxyisobenzofuran-1(3H)-one (3.171 g, 16.33 mmol) was treated with a solution of $KMnO_4$ (2.57 g, 16.26 mmol) and $Na_2CO_3$ (1.542 g, 14.55 mmol) in water (110 ml). The solution was stirred at room temperature for 24 hours, then insoluble material was removed by filtration. The filtrate was cooled with an ice-water bath and acidified with concentrated aqueous HCl. The acidic solution was extracted three times with ethyl acetate (500 ml). The combined organic layers were dried over sodium sulfate and evaporated to dryness to give 600 mg of desired compound. The aqueous phase was then concentrated to 20 ml and a white solid precipitated. After filtration 500 mg desired compound were recovered. The two portions were collected to afford 4,5-dimethoxyphthalic acid as a white powder (1.1 g, 4.87 mmol, 30% yield). MS/ESI$^+$ not detectable [MH]$^+$.

Step 3: Preparation of 5,6-dimethoxyisobenzofuran-1,3-dione (154)

A suspension of 4,5-dimethoxyphthalic acid (600 mg, 2.65 mmol) in acetic anhydride (5 ml) was heated to 120° C. for 1 hour. The solvent was then removed under vacuum to afford 5,6-dimethoxyisobenzofuran-1,3-dione as a yellow solid (552 mg, 2.65 mmol, quantitative yield). MS/ESI$^+$ 208.9 [MH]$^+$. This compound was used as such in the next step.

Step 4: Preparation of 2-(5,6-dimethoxy-1,3-dioxoisoindolin-2-yl)acetic acid (155)

A suspension of 5,6-dimethoxyisobenzofuran-1,3-dione (491 mg, 2.359 mmol) and 2-aminoacetic acid (195 mg, 2.59 mmol) in toluene (10 ml) was heated under MW irradiation at 180° C. for 7 hours. The precipitate was collected by filtration, washed with toluene (5 ml) and dried to afford 2-(5,6-dimethoxy-1,3-dioxoisoindolin-2-yl)acetic acid as a off-white powder (335 mg, 1.263 mmol, 54% yield). MS/ESI$^+$ 265.9 [MH]$^+$.

Step 5: Preparation of (S)-3,5-dichloro-4-(2-(3-(cyclopropylmethoxy)-4-(difluoromethoxy)phenyl)-2-(2-(5,6-dimethoxy-1,3-dioxoisoindolin-2-yl)acetoxy)ethyl)pyridine 1-oxide (156)

To a suspension of 2-(5,6-dimethoxy-1,3-dioxoisoindolin-2-yl)acetic acid (151 mg, 0.571 mmol) in DCM (25 ml), DMAP (69.8 mg, 0.571 mmol), EDC (274 mg, 1.428 mmol) and (S)-3,5-dichloro-4-(2-(3-(cyclopropylmethoxy)-4-(difluoromethoxy)phenyl)-2-hydroxyethyl)pyridine 1-oxide (200 mg, 0.476 mmol) were added in one portion at room temperature, and the resulting mixture was stirred for 4 hours. The solution was diluted with DCM (40 ml) and washed with a saturated solution of $NaHCO_3$ (40 ml), with 1N HCl (30 ml) and finally with brine (30 ml). The organic layer was dried over sodium sulfate, filtered and evaporated to dryness. The crude was purified by crystallization from ethyl acetate (40 ml) to afford (S)-3,5-dichloro-4-(2-(3-(cyclopropylmethoxy)-4-(difluoromethoxy)phenyl)-2-(2-(5,6-dimethoxy-1,3-dioxoisoindolin-2-yl)acetoxy)ethyl)pyridine 1-oxide as a white solid (130 mg, 0.195 mmol, 40.9% yield). MS/ESI$^+$ 667.16 [MH]$^+$; $[\alpha_D]$=−42.80, c=0.25, DCM; $^1$H NMR (300 MHz, DMSO-d$_6$) δ ppm 8.43 (s, 2H), 7.43 (s, 2H), 7.19 (d, 1H), 7.02-7.13 (m, 1H), 6.96 (dd, 1H), 7.08 (t, 1H), 6.01 (dd, 1H), 4.37 (s, 2H), 3.96 (s, 6H), 3.92 (d, 2H), 3.39 (dd, 1H), 3.22 (dd, 1H), 1.12-1.34 (m, 1H), 0.52-0.67 (m, 2H), 0.29-0.46 (m, 2H).

Example 29

(S)-3,5-Dichloro-4-(2-(3-(cyclopropylmethoxy)-4-(difluoromethoxy)-phenyl)-2-(2-(4-(methylsulfonamido)-1,3-dioxoisoindolin-2-yl)acetoxy)-ethyl)pyridine 1-oxide (Compound 162)

145                                                                                         146
Scheme 29.
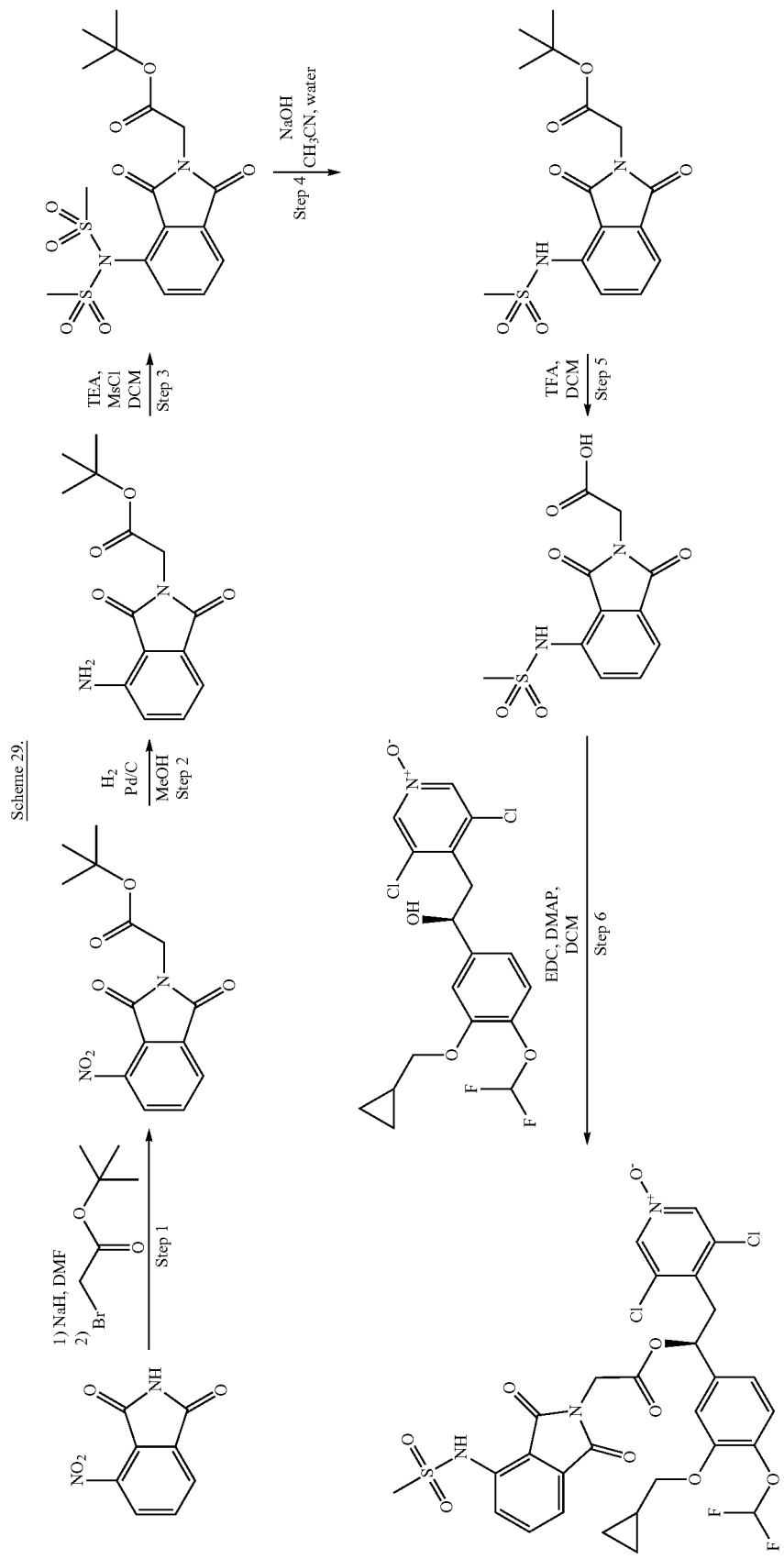

Step 1: Preparation of tert-butyl 2-(4-nitro-1,3-dioxoisoindolin-2-yl)acetate (157)

To a solution of 3-nitrophthalimide (1 g, 5.20 mmol) in dry DMF (35 ml), cooled in an ice bath, NaH (60% w/w dispersion in mineral oil, 0.250 g, 6.25 mmol) was added, followed after 15 minutes by t-butyl bromoacetate (0.845 ml, 5.73 mmol). After stirring for 1 hour at room temperature, the mixture was poured into water and the resulting precipitate was washed with water and with a little amount of Et$_2$O; after drying, tert-butyl 2-(4-nitro-1,3-dioxoisoindolin-2-yl)acetate was obtained (1.44 g, 4.70 mmol, 90% yield, MS/ESI$^+$ 328.9 [MNa]$^+$).

Step 2: Preparation of tert-butyl 2-(4-amino-1,3-dioxoisoindolin-2-yl)acetate (158)

A mixture of tert-butyl 2-(4-nitro-1,3-dioxoisoindolin-2-yl)acetate (1.44 g, 4.70 mmol) and 10% w/w Pd/C (a catalytic amount) in MeOH (150 ml) was hydrogenated in a Parr apparatus at 25 psi for 3 hours. The catalyst was filtered off and the filtrate was evaporated; the residue was purified by a quick flash chromatography on silica gel (Hexane/EtOAc 1/1) to obtain tert-butyl 2-(4-amino-1,3-dioxoisoindolin-2-yl)acetate (712 mg, 2.58 mmol, 54.8% yield, MS/ESI$^+$ 299.0 [MNa]$^+$).

Step 3: Preparation of tert-butyl 2-(4-(N-(methylsulfonyl)-methylsulfonamido)-1,3-dioxoisoindolin-2-yl)acetate (159)

A mixture of tert-butyl 2-(4-amino-1,3-dioxoisoindolin-2-yl)acetate (712 mg, 2.58 mmol), triethylamine (1029 μl, 7.73 mmol) and methanesulfonyl chloride (602 μl, 7.73 mmol) in 20 ml of DCM was stirred overnight at room temperature. The mixture was washed with 1N HCl, brine and finally dried over sodium sulfate and evaporated; the residue was purified by flash chromatography (Hexane/EtOAc 3/1 to 1/1) yielding tert-butyl 2-(4-(N-(methylsulfonyl)methylsulfonamido)-1,3-dioxoisoindolin-2-yl)acetate as an off-white foam (0.96 g, 2.220 mmol, 86% yield, MS/ESI$^+$ 454.8 [MNa]$^+$) and used in the following reaction without further purification.

Step 4: Preparation of tert-butyl 2-(4-(methylsulfonamido)-1,3-dioxoisoindolin-2-yl)acetate (160)

To a solution of tert-butyl 2-(4-(N-(methylsulfonyl)methylsulfonamido)-1,3-dioxoisoindolin-2-yl)acetate (548 mg, 1.267 mmol) in MeCN (5 ml), aqueous 2N NaOH (1457 μl, 2.91 mmol) was added, and the mixture was stirred at room temperature for 24 hours. The solvent was evaporated and the residue was diluted with water, acidified and extracted twice with ethyl acetate; the organic phase was washed with brine, dried over sodium sulfate and evaporated. The residue was purified by flash chromatography on silica gel (EtOAc/hexane 8/2) to obtain tert-butyl 2-(4-(methylsulfonamido)-1,3-dioxoisoindolin-2-yl)acetate as an off-white solid (196 mg, 0.553 mmol, 43.6% yield, MS/ESI$^+$ 376.8 [MNa]$^+$).

Step 5: Preparation of 2-(4-(methylsulfonamido)-1,3-dioxoisoindolin-2-yl)acetic acid (161)

A mixture of tert-butyl 2-(4-(methylsulfonamido)-1,3-dioxoisoindolin-2-yl)acetate (85 mg, 0.240 mmol) and TFA (370 μl, 4.80 mmol) in 5 ml of DCM was stirred at room temperature overnight. The mixture was evaporated to obtain 2-(4-(methylsulfonamido)-1,3-dioxoisoindolin-2-yl)acetic acid (72 mg, 0.240 mmol, 100% yield, MS/ESI$^+$ 298.9 [MH]$^+$) and used as such in the following reaction without further purification.

Step 6: Preparation of (S)-3,5-dichloro-4-(2-(3-(cyclopropylmethoxy)-4-(difluoromethoxy)phenyl)-2-(2-(4-(methylsulfonamido)-1,3-dioxoisoindolin-2-yl)acetoxy)ethyl)pyridine 1-oxide (162)

A mixture of 2-(4-(methylsulfonamido)-1,3-dioxoisoindolin-2-yl)acetic acid (78 mg, 0.262 mmol), (S)-3,5-dichloro-4-(2-(3-(cyclopropylmethoxy)-4-(difluoromethoxy)-phenyl)-2-hydroxyethyl)pyridine 1-oxide (110 mg, 0.262 mmol), DMAP (15.97 mg, 0.131 mmol) and EDC (125 mg, 0.654 mmol) in 15 ml of THF was stirred at room temperature for 2 days. The mixture was diluted with water, acidified and extracted twice with EtOAc; the organic layer was then washed with brine, dried over sodium sulfate and evaporated. The residue was triturated with methanol and the title compound was obtained as a pale yellow solid (39 mg, 0.056 mmol, 21.29% yield, MS/ESI$^+$ 700.11 [MH]$^+$, [α$_D$]=−63.94, c=0.355 in DCM). $^1$H NMR (300 MHz, DMSO-d$_6$) δ ppm 9.29 (br. s., 1H), 8.47 (s, 2H), 7.86 (dd, 1H), 7.81 (dd, 1H), 7.63 (dd, 1H), 7.19 (d, 1H), 7.10 (d, 1H), 6.97 (dd, 1H), 7.08 (t, 1H), 6.02 (dd, 1H), 4.46 (d, 1H), 4.38 (d, 1H), 3.93 (d, 2H), 3.41 (dd, 1H), 3.30 (s, 3H), 3.24 (dd, 1H), 1.10-1.31 (m, 1H), 0.48-0.66 (m, 2H), 0.27-0.48 (m, 2H)

Example 30

(S)-3,5-Dichloro-4-(2-(3-(cyclopropylmethoxy)-4-(difluoromethoxy)phenyl)-2-(2-(5-(methylsulfonamido)-1,3-dioxoisoindolin-2-yl)acetoxy)-ethyl)pyridine 1-oxide (Compound 167)

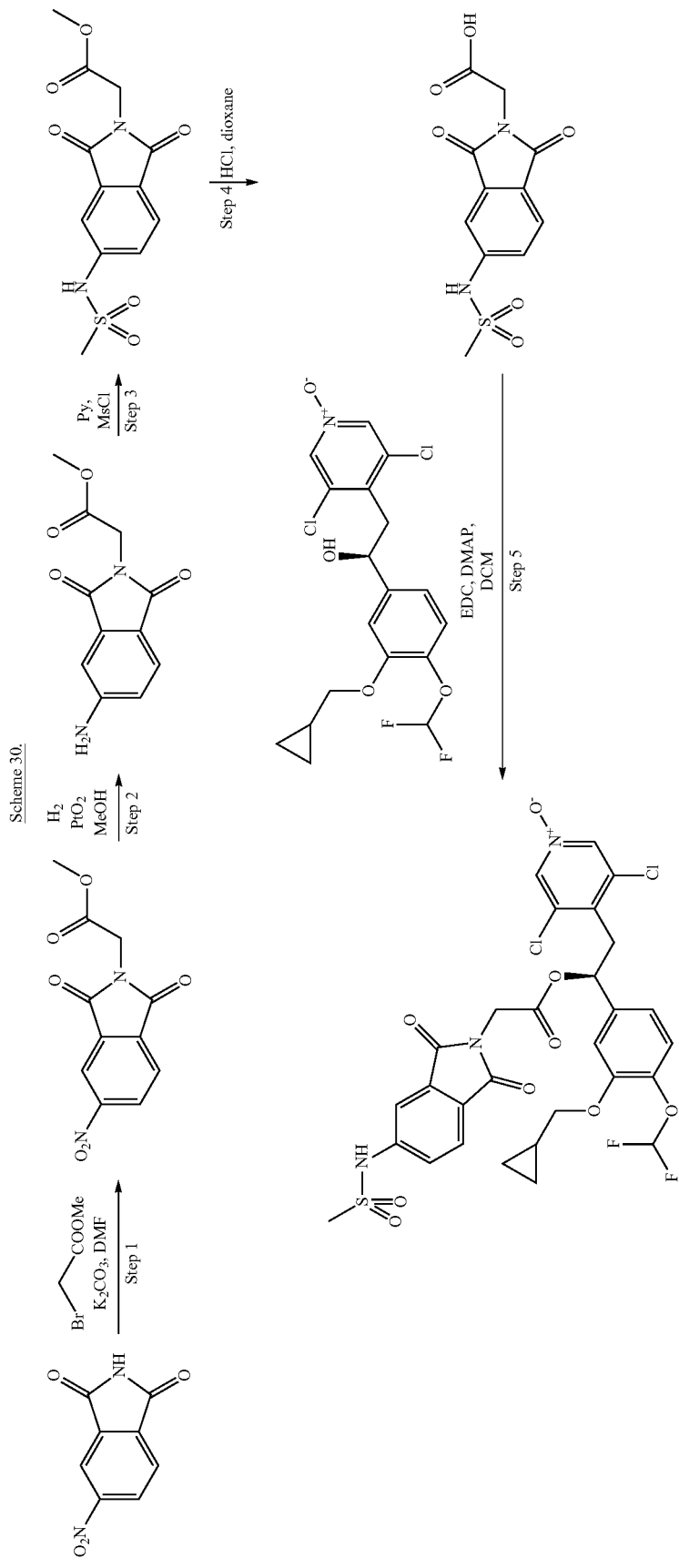
Scheme 30.

Step 1: Preparation of methyl 2-(5-nitro-1,3-dioxoisoindolin-2-yl)acetate (163)

To a solution of 5-nitroisoindoline-1,3-dione (2 g, 10.41 mmol) in DMF (10 ml), $K_2CO_3$ (1.439 g, 10.41 mmol) and methyl 2-bromoacetate (1.930 ml, 20.82 mmol) were added, and the mixture was reacted under MW irradiation for 2 hr at 140° C. Then the solid $K_2CO_3$ was filtered off, the solvent was evaporated and the resulting crude was triturated with EtOH obtaining the title compound as a pale brown solid (1.8 g, 6.82 mmol, 65.5% yield, UPLC-MS purity 90%, MS/ESI$^+$ 265.1 [MH]$^+$) which was used without any additional purification.

Step 2: Preparation of methyl methyl 2-(5-amino-1,3-dioxoisoindolin-2-yl)acetate (164)

To a solution of methyl 2-(5-nitro-1,3-dioxoisoindolin-2-yl)acetate (500 mg, 1.893 mmol) in MeOH (10 ml) a catalytic amount of $PtO_2$ was added and the mixture was reacted under $H_2$ atmosphere (15 psi) in a Parr apparatus for 15 minutes. The catalyst was filtered off and after evaporation of the solvent, the desired product was obtained as a yellow solid (380 mg, 1.62 mmol, 86% yield, MS/ESI$^+$ 235.0 [MH]$^+$) and was used in the next step without any additional purification.

Step 3: Preparation of methyl 2-(5-(methylsulfonamido)-1,3-dioxoisoindolin-2-yl)acetate (165)

To a solution of methyl 2-(5-amino-1,3-dioxoisoindolin-2-yl)acetate (380 mg, 1.622 mmol) in pyridine (10 ml), methanesulfonyl chloride (190 µl, 2.434 mmol) was added, and the mixture was reacted overnight at room temperature. The solvent was evaporated and the resulting crude was partitioned between 1N HCl (10 ml) and EtOAc (10 ml); aqueous phase was extracted with EtOAc (3×20 ml) and the organic phase was dried over sodium sulfate. The solvent was removed affording title compound as a brown solid (550 mg, MS/ESI$^+$ 312.9 [MH]$^+$). It was used in the next step without any additional purification.

Step 4: Preparation of 2-(5-(methylsulfonamido)-1,3-dioxoisoindolin-2-yl)acetic acid (166)

To a solution of methyl 2-(5-(methylsulfonamido)-1,3-dioxoisoindolin-2-yl)acetate (obtained as described in Example 30, Step 3, theoretical amount 1.622 mmol) in dioxane (10 ml), a 36% solution of HCl in water (10 ml) was added, and the mixture was stirred for 3 hours at room temperature. The volatiles were evaporated and the resulting crude was purified by flash chromatography on silica gel (eluent: DCM/MeOH 95:5). The title compound was obtained as a pale yellow solid (230 mg, 0.772 mmol, 47.6% yield over 2 steps, MS/ESI$^+$ 299.1 [MH]$^+$).

Step 5: Preparation of (S)-3,5-dichloro-4-(2-(3-(cyclopropylmethoxy)-4-(difluoromethoxy)phenyl)-2-(2-(5-(methylsulfonamido)-1,3-dioxoisoindolin-2-yl)acetoxy)ethyl)pyridine 1-oxide (167)

To a solution of 2-(5-(methylsulfonamido)-1,3-dioxoisoindolin-2-yl)acetic acid (130 mg, 0.436 mmol) in DCM (10 ml), (S)-3,5-dichloro-4-(2-(3-(cyclopropylmethoxy)-4-(difluoromethoxy)phenyl)-2-hydroxyethyl)pyridine 1-oxide (183 mg, 0.436 mmol), EDC (251 mg, 1.308 mmol) and DMAP (26.6 mg, 0.218 mmol) were added, and the mixture was reacted at room temperature overnight. The solvent was evaporated and the resulting crude was partitioned between 1N HCl (10 ml) and EtOAc (10 ml). The desired compound was extracted with EtOAc (3×20 ml), the organic phase was dried over sodium sulfate and evaporated to dryness. The resulting crude was purified by trituration with MeOH obtaining (111 mg, 0.158 mmol, 36% yield). MS/ESI$^+$ 700.14 [MH]$^+$; [α$_D$]=−70.16, c=0.25 in DCM; $^1$H NMR (300 MHz, DMSO-d$_6$) δ ppm 10.68 (br. s., 1H) 8.45 (s, 2H) 7.88 (d, 1H) 7.64 (d, 1H) 7.58 (dd, 1H) 7.19 (d, 1H) 7.06-7.09 (m, 1H) 6.96 (dd, 1H) 7.08 (t, 1H) 6.01 (dd, 1H) 4.43 (d, 1H) 4.37 (d, 1H) 3.93 (d, 2H) 3.40 (dd, 1H) 3.23-3.27 (m, 1H) 3.20 (s, 3H) 1.15-1.31 (m, 1H) 0.53-0.65 (m, 2H) 0.32-0.42 (m, 2H)

Example 31

(S)-3,5-Dichloro-4-(2-(3-(cyclopropylmethoxy)-4-(difluoromethoxy)phenyl)-2-(2-(5-(hydroxyamino)-1,3-dioxoisoindolin-2-yl)acetoxy)ethyl)pyridine 1-oxide (Compound 169)

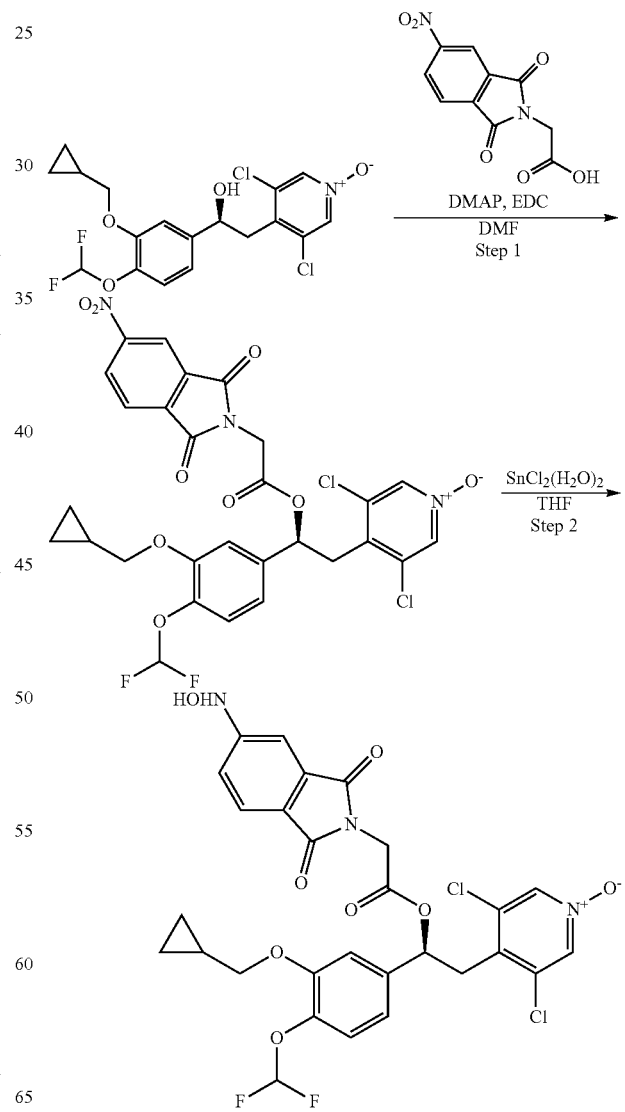

Scheme 31.

Step 1. Preparation of (S)-3,5-dichloro-4-(2-(3-(cyclopropylmethoxy)-4-(difluoromethoxy)phenyl)-2-(2-(5-nitro-1,3-dioxoisoindolin-2-yl)acetoxy)-ethyl)pyridine 1-oxide (168)

(S)-3,5-dichloro-4-(2-(3-(cyclopropylmethoxy)-4-(difluoromethoxy)phenyl)-2-hydroxyethyl)pyridine 1-oxide (100 mg, 0.238 mmol) was placed in a 50 ml round bottom flask and dissolved in DMF (3 ml), and 2-(4-nitro-1,3-dioxoisoindolin-2-yl)acetic acid (60 mg, 0.238 mmol) and EDC (45.6 mg, 0.238 mmol) were added to it followed by DMAP (29.1 mg, 0.238 mmol). The reaction was stirred at RT for 6 hours by adding 30 ml of HCl/H2O (1M) and extracted with EtOAc (30 ml). The organic phase (EtOAc) was extracted with HCl/H2O (1M; 30 ml; ×3) and subsequently with K2CO3/H2O (15% w/w; 20 ml; ×3) by using a 100 ml extracting funnel. The resulting organic extract was dried over Na2SO4, filtered on a filter paper, and the solvent removed under vacuum. The oil residue was purified by preparative HPLC (Method 2) to yield 120 mg of title compound (0.184 mmol, 77% yield)

Step 2. Preparation of (S)-3,5-dichloro-4-(2-(3-(cyclopropylmethoxy)-4-(difluoromethoxy)phenyl)-2-(2-(5-(hydroxyamino)-1,3-dioxoisoindolin-2-yl)acetoxy)ethyl)pyridine 1-oxide (169)

(S)-3,5-dichloro-4-(2-(3-(cyclopropylmethoxy)-4-(difluoromethoxy)phenyl)-2-(2-(5-nitro-1,3- dioxoisoindolin-2-yl)acetoxy)ethyl)pyridine 1-oxide (60 mg, 0.092 mmol) was dissolved in THF (5 ml), and added with tin(II) chloride dihydrate (25.0 mg, 0.111 mmol). The reaction was stirred at RT for 18 hours. THF was evaporated under vacuum at RT, and the residue quenched by addition of K2CO3/H2O (15% w/w; 50 ml) and extracted with EtOAc (50 ml). The organic phase was extracted with $K_2CO_3/H_2O$ (15% w/w) (×3), dried over $Na_2SO_4$ and the solvent removed under reduced pressure to yield the title compound (35.0 mg, 0.055 mmol, 60% yield). $^1$H NMR (400 MHz, acetone) ppm 8.80 (bs, 1H), 8.32 (bs, 1H), 8.18 (s, 2H), 7.70 (d, J=8.38 Hz, 1H), 7.36 (d, J=1.76 Hz, 1H), 7.28 (dd, J=8.16, 1.98 Hz, 1H), 7.15-7.23 (m, 2H), 7.03 (dd, J=8.38, 1.76 Hz, 1H), 6.93 (t, 1H, CHF2), 6.13 (dd, J=9.48, 4.63 Hz, 1H), 4.39 (s, 2H), 4.00 (dd, J=7.06, 3.09 Hz, 2H), 3.51 (dd, J=14.33, 9.48 Hz, 1H), 3.31 (dd, J=14.11, 4.41 Hz, 1H), 1.24-1.36 (m, 1H), 0.53-0.71 (m, 2H), 0.31-0.49 (m, 2H). MS/ESI$^+$ [MH]$^+$=637.9

The compound listed in Table 11 was prepared with analogous synthetic steps and procedures to that described in Example 31, by reacting the appropriate precursors (commercially available or synthesized by a person skilled in the art) with suitable reagents. Specific variations in the experimentals or purification methods are indicated in the table.

TABLE 11

| Entry | Structure | NMR characterization | MS/ESI$^+$ [MH]$^+$ | Purification and yield | Starting material (precursor) |
|---|---|---|---|---|---|
| 170 | 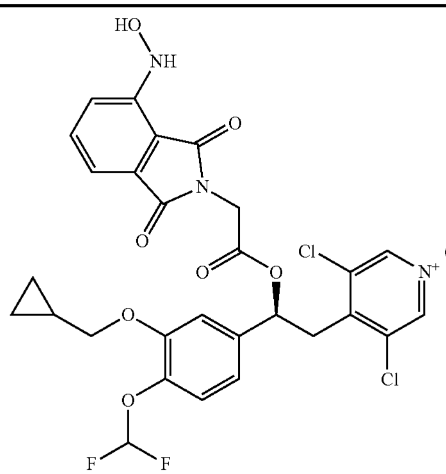 | $^1$H NMR (400 MHz, acetone) δ ppm 8.60 (bs, 1H), 8.41-8.53 (bs, 1H), 8.17 (s, 2H), 7.69-7.81 (m, 1H), 7.57 (d, J = 8.38Hz, 1H), 7.26-7.34 (m, 1H), 7.19 (m, 2H), 7.05 (dd, J = 8.16, 1.98 Hz, 1H), 6.93 (t, J = 75.00 Hz, 1H), 6.14 (dd, J = 9.92, 4.63Hz, 1H), 4.26-4.45 (m, 2H), 4.00 (dd, J = 6.84, 1.54 Hz, 2H), 3.52 (dd, J = 14.33, 9.92 Hz, 1H), 3.31 (dd, J = 14.11, 4.41 Hz, 1H), 1.25-1.37 (m, 1H), 0.53-0.69 (m, 2H), 0.35-0.45 (m, 2H). | 637.9 | Yield 38% | |

Example 32

(S)-3,5-Dichloro-4-(2-(3-(cyclopropylmethoxy)-4-(difluoromethoxy)-phenyl)-2-(2-(5-nitro-1,3-dioxoisoindolin-2-yl)acetoxy)ethyl)pyridine 1-oxide (Compound 171), (S)-4-(2-(2-(4-Amino-1,3-dioxoisoindolin-2-yl)acetoxy)-2-(3-(cyclopropylmethoxy)-4-(difluoromethoxy)phenyl)ethyl)-3,5-dichloropyridine 1-oxide (Compound 172) and (S)-3,5-Dichloro-4-(2-(3-(cyclopropylmethoxy)-4-(difluoromethoxy)phenyl)-2-(2-(4-(2-methoxyacetamido)-1,3-dioxoisoindolin-2-yl)acetoxy)ethyl)pyridine 1-oxide (Compound 173)

Scheme 32.
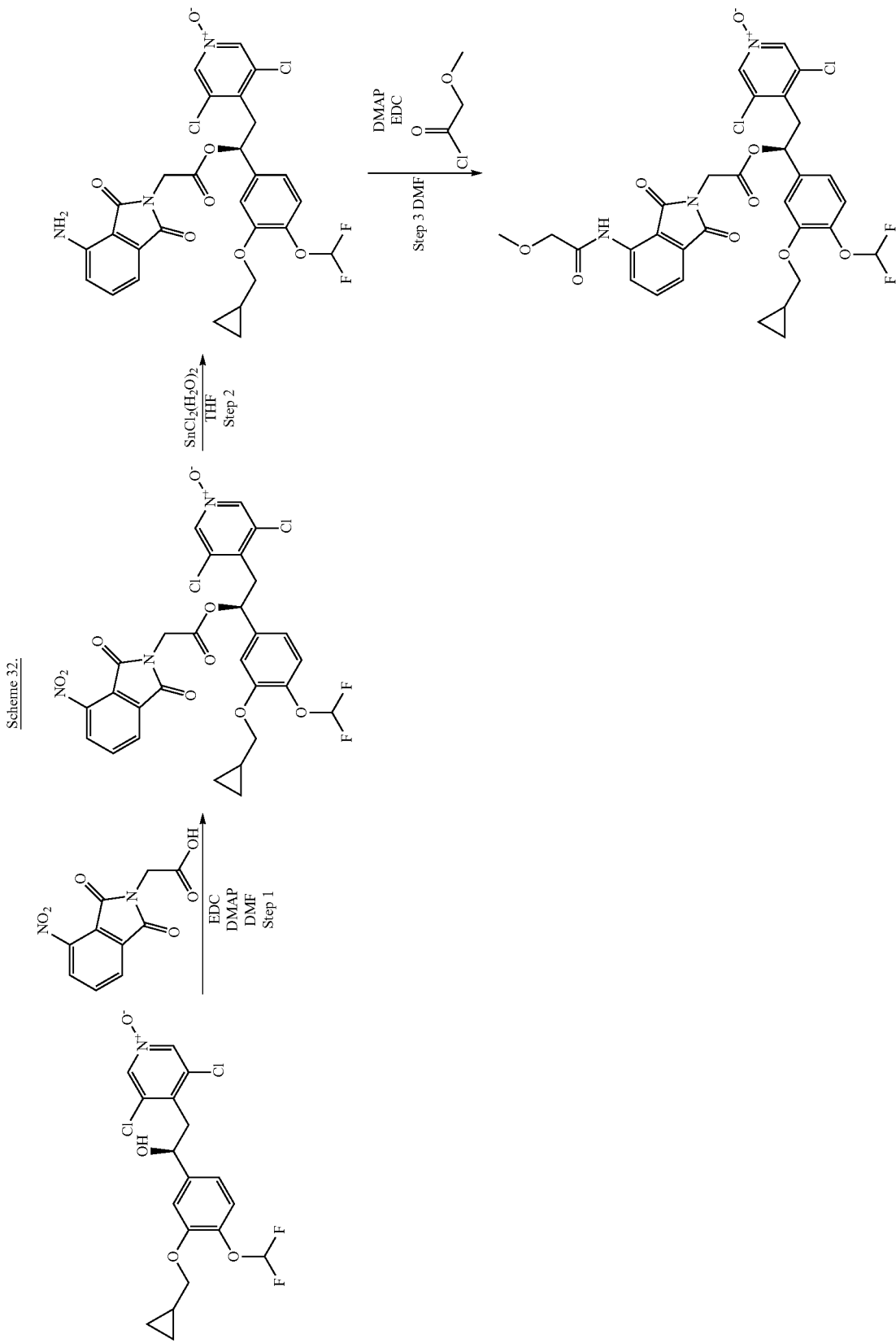

Step 1. Preparation of (S)-3,5-dichloro-4-(2-(3-(cyclopropylmethoxy)-4-(difluoromethoxy)phenyl)-2-(2-(5-nitro-1,3-dioxoisoindolin-2yl)acetoxy)ethyl)pyridine 1-oxide (171)

(S)-3,5-dichloro-4-(2-(3-(cyclopropylmethoxy)-4-(difluoromethoxy)phenyl)-2-hydroxyethyl)pyridine 1-oxide (100 mg, 0.238 mmol) was placed in a 50 ml round bottom flask and dissolved in DMF (3 ml), EDC (45.6 mg, 0.238 mmol), and 2-(5-nitro-1,3-dioxoisoindolin-2-yl)acetic acid (60 mg, 0.238 mmol) were added to it followed by DMAP (29.1 mg, 0.238 mmol). The reaction was stirred at RT for 6 hours. The reaction was quenched by adding 30 ml of HCl/H₂O (1M) and extracted with EtOAc (30 ml). The organic phase (EtOAc) was extracted with HCl/H₂O (1M; 30 ml; ×3) and subsequently with K₂CO₃/H₂O (15% w/w; 20 ml; ×3) by using a 100 ml extracting funnel. The resulting organic extract was dried over Na₂SO₄ (0.5 g), filtered on a filter paper, and the solvent removed under reduced pressure. The oil residue was purified by preparative HPLC (Method 2) to yield 120 mg of desired product (yield=77%). ¹H NMR (400 MHz, acetone) δ ppm 8.35 (d, J=7.50 Hz, 1H), 8.24-8.30 (m, 1H), 8.16-8.24 (m, 3H), 7.16-7.25 (m, 2H), 7.05 (dd, J=8.16, 1.98 Hz, 1H), 6.94 (t, 1H, CHF2), 6.14 (dd, J=9.48, 4.63 Hz, 1H), 4.52 (s, 2H), 4.01 (dd, J=6.62, 3.97 Hz, 2H), 3.54 (dd, J=14.33, 9.48 Hz, 1H), 3.26-3.40 (m, 1H), 1.25-1.38 (m, 1H), 0.56-0.73 (m, 2H), 0.36-0.48 (m, 2H). MS/ESI⁺ [MH]⁺=652.1

Step 2. Preparation of (S)-4-(2-(2-(4-amino-1,3-dioxoisoindolin-2-yl)acetoxy)-2-(3-(cyclopropylmethoxy)-4-(difluoromethoxy)phenyl)ethyl)-3,5-dichloropyridine 1-oxide (172)

(S)-3,5-dichloro-4-(2-(3-(cyclopropylmethoxy)-4-(difluoromethoxy)phenyl)-2-(2-(5-nitro-1,3-dioxoisoindolin-2-yl)acetoxy)ethyl)pyridine 1-oxide (80 mg, 0.123 mmol) was dissolved in THF (10 ml), and added with tin(II) chloride dihydrate (80.0 mg, 0.355 mmol). The reaction was stirred at RT for 3 days. The reaction was quenched by addition of K₂CO₃/H₂O (15% w/w; 50 ml). The solid precipitated was filtered on paper, and the solution extracted with EtOAc (50 ml). The organic phase was washed with K₂CO₃/H₂O conc. (×3), dried over Na₂SO₄ and the solvent removed to yield the titled compound (50.0 mg) as yellow oil (yield=66%). ¹H NMR (400 MHz, acetone) ppm 8.20 (s, 2H), 7.50 (d, J=7.50 Hz, 1H), 7.14-7.24 (m, 2H), 7.01-7.13 (m, 3H), 6.92 (t, J=75.00 Hz, 1H), 6.17 (dd, J=9.48, 5.07 Hz, 3H), 4.37 (d, J=7.50 Hz, 2H), 4.00 (dd, J=7.06, 3.09 Hz, 2H), 3.53 (m, 1H), 3.34 (d, J=4.41 Hz, 1H), 1.30 (br. s., 2H), 0.56-0.68 (m, 2H), 0.41 (d, J=4.41 Hz, 2H). MS/ESI⁺ [MH]⁺=608.39.

Step 3. Preparation of (S)-3,5-dichloro-4-(2-(3-(cyclopropylmethoxy)-4-(difluoromethoxy)phenyl)-2-(2-(4-(2-methoxyacetamido)-1,3-dioxoisoindolin-2-yl)acetoxy)ethyl)pyridine 1-oxide (173)

(S)-4-(2-(2-(4-amino-1,3-dioxoisoindolin-2-yl)acetoxy)-2-(3-(cyclopropylmethoxy)-4 (difluoromethoxy)phenyl) ethyl)-3,5-dichloropyridine 1-oxide (20.0 mg; 0.032 mmol) was dissolved in DMF (2 ml) and cooled down to 0° C. in a ice bath. 2-methoxyacetyl chloride (20.0 mg; 0.184 mmol) and DMAP (0.048 mmol; 5.89 mg) were added to the reaction solution that was stirred a 0° C. for 2 hours. After that time, the reaction was quenched with aqueous HCl (1M) (20 ml) and extracted with EtOAc (20 ml). The organic phase was further washed with HCl (1M) (3×20 ml), dried over Na₂SO₄ and the solvent removed under reduced pressure to afford the titled compound (15.0 mg; 67% yield). ¹H NMR (400 MHz, acetone) δ ppm 10.33-10.47 (m, 1H), 8.80-8.93 (m, 1H), 8.22 (s, 2H), 7.83-7.95 (m, 1H), 7.57-7.67 (m, 1H), 7.16-7.24 (m, 2H), 7.04-7.11 (m, 1H), 6.94 (t, J=75.00 Hz, 1H), 6.13-6.22 (m, 1H), 4.46 (s, 2H), 4.14 (d, J=3.09 Hz, 2H), 3.91-4.06 (m, 2H), 3.65 (s, 3H), 3.49-3.58 (m, 1H), 3.26-3.38 (m, 1H), 1.17-1.39 (m, 1H), 0.54-0.69 (m, 2H), 0.36-0.48 (m, 2H). MS/ESI⁺ [MH]⁺=694.1.

Example 33

(S)-3,5-Dichloro-4-(2-(3-(cyclopropylmethoxy)-4-(difluoromethoxy)-phenyl)-2-(2-(4-(N-(2-morpholinoethyl)methylsulfonamido)-1,3-dioxoisoindolin-2-yl)acetoxy)ethyl)pyridine 1-oxide 2,2,2-trifluoroacetic acid salt (Compound 176)

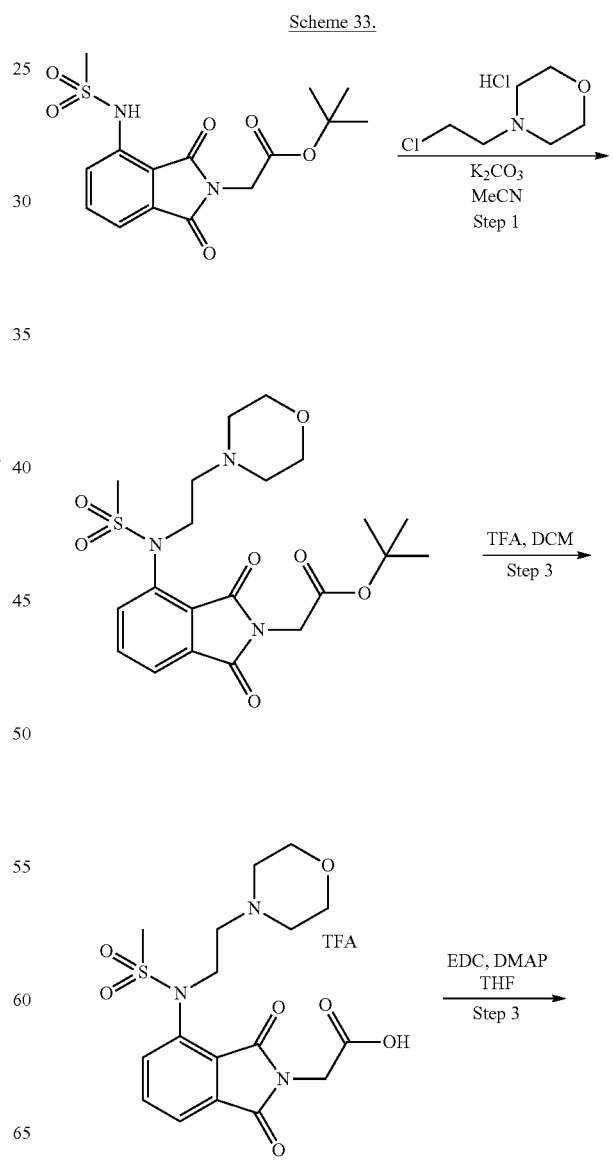

Scheme 33.

-continued

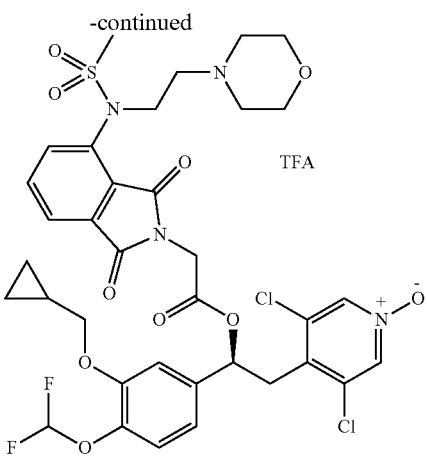

Step 1: Preparation of tert-butyl 2-(4-(N-(2-morpholinoethyl)-methylsulfonamido)-1,3-dioxoisoindolin-2-yl)acetate (174)

A mixture of tert-butyl 2-(4-(methylsulfonamido)-1,3-dioxoisoindolin-2-yl)acetate (196 mg, 0.553 mmol) (prepared with an analogous procedure to that described in, Example 29, Scheme 29, Steps 1, 2, 3, 4 for the preparation of Compound 160), 4-(2-chloroethyl)morpholine hydrochloride (108 mg, 0.581 mmol), and $K_2CO_3$ (168 mg, 1.217 mmol) in acetonitrile (10 ml) was stirred at 75° C. overnight. The solvent was removed under vacuum, and the residue was taken up in a EtOAc/DCM/Et2O mixture and filtered through Na2SO4 to remove the inorganic salts. After evaporation of the solvent, tert-butyl 2-(4-(N-(2-morpholinoethyl)methylsulfonamido)-1,3-dioxoisoindolin-2-yl)acetate was obtained (256 mg, 0.548 mmol, 99% yield, MS/ESI+ 467 [MH]+).

Step 2: Preparation of 2-(4-(N-(2-morpholinoethyl)methylsulfonamido)-1,3-dioxoisoindolin-2-yl)acetic acid 2,2,2-trifluoroacetic acid salt (175)

A mixture of tert-butyl 2-(4-(N-(2-morpholinoethyl)methylsulfonamido)-1,3-dioxoisoindolin-2-yl)acetate (256 mg, 0.548 mmol) and TFA (844 µl, 10.95 mmol) in DCM (5 ml) was stirred at room temperature for 48 hours. The mixture was evaporated and so obtained crude of 2-(4-(N-(2-morpholinoethyl)-methylsulfonamido)-1,3-dioxoisoindolin-2-yl)acetic acid 2,2,2-trifluoroacetic acid salt (MS/ESI+ 412 [MH]+) was used as such in the following reaction.

Step 3: Preparation of (S)-3,5-dichloro-4-(2-(3-(cyclopropylmethoxy)-4-(difluoromethoxy)phenyl)-2-(2-(4-(N-(2-morpholinoethyl)methylsulfonamido)-1,3-dioxoisoindolin-2-yl)acetoxy)ethyl)pyridine 1-oxide 2,2,2-trifluoroacetic acid salt (176)

A mixture of crude 2-(4-(N-(2-morpholinoethyl)methylsulfonamido)-1,3-dioxoisoindolin-2-yl)acetic acid 2,2,2-trifluoroacetic acid salt (−) (obtained as described in Example 33, Step 2, theoretical amount 0.548 mmol), (S)-3,5-dichloro-4-(2-(3-(cyclopropylmethoxy)-4-(difluoromethoxy)phenyl)-2-hydroxyethyl)pyridine 1-oxide (192 mg, 0.457 mmol), EDC (219 mg, 1.142 mmol), and DMAP (84 mg, 0.685 mmol) in dry THF (15 ml) was stirred at room temperature overnight. Additional EDC (175 mg, 0.917 mmol), DMAP (83.7, 0.685 mmol) and (S)-3,5-dichloro-4-(2-(3-(cyclopropylmethoxy)-4-(difluoromethoxy)phenyl)-2-hydroxyethyl)pyridine 1-oxide (57.6 mg, 0.137 mmol) were added over 24 hours, then the mixture was diluted with DCM (10 ml) and heated to 70° C. for 7 hours. The mixture was diluted with EtOAc, washed with 1N HCl and brine, then dried over sodium sulfate and evaporated. The residue was purified by preparative HPLC (Method 1) to obtain (S)-3,5-dichloro-4-(2-(3-(cyclopropylmethoxy)-4-(difluoromethoxy)phenyl)-2-(2-(4-(N-(2-morpholinoethyl)-methylsulfonamido)-1,3-dioxoisoindolin-2-yl)acetoxy)ethyl) pyridine 1-oxide 2,2,2-trifluoroacetate (204 mg, 0.220 mmol, 48% yield, MS/ESI+ 813.34 [MH]+, $[\alpha_D]$=−51.5, c=0.465 in DCM). $^1$H NMR (300 MHz, DMSO-$d_6$) δ ppm 9.38 (br. s., 1H) 8.54 (s, 2H) 7.91-8.05 (m, 2H) 7.81-7.91 (m, 1H) 7.22 (d, 1H) 7.15 (d, 1H) 7.02 (dd, 1H) 7.08 (t, 1H) 6.09 (dd, 1H) 4.57 (d, 1H) 4.33 (d, 1H) 3.95 (d, 2H) 3.83-4.24 (m, 8H) 3.47 (dd, 1H) 3.27 (dd, 1H) 3.14 (s, 3H) 2.99-3.53 (m, 4H) 1.21-1.28 (m, 1H) 0.52-0.68 (m, 2H) 0.28-0.45 (m, 2H).

Example 34

(S)-3,5-Dichloro-4-(2-(3-(cyclopropylmethoxy)-4-(difluoromethoxy)-phenyl)-2-(2-(5-(N-(2-morpholinoethyl)methylsulfonamido)-1,3-dioxoisoindolin-2-yl)acetoxy)ethyl)pyridine 1-oxide 2,2,2 trifluoroacetic acid salt (Compound 182)

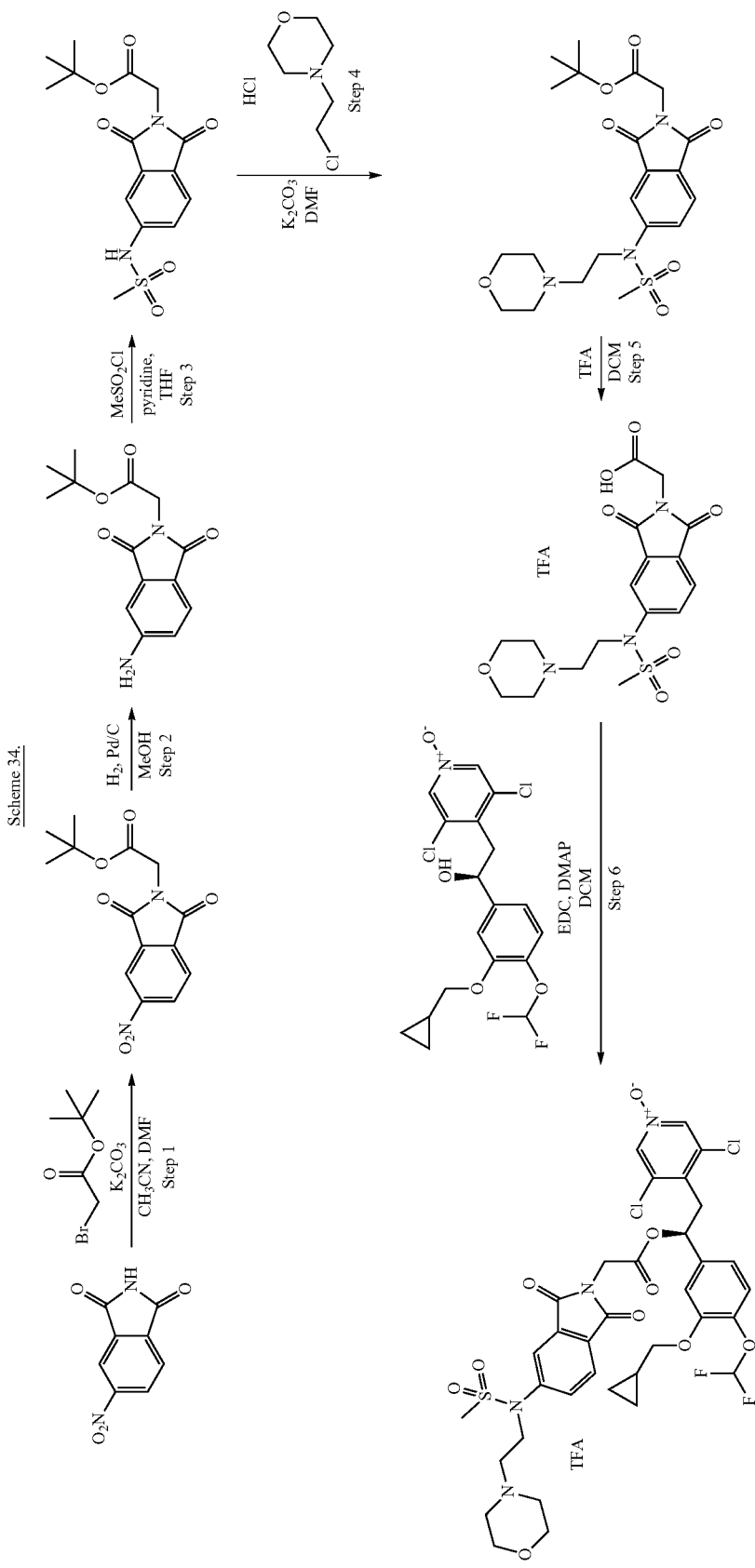

Step 1: Preparation of tert-butyl 2-(5-nitro-1,3-dioxoisoindolin-2-yl)acetate (177)

To a solution of 5-nitroisoindoline-1,3-dione (10.5 g, 53.6 mmol) in a mixture of acetonitrile (80 ml) and DMF (20 ml), potassium carbonate (9.99 g, 72.3 mmol) and tert-butyl 2-bromoacetate (10.29 ml, 69.6 mmol) were added, and the reaction was heated to reflux for 3 hours. The insoluble inorganic salts were filtered off, and the filtrate was evaporated to dryness. The residue was diluted with EtOH (60 ml) and precipitation of the desired product was observed. The precipitate was collected by filtration affording tert-butyl 2-(5-nitro-1,3-dioxoisoindolin-2-yl)acetate (15.7 g, 51.3 mmol, 96% yield, MS/ESI$^+$ 328.9 [MNa]$^+$).

Step 2: Preparation of tert-butyl 2-(5-amino-1,3-dioxoisoindolin-2-yl)acetate (178)

To a solution of tert-butyl 2-(5-nitro-1,3-dioxoisoindolin-2-yl)acetate (15.7 g, 51.3 mmol) in a mixture of ethyl acetate (400 ml) and MeOH (200 ml), 10% w/w Pd/C (0.900 g) was added, and the mixture was hydrogenated in a Parr apparatus at 30 psi for 2 hours. The catalyst was filtered off, and the filtrate was evaporated to dryness affording tert-butyl 2-(5-amino-1,3-dioxoisoindolin-2-yl)acetate (14 g, 50.7 mmol, 99% yield, MS/ESI$^+$ 276.9 [MH]$^+$). This product was used in the following step without any further purification.

Step 3: Preparation of tert-butyl 2-(5-(methylsulfonamido)-1,3-dioxoisoindolin-2-yl)acetate (179)

To a solution of tert-butyl 2-(5-amino-1,3-dioxoisoindolin-2-yl)acetate (14 g, 50.7 mmol) in THF (100 ml), pyridine (8.20 ml, 101 mmol) was added followed by methanesulfonyl chloride (7.74 ml, 101 mmol), and the resulting mixture was heated to reflux for 5 hours. The volatiles were removed under vacuum, the residue was dissolved in DCM (200 ml) and washed with 0.2M HCl (3×50 ml) and brine; the organic phase was dried over Na$_2$SO$_4$ and evaporated to dryness. The resulting solid was triturated with ethyl acetate, and the title compound was recovered by filtration (12.5 g). The mother liquors were evaporated in vacuo and purified by silica gel chromatography (DCM:AcOEt 10:1), affording additional 2.6 g of the title compound. These two batches were dissolved in DCM, combined, and the solvent was evaporated in vacuo to afford tert-butyl 2-(5-(methylsulfonamido)-1,3-dioxoisoindolin-2-yl)acetate (15.1 g, 42.6 mmol, 84% yield, MS/ESI$^+$ 354.9 [MH]$^+$).

Step 4: Preparation of tert-butyl 2-(5-(N-(2-morpholinoethyl)-methylsulfonamido)-1,3-dioxoisoindolin-2-yl)acetate (180)

To a solution of tert-butyl 2-(5-(methylsulfonamido)-1,3-dioxoisoindolin-2-yl)acetate (501 mg, 1.414 mmol) in dry DMF (15 ml) maintained under nitrogen atmosphere, K$_2$CO$_3$ (391 mg, 2.83 mmol) and 4-(2-chloroethyl)morpholine hydrochloride (526 mg, 2.83 mmol) were added, and the mixture was stirred at 60° C. for 3 hours. The solid was filtered off, the solvent was evaporated and the resulting crude was purified by filtration on a silica gel cartridge (DCM/MeOH 9/1), obtaining tert-butyl 2-(5-(N-(2-morpholinoethyl)methylsulfonamido)-1,3-dioxoisoindolin-2-yl)acetate (570 mg, 1.22 mmol, 86% yield, MS/ESI$^+$ 468.2 [MH]$^+$).

Step 5: Preparation of 2-(5-(N-(2-morpholinoethyl) methylsulfonamido)-1,3-dioxoisoindolin-2-yl)acetic acid 2,2,2-trifluoroacetic acid salt (181)

To a solution of tert-butyl 2-(5-(N-(2-morpholinoethyl) methylsulfonamido)-1,3-dioxoisoindolin-2-yl)acetate (570 mg, 1.219 mmol) in DCM (15 ml), trifluoroacetic acid (939 µl, 12.19 mmol) was added, and the mixture was reacted for 1 hour at room temperature. The solvent was evaporated and crude 2-(5-(N-(2-morpholinoethyl)-methylsulfonamido)-1,3-dioxoisoindolin-2-yl)acetic acid 2,2,2-trifluoroacetic acid salt was obtained (408 mg, 0.776 mmol, 64% yield).MS/ESI$^+$ 411.8 [MH]$^+$) and used without purification.

Step 6: Preparation of (S)-3,5-dichloro-4-(2-(3-(cyclopropylmethoxy)-4-(difluoromethoxy)phenyl)-2-(2-(5-(N-(2-morpholinoethyl)methylsulfonamido)-1,3-dioxoisoindolin-2-yl)acetoxy)ethyl)pyridine 1-oxide 2,2,2 trifluoroacetic acid salt (182)

To a solution of 2-(5-(N-(2-morpholinoethyl)methylsulfonamido)-1,3-dioxoisoindolin-2-yl)acetic acid 2,2,2-trifluoroacetic acid salt (230 mg, 0.438 mmol) in DCM (10 ml), (S)-3,5-dichloro-4-(2-(3-(cyclopropylmethoxy)-4-(difluoromethoxy)-phenyl)-2-hydroxyethyl)pyridine 1-oxide (184 mg, 0.438 mmol), EDC (252 mg, 1.313 mmol), and DMAP (80 mg, 0.657 mmol) were added, and the mixture was stirred overnight at room temperature. The solvent was evaporated and the resulting crude was purified by preparative HPLC (Method 1) obtaining (S)—(S)-3,5-dichloro-4-(2-(3-(cyclopropylmethoxy)-4-(difluoromethoxy)phenyl)-2-(2-(5-(N-(2-morpholinoethyl)-methylsulfonamido)-1,3-dioxoisoindolin-2-yl)acetoxy)ethyl)pyridine 1-oxide 2,2,2-trifluoroacetic acid salt (116 mg, 28.6% yield, MS/ESI$^+$ 813.19 [MH]$^+$, [α$_D$]=−7.37, c=0.6 in DCM). $^1$H NMR (300 MHz, DMSO-d$_6$) δ ppm 9.77 (br. s., 1H), 8.44 (s, 2H), 8.08 (d, 1H), 8.03 (d, 1H), 7.98 (dd, 1H), 7.21 (d, 1H), 7.12 (d, 1H), 6.98 (dd, 1H), 7.09 (t, 1H), 6.02 (dd, 1H), 4.46 (s, 2H), 4.20 (t, 2H), 3.86-4.08 (m, 2H), 3.41 (dd, 1H), 3.25 (dd, 1H), 3.16 (s, 3H), 2.98-4.13 (m, 10H), 1.04-1.40 (m, 1H), 0.50-0.71 (m, 2H), 0.31-0.50 (m, 2H)

The compounds listed in Table 12 were prepared with analogous synthetic steps and procedures to that described in Example 34, by reacting the appropriate precursors (commercially available or synthesized by a person skilled in the art) with suitable reagents. Specific variations in the experimentals or purification methods are indicated in the table.

TABLE 12

| Entry | Structure | NMR characterization | MS/ESI+ [MH]+ | [α]D | Experimental procedure | Purification and yield | Starting material (precursor) | Alkylating agent |
|---|---|---|---|---|---|---|---|---|
| 183 | 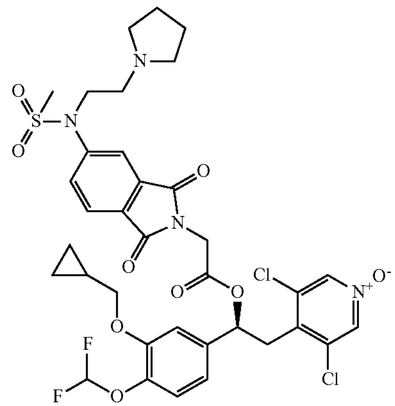 | 1H NMR (300 MHz, DMSO-d6) δ ppm 8.43 (s, 2H), 7.94-7.99 (m, 2H), 7.89 (dd, 1H), 7.19 (d, 1H), 7.09 (d, 1H), 6.97 (dd, 1H), 7.08 (t, 1H), 6.02 (dd, 1H), 4.43 (s, 2H), 3.70-4.07 (m, 4H), 3.39 (dd, 1H), 3.23 (dd, 1H), 3.14 (s, 3H), 2.39 (br. s.., 6H), 1.44-1.72 (m, 4H), 1.26-1.33 (m, 1H), 0.46-0.69 (m, 2H), 0.26-0.45 (m, 2H) | 797.28 | −30.52 c = 0.500; DCM | Step 4: 110° C., 3 h | Flash chromatography on silica gel (DCM/MeOH 96/4) 14.6% yield No salt | | |
| 184 | 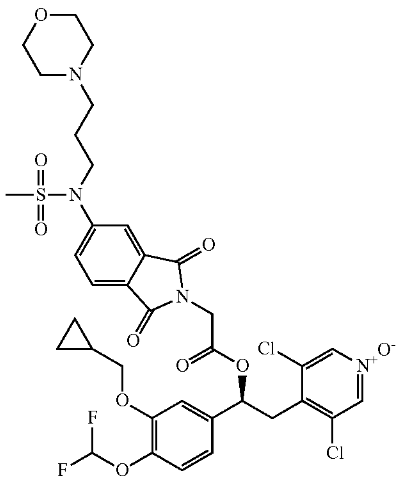 | 1H NMR (300 MHz, DMSO-d6) δ ppm 8.44 (s, 2H), 7.97 (d, 1H), 7.96 (d, 1H), 7.89 (dd, 1H), 7.19 (d, 1H), 7.09 (d, 1H), 6.97 (dd, 1H), 7.08 (t, 1H), 6.02 (dd, 1H), 4.43 (s, 2H), 3.89-4.04 (m, 2H), 3.79-3.88 (m, 2H), 3.46-3.54 (m, 4H), 3.39 (dd, 1H), 3.23 (dd, 1H), 3.11 (s, 3H), 2.11-2.33 (m, 6H), 1.46-1.67 (m, 2H), 1.12-1.32 (m, 1H), 0.50-0.70 (m, 2H), 0.30-0.44 (m, 2H) | 827.1 | −13.01 c = 0.518 MeOH | Step 4: 100° C., 2 h | Flash chromatography on silica gel (DCM/MeOH 97/3) 11% yield No salt | | |

TABLE 12-continued

| Entry | Structure | NMR characterization | MS/ESI+ [MH]+ | [α]D | Experimental procedure | Purification and yield | Starting material (precursor) | Alkylating agent |
|---|---|---|---|---|---|---|---|---|
| 185 | (structure with pyridine N-oxide, dichloro, cyclopropylmethoxy, difluoromethoxy phenyl, methanesulfonyl isoindoline-dione) | 1H NMR (300 MHz, DMSO-d6) δ ppm 8.43-8.52 (m, 2H), 8.37 (s, 2H), 8.01 (dd, 1H), 7.92 (dd, 1H), 7.88 (dd, 1H), 7.33-7.39 (m, 2H), 7.18 (d, 1H), 7.07 (d, 1H), 6.95 (dd, 1H), 7.08 (t, 1H), 5.99 (dd, 1H), 5.13 (s, 2H), 4.38 (s, 2H), 3.95 (dd, 1H), 3.92 (dd, 1H), 3.35 (dd, 1H), 3.27 (s, 3H), 3.21 (dd, 1H), 1.17-1.35 (m, 1H), 0.52-0.67 (m, 2H), 0.29-0.45 (m, 2H) | 791.01 | −21.8 c = 0.43 DCM | Step 4: CH3CN MW irrad. 110° C., 2 h | Flash chromatography on silica gel (EtOAc/DCM 1/1; then EtOAc; then EtOAc/MeOH 9/1) followed by trituration with Et2O/iPrOH 70% yield No salt | (5-nitroisoindoline-1,3-dione precursor) | (4-pyridylmethyl chloride) |
| 186 | (structure with pyridine, dichloro pyridine N-oxide, cyclopropylmethoxy, difluoromethoxy phenyl, methanesulfonyl isoindoline-dione) | 1H NMR (300 MHz, DMSO-d6) δ ppm 8.55 (d, 1H), 8.46 (dd, 1H), 8.38 (s, 2H), 7.99 (t, 1H), 7.83-7.87 (m, 1H), 7.89 (d, 2H), 7.42 (dd, 1H), 7.19 (d, 1H), 7.02-7.13 (m, 1H), 6.95 (dd, 1H), 7.08 (t, 1H), 5.99 (dd, 1H), 5.14 (s, 2H), 4.38 (s, 2H), 3.94 (dd, 2H), 3.30-3.37 (m, 1H), 3.28 (s, 3H), 3.21 (dd, 1H), 1.17-1.33 (m, 1H), 0.49-0.66 (m, 2H), 0.22-0.45 (m, 2H) | 791.2 | −30.72 c = 0.515; DCM | Step 4: K2CO3, MeCN, 5 h, 130° C., MW Step 5: HCl/dioxane MeCN 100° C., MW, 2 h, | Flash chromatography on silica gel (DCM/MeOH 98/2) 44.7% yield No salt | (5-nitroisoindoline-1,3-dione precursor) | (3-pyridylmethyl chloride) |

Example 35

(S)-3,5-Dichloro-4-(2-(3-(cyclopropylmethoxy)-4-(difluoromethoxy)phenyl)-2-(2-(1,3-dioxo-5-(N-(2-(piperidin-1-yl)ethyl)methylsulfonamido)-isoindolin-2-yl)acetoxy)ethyl)pyridine 1-oxide (Compound 189)

Scheme 35.

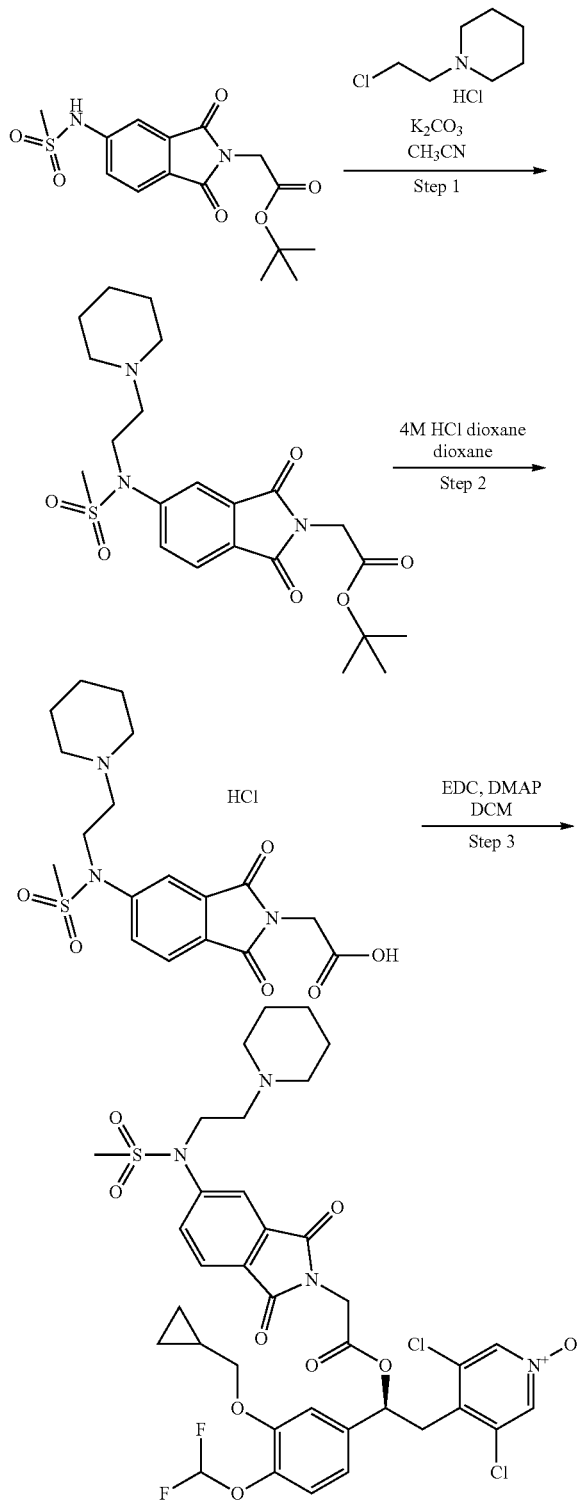

Step 1: Preparation of tert-butyl 2-(1,3-dioxo-5-(N-(2-(piperidin-1-yl)ethyl)methylsulfonamido)isoindolin-2-yl)acetate (187)

To a stirred solution of tert-butyl 2-(5-(methylsulfonamido)-1,3-dioxoisoindolin-2-yl)acetate (prepared in an analogous manner as previously described in Example 34, Scheme 34, Steps 1, 2, 3) (400 mg, 1.129 mmol) in acetonitrile (10 ml), potassium carbonate (312 mg, 2.257 mmol), and 1-(2-chloroethyl)piperidine hydrochloride (249 mg, 1.354 mmol) were added. The reaction was heated at 90° C. under microwave irradiation for 2 hours. The solid inorganic salts were filtered off and the filtrate was evaporated to dryness. The resulting crude was crystallized from EtOH affording tert-butyl 2-(1,3-dioxo-5-(N-(2-(piperidin-1-yl)ethyl)methylsulfonamido)isoindolin-2-yl)acetate (450 mg, 0.967 mmol, 86% yield, MS/ESI$^+$ 465.9 [MH]$^+$).

Step 2: Preparation of 2-(1,3-dioxo-5-(N-(2-(piperidin-1-yl)ethyl)methylsulfonamido)isoindolin-2-yl) acetic acid hydrochloride (188)

To a stirred solution of tert-butyl 2-(1,3-dioxo-5-(N-(2-(piperidin-1-yl)ethyl)methylsulfonamido)isoindolin-2-yl)acetate (450 mg, 0.967 mmol) in dioxane (7 ml), 4 M HCl in dioxane (2.5 ml, 10.00 mmol) was added. The reaction was heated at 100° C. under microwave irradiation for 4 hours. The volatiles were removed under vacuum and the resulting solid was triturated with Et$_2$O and recovered by filtration affording 2-(1,3-dioxo-5-(N-(2-(piperidin-1-yl)ethyl)methylsulfonamido)isoindolin-2-yl)acetic acid hydrochloride (407 mg, 0.913 mmol, 94% yield, MS/ESI$^+$ 409.8 [MH]$^+$).

Step 3: Preparation of CHD-026420, (S)-3,5-dichloro-4-(2-(3-(cyclopropylmethoxy)-4-(difluoromethoxy)phenyl)-2-(2-(1,3-dioxo-5-(N-(2-(piperidin-1-yl)ethyl)methylsulfonamido)isoindolin-2-yl)acetoxy)ethyl)pyridine 1-oxide (189)

To a stirred solution of (S)-3,5-dichloro-4-(2-(3-(cyclopropylmethoxy)-4-(difluoromethoxy)phenyl)-2-hydroxyethyl)pyridine 1-oxide (188 mg, 0.449 mmol), DMAP (110 mg, 0.897 mmol) and EDC (129 mg, 0.673 mmol) in DCM (10 ml), 2-(1,3-dioxo-5-(N-(2-(piperidin-1-yl)ethyl)methylsulfonamido)isoindolin-2-yl)acetic acid hydrochloride (200 mg, 0.449 mmol) was added portion wise over 5 hours, and the resulting mixture was stirred at room and for 96 hours. The solvent was removed and the crude was purified by silica gel chromatography (EtOAc/DCM 2/1 then DCM/MeOH 100/3). The resulting white solid was triturated with EtOH and recovered by filtration affording (S)-3,5-dichloro-4-(2-(3-(cyclopropylmethoxy)-4-(difluoromethoxy)phenyl)-2-(2-(1,3-dioxo-5-(N-(2-(piperidin-1-yl)ethyl)methylsulfonamido)isoindolin-2-yl)acetoxy)ethyl)pyridine 1-oxide (190 mg, 0.234 mmol, 52.2% yield, LC-MS purity (BPI): 98.3%, MS/ESI$^+$ 811.21 [MH]$^+$, [α$_D$]=+28.12, c=0.653 DCM). $^1$H NMR (300 MHz, DMSO-d6) δ ppm 8.44 (s, 2H), 7.97 (d, 1H), 7.95 (d, 1H), 7.89 (dd, 1H), 7.19 (d, 1H), 7.09 (d, 1H), 6.96 (dd, 1H), 7.08 (t, 1H), 6.02 (dd, 1H), 4.43 (s, 2H), 3.91-4.04 (m, 2H), 3.88 (t, 2H), 3.38 (dd, 1H), 3.23 (dd, 1H), 3.15 (s, 3H), 2.35 (t, 2H), 2.17-2.31 (m, 4H), 1.03-1.53 (m, 7H), 0.49-0.68 (m, 2H), 0.28-0.46 (m, 2H).

The compound listed in Table 13 was prepared with analogous synthetic steps and procedures to that described in Example 35, by reacting the appropriate precursors (commercially available or synthesized by a person skilled in the art) with suitable reagents. Specific variations in the experimentals or purification methods are indicated in the table.

TABLE 13

| Entry | Structure | NMR characterization | MS/ESI+ [MH]+ | [α_D] | Experimental procedure | Purification and yield | Starting material (precursor) | Alkylating agent |
|---|---|---|---|---|---|---|---|---|
| 190 | 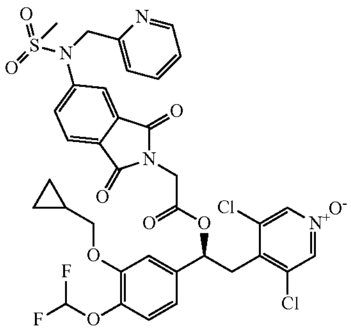 | 1H NMR (300 MHz, DMSO-d6) δ ppm 8.46 (ddd, 1H), 8.39 (s, 2H), 7.98 (dd, 1H), 7.91 (dd, 1H), 7.87 (dd, 1H), 7.75 (td, 1H), 7.45 (dt, 1H), 7.24 (ddd, 1H), 7.19 (d, 1H), 7.07 (d, 1H), 6.95 (dd, 1H), 7.08 (t, 1H), 6.00 (dd, 1H), 5.18 (s, 2H), 4.38 (s, 2H), 3.95 (dd, 1H), 3.91 (dd, 1H), 3.36 (dd, 1H), 3.29 (s, 3H), 3.21 (dd, 1H), 1.08-1.39 (m, 1H), 0.49-0.68 (m, 2H), 0.21-0.47 (m, 2H) | 791.14 | −29.20 c = 0.463 DCM | Step 1: MW, 120° C., 8 h Step 2: CH3CN, MW, 100° C., 2 h | Flash chromatography on silica gel (EtOAc/DCM 2/1, then DCM/MeOH 100/3) followed by trituration with EtOH 58.4% yield No salt | | |
| 191 | 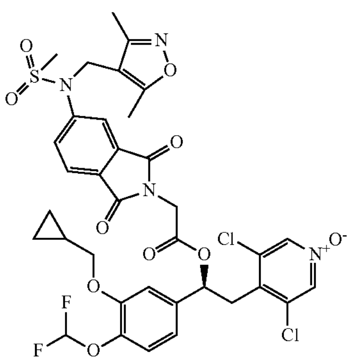 | 1H NMR (300 MHz, DMSO-d6) δ ppm 8.37 (s, 2H), 7.98 (d, 1H), 7.92 (d, 1H), 7.86 (dd, 1H), 7.19 (d, 1H), 7.09 (d, 1H), 6.96 (dd, 1H), 7.08 (t, 1H), 6.01 (dd, 1H), 4.86 (s, 2H), 4.40 (s, 2H), 3.37(dd, 1H), 3.19 (s, 3H), 3.13-3.24 (m, 1H), 2.21 (s, 3H), 2.15 (s, 3H), 1.11-1.40 (m, 1H), 0.52-0.72 (m, 2H), 0.24-0.46 (m, 2H) | 809.01 | −37.62 c = 0.463 DCM | Step 1: MW, 80° C., 4 h Step 2: Dioxane, MW, 100° C., 2 h | Flash chromatography on silica gel (EtOAc/DCM 8/2) 69% yield No salt | | |

TABLE 13-continued

| Entry | Structure | NMR characterization | MS/ESI+ [MH]+ | [α]D | Experimental procedure | Purification and yield | Starting material (precursor) | Alkylating agent |
|---|---|---|---|---|---|---|---|---|
| 192 | 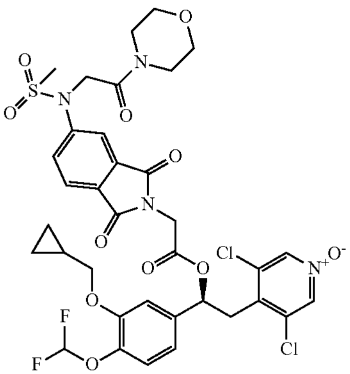 | 1H NMR (300 MHz, DMSO-d6) δ ppm 8.42 (s, 2H), 7.94 (dd, 1H), 7.91 (d, 1H), 7.88 (dd, 1H), 7.20 (d, 1H), 7.09 (d, 1H), 6.96 (dd, 1H), 7.08 (t, 1H), 6.02 (dd, 1H), 4.89 (s, 2H), 4.45 (d, 1H), 4.38(d, 1H), 3.95 (dd, 2H), 3.40-3.68 (m, 8H), 3.38 (dd, 1H), 3.25 (s, 3H), 3.23 (dd, 1H), 1.14-1.35 (m, 1H), 0.51-0.66 (m, 2H), 0.25-0.47 (m, 2H) | 827.17 | −28.15 c = 0.417 DCM | Step 1: MW, 100° C., 4 h Step 2: dioxane, MW, 100° C., 3 h | Flash chromatography on silica gel (EtOAc/DCM 2/1, then DCM/MeOH 100/3) 35.4% yield No salt | | |
| 193 | 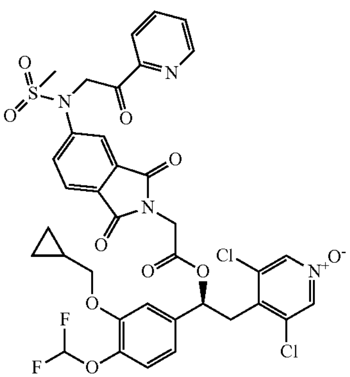 | 1H NMR (300 MHz, DMSO-d6) δ ppm 8.77 (ddd, 1H), 8.41 (s, 2H), 8.05 (td, 1H), 7.94-8.01 (m, 3H), 7.92 (dd, 1H), 7.73 (ddd, 1H), 7.19 (d, 1H), 7.08 (d, 1H), 6.96 (dd, 1H), 7.08 (t, 1H), 6.01 (dd, 1H), 5.71 (s, 2H), 4.41 (s, 2H), 3.96 (dd, 1H), 3.92 (dd, 1H), 3.38 (dd, 1H), 3.30 (s, 3H), 3.20 (dd, 1H), 1.05-1.32 (m, 1H), 0.49-0.70 (m, 2H), 0.27-0.45 (m, 2H) | 819 | −32.40 c = 0.15, DCM | Step 1: MW, 80° C., 5 h Step 2: dioxane, MW, 100° C., 2 h | Flash chromatography on silica gel (EtOAc/DCM 2/1) followed by preparative HPLC (Method 1)10.5% yield No salt | | |

TABLE 13-continued

| Entry | Structure | NMR characterization | MS/ESI+ [MH]+ | [α]D | Experimental procedure | Purification and yield | Starting material (precursor) | Alkylating agent |
|---|---|---|---|---|---|---|---|---|
| 194 | 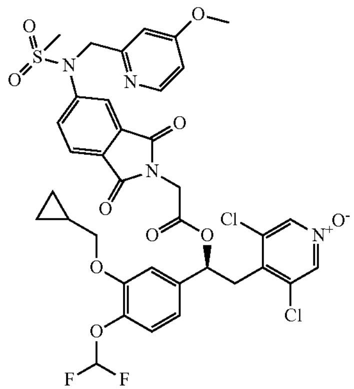 | 1H NMR (300 MHz, DMSO-d6) δ ppm 8.38 (s, 2H), 8.28 (d, 1H), 7.98 (d, 1H), 7.91 (dd, 1H), 7.87 (d, 1H), 7.19 (d, 1H), 7.07 (d, 1H), 6.95 (dd, 2H), 7.08 (t, 1H), 6.83 (dd, 1H), 6.00 (dd, 1H), 5.12 (s, 2H), 4.41 (d, 1H), 4.35 (d, 1H), 3.86-3.99 (m, 2H), 3.78 (s, 3H), 3.35 (dd, 1H), 3.30 (s, 3H), 3.21 (dd, 1H), 1.17-1.32 (m, 1H), 0.50-0.67 (m, 2H), 0.29-0.44 (m, 2H) | 821.08 | −27.95 c = 0.453 DCM | Step 1: MW, 100° C., 2 h Step 2: CH3CN, MW, 100° C., 1 h | Flash chromatography on silica gel (EtOAc/DCM 2/1; then DCM/MeOH 100/3) 49.5% yield No salt | | |
| 195 | 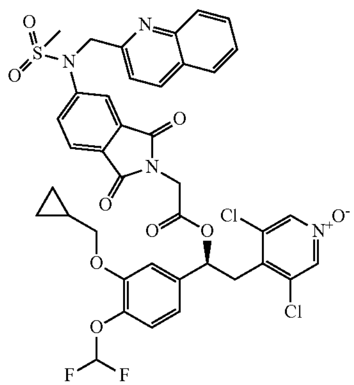 | 1H NMR (300 MHz, DMSO-d6) δ ppm 8.36 (s, 2H), 8.34 (d, 1H), 8.06 (d, 1H), 7.97 (dd, 1H), 7.84-7.94 (m, 3H), 7.70 (ddd, 1H), 7.63 (d, 1H), 7.54 (ddd, 1H), 7.17 (d, 1H), 7.05 (d, 1H), 6.93 (dd, 1H), 7.07 (t, 1H), 5.97 (dd, 1H), 5.39 (s, 2H), 4.38 (d, 1H), 4.32 (d, 1H), 3.94 (dd, 1H), 3.90 (dd, 1H), 3.37 (s, 3H), 3.30-3.35 (m, 1H), 3.18(dd, 1H), 1.14-1.32 (m, 1H), 0.49-0.65 (m, 2H), 0.28-0.43 (m, 2H) | 841.11 | −21.6 c = 0.71 DCM | Step 1: MW, 120° C., 2 h Step 2: CH3CN, r.t. 42 h | Flash chromatography on silica gel (DCM/EtOAc 7/3,then DCM/EtOAc/ MeOH 70/30/3 49% yield No salt | | |

TABLE 13-continued

| Entry | Structure | NMR characterization | MS/ESI⁺ [MH]⁺ | [α]_D | Experimental procedure | Purification and yield | Starting material (precursor) | Alkylating agent |
|---|---|---|---|---|---|---|---|---|
| 196 | 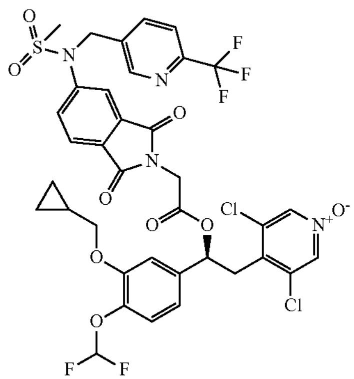 | ¹H NMR (300 MHz, DMSO-d₆) δ ppm 8.71 (d, 1H), 8.37 (s, 2H), 8.00-8.11 (m, 2H), 7.87-7.96 (m, 2H), 7.84 (d, 1H), 7.19 (d, 1H), 7.07 (d, 1H), 6.95 (dd, 1H), 7.08 (t, 1H), 5.99 (dd, 1H), 5.24 (s, 2H), 4.38 (s, 2H), 3.96 (dd, 1H), 3.92 (dd, 1H), 3.35 (dd, 1H), 3.30 (s, 3H), 3.21 (dd, 1H), 1.07-1.34 (m, 1H), 0.49-0.71 (m, 2H), 0.25-0.46 (m, 2H) | 859.13 | −27.92 c = 0.475 DCM | Step 1: 120° C., 4 h Step 2: CH₃CN, MW, 110° C., 1 h | Flash chromatography on silica gel (EtOAc/DCM 2/1, then DCM/MeOH 100/3) followed by crystallization from iPrOH 49% yield No salt | | |
| 197 | 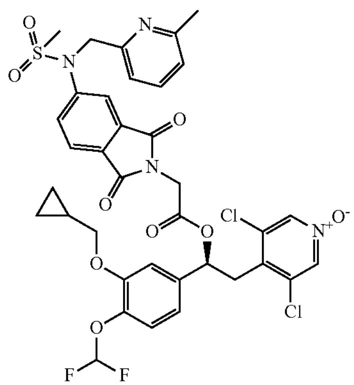 | ¹H NMR (300 MHz, DMSO-d₆) δ ppm 8.38 (s, 2H), 8.00 (dd, 1H), 7.92 (dd, 1H), 7.88 (dd, 1H), 7.66 (t, 1H), 7.26 (d, 1H), 7.18 (d, 1H), 7.13 (d, 1H), 7.07 (d, 1H), 6.95 (dd, 1H), 7.08 (t, 1H), 5.99 (dd, 1H), 5.14 (s, 2H), 4.38 (d, 2H), 3.85-3.98 (m, 2H), 3.30 (s, 3H), 2.41 (s, 3H), 3.13-3.32 (m, 2H), 1.13-1.33 (m, 1H), 0.49-0.68 (m, 2H), 0.27-0.44 (m, 2H) | 804.99 | −25 c = 0.43 DCM | Step 1: MW, 120° C., 4 h Step 2: DCM, r.t. 72 h | Flash chromatography on silica gel (EtOAc). The obtained product was dissolved in DCM and 4M HCl in dioxane was added; the solvent was removed and the residue was purified by trituration with iPrOH 42.3% yield Hydrochloride | | |

TABLE 13-continued

| Entry | Structure | NMR characterization | MS/ESI+ [MH]+ | [α]D | Experimental procedure | Purification and yield | Starting material (precursor) | Alkylating agent |
|---|---|---|---|---|---|---|---|---|
| 198 | (structure shown) | 1H NMR (300 MHz, DMSO-d6) δ ppm 8.38 (s, 2H), 8.23 (dd, 1H), 7.92 (t, 1H), 7.85 (d, 2H), 7.54 (dd, 1H), 7.19 (d, 1H), 7.14 (dd, 1H), 7.07 (d, 1H), 6.95 (dd, 1H), 7.08 (t, 1H), 5.99 (dd, 1H), 5.23 (s, 2H), 4.20-4.51 (m, 2H), 3.79-4.05 (m, 2H), 3.30-3.42 (m, 1H), 3.27 (s, 3H), 3.15-3.25 (m, 1H), 2.38 (s, 3H), 1.11-1.35 (m, 1H), 0.50-0.66 (m, 2H), 0.27-0.44 (m, 2H) | 805.02 | −23.6 c = 0.5 DCM | Step 1: MW, 120° C., 2 h Step 2: CH3CN, MW, 100° C., 1 h | Flash chromatography on silica gel (EtOAc) followed by trituration with iPrOH 55% yield No salt | (structure shown) | (structure shown) |
| 199 | (structure shown) | 1H NMR (300 MHz, DMSO-d6) δ ppm 8.77 (d, 2H), 8.41 (s, 2H), 7.96 (dd, 1H), 7.92 (dd, 1H), 7.88 (dd, 1H), 7.39 (t, 1H), 7.19 (d, 1H), 7.07 (d, 1H), 6.95 (dd, 1H), 7.08 (t, 1H), 6.00 (dd, 1H), 5.31 (s, 2H), 4.42 (d, 1H), 4.36 (d, 1H), 3.81-3.99 (m, 2H), 3.34 (s, 3H), 3.36 (dd, 1H), 3.21 (dd, 1H), 1.07-1.34 (m, 1H), 0.49-0.66 (m, 2H), 0.31-0.47 (m, 2H) | 792.04 | −41.6 c = 0.31 DCM | Step 1: MW, 120° C., 6 h Step 2: DCM, r.t. 5 days | Flash chromatography on silica gel (EtOAc, then EtOAc/MeOH 9/1) 20% yield No salt | (structure shown) | (structure shown) |

TABLE 13-continued

| Entry | Structure | NMR characterization | MS/ESI+ [MH]+ | [α]D | Experimental procedure | Purification and yield | Starting material (precursor) | Alkylating agent |
|---|---|---|---|---|---|---|---|---|
| 200 | (structure) | 1H NMR (300 MHz, DMSO-d6) δ ppm 8.71 (d, 1H), 8.55 (dd, 1H), 8.51 (d, 1H), 8.40 (s, 2H), 8.03 (dd, 1H), 7.93 (dd, 1H), 7.89 (dd, 1H), 7.19 (d, 1H), 7.07 (d, 1H), 6.95 (dd, 1H), 7.08 (t, 1H), 6.00 (dd, 1H), 5.27 (s, 2H), 4.39 (s, 1H), 3.79-4.09 (m, 2H), 3.36 (dd, 1H), 3.30 (s, 3H), 3.21 (dd, 1H), 1.16-1.34 (m, 1H), 0.49-0.70 (m, 2H), 0.28-0.49 (m, 2H) | 792.04 | −26.96 (c = 0.523, DCM) | Step 1: MW, 120° C., 2 h Step 2: MW, 100° C., 3 h | Preparative HPLC (Method 1), followed by dissolution in DCM, washing with aq. NaHCO3, and evaporation 21% yield No salt | (structure) | (structure) |
| 201 | (structure) | 1H NMR (300 MHz, DMSO-d6) δ ppm 8.41 (s, 2H), 8.04 (t, 1H), 7.94 (d, 2H), 7.70 (d, 1H), 7.67 (d, 1H), 7.19 (d, 1H), 7.08 (d, 1H), 6.96 (dd, 1H), 7.08 (t, 1H), 6.01 (dd, 1H), 5.41 (s, 2H), 4.40 (s, 2H), 3.79-4.01 (m, 2H), 3.37 (dd, 1H), 3.27 (s, 3H), 3.22 (dd, 1H), 1.12-1.36 (m, 1H), 0.45-0.68 (m, 2H), 0.21-0.45 (m, 2H) | 796.97 | −26.75 (c = 0.51, DCM) | Step 1: MW, 110° C., 5 h Step 2: MW, 100° C., 5 h | Flash chromatography on silica gel (EtOAc/DCM = 2/1, then DCM/MeOH = 100/3) followed by trituration with iPr2O; the dissolution in DCM, washing with 0.05N HCl and evaporation 57% No salt | (structure) | (structure) |

| Entry | Structure | NMR characterization | MS/ESI+ [MH]+ [α_D] | Experimental procedure | Purification and yield | Starting material (precursor) | Alkylating agent |
|---|---|---|---|---|---|---|---|
| 202 | (structure shown) | 1H NMR (300 MHz, DMSO-d6) δ ppm 8.43 (s, 2H), 7.96 (d, 1H), 7.94 (d, 1H), 7.88 (dd, 1H), 7.20 (d, 1H), 7.09 (d, 1H), 6.97 (dd, 1H), 7.08 (t, 1H), 6.02 (dd, 1H), 4.43 (s, 2H), 3.82-4.07 (m, 4 H), 3.42 (t, 2H), 3.39 (dd, 1H), 3.23 (dd, 1H), 3.17 (s, 3H), 3.14 (s, 3H), 1.13-1.40 (m, 1H), 0.53-0.67 (m, 2H), 0.30-0.47 (m, 2H) | 758.04 −26.8 c = 0.82 DCM | Step 1: MW, 100° C., 2 h Step 2: CH3CN, r.t. 18 h | Flash chromatography on silica gel (DCM/EtOAc 1/2, then EtOAc) followed by flash chromatography on silica gel (EtOAc) 31.6% yield No salt | (structure shown) | (structure shown) |

Example 36

(S)-3,5-Dichloro-4-(2-(3-(cyclopropylmethoxy)-4-(difluoromethoxy)phenyl)-2-(2-(1,3-dioxo-5-(N-(thiophen-2-ylmethyl)methylsulfonamido)-isoindolin-2-yl)acetoxy)ethyl)pyridine 1-oxide (Compound 205)

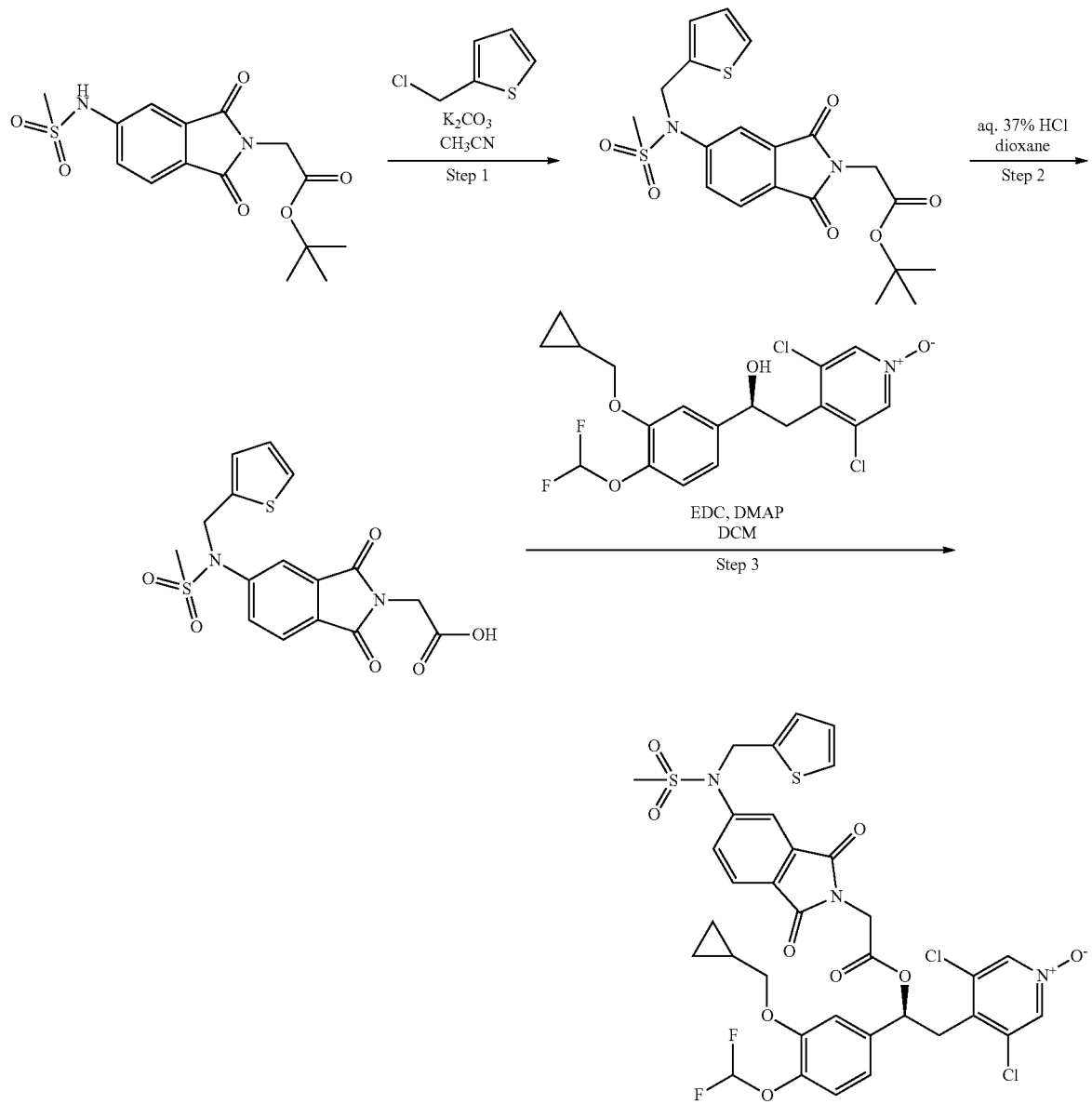

Scheme 36.

Step 1: Preparation of tert-butyl 2-(1,3-dioxo-5-(N-(thiophen-2-ylmethyl)methylsulfonamido)isoindolin-2-yl)acetate (203)

To a solution of tert-butyl 2-(5-(methylsulfonamido)-1,3-dioxoisoindolin-2-yl)acetate (500 mg, 1.411 mmol) (prepared in an analogous manner as previously described in Example 34, Scheme 34, Steps 1, 2, 3) in acetonitrile (10 ml), K$_2$CO$_3$ (390 mg, 2.82 mmol) and 2-(chloromethyl)thiophene (281 mg, 2.116 mmol) (obtainable as described in U.S. Pat. No. 5,716,943, which is incorporated herein by reference in its entirety) were added, and the reaction was heated under microwave irradiation at 120° C. for 3 hours. The mixture was filtered and the filtrate was evaporated to dryness. The resulting crude was purified by flash chromatography on silica gel (hexane/EtOAc 2/1) affording tert-butyl 2-(1,3-dioxo-5-(N-(thiophen-2-ylmethyl)methylsulfonamido)-isoindolin-2-yl) acetate (600 mg, 1.332 mmol, 94% yield, MS/ESI$^+$ 472.9 [MNa]$^+$).

Step 2: Preparation of 2-(1,3-dioxo-5-(N-(thiophen-2-ylmethyl)-methylsulfonamido) isoindolin-2-yl) acetic acid (204)

To a stirred solution of tert-butyl 2-(1,3-dioxo-5-(N-(thiophen-2-ylmethyl)methylsulfonamido)isoindolin-2-yl) acetate (580 mg, 1.287 mmol) in dioxane (15 ml), aqueous 12M HCl (1 ml, 12.00 mmol) was added drop wise. The resulting mixture was stirred at 50° C. for 4 hours. The volatiles were removed under vacuum and the crude 2-(1,3-dioxo-5-(N-(thiophen-2-ylmethyl)methylsulfonamido) isoindolin-2-yl)acetic acid (490 mg, 1.242 mmol, 97% yield, MS/ESI⁺ 395.0 [MH]⁺). was used without further purification.

Step 3: Preparation of (S)-3,5-dichloro-4-(2-(3-(cyclopropylmethoxy)-4-(difluoromethoxy)phenyl)-2-(2-(1,3-dioxo-5-(N-(thiophen-2-ylmethyl)methylsulfonamido)isoindolin-2-yl)acetoxy)ethyl)pyridine 1-oxide (205)

To a stirred solution of (S)-3,5-dichloro-4-(2-(3-(cyclopropylmethoxy)-4-(difluoromethoxy)phenyl)-2-hydroxyethyl) pyridine 1-oxide (200 mg, 0.476 mmol), DMAP (116 mg, 0.952 mmol), and EDC (182 mg, 0.952 mmol) in DCM (10 ml), 2-(1,3-dioxo-5-(N-(thiophen-2-ylmethyl)methylsulfonamido)isoindolin-2-yl)acetic acid (225 mg, 0.571 mmol) was added portion wise, and the resulting mixture was stirred at room temperature for 18 hours. The solvent was evaporated, and the crude was purified by flash chromatography on silica gel (DCM/MeOH 10/0.5). The resulting product was triturated with iPr₂O affording after filtration 227 mg of crude desired product. A further purification by flash chromatography on silica gel (DCM/acetone 8/1) was performed to afford (S)-3,5-dichloro-4-(2-(3-(cyclopropylmethoxy)-4-(difluoromethoxy)phenyl)-2-(2-(1,3-dioxo-5-(N-(thiophen-2-ylmethyl)methylsulfonamido)isoindolin-2-yl)acetoxy)ethyl)pyridine 1-oxide (155 mg, 0.195 mmol, 40.9% yield, MS/ESI⁺ 796.02 [MH]⁺, [α$_D$]=−30.31, c=0.415, DCM). ¹H NMR (300 MHz, DMSO-d₆) δ ppm 8.38 (s, 2H), 7.96 (d, 1H), 7.91 (d, 1H), 7.86 (dd, 1H), 7.40 (dd, 1H), 7.19 (d, 1H), 7.08 (d, 1H), 6.92-6.99 (m, 1H), 7.08 (t, 1H), 6.86 (d, 1H), 6.84 (d, 1H), 6.00 (dd, 1H), 5.25 (s, 2H), 4.39 (s, 2H), 3.81-4.09 (m, 2H), 3.37 (dd, 1H), 3.21 (s, 3H), 3.21 (dd, 1H), 1.17-1.37 (m, 1H), 0.50-0.69 (m, 2H), 0.21-0.46 (m, 2H)

Example 37

(S)-3,5-Dichloro-4-(2-(3-(cyclopropylmethoxy)-4-(difluoromethoxy)-phenyl)-2-(2-(5-(N-(2-(dimethylamino)ethyl)methylsulfonamido)-1,3-dioxoisoindolin-2-yl)acetoxy)ethyl)pyridine 1-oxide (Compound 208)

Scheme 37.

-continued

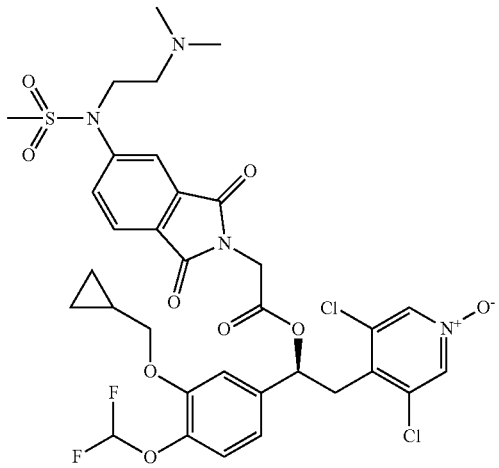

Step 1: Preparation of tert-butyl 2-(5-(N-(2-(dimethylamino)-ethyl)methylsulfonamido)-1,3-dioxoisoindolin-2-yl)acetate (206)

To a solution of tert-butyl 2-(5-(methylsulfonamido)-1,3-dioxoisoindolin-2-yl)acetate (600 mg, 1.693 mmol) (prepared in an analogous manner as previously described in Example 34, Scheme 34, Steps 1, 2, 3) in acetone (20 ml), 2-chloro-N,N-dimethylethanamine hydrochloride (366 mg, 2.54 mmol), potassium carbonate (468 mg, 3.39 mmol) and potassium iodide (281 mg, 1.693 mmol) were added. The resulting mixture was stirred at 50° C. for 48 hours. The insoluble inorganic salts were filtered off, and the filtrate was evaporated. The crude was purified by was crystallization from EtOH affording tert-butyl 2-(5-(N-(2-(dimethylamino)ethyl)methylsulfonamido)-1,3-dioxoisoindolin-2-yl)acetate (300 mg, 0.705 mmol, 41.6% yield, MS/ESI$^+$ 426.0 [MH]$^+$).

Step 2: Preparation of 2-(5-(N-(2-(dimethylamino)ethyl)-methylsulfonamido)-1,3-dioxoisoindolin-2-yl)acetic acid hydrochloride (207)

To a solution of tert-butyl 2-(5-(N-(2-(dimethylamino)ethyl)-methylsulfonamido)-1,3-dioxoisoindolin-2-yl)acetate (300 mg, 0.705 mmol) in dioxane (8 ml), 4M HCl in dioxane (1.763 ml, 7.05 mmol) was added, and the mixture was heated under microwave irradiation at 100° C. for 2 hours. The volatiles were removed under vacuum and the crude was purified by trituration with Et$_2$O affording after filtration 2-(5-(N-(2-(dimethylamino)ethyl)methylsulfonamido)-1,3-dioxoisoindolin-2-yl)acetic acid hydrochloride (250 mg, 0.616 mmol, 87% yield), MS/ESI$^+$ 370.0 [MH]$^+$).

Step 3: Preparation of (S)-3,5-dichloro-4-(2-(3-(cyclopropylmethoxy)-4-(difluoromethoxy)phenyl)-2-(2-(5-(N-(2-(dimethylamino)ethyl)-methylsulfonamido)-1,3-dioxoisoindolin-2-yl)acetoxy)ethyl) pyridine 1-oxide (208)

To a solution of (S)-3,5-dichloro-4-(2-(3-(cyclopropylmethoxy)-4-(difluoromethoxy)phenyl)-2-hydroxyethyl)pyridine 1-oxide (180 mg, 0.428 mmol), DMAP (52.3 mg, 0.428 mmol) and EDC (164 mg, 0.857 mmol) in DCM (10 ml), 2-(5-(N-(2-(dimethylamino)ethyl)methylsulfonamido)-1,3-dioxoisoindolin-2-yl)acetic acid hydrochloride (191 mg, 0.471 mmol) was added portion wise within 4 hours, and the reaction was stirred at room temperature for 24 hours. The solvent was evaporated and the crude was purified by flash silica gel chromatography (DCM/MeOH 10/0.2) affording (S)-3,5-dichloro-4-(2-(3-(cyclopropylmethoxy)-4-(difluoromethoxy)phenyl)-2-(2-(5-(N-(2-(dimethylamino)ethyl)methylsulfonamido)-1,3-dioxoisoindolin-2-yl)acetoxy)ethyl)pyridine 1-oxide as a white solid (253 mg, 0.328 mmol, 77% yield). MS/ESI$^+$ 771.15 [MH]$^+$, [$\alpha_D$]=−32.18, c=0.353, DCM). $^1$H NMR (300 MHz, DMSO-d$_6$) δ ppm 8.43 (s, 2H), 7.93-8.00 (m, 2H), 7.89 (dd, 1H), 7.19 (d, 1H), 7.09 (d, 1H), 6.97 (dd, 1H), 7.08 (t, 1H), 6.02 (dd, 1H), 4.43 (s, 2H), 3.92-4.05 (m, 2H), 3.88 (t, 2H), 3.39 (dd, 1H), 3.23 (dd, 1H), 3.13 (s, 3H), 2.31 (t, 2H), 2.10 (s, 6H), 1.07-1.33 (m, 1H), 0.49-0.71 (m, 2H), 0.27-0.49 (m, 2H)

Example 38

(S)-3,5-Dichloro-4-(2-(3-(cyclopropylmethoxy)-4-(difluoromethoxy)-phenyl)-2-(2-(5-(N-(2-(4-methylpiperazin-1-yl)ethyl)methylsulfonamido)-1,3-dioxoisoindolin-2-yl)acetoxy)ethyl)pyridine 1-oxide (Compound 213)

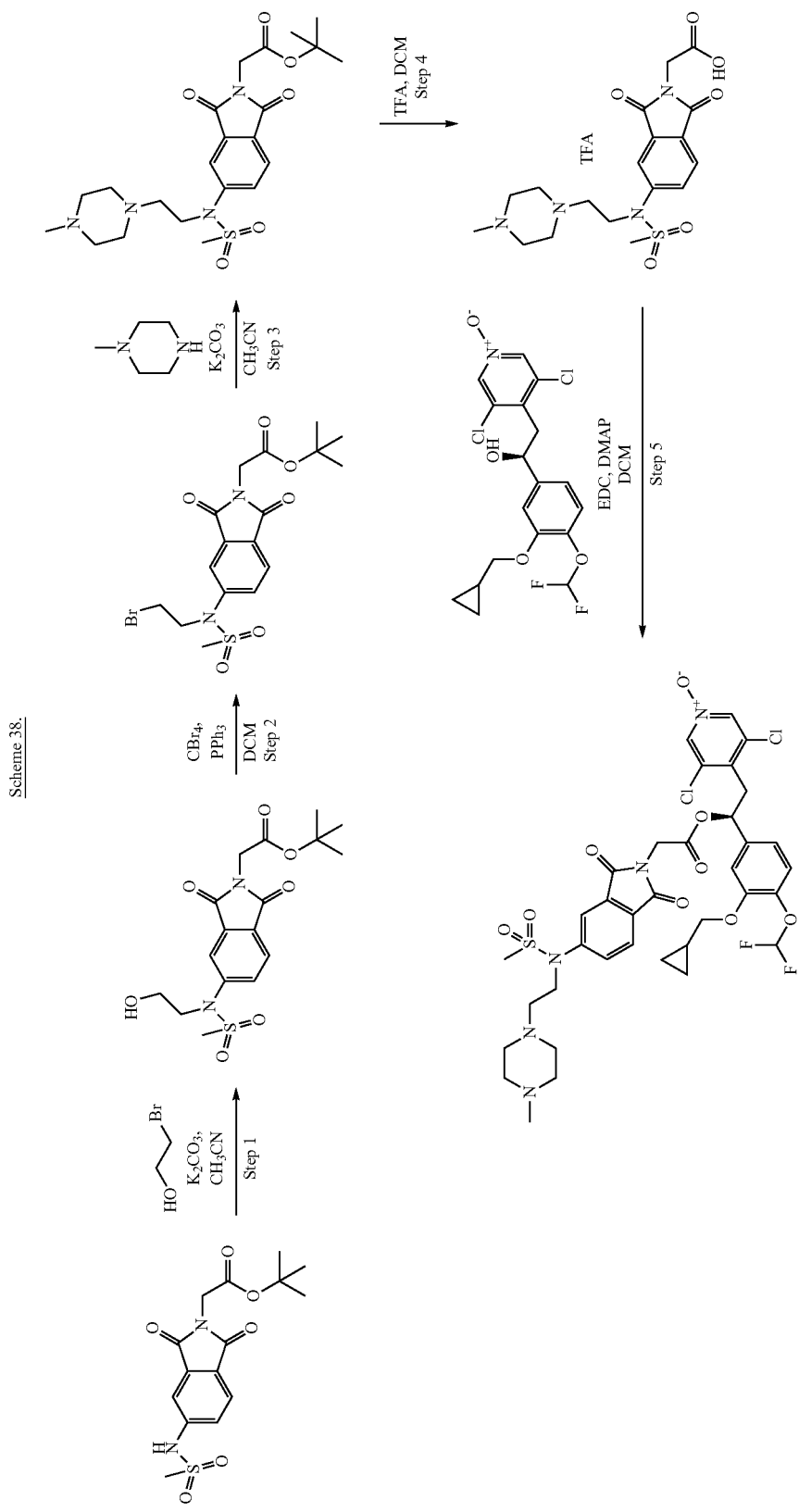

Step 1: Preparation of tert-butyl 2-(5-(N-(2-hydroxyethyl)-methylsulfonamido)-1,3-dioxoisoindolin-2-yl)acetate (209)

To a stirred solution of tert-butyl 2-(5-(methylsulfonamido)-1,3-dioxoisoindolin-2-yl)acetate (1 g, 2.82 mmol) (prepared in an analogous manner as previously described in Example 34, Scheme 34, Steps 1, 2, 3) in acetonitrile (15 ml), $K_2CO_3$ (0.585 g, 4.23 mmol) and 2-bromoethanol (0.500 ml, 7.05 mmol) were added, and the reaction was heated under MW irradiation at 110° C. for 3 hours. The insoluble inorganic salts were filtered off, and the filtrate was evaporated to dryness. The resulting crude tert-butyl 2-(5-(N-(2-hydroxyethyl)methylsulfonamido)-1,3-dioxoisoindolin-2-yl)acetate (1.12 g, 2.81 mmol, 100% yield MS/ESI$^+$ not detectable [MH]$^+$) was used without further purification.

Step 2: Preparation of tert-butyl 2-(5-(N-(2-bromoethyl)-methylsulfonamido)-1,3-dioxoisoindolin-2-yl)acetate (210)

To a stirred solution of tert-butyl 2-(5-(N-(2-hydroxyethyl)methylsulfonamido)-1,3-dioxoisoindolin-2-yl)acetate (as obtained from Example 38, step 1, 1.12 g, 2.81 mmol) in DCM (20 ml), triphenylphosphine (0.958 g, 3.65 mmol) was added. After 10 minutes at room temperature under stirring, $CBr_4$ (1.212 g, 3.65 mmol) was added, and the mixture was stirred at the same temperature for additional 14 hours. The volatiles were removed under vacuum and the crude was purified by chromatography on silica gel column (petroleum ether:ethyl acetate=7:3) affording tert-butyl 2-(5-(N-(2-bromoethyl)methylsulfonamido)-1,3-dioxoisoindolin-2-yl)acetate that crystallized on standing (0.980 g, 2.124 mmol, 76% yield).

Step 3: Preparation of tert-butyl 2-(5-(N-(2-(4-methylpiperazin-1-yl)ethyl)methylsulfonamido)-1,3-dioxoisoindolin-2-yl)acetate (211)

To a solution of tert-butyl 2-(5-(N-(2-bromoethyl)methylsulfonamido)-1,3-dioxoisoindolin-2-yl)acetate (300 mg, 0.650 mmol) in acetonitrile (15 ml), $K_2CO_3$ (135 mg, 0.975 mmol) and 1-methylpiperazine (0.080 ml, 0.715 mmol) were added, and the resulting mixture was heated under MW irradiation at 130° C. for 1 hour. Additional $K_2CO_3$ (44.8 mg, 0.325 mmol) and 1-methylpiperazine (0.036 ml, 0.325 mmol) were added, and the reaction was submitted to a second microwave cycle at 130° C. for 1 hour. The mixture was diluted with acetonitrile, the insoluble inorganic salts were filtered off, and the filtrate was evaporated under vacuum. Purification by flash chromatography (DCM/MeOH 95/5) afforded tert-butyl 2-(5-(N-(2-(4-methylpiperazin-1-yl)ethyl)methylsulfonamido)-1,3-dioxoisoindolin-2-yl)acetate (149 mg, 0.310 mmol, 47.7% yield, MS/ESI$^+$ 480.9 [MH]$^+$).

Step 4: Preparation of 2-(5-(N-(2-(4-methylpiperazin-1-yl)ethyl)-methylsulfonamido)-1,3-dioxoisoindolin-2-yl)acetic acid 2,2,2-trifluoroacetic acid salt (212)

To a solution of tert-butyl 2-(5-(N-(2-(4-methylpiperazin-1-yl)ethyl)methylsulfonamido)-1,3-dioxoisoindolin-2-yl)acetate (140 mg, 0.291 mmol) in dry DCM (4 ml) cooled to 0° C., TFA (0.449 ml, 5.83 mmol) was added, and the mixture was stirred at room temperature for 24 hours. The volatiles were removed under vacuum and the crude residue was dried affording 2-(5-(N-(2-(4-methylpiperazin-1-yl)ethyl)methylsulfonamido)-1,3-dioxoisoindolin-2-yl)acetic acid 2,2,2-trifluoroacetic acid salt (152 mg, 0.282 mmol, 97% yield, MS/ESI$^+$ 424.8 [MH]$^+$).

Step 5: Preparation of ((S)-3,5-dichloro-4-(2-(3-(cyclopropylmethoxy)-4-(difluoromethoxy)phenyl)-2-(2-(5-(N-(2-(4-methylpiperazin-1-yl)ethyl)-methylsulfonamido)-1,3-dioxoisoindolin-2-yl)acetoxy)ethyl)pyridine 1-oxide (213)

A mixture of 2-(5-(N-(2-(4-methylpiperazin-1-yl)ethyl)methylsulfonamido)-1,3-dioxoisoindolin-2-yl)acetic acid 2,2,2-trifluoroacetic acid salt (128 mg, 0.237 mmol), (S)-3,5-dichloro-4-(2-(3-(cyclopropylmethoxy)-4-(difluoromethoxy)phenyl)-2-hydroxyethyl)pyridine 1-oxide (83 mg, 0.198 mmol), EDC (53.0 mg, 0.277 mmol) and DMAP (48.3 mg, 0.395 mmol) in DCM (4 ml) was stirred at room temperature overnight. Additional EDC (18.93 mg, 0.099 mmol) was added, and the reaction was stirred at the same temperature for further 4 hours. The mixture was diluted with DCM and washed with 1N HCl and brine. The organic phase was dried over $Na_2SO_4$, filtered and evaporated. The crude was purified by flash chromatography on silica gel (DCM/MeOH 96/4, then DCM/MeOH 92/8) affording (S)-3,5-dichloro-4-(2-(3-(cyclopropylmethoxy)-4-(difluoromethoxy)phenyl)-2-(2-(5-(N-(2-(4-methylpiperazin-1-yl)ethyl)methylsulfonamido)-1,3-dioxoisoindolin-2-yl)acetoxy)-ethyl)pyridine 1-oxide as a white solid (29 mg, 0.035 mmol, 17.76% yield, MS/ESI$^+$ 826.03 [MH]$^+$, $[\alpha_D]$=−23.91, c=0.466, MeOH). $^1$H NMR (300 MHz, DMSO-$d_6$) δ ppm 8.44 (s, 2H), 7.92-7.99 (m, 2H), 7.88 (dd, 1H), 7.19 (d, 1H), 7.09 (d, 1H), 6.97 (dd, 1H), 7.08 (t, 1H), 6.02 (dd, 1H), 4.43 (s, 2H), 3.95 (dd, 2H), 3.80-3.92 (m, 2H), 3.32-3.45 (m, 1H), 3.17-3.24 (m, 1H), 3.15 (s, 3H), 2.39 (t, 2H), 2.25-2.34 (m, 4H), 2.12-2.22 (m, 4H), 2.07 (s, 3H), 1.15-1.32 (m, 1H), 0.53-0.67 (m, 2H), 0.31-0.45 (m, 2H).

The compounds listed in Table 14 were prepared with analogous synthetic steps and procedures to that described in Example 38, by reacting the appropriate precursors (commercially available or synthesized by a person skilled in the art) with suitable reagents. Specific variations in the experimentals or purification methods are indicated in the table.

TABLE 14

| Entry | Structure | NMR characterization | MS/ESI+ [MH]+ | [α_D] | Experimental procedure | Purification and yield | Starting material (precursor) | Nucleophilic agent |
|---|---|---|---|---|---|---|---|---|
| 214 | (structure shown) | $^1$H NMR (300 MHz, DMSO-d$_6$) δ ppm 8.44 (s, 2H), 7.88-8.05 (m, 3H), 7.20 (d, 1H), 7.03-7.14 (m, 1H), 6.97 (d, 1H), 7.08 (t, 1H), 6.02 (dd, 1H), 4.44 (s, 2H), 3.95 (dd, 2H), 3.82-4.06 (m, 2H), 3.31-3.48 (m, 3H), 3.10-3.24 (m, 3H), 3.15 (s, 3H), 2.17-2.44 (m, 6H), 1.81-2.07 (m, 3H), 1.18-1.33 (m, 1H), 0.51-0.70 (m, 2H), 0.25-0.48 (m, 2H) | 854.2 | −24.39 c = 0.51, MeOH | Step 3: MW, 110° C., 4 h | Flash chromatography on silica gel (DCM/ MeOH 99/1) 65.5% yield No salt | (structure shown) | (structure shown) |
| 215 | (structure shown) | $^1$H NMR (300 MHz, DMSO-d$_6$) δ ppm 8.44 (s, 2H), 8.06 (d, 1H), 8.03 (d, 1H), 7.96 (dd, 1H), 7.21 (d, 1H), 7.12 (d, 1H), 6.98 (dd, 1H), 7.09 (t, 1H), 6.02 (dd, 1H), 4.46 (s, 2H), 4.09-4.27 (m, 2H), 3.96 (d, 2H), 3.52-3.82 (dd, 1H), 3.41 (dd, 1H), 3.25 (m, 6H), 3.16 (s, 3H), 2.89 (br. s., 4H), 1.15-1.31 (m, 1H), 0.54-0.68 (m, 2H), 0.31-0.42 (m, 2H) | 829.2 | −30.37 c = 0.513, MeOH | Step 3: MW, 130° C., 2 h | Flash chromatography on silica gel (DCM/ MeOH 97/3) followed by preparative HPLC (Method 1) 42% yield TFA salt | (structure shown) | (structure shown) |

TABLE 14-continued

| Entry | Structure | NMR characterization | MS/ESI+ [MH]+ | [α_D] | Experimental procedure | Purification and yield | Starting material (precursor) | Nucleophilic agent |
|---|---|---|---|---|---|---|---|---|
| 216 | (structure) | 1H NMR (300 MHz, DMSO-d6) δ ppm 8.44 (s, 2H), 8.02 (d, 1H), 8.00 (d, 1H), 7.93 (dd, 1H), 7.20 (d, 1H), 7.11 (d, 1H), 6.98 (dd, 1H), 7.09 (t, 1H), 6.02 (dd, 1H), 4.45 (s, 2H), 4.02 (br. s., 2H), 3.89-3.98 (m, 2H), 3.41 (dd, 1H), 3.25 (dd, 1H), 3.18 (br. s., 2H), 3.12 (s, 3H), 2.76 (s, 6H), 2.69-2.93 (m, 2H), 2.37 (br. s., 2H), 1.09-1.33 (m, 1H), 0.48-0.69 (m, 2H), 0.29-0.47 (m, 2H) | 828.2 | −17.24 c = 0.667, MeOH | Step 3: MW, 130° C., 1 h | Flash chromatography on silica gel (DCM/MeOH 97/3 to 90/10) followed by preparative HPLC (Method 1) 3% yield TFA salt | (structure) | (structure) |
| 217 | (structure) | 1H NMR (300 MHz, DMSO-d6) δ ppm 8.44 (s, 2H), 7.91 (d, 1H), 7.85 (d, 1H), 7.74 (dd, 1H), 7.50 (t, 1H), 7.20 (d, 1H), 7.09-7.12 (m, 2H), 6.97 (dd, 1H), 7.08 (t, 1H), 6.79 (t, 1H), 6.02 (dd, 1H), 4.43 (s, 2H), 4.15-4.25 (m, 2H), 4.07-4.15 (m, 2H), 3.78-4.01 (m, 2H), 3.40 (dd, 1H), 3.24 (dd, 1H), 3.03 (s, 3H), 1.19-1.36 (m, 1H), 0.52-0.68 (m, 2H), 0.30-0.46 (m, 2H) | 794.11 | −30.91 c = 0.383, DCM | Step 3: MW, 120° C., 2 h Step 4: dioxane, 4 M HCl dioxane, 100° C., 1 h (see Example 5) | Flash chromatography on silica gel (DCM/MeOH 10/0.5) 45.4% yield No salt | (structure) | (structure) |

Example 39

(S)-3,5-Dichloro-4-(2-(3-(cyclopropylmethoxy)-4-(difluoromethoxy)phenyl)-2-(2-(5-(N-(2-(2-methoxyethylamino)ethyl)methylsulfonamido)-1,3-dioxoisoindolin-2-yl)acetoxy)ethyl)pyridine 1-oxide (Compound 227)

Scheme 39.
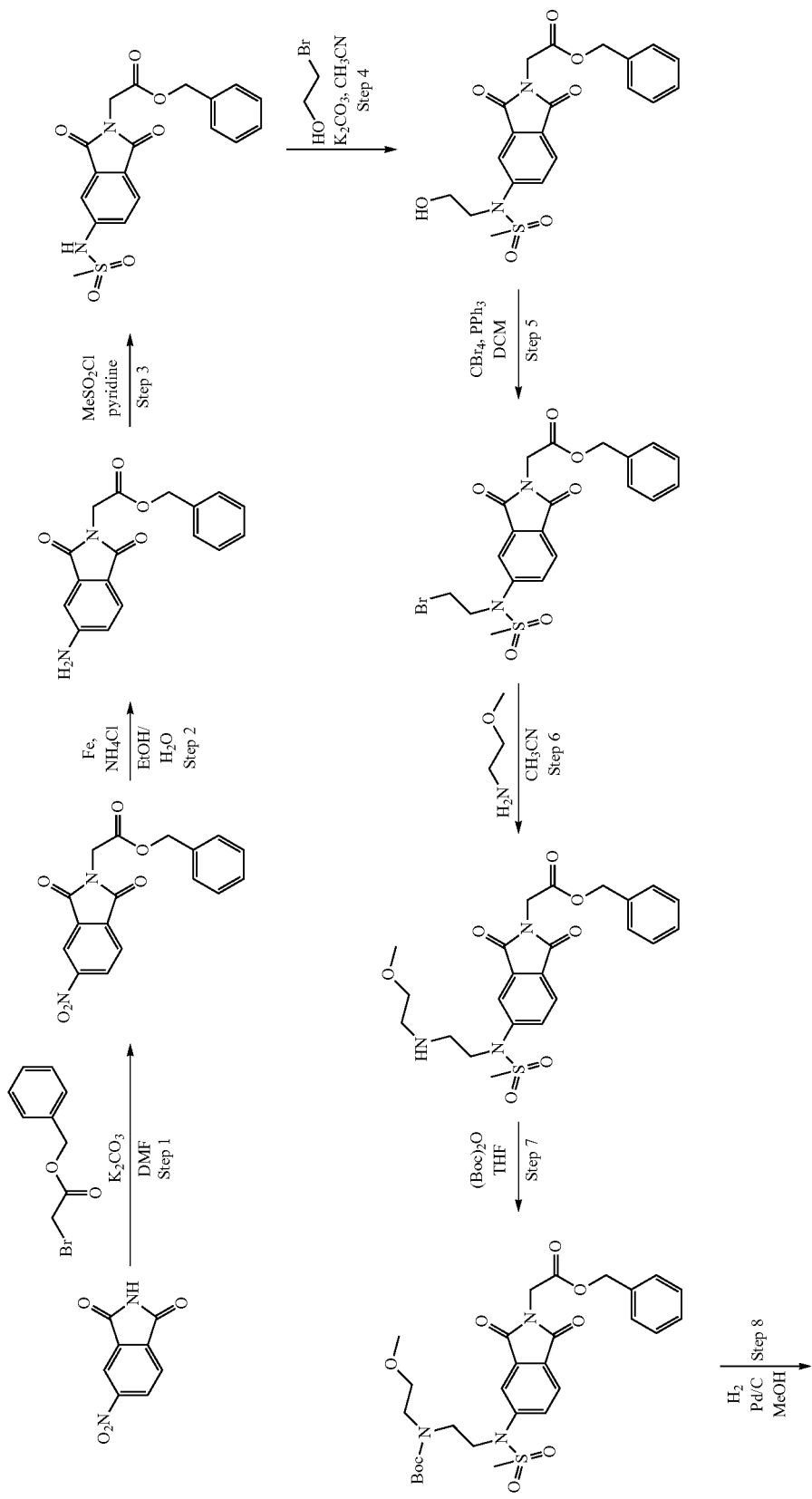

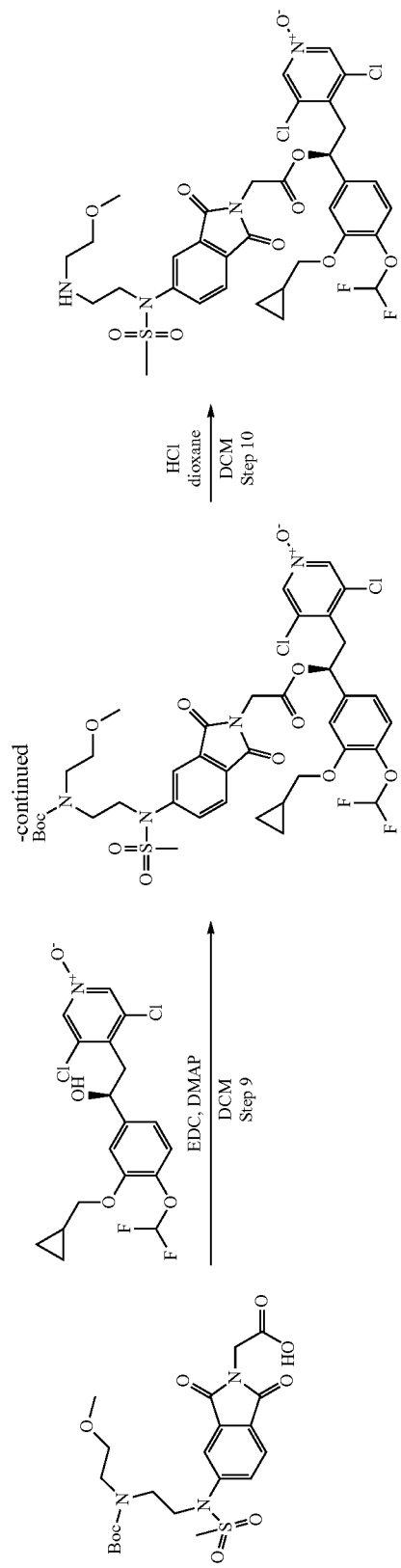

Step 1: Preparation of benzyl 2-(5-nitro-1,3-dioxoisoindolin-2-yl)acetate (218)

A solution of 5-nitroisoindoline-1,3-dione (1.00 g, 5.20 mmol), benzyl 2-bromoacetate (1.225 ml, 7.81 mmol) and $K_2CO_3$ (1.079 g, 7.81 mmol) in DMF (10 ml) was heated at 90° C. for 2 hours. The insoluble inorganic salts were filtered off, and the filtrate was diluted with ethyl acetate and washed with 1N HCl and with brine. The organic layer was dried over $Na_2SO_4$ and the solvent was removed under vacuum. The residue was purified by crystallization from MeOH to afford benzyl 2-(5-nitro-1,3-dioxoisoindolin-2-yl)acetate (1.39 g, 4.08 mmol, 78% yield, MS/ESI$^+$ not detectable [MH]$^+$).

Step 2: Preparation of benzyl 2-(5-amino-1,3-dioxoisoindolin-2-yl)acetate (219)

To a suspension of benzyl 2-(5-nitro-1,3-dioxoisoindolin-2-yl)acetate (1.2 g, 3.528 mmol) in a mixture of ethanol (23 ml) and water (11.5 ml), iron powder (1.182 g, 21.16 mmol) and ammonium chloride (0.132 g, 2.468 mmol) were added, and the mixture was heated to reflux for 1 hour. The insoluble was filtered off and the filtrate was evaporated to dryness. The residue was dissolved in ethyl acetate and washed with water and brine (×3). The organic phase was dried over $Na_2SO_4$ and the solvent was removed to give benzyl 2-(5-amino-1,3-dioxoisoindolin-2-yl)acetate (1.035 g, 3.335 mmol, 94.5% yield, MS/ESI$^+$ 310.9 [MH]$^+$). This product was used in the following step without further purification.

Step 3: Preparation of benzyl 2-(5-(methylsulfonamido)-1,3-dioxoisoindolin-2-yl)acetate (220)

To a solution of benzyl 2-(5-amino-1,3-dioxoisoindolin-2-yl)acetate (1.0 g, 3.22 mmol) in pyridine (8 ml) cooled to 0° C., methanesulfonyl chloride (0.377 ml, 4.83 mmol) was added drop wise, and the resulting mixture was stirred at room temperature for 3 hours. The solvent was removed under vacuum and the residue was partitioned between 2N HCl and DCM; the aqueous phase was extracted with DCM and the combined organic layers were dried over $Na_2SO_4$ and evaporated to dryness. The crude was triturated with $Et_2O$ (15 ml) to give benzyl 2-(5-(methylsulfonamido)-1,3-dioxoisoindolin-2-yl)acetate (1.1 g, 2.83 mmol, 88% yield, MS/ESI$^+$ 388.8 [MH]$^+$).

Step 4: Preparation of benzyl 2-(5-(N-(2-hydroxyethyl)-methylsulfonamido)-1,3-dioxoisoindolin-2-yl)acetate (221)

To a solution of benzyl 2-(5-(methylsulfonamido)-1,3-dioxoisoindolin-2-yl)acetate (0.700 g, 1.802 mmol) in acetonitrile (20 ml), $K_2CO_3$ (0.498 g, 3.605 mmol) and 2-bromoethanol (0.509 ml, 7.21 mmol) were further added. The mixture was heated under MW irradiation at 110° C. for 2 hours. 2-Bromoethanol (0.272 ml, 3.734 mmol) and $K_2CO_3$ (0.268 g, 1.931 mmol) were added, and the reaction was heated under MW irradiation at 110° C. for additional 3 hours. The mixture was then diluted with acetonitrile, the insoluble inorganic salts were filtered off and the filtrate was evaporated to dryness. The crude was purified by trituration with $Et_2O$ affording benzyl 2-(5-(N-(2-hydroxyethyl)methylsulfonamido)-1,3-dioxoisoindolin-2-yl)acetate (0.746 g, 1.725 mmol, 96% yield, MS/ESI$^+$ 432.9 [MH]$^+$).

Step 5: Preparation of benzyl 2-(5-(N-(2-bromoethyl)methylsulfonamido)-1,3-dioxoisoindolin-2-yl)acetate (222)

To a solution of benzyl 2-(5-(N-(2-hydroxyethyl)methylsulfonamido)-1,3-dioxoisoindolin-2-yl)acetate (0.690 g, 1.595 mmol) in DCM (18 ml), $CBr_4$ (0.688 g, 2.075 mmol) was added stirring at room temperature. After few minutes triphenylphosphine (0.544 g, 2.075 mmol) was added, and the mixture was stirred at room temperature for 2 hours. The solvent was evaporated under vacuum and the crude was purified by flash chromatography on silica gel column (petroleum ether:ethyl acetate=60:40) affording benzyl 2-(5-(N-(2-bromoethyl)methylsulfonamido)-1,3-dioxoisoindolin-2-yl)acetate (0.759 g, 1.532 mmol, 96% yield, MS/ESI$^+$ 494.8-496.7 [MH]$^+$).

Step 6: Preparation of benzyl 2-(5-(N-(2-(2-methoxyethylamino)-ethyl)methylsulfonamido)-1,3-dioxoisoindolin-2-yl)acetate (223)

To a solution of benzyl 2-(5-(N-(2-bromoethyl)methylsulfonamido)-1,3-dioxoisoindolin-2-yl)acetate (0.300 g, 0.606 mmol) in acetonitrile (6 ml), $K_2CO_3$ (0.126 g, 0.908 mmol) and 2-methoxyethanamine (0.079 ml, 0.908 mmol) were added, and the resulting mixture was heated under MW irradiation for 1 hour at 130° C. The insoluble inorganic salts were filtered off and the filtrate was evaporated to dryness. The crude was purified by flash chromatography on silica gel column (DCM:MeOH=95:5) affording benzyl 2-(5-(N-(2-(2-methoxyethylamino)ethyl)methylsulfonamido)-1,3-dioxoisoindolin-2-yl)acetate (0.154 g, 0.315 mmol, 52.0% yield, MS/ESI$^+$ 490.0 [MH]$^+$).

Step 7: Preparation of benzyl 2-(5-(N-(2-(tert-butoxycarbonyl(2-methoxyethyl)amino)ethyl)methylsulfonamido)-1,3-dioxoisoindolin-2-yl)acetate (224)

To a solution of benzyl 2-(5-(N-(2-(2-methoxyethylamino)ethyl)-methylsulfonamido)-1,3-dioxoisoindolin-2-yl)acetate (0.154 g, 0.315 mmol) in dry THF (2 ml), di-tert-butyl dicarbonate (0.103 g, 0.472 mmol) was added, and the mixture was stirred for 1 hour at room temperature. The solvent was evaporated to dryness, and the residue was diluted with ethyl acetate and washed with aqueous sat. $NaHCO_3$. The organic phase was dried over $Na_2SO_4$ and the solvent was removed affording benzyl 2-(5-(N-(2-(tert-butoxycarbonyl (2-methoxyethyl)amino)ethyl)methylsulfonamido)-1,3-dioxoisoindolin-2-yl)acetate (0.166 g, 0.282 mmol, 89% yield). This product was used without any further purification.

Step 8: Preparation of 2-(5-(N-(2-(tert-butoxycarbonyl(2-methoxyethyl)-amino)ethyl)methylsulfonamido)-1,3-dioxoisoindolin-2-yl)acetic acid (225)

A mixture of benzyl 2-(5-(N-(2-(tert-butoxycarbonyl(2-methoxyethyl)-amino)ethyl)methylsulfonamido)-1,3-dioxoisoindolin-2-yl)acetate (0.166 g, 0.282 mmol) and 10% w/w Pd/C (a catalytic amount) in MeOH was hydrogenated in a Parr apparatus at 30 psi for 3 hours. The catalyst was filtered off and the filtrate was evaporated to dryness affording 2-(5-(N-(2-(tert-butoxycarbonyl(2-methoxyethyl)amino)ethyl)-methylsulfonamido)-1,3-dioxoisoindolin-2-yl)acetic acid (0.138 g, 0.276 mmol, 98% yield, MS/ESI$^+$ 522.0 [MNa]$^+$).

Step 9: Preparation of (S)-4-(2-(2-(5-(N-(2-(tert-butoxycarbonyl(2-methoxyethyl)amino)ethyl)methylsulfonamido)-1,3-dioxoisoindolin-2-yl)acetoxy)-2-(3-(cyclopropylmethoxy)-4-(difluoromethoxy)phenyl)ethyl)-3,5-dichloropyridine 1-oxide (226)

A mixture of 2-(5-(N-(2-(tert-butoxycarbonyl(2-methoxyethyl)amino)ethyl)methylsulfonamido)-1,3-dioxoisoindolin-2-yl)acetic acid (0.138 g, 0.276 mmol), DMAP (0.0675 g, 0.553 mmol), EDC (0.079 g, 0.414 mmol) and (S)-3,5-dichloro-4-(2-(3-(cyclopropylmethoxy)-4-(difluoromethoxy)phenyl)-2-hydroxyethyl)pyridine 1-oxide (0.116 g, 0.276 mmol) in dry DCM (4 ml) was stirred overnight at room temperature under nitrogen. Additional EDC (0.106 g, 0.552 mmol) and DMAP (0.034 g, 0.276 mmol) were added, and the mixture was stirred at room temperature for further 24 hours. The reaction mixture was washed with 1N HCl and brine; the organic phase was dried over sodium sulfate and the solvent was removed. The crude was purified by flash chromatography on silica gel column (DCM:MeOH=98:2) affording (S)-4-(2-(2-(5-(N-(2-(tert-butoxycarbonyl(2-methoxyethyeamino)ethyl)methylsulfonamido)-1,3-dioxoisoindolin-2-yl)acetoxy)-2-(3-(cyclopropylmethoxy)-4-(difluoromethoxy)phenyl)ethyl)-3,5-dichloropyridine 1-oxide (0.078 g, 0.086 mmol, 31.3% yield, MS/ESI$^+$ 901.2 [MH]$^+$).

Step 10: Preparation of (S)-3,5-dichloro-4-(2-(3-(cyclopropylmethoxy)-4-(difluoromethoxy)phenyl)-2-(2-(5-(N-(2-(2-methoxyethylamino)ethyl)methylsulfonamido)-1,3-dioxoisoindolin-2-yl)acetoxy)ethyl)pyridine 1-oxide (227)

To a solution of (S)-4-(2-(2-(5-(N-(2-(tert-butoxycarbonyl(2-methoxyethyl)amino)ethyl)methylsulfonamido)-1,3-dioxoisoindolin-2-yl)acetoxy)-2-(3-(cyclopropylmethoxy)-4-(difluoromethoxy)phenyl)ethyl)-3,5-dichloropyridine 1-oxide (0.078 g, 0.086 mmol) in dry DCM (3 ml), 4M HCl in dioxane (0.103 ml, 0.412 mmol) was added, and the mixture was stirred for at room temperature overnight. Additional 4M HCl in dioxane (0.086 ml, 0.344 ml) was added, and the reaction was stirred at the same temperature for 72 hours. The mixture was washed with aqueous sat. NaHCO$_3$; the organic phase was dried over sodium sulfate and the solvent was removed affording (S)-3,5-dichloro-4-(2-(3-(cyclopropylmethoxy)-4-(difluoromethoxy)phenyl)-2-(2-(5-(N-(2-(2-methoxyethylamino)ethyl)methylsulfonamido)-1,3-dioxoisoindolin-2-yl)acetoxy)ethyl)pyridine 1-oxide as a yellow solid (54.72 mg, 0.068 mmol, 79% yield, MS/ESI$^+$ 801.13 [MH]$^+$, [$\alpha_D$]=−20.82, c=0.512, MeOH). $^1$H NMR (300 MHz, DMSO-d$_6$) δ ppm 8.43 (s, 2H), 7.98 (s, 1H), 7.96 (dd, 1H), 7.90 (dd, 1H), 7.19 (d, 1H), 7.09 (d, 1H), 6.97 (dd, 1H), 7.08 (t, 1H), 6.02 (dd, 1H), 4.43 (s, 2H), 3.91-4.02 (m, 2H), 3.86 (t, 2H), 3.39 (dd, 1H), 3.30 (t, 2H), 3.23 (dd, 1H), 3.19 (s, 3H), 3.13 (s, 3H), 2.56-2.67 (m, 4H), 1.05-1.38 (m, 1H), 0.48-0.69 (m, 2H), 0.27-0.48 (m, 2H).

Example 40

(S)-3,5-Dichloro-4-(2-(3-(cyclopropylmethoxy)-4-(difluoromethoxy)-phenyl)-2-(2-(5-(N-(2-morpholinoethyl)methylsulfonamido)-1H-indol-1-yl)acetoxy)ethyl)pyridine 1-oxide hydrochloride (Compound 230)

Scheme 40.

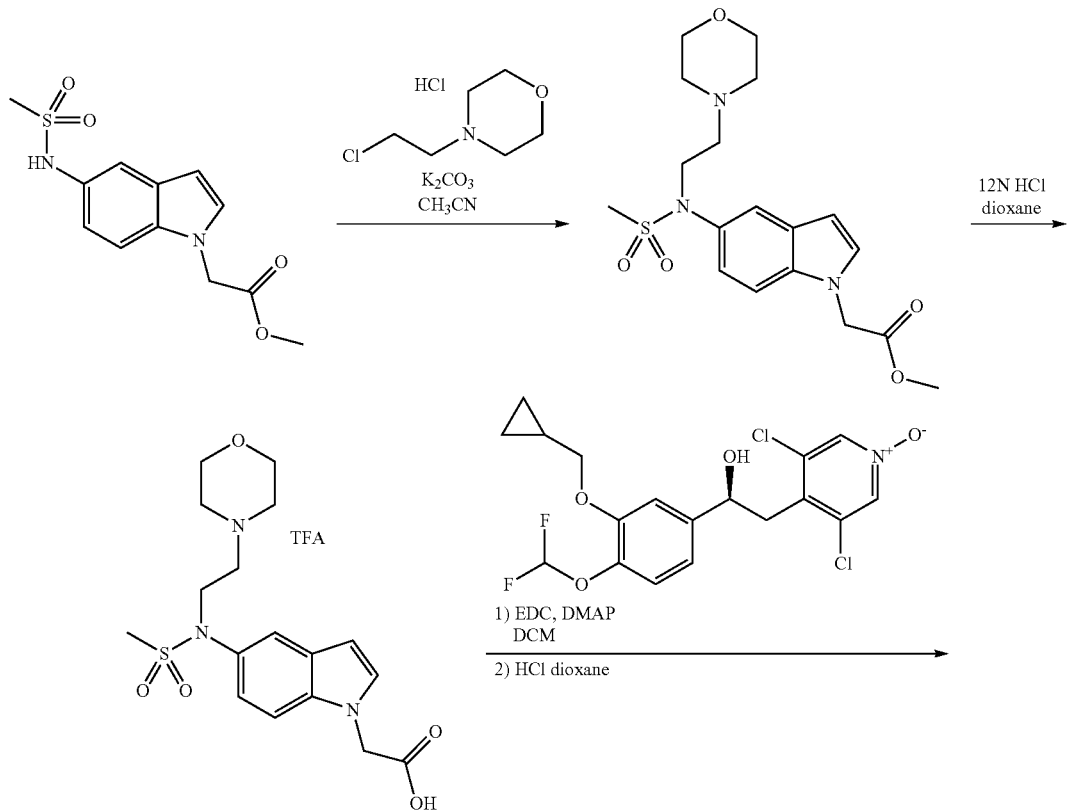

-continued

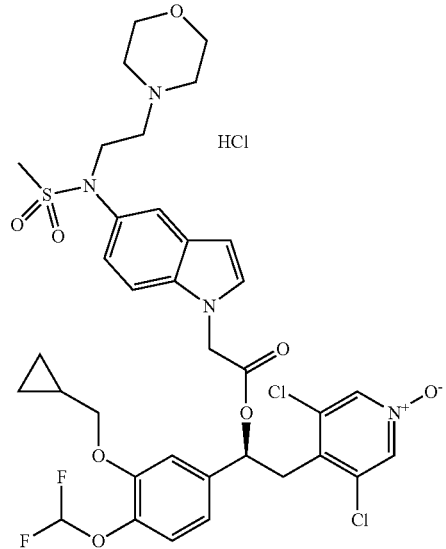

Step 1: Preparation of methyl 2-(5-(N-(2-morpholinoethyl)methylsulfonamido)-1H-indol-1-yl)acetate (228)

To a solution of methyl 2-(5-(methylsulfonamido)-1H-indol-1-yl)acetate (1.8 g, 6.38 mmol) (prepared in an analogous manner as described in, Example 14, Scheme 14, Steps 1, 2, 3) in CH$_3$CN (30 ml), K$_2$CO$_3$ (1.762 g, 12.75 mmol) and 4-(2-chloroethyl)morpholine hydrochloride (1.186 g, 6.38 mmol) were added, and the mixture heated to reflux for 3 hours. The solvent was removed and the residue was purified by flash chromatography on silica gel (DCM/MeOH 99:1 to 97:3) recovering methyl 2-(5-(N-(2-morpholinoethyl)methylsulfonamido)-1H-indol-1-yl)acetate (1.5 g, 3.79 mmol, 59.5% yield, UPLC-MS purity: 96%, MS/ESI$^+$ 396.2 [MH]$^+$).

Step 2: Preparation of 2-(5-(N-(2-morpholinoethyl)methylsulfonamido)-1H-indol-1-yl)acetic acid 2,2,2-trifluoroacetic acid salt (229)

To a solution of methyl 2-(5-(N-(2-morpholinoethyl)methylsulfonamido)-1H-indol-1-yl)acetate (1.5 g, 3.79 mmol) in dioxane (30 ml), aqueous 12 N HCl was added, and the mixture was reacted at room temperature for 3 hours. The volatiles were removed under vacuum recovering the crude desired product as hydrochloride salt (1.5 g, 3.60 mmol, 95% yield of crude). A portion of this brown crude (300 mg, 0.719 mmol) was purified by preparative HPLC (Method 2) affording 2-(5-(N-(2-morpholinoethyl)methylsulfonamido)-1H-indol-1-yl)acetic acid 2,2,2-trifluoroacetic acid salt (150 mg, 0.303 mmol, 42% yield of purification, MS/ESI$^+$ 381.9 [MH]$^+$).

Step 3: Preparation of (S)-3,5-dichloro-4-(2-(3-(cyclopropylmethoxy)-4-(difluoromethoxy)phenyl)-2-(2-(5-(N-(2-morpholinoethyl)methylsulfonamido)-1H-indol-1-yl)acetoxy)ethyl)pyridine 1-oxide hydrochloride (230)

To a solution of crude 2-(5-(N-(2-morpholinoethyl)methylsulfonamido)-1H-indol-1-yl)acetic acid 2,2,2-trifluoroacetate (150 mg, 0.303 mmol) in DCM, (S)-3,5-dichloro-4-(2-(3-(cyclopropylmethoxy)-4-(difluoromethoxy)phenyl)-2-hydroxyethyl)pyridine 1-oxide (165 mg, 0.393 mmol), EDC (226 mg, 1.180 mmol) and DMAP (24.02 mg, 0.197 mmol) were added, and the resulting mixture was stirred overnight at room temperature. The solvent was removed, and the residue was purified by flash chromatography on silica gel (DCM/MeOH 95/5). The obtained compound was treated with 4N HCl in dioxane (30 ml) affording after evaporation of the volatiles (S)-3,5-dichloro-4-(2-(3-(cyclopropylmethoxy)-4-(difluoromethoxy)-phenyl)-2-(2-(5-(N-(2-morpholinoethyl)methylsulfonamido)-1H-indol-1-yl)acetoxy)ethyl)pyridine 1-oxide hydrochloride (76.3 mg, 0.093 mmol, 32% yield, MS/ESI$^+$ 783.47 [MH]$^+$, [α$_D$]=−17.52, c=0.25 in DCM). $^1$H NMR (300 MHz, DMSO-d$_6$+Na$_2$CO$_3$) δ ppm 8.50 (s, 2H), 7.34 (d, 1H), 7.07-7.23 (m, 5H), 6.89 (dd, 1H), 7.06 (t, 1H), 6.55 (d, 1H), 6.02 (dd, 1H), 5.25 (d, 1H), 5.10 (d, 1H), 3.91 (d, 2H), 3.77-3.85 (m, 2H), 3.46-3.52 (m, 4H), 3.39-3.47 (m, 1H), 3.16-3.25 (m, 1H), 3.09 (s, 3H), 2.30-2.36 (m, 2H), 2.24-2.31 (m, 4H), 1.10-1.24 (m, 1H), 0.52-0.67 (m, 2H), 0.23-0.47 (m, 2H).

Example 41

(S)-3,5-Dichloro-4-(2-(3-(cyclopropylmethoxy)-4-(difluoromethoxy)-phenyl)-2-(2-(4-(N-(2-morpholinoethyl)methylsulfonamido)-1H-indol-1-yl)acetoxy)ethyl)pyridine 1-oxide (Compound 233)

Scheme 41.

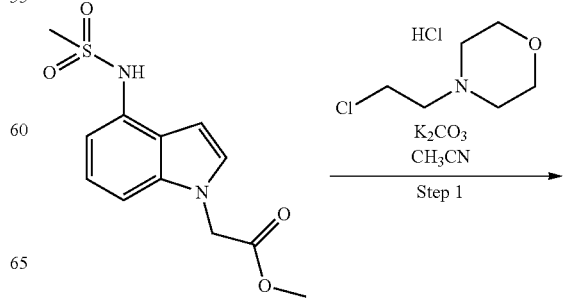

-continued

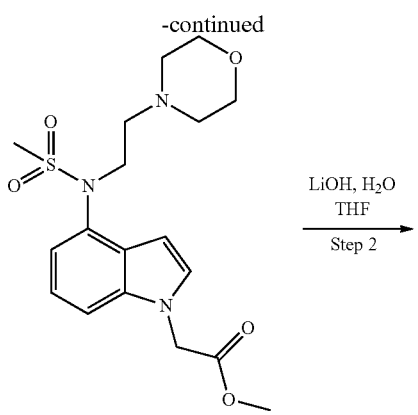

LiOH, H₂O
THF
Step 2

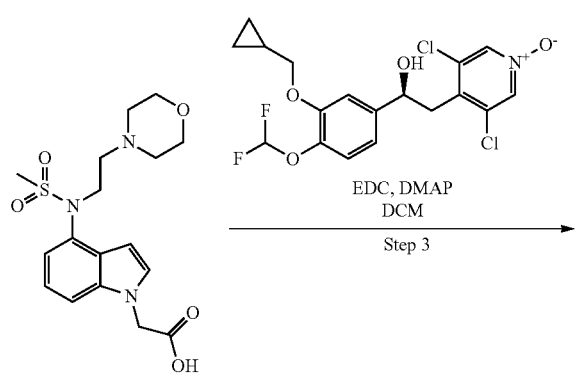

EDC, DMAP
DCM
Step 3

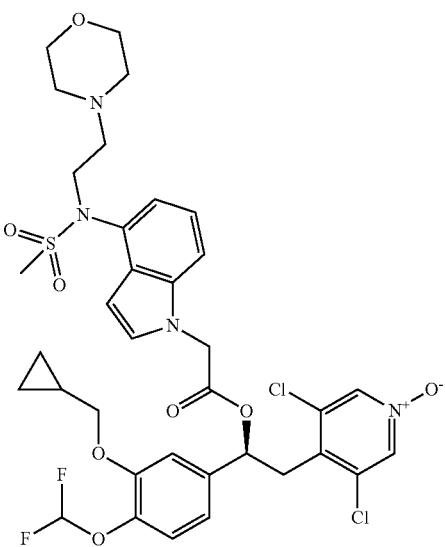

Step 1: Preparation of methyl 2-(4-(N-(2-morpholinoethyl)-methylsulfonamido)-1H-indol-1-yl)acetate (231)

To a solution of methyl 2-(4-(methylsulfonamido)-1H-indol-1-yl)acetate (1.0 g, 3.54 mmol) (prepared in an analogous manner as described Example 15, Scheme 15, Steps 1, 2, 3) in CH₃CN (30 ml), K₂CO₃ (0.734 g, 5.31 mmol) and 4-(2-chloroethyl)-morpholine hydrochloride (0.989 g, 5.31 mmol) were added, and the resulting mixture heated to reflux for 3 hours. The insoluble inorganic salts were filtered off and the filtrate was evaporated to dryness affording methyl 2-(4-(N-(2-morpholinoethyl)-methylsulfonamido)-1H-indol-1-yl) acetate (1.08 g, 2.73 mmol, 77% yield, MS/ESI⁺ 395.9 [MH]⁺) which was used without any additional purification.

Step 2: Preparation of 2-(4-(N-(2-morpholinoethyl) methylsulfonamido)-1H-indol-1-yl)acetic acid (232)

To a solution of methyl 2-(4-(N-(2-morpholinoethyl)methylsulfonamido)-1H-indol-1-yl)acetate (1.08 g, 2.73 mmol) in a 1/1 mixture of THF and water (30 ml), lithium hydroxide (0.654 g, 27.3 mmol) was added, and the mixture reacted for 1 hour at room temperature. The mixture was acidified with aqueous 12 N HCl (pH=5) and the desired compound was extracted with EtOAc (3×50 ml). The organic phase was dried over sodium sulfate and the solvent was removed; the residue was purified by flash chromatography (DCM/MeOH 9/1) recovering 2-(4-(N-(2-morpholinoethyl)-methylsulfonamido)-1H-indol-1-yl)acetic acid (650 mg, 1.704 mmol 62.4% yield, MS/ESI⁺ 381.9 [MH]⁺).

Step 3: Preparation of (S)-3,5-dichloro-4-(2-(3-(cyclopropylmethoxy)-4-(difluoromethoxy)phenyl)-2-(2-(4-(N-(2-morpholinoethyl)methylsulfonamido)-1H-indol-1-yl)acetoxy)ethyl)pyridine 1-oxide (233)

To a solution of 2-(4-(N-(2-morpholinoethyl)methylsulfonamido)-1H-indol-1-yl)acetic acid (100 mg, 0.262 mmol) in DCM (5 ml), (S)-3,5-dichloro-4-(2-(3-(cyclopropylmethoxy)-4-(difluoromethoxy)phenyl)-2-hydroxyethyl)pyridine 1-oxide (110 mg, 0.262 mmol), EDC (151 mg, 0.786 mmol) and DMAP (64.1 mg, 0.524 mmol) were added, and the mixture was reacted overnight at room temperature. The solvent was evaporated and the residue was partitioned between 1N HCl (10 ml) and EtOAc; the aqueous phase was extracted with EtOAc, the combined organic layers were dried over sodium sulfate and the solvent was removed under vacuum. Three flash chromatographic column on silica gel (DCM/MeOH 97/3) were required to afford (S)-3,5-dichloro-4-(2-(3-(cyclopropylmethoxy)-4-(difluoromethoxy)phenyl)-2-(2-(4-(N-(2-morpholinoethyl)methylsulfonamido)-1H-indol-1-yl)acetoxy)ethyl)pyridine 1-oxide (21.4 mg, 0.027 mmol, 10.4% yield, MS/ESI⁺ 783.19 [MH]⁺, [α$_D$]=+14.1, c=0.2 DCM). ¹H NMR (300 MHz, DMSO-d₆) δ ppm 8.50 (s, 2H), 7.34 (d, 1H), 7.07-7.21 (m, 5H), 6.90 (dd, 1H), 7.06 (t, 1H), 6.55 (d, 1H), 6.02 (dd, 1H), 5.25 (d, 1H), 5.10 (d, 1H), 3.91 (d, 2H), 3.80 (t, 2H), 3.46-3.54 (m, 4H), 3.41 (dd, 1H), 3.21 (dd, 1H), 3.09 (s, 3H), 2.32 (dd, 2H), 2.23-2.31 (m, 4H), 1.07-1.36 (m, 1H), 0.54-0.65 (m, 2H), 0.29-0.47 (m, 2H).

Example 42

(S)-3,5-Dichloro-4-(2-(3-(cyclopropylmethoxy)-4-(difluoromethoxy)-phenyl)-2-(2-(6-(N-(2-morpholinoethyl)methylsulfonamido)-2-oxobenzo[d]oxazol-3(2H)-yl)acetoxy)ethyl)pyridine 1-oxide (Compound 236)

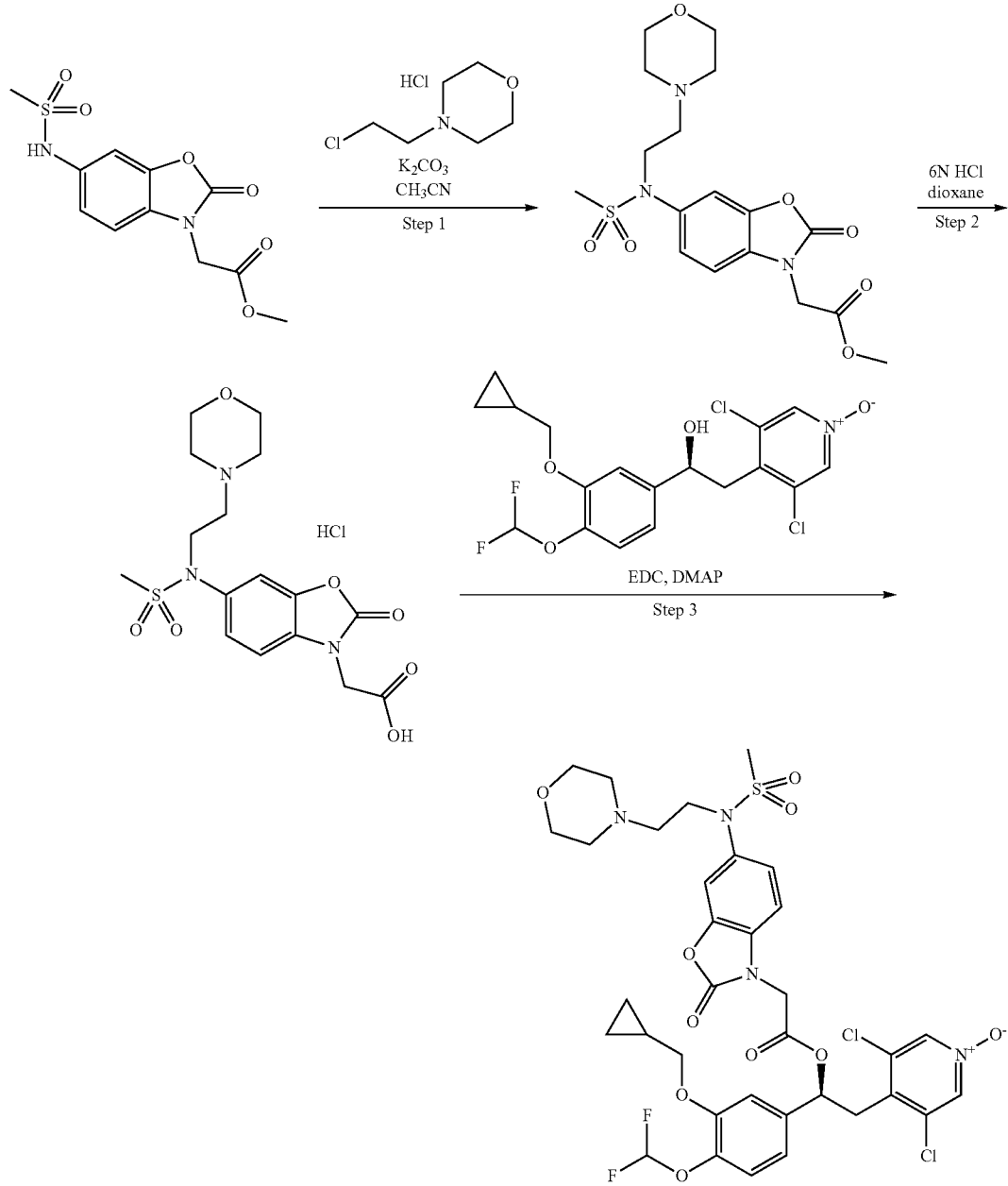

Scheme 42.

Step 1: Preparation of methyl 2-(6-(N-(2-morpholinoethyl)-methylsulfonamido)-2-oxobenzo[d]oxazol-3(2H)-yl)acetate (234)

To a solution of methyl 2-(6-(methylsulfonamido)-2-oxobenzo[d]oxazol-3(2H)-yl)acetate (300 mg, 0.999 mmol) (prepared in an analogous manner as described in Example 24, Scheme 24, Steps 1, 2, 3) in $CH_3CN$ (15 ml), 4-(2-chloroethyl)morpholine hydrochloride (186 mg, 0.999 mmol) and $K_2CO_3$ (138 mg, 0.999 mmol) were added. The mixture was heated at 100° C. under microwaves irradiation for 1 hour. The solvent was removed under vacuum, and the residue was portioned between EtOAc and water. The organic phase was washed several times with brine and dried over sodium sulfate; the solvent was evaporated to dryness and the crude was purified by flash chromatography on silica gel (DCM/MeOH 98/2) to afford methyl 2-(6-(N-(2-morpholinoethyl)methylsulfonamido)-2-oxobenzo[d]oxazol-3(2H)-yl)acetate (340 mg, 0.822 mmol, 82% yield, MS/ESI$^+$ 414.0 [MH]$^+$).

Step 2: Preparation of 2-(6-(N-(2-morpholinoethyl) methylsulfonamido)-2-oxobenzo[d]oxazol-3(2H)-yl) acetic acid hydrochloride (235)

To a solution of methyl 2-(6-(N-(2-morpholinoethyl)methylsulfonamido)-2-oxobenzo[d]oxazol-3(211)-yl)acetate (340 mg, 0.822 mmol) in dioxane (6 ml) aqueous 6N HCl (1.645 ml, 9.870 mmol) was added, and the reaction mixture was heated at 100° C. for 2 hours. All the volatiles were removed under reduced pressure and the residue was treated with toluene and dried to give 2-(6-(N-(2-morpholinoethyl) methylsulfonamido)-2-oxobenzo[d]oxazol-3(2H)-yl)acetic acid hydrochloride (350 mg, 0.803 mmol, 98% yield, MS/ESI$^+$ 400.0 [MH]$^+$).

Step 3: Preparation of (S)-3,5-dichloro-4-(2-(3-(cyclopropylmethoxy)-4-(difluoromethoxy)phenyl)-2-(2-(6-(N-(2-morpholinoethyl)methylsulfonamido)-2-oxobenzo[d]oxazol-3(2H)-yl)acetoxy)ethyl)pyridine 1-oxide (236)

(S)-3,5-dichloro-4-(2-(3-(cyclopropylmethoxy)-4-(difluoromethoxy)phenyl)-2-hydroxyethyl)pyridine 1-oxide (281 mg, 0.669 mmol), 2-(6-(N-(2-morpholinoethyl)-methylsulfonamido)-2-oxobenzo[d]oxazol-3(2H)-yl)acetic acid hydrochloride (350 mg, 0.803 mmol), EDC (192 mg, 1.004 mmol) and DMAP (204 mg, 1.673 mmol) were dissolved in dry DCM (8 ml), and the mixture was reacted at room temperature for 5 hours. Additional EDC (128 mg, 0.669 mmol) and DMAP (82 mg, 0.669 mmol) were added, and the reaction was stirred at the same temperature overnight. Thus, the mixture was treated with 1N HCl (30 ml) and extracted with DCM (2×100 ml). The organic phase was washed with brine and dried over Na$_2$SO$_4$; the solvent was removed under reduced pressure and the resulting crude was purified by flash chromatography (DCM/MeOH 98/2 to 90/10) yielding (S)-3,5-dichloro-4-(2-(3-(cyclopropylmethoxy)-4-(difluoromethoxy)phenyl)-2-(2-(6-(N-(2-morpholinoethyl)methylsulfonamido)-2-oxobenzo[d]oxazol-3(2H)-yl)acetoxy) ethyl)pyridine 1-oxide (203 mg, 0.253 mmol, 37.8% yield, MS/ESI$^+$ 801.15 [MH]$^+$, [α$_D$]=−20.63, c=0.505, DCM). $^1$H NMR (300 MHz, DMSO-d$_6$) δ ppm 8.39 (s, 2H), 7.52 (d, 1H), 7.27 (dd, 1H), 7.22 (d, 1H), 7.20 (d, 1H), 7.11 (d, 1H), 6.97 (dd, 1H), 7.08 (t, 1H), 6.04 (dd, 1H), 4.86 (d, 1H), 4.72 (d, 1H), 3.94 (d, 2H), 3.74 (t, 2H), 3.46-3.57 (m, 4H), 3.38 (dd, 1H), 3.22 (dd, 1H), 3.09 (s, 3H), 2.22-2.44 (m, 6H), 1.16-1.31 (m, 1H), 0.50-0.66 (m, 2H), 0.28-0.46 (m, 2H).

The compound listed in Table 15 was prepared with analogous synthetic steps and procedures to that described in Example 42, by reacting the appropriate precursors (commercially available or synthesized by a person skilled in the art) with suitable reagents. Specific variations in the experimentals or purification methods are indicated in the table.

TABLE 15

| Entry | Structure | NMR characterization | MS/ESI$^+$ [MH]$^+$ | [α$_D$] | Experimental procedure | Purification and yield | Starting material (precursor) | Alkylating agent |
|---|---|---|---|---|---|---|---|---|
| 237 | 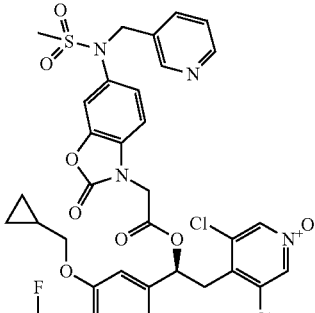 | $^1$H NMR (300 MHz, DMSO-d$_6$) δ ppm 8.43 (dd, 1H), 8.40 (dd, 1H), 8.33 (s, 2H), 7.72 (dt, 1H), 7.53 (d, 1H), 7.31 (ddd, 1H), 7.12-7.24 (m, 3H), 7.08 (d, 1H), 6.94 (dd, 1H), 7.07 (t, 1H), 6.00 (dd, 1H), 4.92 (s, 2H), 4.79 (d, 1H), 4.65 (d, 1H), 3.92 (d, 2H), 3.34 (dd, 1H), 3.19 (dd, 1H), 3.18 (s, 3H), 0.99-1.35 (m, 1H), 0.44-0.72 (m, 2H), 0.18-0.44 (m, 2H) | 779.04 | −13.80 c = 0.500 DCM | Step 2: 100° C., 3 h | Flash chromatography on silica gel (DCM/MeOH 98/2 to 90/10) 28% yield No salt | 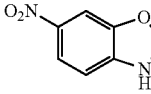 | 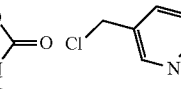 |

Example 43
(S)-3,5-Dichloro-4-(2-(3-(cyclopropylmethoxy)-4-(difluoromethoxy)-phenyl)-2-(2-(5-(N-(2-morpholinoethyl)methylsulfonamido)-2,3-dioxoindolin-1-yl)acetoxy)ethyl)pyridine 1-oxide (Compound 240)
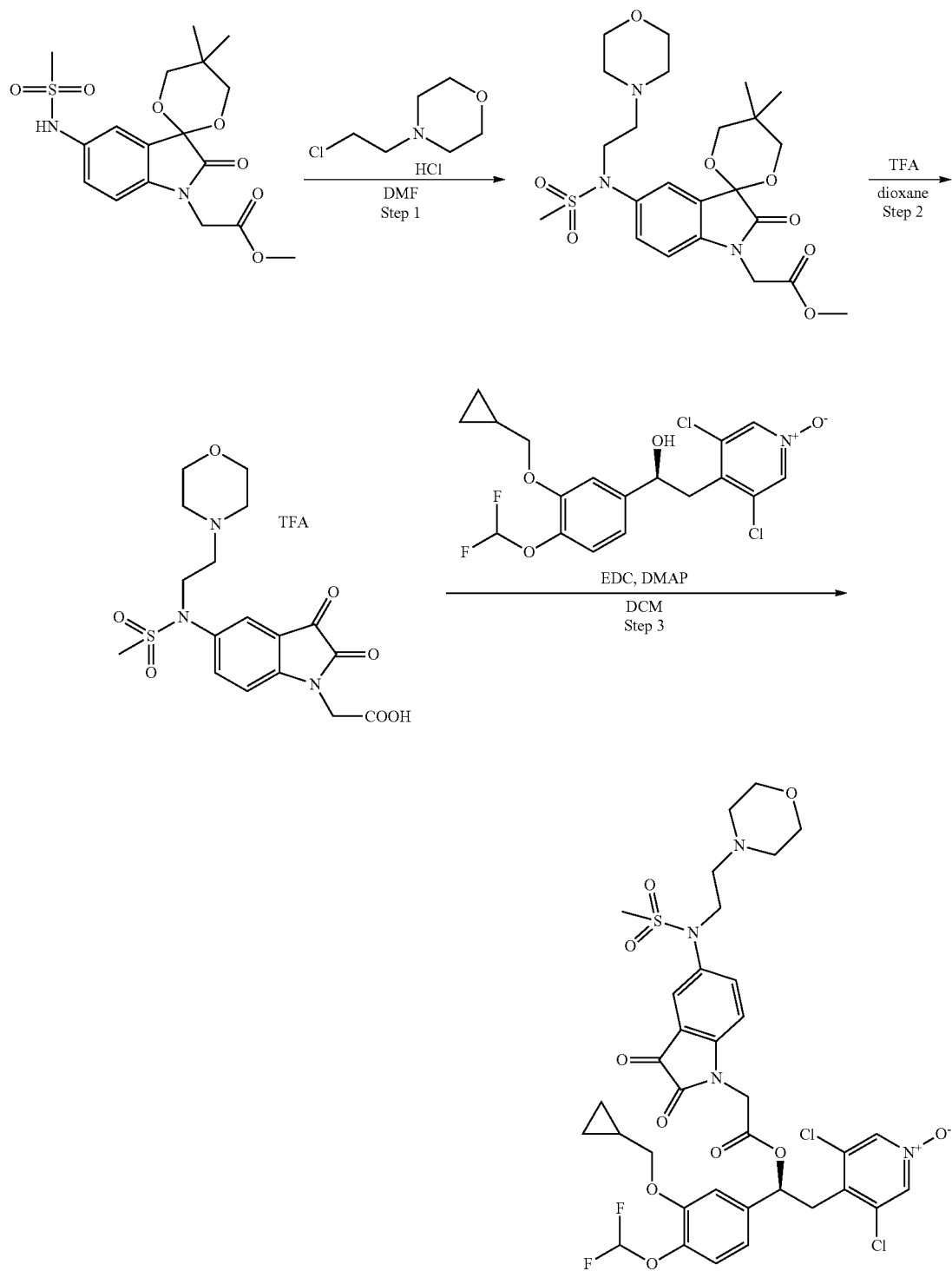
Scheme 43.

Step 1: Preparation of methyl 2-(5,5-dimethyl-5'-(N-(2-morpholinoethyl)-methylsulfonamido)-2'-oxospiro[1,3]dioxane-2,3'-indoline]-1'-yl)acetate (238)

A mixture of methyl 2-(5,5-dimethyl-5'-(methylsulfonamido)-2'-oxospiro[[1,3]dioxane-2,3'-indoline]-1'-yl)acetate (0.400 g, 1.004 mmol), 4-(2-chloroethyl)morpholine hydrochloride (0.224 g, 1.204 mmol) (prepared in an analogous manner as described in Example 17, Scheme 17, Steps 1, 2, 3, 4) and K$_2$CO$_3$ (0.306 g, 2.208 mmol) in DMF (8 ml) was heated at 70° C. for 3 hours. The mixture was partitioned between ethyl acetate and water, and the aqueous phase was extracted with ethyl acetate. The combined organic layers were washed several times with brine and dried over sodium sulfate; the solvent was removed and the crude was purified by chromatography on silica gel cartridge (DCM:MeOH=99:1 to 97:3) affording methyl 2-(5,5-dimethyl-5'-(N-(2-morpholinoethyl)-methylsulfonamido)-2'-oxospiro[[1,3]dioxane-2,3'-indoline]-1'-yl)acetate (0.453 g, 0.885 mmol, 88% yield, MS/ESI$^+$ 512.1 [MH]$^+$).

Step 2: Preparation of 2-(5-(N-(2-morpholinoethyl)methylsulfonamido)-2,3-dioxoindolin-1-yl)acetic acid 2,2,2-trifluoroacetic acid salt (239)

A mixture of methyl 2-(5,5-dimethyl-5'-(N-(2-morpholinoethyl)-methylsulfonamido)-2'-oxospiro[[1,3]dioxane-2,3'-indoline]-1'-yl)acetate (0.450 g, 0.880 mmol) and TFA (0.678 ml, 8.80 mmol) in dioxane/water 1/1 (15 ml) was heated at 80° C. for 24 hours. Additional TFA (1.356 ml, 17.6 mmol) was added over 5 days with stirring at the same temperature. The volatiles were removed under vacuum, and the crude was triturated with diethyl ether. The insoluble was collected by filtration and dried under vacuum affording 2-(5-(N-(2-morpholinoethyl)methylsulfonamido)-2,3-dioxoindolin-1-yl)acetic acid 2,2,2-trifluoroacetic acid salt (0.319 g, 0.607 mmol, 69.0% yield, MS/ESI$^+$ 412.0 [MH]$^+$).

Step 3: Preparation of (S)-3,5-dichloro-4-(2-(3-(cyclopropylmethoxy)-4-(difluoromethoxy)phenyl)-2-(2-(5-(N-(2-morpholinoethyl)methylsulfonamido)-2,3-dioxoindolin-1-yl)acetoxy)ethyl)pyridine 1-oxide (240)

A mixture of 2-(5-(N-(2-morpholinoethyl)methylsulfonamido)-2,3-dioxoindolin-1-yl)acetic acid 2,2,2-trifluoroacetic acid salt (0.319 g, 0.607 mmol), (S)-3,5-dichloro-4-(2-(3-(cyclopropylmethoxy)-4-(difluoromethoxy)phenyl)-2-hydroxyethyl)pyridine 1-oxide (0.170 g, 0.405 mmol), EDC (0.233 g, 1.214 mmol), and DMAP (0.099 g, 0.809 mmol) in DCM (25 ml) was stirred at room temperature for 3 days. The mixture was diluted with DCM and washed with aqueous 5% NaHCO$_3$ and with sat. NH$_4$Cl; the organic phase was dried over sodium sulfate, and the solvent was removed. The crude was purified by flash chromatography on silica gel cartridge (DCM:MeOH=99:1 to 95:5). An additional purification by chromatography on silica gel column (DCM:MeOH=98:2 to 97:3) was performed to afford (S)-3,5-dichloro-4-(2-(3-(cyclopropylmethoxy)-4-(difluoromethoxy)phenyl)-2-(2-(5-(N-(2-morpholinoethyl)methylsulfonamido)-2,3-dioxoindolin-1-yl)acetoxy)ethyl)pyridine 1-oxide (0.113 g, 0.139 mmol, 34.3% yield, MS/ESI$^+$ 813.19 [MH]$^+$, [α$_D$]=−26.83, c=0.24, MeOH). $^1$H NMR (300 MHz, DMSO-d$_6$) δ ppm 8.43 (s, 2H), 7.69 (d, 1H), 7.68 (dd, 1H), 7.19 (d, 1H), 7.10 (d, 1H), 7.09 (d, 1H), 6.96 (dd, 1H), 7.08 (t, 1H), 6.04 (dd, 1H), 4.69 (d, 1H), 4.58 (d, 1H), 3.93 (d, 2H), 3.74 (t, 2H), 3.46-3.55 (m, 4H), 3.40 (dd, 1H), 3.23 (dd, 1H), 3.08 (s, 3H), 2.37 (t, 2H), 2.28-2.34 (m, 4H), 1.08-1.36 (m, 1H), 0.47-0.66 (m, 2H), 0.27-0.49 (m, 2H).

Example 44

(S)-3,5-Dichloro-4-(2-(3-(cyclopropylmethoxy)-4-(difluoromethoxy)-phenyl)-2-(2-(5-(N-(2-morpholinoethyl)methylsulfonamido)-2-oxoindolin-1-yl)acetoxy)ethyl)pyridine 1-oxide (Compound 243)

Scheme 44.

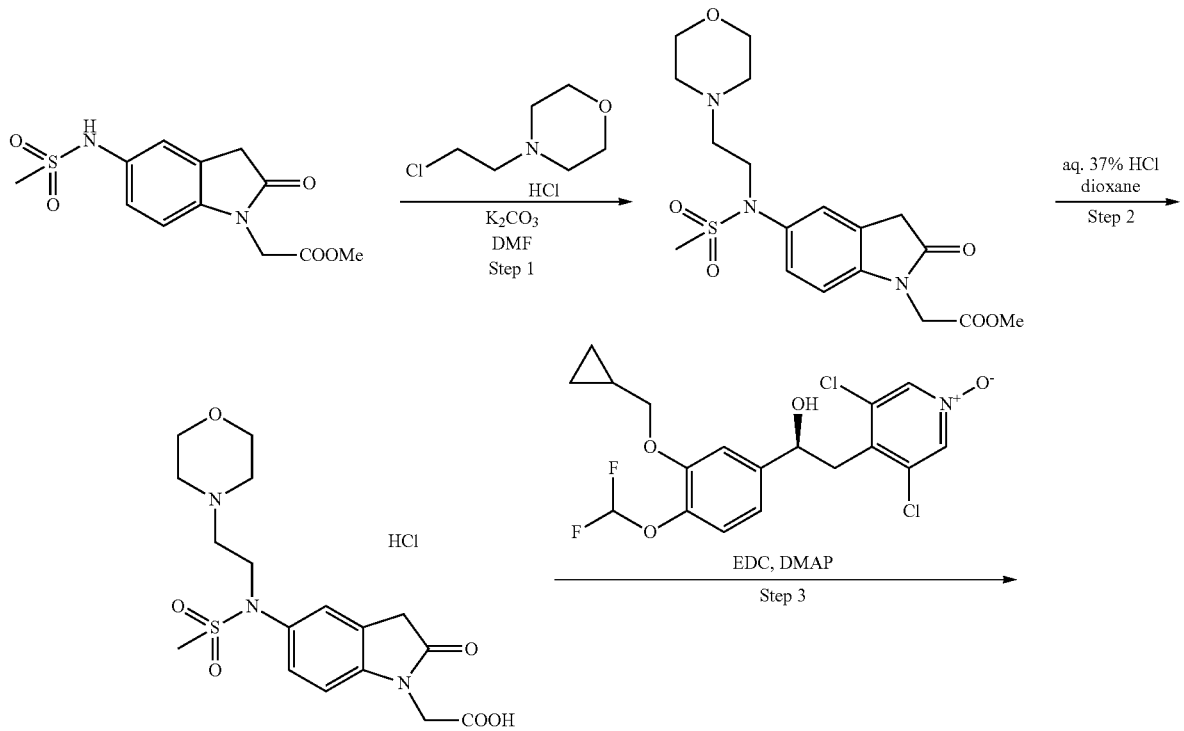

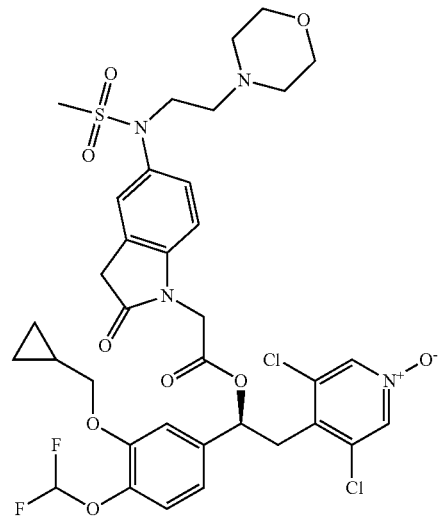

Step 1: Preparation of methyl 2-(5-(N-(2-morpholinoethyl)-methylsulfonamido)-2-oxoindolin-1-yl)acetate (241)

A mixture of methyl 2-(5-(methylsulfonamido)-2-oxoindolin-1-yl)acetate (0.500 g, 1.607 mmol) (prepared in an analogous manner as described in Example 20, Scheme 20, Steps 1, 2, 3, 4), 4-(2-chloroethyl)morpholine hydrochloride (0.393 g, 2.112 mmol), and $K_2CO_3$ (0.524 g, 3.788 mmol) in DMF (25 ml) was heated at 65° C. for 2 hours. The mixture was partitioned between ethyl acetate and aqueous 5% $NaHCO_3$; the organic phase was washed several times with brine and dried over sodium sulfate. The solvent was removed under vacuum and the dark crude was purified by flash chromatography on silica gel column (DCM:MeOH=99:1 to 97:3) affording methyl 2-(5-(N-(2-morpholinoethyl)methylsulfonamido)-2-oxoindolin-1-yl)acetate (0.100 g, 0.243 mmol, 14.5% yield, MS/ESI$^+$ 412.0 [MH]$^+$).

Step 2: Preparation of 2-(5-(N-(2-morpholinoethyl)methylsulfonamido)-2-oxoindolin-1-yl)acetic acid hydrochloride (242)

To a solution of methyl 2-(5-(N-(2-morpholinoethyl)methylsulfonamido)-2-oxoindolin-1-yl)acetate (0.100 g, 0.243 mmol) in dioxane (5 ml), aqueous 37% HCl (5 ml) was added, and the mixture was stirred at room temperature overnight. The volatiles were removed under vacuum and crude 2-(5-(N-(2-morpholinoethyl)-methylsulfonamido)-2-oxoindolin-1-yl)acetic acid hydrochloride (0.105 g, 0.242 mmol, 100% yield, MS/ESI$^+$ 398.0 [MH]$^+$) was used as such in the next step.

Step 3: Preparation of (S)-3,5-dichloro-4-(2-(3-(cyclopropylmethoxy)-4-(difluoromethoxy)phenyl)-2-(2-(5-(N-(2-morpholinoethyl)methylsulfonamido)-2-oxoindolin-1-yl)acetoxy)ethyl)pyridine 1-oxide (243)

A mixture of 2-(5-(N-(2-morpholinoethyl)methylsulfonamido)-2-oxoindolin-1-yl)acetic acid hydrochloride (0.105 g, 0.242 mmol), (S)-3,5-dichloro-4-(2-(3-(cyclopropylmethoxy)-4-(difluoromethoxy)phenyl)-2-hydroxyethyl)pyridine 1-oxide (0.092 g, 0.220 mmol), EDC (0.127 g, 0.660 mmol), and DMAP (0.054 g, 0.440 mmol) in DCM (15 ml) was stirred at room temperature for 24 hours. The mixture was diluted with DCM and washed with aqueous sat. $NH_4Cl$ and aqueous 5% $NaHCO_3$; the organic phase was dried over sodium sulfate and the solvent was removed. The crude was purified by flash chromatography on silica gel column (DCM:MeOH=99:1 to 96:4) affording (S)-3,5-dichloro-4-(2-(3-(cyclopropylmethoxy)-4-(difluoromethoxy)phenyl)-2-(2-(5-(N-(2-morpholinoethyl)-methylsulfonamido)-2-oxoindolin-1-yl)acetoxy)ethyl)pyridine 1-oxide (0.070 g, 0.088 mmol, 39.8% yield, MS/ESI$^+$ 799.46 [MH]$^+$, [$\alpha_D$]=−40.88, c=0.25, MeOH). $^1$H NMR (300 MHz, DMSO-d$_6$) δ ppm 8.44 (s, 2H), 7.32 (s, 1H), 7.26 (dd, 1H), 7.19 (d, 1H), 7.11 (d, 1H), 6.97 (dd, 1H), 6.83 (d, 1H), 7.07 (t, 1H), 6.03 (dd, 1H), 4.61 (d, 1H), 4.50 (d, 1H), 3.95 (d, 2H), 3.70 (t, 2H), 3.67 (s, 2H), 3.48-3.57 (m, 4H), 3.39 (dd, 1H), 3.22 (dd, 1H), 3.07 (s, 3H), 2.30-2.43 (m, 6H), 1.14-1.34 (m, 1H), 0.50-0.69 (m, 2H), 0.25-0.46 (m, 2H).

Example 45

(S)-3,5-Dichloro-4-(2-(3-(cyclopropylmethoxy)-4-(difluoromethoxy)phenyl)-2-(2-(1,3-dioxo-5-(pyridin-3-ylmethoxy)isoindolin-2-yl)acetoxy)ethyl)pyridine 1-oxide 2,2,2-trifluoroacetic acid salt
(Compound 248)

Scheme 45.
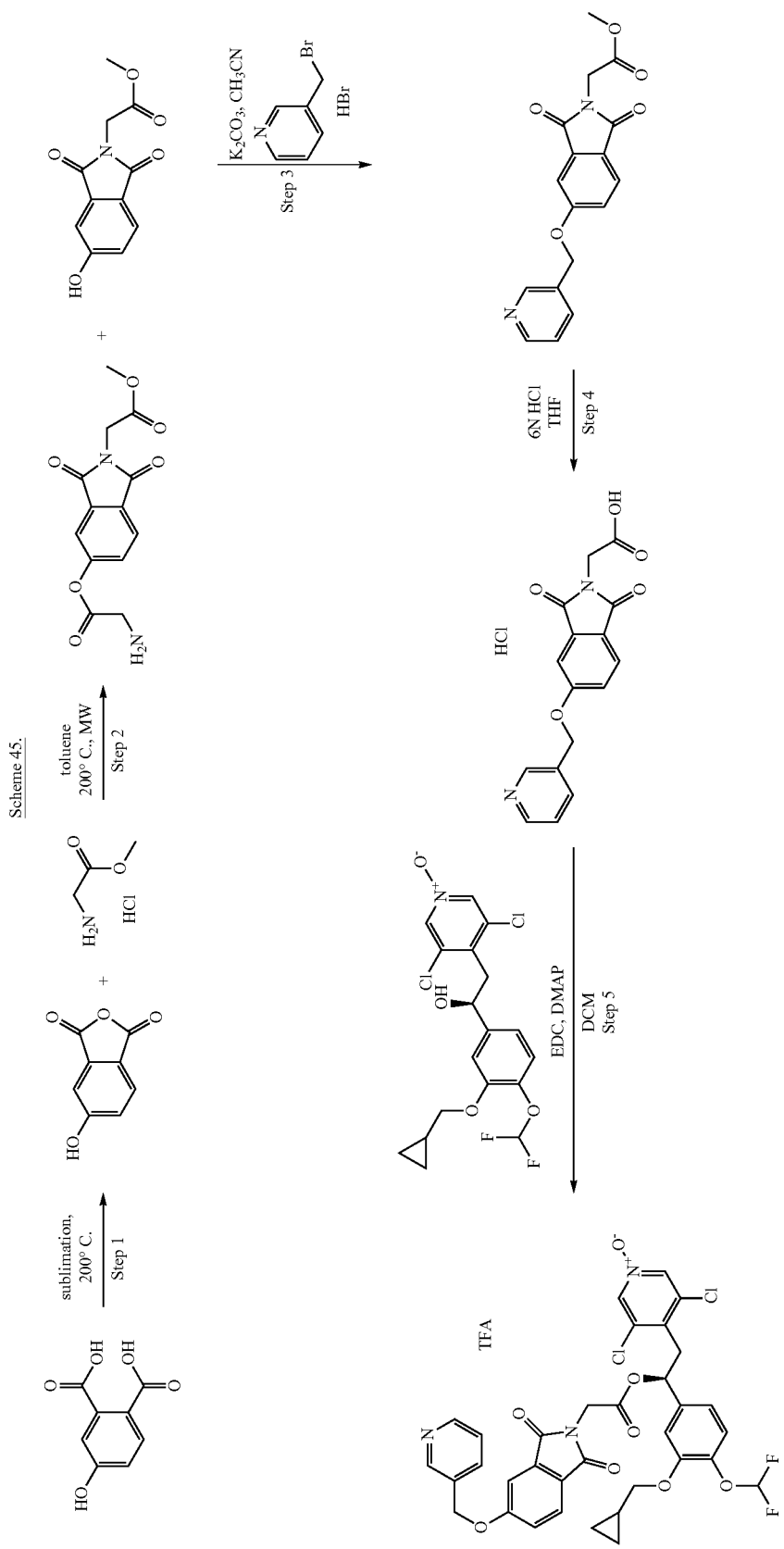

Step 1: Preparation of 5-hydroxyisobenzofuran-1,3-dione (244)

4-Hydroxyphthalic acid (1 g, 5.49 mmol) was sublimated at 220° C. under vacuum (about 10 mbar). The obtained white solid 5-hydroxyisobenzofuran-1,3-dione (675 mg, 4.11 mmol, 74.9% yield, MS/ESI$^+$ 164.9 [MH]$^+$) was collected, stored under vacuum and used as such in the next step.

Step 2: Preparation of methyl 2-(5-hydroxy-1,3-dioxoisoindolin-2-yl)acetate (245)

In a MW vial 5-hydroxyisobenzofuran-1,3-dione (561 mg, 3.42 mmol) and methyl 2-aminoacetate hydrochloride (386 mg, 3.08 mmol) were suspended in toluene (15 ml). The obtained mixture was heated under microwave irradiation at 200° C. for 5 hours. A mixture of the desired compound with an undesired byproduct (about 1:2 ratio) was obtained. After filtration, the obtained beige solid was purified by silica gel flash chromatography (petroleum ether/EtOAc 1/1 to EtOAc) to give 7 methyl 2-(5-hydroxy-1,3-dioxoisoindolin-2-yl)acetate (78 mg, 0.332 mmol, 9.70% yield, MS/ESI$^+$ 235.9 [MH]$^+$).

Step 3: Preparation of methyl 2-(1,3-dioxo-5-(pyridin-3-ylmethoxy)-isoindolin-2-yl)acetate (246)

To a solution of methyl 2-(5-hydroxy-1,3-dioxoisoindolin-2-yl)acetate (78 mg, 0.332 mmol) in CH$_3$CN (20 mL), K$_2$CO$_3$ (115 mg, 0.829 mmol) and 3-(bromomethyl)-pyridine hydrobromide (126 mg, 0.497 mmol) were added at room temperature. The reaction was heated at 80° C. for 2 hours. The insoluble was filtered off and washed with DCM; the filtrated was evaporated under vacuum; and the crude was partitioned between a saturated solution of Na$_2$CO$_3$ and DCM. The organic phase was washed with brine, dried over sodium sulfate, filtered and evaporated to dryness. The crude was purified by filtration on silica gel cartridge (petroleum ether/EtOAc 1/1 to petroleum ether/EtOAc 2/8) to afford methyl 2-(1,3-dioxo-5-(pyridin-3-ylmethoxy)isoindolin-2-yl)acetate (60 mg, 0.184 mmol, 55.4% yield, MS/ESI$^+$ 327.0 [MH]$^+$).

Step 4: Preparation 2-(1,3-dioxo-5-(pyridin-3-ylmethoxy)isoindolin-2-yl)acetic acid hydrochloride (247)

To a solution of methyl 2-(1,3-dioxo-5-(pyridin-3-ylmethoxy)isoindolin-2-yl)acetate (56 mg, 0.172 mmol) in THF (3 ml), aqueous 6N HCl (2002 μL, 12.01 mmol) was added, and the reaction mixture was stirred for 16 hours at room temperature and then heated at 50° C. for 5 hours. The volatiles were removed under vacuum and the crude was dried yielding 2-(1,3-dioxo-5-(pyridin-3-ylmethoxy)isoindolin-2-yl)acetic acid hydrochloride (54 mg, 0.155 mmol, 90% yield, MS/ESI$^+$ 313.0 [MH]$^+$).

Step 5: Preparation of (S)-3,5-dichloro-4-(2-(3-(cyclopropylmethoxy)-4-(difluoromethoxy)phenyl)-2-(2-(1,3-dioxo-5-(pyridin-3-ylmethoxy)isoindolin-2-yl)acetoxy)ethyl)pyridine 1-oxide 2,2,2-trifluoroacetic acid salt (248)

A mixture of (S)-3,5-dichloro-4-(2-(3-(cyclopropylmethoxy)-4-(difluoromethoxy)phenyl)-2-hydroxyethyl)pyridine 1-oxide (65.1 mg, 0.155 mmol), 2-(1,3-dioxo-5-(pyridin-3-ylmethoxy)isoindolin-2-yl)acetic acid hydrochloride (54 mg, 0.155 mmol), EDC (89 mg, 0.465 mmol), and DMAP (37.8 mg, 0.310 mmol) in DCM (10 ml) was stirred at room temperature for 5 hours. The mixture was diluted with DCM and washed with a saturated solution of Na$_2$CO$_3$ and finally with brine. The organic phase was dried over sodium sulfate, filtered and evaporated under vacuum. The crude was purified by preparative HPLC (Method 1) affording (S)-3,5-dichloro-4-(2-(3-(cyclopropylmethoxy)-4-(difluoromethoxy)phenyl)-2-(2-(1,3-dioxo-5-(pyridin-3-ylmethoxy)isoindolin-2-yl)acetoxy)ethyl)pyridine 1-oxide 2,2,2-trifluoroacetic acid salt (65 mg, 0.080 mmol, 50.6% yield, MS/ESI$^+$ 714.09 [MH]$^+$, [α$_D$]=−25.80, c=0.4, DCM). $^1$H NMR (300 MHz, DMSO-d$_6$) δ ppm 8.78 (d, 1H), 8.63 (dd, 1H), 8.44 (s, 2H), 7.98-8.09 (m, 1H), 7.87 (d, 1H), 7.56 (d, 1H), 7.55 (dd, 1H), 7.48 (dd, 1H), 7.19 (d, 1H), 7.07 (d, 1H), 6.96 (dd, 1H), 7.08 (t, 1H), 6.01 (dd, 1H), 5.43 (s, 2H), 4.40 (s, 2H), 3.92 (d, 2H), 3.39 (dd, 1H), 3.22 (dd, 1H), 1.15-1.33 (m, 1H), 0.51-0.70 (m, 2H), 0.30-0.47 (m, 2H).

Example 46

(S)-3,5-dichloro-4-(2-(3-(cyclopropylmethoxy)-4-(difluoromethoxy)-phenyl)-2-(2-(5-(methylsulfonamidomethyl)-1,3-dioxoisoindolin-2-yl)acetoxy)ethyl)pyridine 1-oxide (Compound 254)

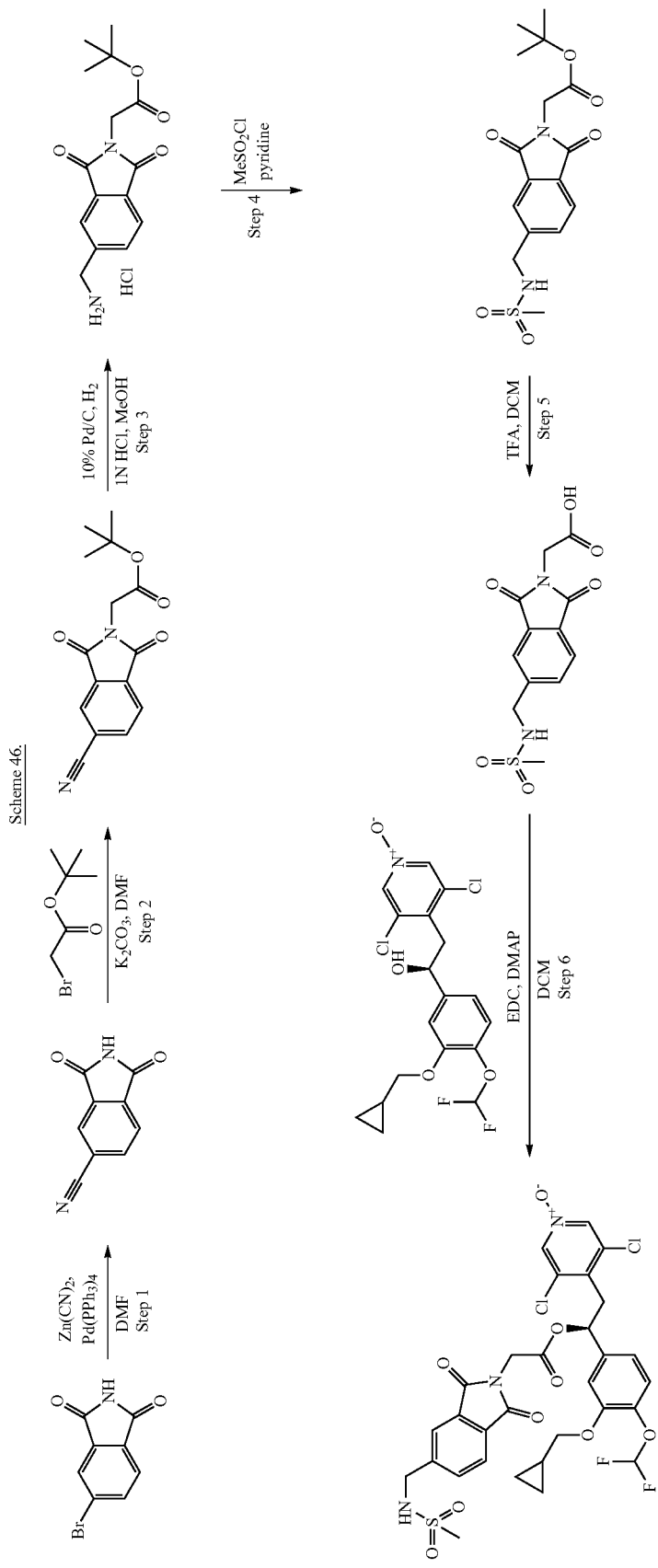

Step 1: Preparation of 1,3-dioxoisoindoline-5-carbonitrile (249)

A mixture of 5-bromoisoindoline-1,3-dione (2.5 g, 11.06 mmol) and Pd(Ph$_3$P)$_4$ (1.406 g, 1.217 mmol) in DMF (50 ml) was accurately degassed with nitrogen, then Zn(CN)$_2$ (1.299 g, 11.06 mmol) was added, and the solution, splitted in 5 vials, was heated under microwave irradiation at 200° C. for 1 hour. A 3% aqueous solution of NH$_4$OH (200 ml) was added, and the organic phase was extracted with ethyl acetate (3×150 ml). The combined organic layers were washed with brine (150 ml), dried over sodium sulfate and concentrated to dryness. The crude was purified by silica gel flash chromatography (100% DCM to DCM:MeOH=99:1) to afford 1,3-dioxoisoindoline-5-carbonitrile as (0.522 g, 3.03 mmol, 27.4% yield, MS/ESI$^+$ 172.9 [MH]$^+$).

Step 2: Preparation of tert-butyl 2-(5-cyano-1,3-dioxoisoindolin-2-yl)acetate (250)

1,3-Dioxoisoindoline-5-carbonitrile (0.522 g, 3.03 mmol) was dissolved in dry DMF (10 ml), then tert-butyl 2-bromoacetate (0.672 ml, 4.55 mmol) and K$_2$CO$_3$ (0.629 g, 4.55 mmol) were added. The resulting suspension was stirred at 90° C. for 3 hours. The solvent was evaporated under vacuum, and the crude was dissolved in ethyl acetate. The precipitate was filtered and washed with ethyl acetate; the filtrate was evaporated under vacuum and the residue was purified by silica gel flash chromatography (petroleum ether:ethyl acetate=9:1 to 70:30) affording tert-butyl 2-(5-cyano-1,3-dioxoisoindolin-2-yl)acetate (0.507 g, 1.771 mmol, 58.4% yield, MS/ESI$^+$ not detectable [MH]$^+$).

Step 3: Preparation of tert-butyl 2-(5-(aminomethyl)-1,3-dioxoisoindolin-2-yl)acetate hydrochloride (251)

A mixture of tert-butyl 2-(5-cyano-1,3-dioxoisoindolin-2-yl)acetate (0.440 g, 1.537 mmol), aqueous 1M HCl (0.768 ml, 0.768 mmol) and 10% w/w Pd/C (a catalytic amount) in MeOH (30 ml) was hydrogenated in a Parr apparatus at 40 psi for 4 hours. 37% HCl aqueous solution (0.0316 ml, 0.384 mmol) was added, and the mixture hydrogenated at 45 psi for additional 4 hours. The mixture was filtered, and the solution evaporated under vacuum. The crude was dissolved in MeOH (25 ml) and added to a suspension of new 10% w/w Pd/C (a catalytic amount) in MeOH (5 ml); 37% HCl (0.0316 ml, 0.384 mmol) was added at 0° C., and the mixture was hydrogenated at 45 psi 3 hours. The catalyst was filtered off, and the solution concentrated under vacuum. The crude was triturated with diethyl ether to afford tert-butyl 2-(5-(aminomethyl)-1,3-dioxoisoindolin-2-yl)acetate hydrochloride (0.409 g, 1.252 mmol, 81% yield, MS/ESI$^+$ 291.1 [MH]$^+$).

Step 4: Preparation of tert-butyl 2-(5-(methylsulfonamidomethyl)-1,3-dioxoisoindolin-2-yl)acetate (252)

To a solution of tert-butyl 2-(5-(aminomethyl)-1,3-dioxoisoindolin-2-yl)acetate hydrochloride (0.409 g, 1.252 mmol) in dry pyridine (10 ml) cooled to 0° C., methanesulfonyl chloride (0.117 ml, 1.502 mmol) was added. The reaction was warmed to room temperature and stirred overnight. Additional methanesulfonyl chloride (0.148 ml, 1.878 mmol) was added over 24 hours cooling at 0° C. and stirring at room temperature. The solvent was removed under vacuum and the residue was portioned between ethyl acetate and 1N HCl. The organic phase was washed with brine and dried over sodium sulfate. The solvent was evaporated to dryness affording tert-butyl 2-(5-(methylsulfonamidomethyl)-1,3-dioxoisoindolin-2-yl)acetate (0.461 g, 1.251 mmol, MS/ESI$^+$ 390.9 [MNa]$^+$). This crude was used in the following steps without purification.

Step 5: Preparation of 2-(5-(methylsulfonamidomethyl)-1,3-dioxoisoindolin-2-yl)acetic acid (253)

To a solution of tert-butyl 2-(5-(methylsulfonamidomethyl)-1,3-dioxoisoindolin-2-yl)acetate (0.200 g, 0.543 mmol) in DCM (10 ml) cooled to 0° C., TFA (0.418 ml, 5.43 mmol) was added drop wise, and the solution stirred at room temperature for 24 hours. The solvent was removed under vacuum and dried to give 2-(5-(methylsulfonamidomethyl)-1,3-dioxoisoindolin-2-yl)acetic acid as a yellow solid (0.170 g, 0.544 mmol, yield considered to be quantitative, MS/ESI$^+$ 312.9 [MH]$^+$). This product was used without any further purification.

Step 6: Preparation of (S)-3,5-dichloro-4-(2-(3-(cyclopropylmethoxy)-4-(difluoromethoxy)phenyl)-2-(2-(5-(methylsulfonamidomethyl)-1,3-dioxoisoindolin-2-yl)acetoxy)ethyl)pyridine 1-oxide (254)

(S)-3,5-dichloro-4-(2-(3-(cyclopropylmethoxy)-4-(difluoromethoxy)phenyl)-2-hydroxyethyl)pyridine 1-oxide (0.229 g, 0.544 mmol), 2-(5-(methylsulfonamidomethyl)-1,3-dioxoisoindolin-2-yl)acetic acid (0.170 g, 0.544 mmol), EDC (0.313 g, 1.633 mmol) and DMAP (0.133 g, 1.089 mmol) were dissolved in DCM (20 ml), and the solution was stirred at room temperature for 20 hours. The mixture was diluted with DCM and washed with 0.5N HCl, aqueous 5% NaHCO$_3$ and brine. The organic phase was dried over sodium sulfate, and the solvent removed under vacuum. The crude was purified by preparative HPLC (Method 1) to afford (S)-3,5-dichloro-4-(2-(3-(cyclopropylmethoxy)-4-(difluoromethoxy)phenyl)-2-(2-(5-(methylsulfonamido methyl)-1,3-dioxoisoindolin-2-yl)acetoxy)ethyl)pyridine 1-oxide (0.120 g, 0.168 mmol, 30.9% yield, MS/ESI$^+$ 714.06 [MH]$^+$, [a$_D$]=−27.89, c=0.9, DCM; $^1$H NMR (300 MHz, DMSO-d$_6$) δ ppm 8.44 (s, 2H), 7.88-7.94 (m, 2H), 7.85 (dd, 1H), 7.77 (t, 1H), 7.19 (d, 1H), 7.08 (s, 1H), 6.96 (dd, 1H), 7.08 (t, 1H), 6.01 (dd, 1H), 4.42 (s, 2H), 4.23-4.56 (m, 2H), 3.83-4.00 (m, 2H), 3.39 (dd, 1H), 3.22 (dd, 1H), 2.95 (s, 3H), 1.10-1.34 (m, 1H), 0.49-0.67 (m, 2H), 0.30-0.46 (m, 2H)

The compound listed in Table 16 was prepared with analogous synthetic steps and procedures to that described in Example 46, Steps 1, 2, 5 and 6, by reacting the appropriate precursors (commercially available or synthesized by a person skilled in the art) with suitable reagents. Specific variations in the experimentals or purification methods are indicated in the table.

TABLE 16

| Entry | Structure | NMR characterization | MS/ESI+ [MH]+ | [α_D] | Experimental procedure | Purification and yield | Starting material (precursor) |
|---|---|---|---|---|---|---|---|
| 255 | 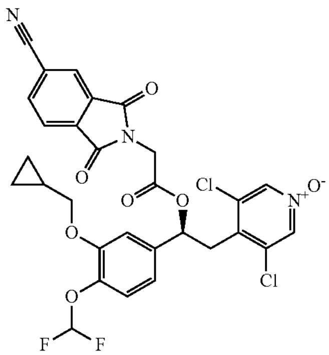 | 1H NMR (300 MHz, DMSO-d6) δ ppm 8.45 (s, 1H), 8.46 (s, 2H), 8.38 (dd, 1H), 8.11 (dd, 1H), 7.19 (d, 1H), 7.08 (s, 1H), 6.96 (dd, 1H), 7.08 (t, 1H), 6.01 (dd, 1H), 4.46 (s, 2H), 3.92 (d, 2H), 3.39 (dd, 1H), 3.16-3.24 (m, 1H), 1.11-1.32 (m, 1H), 0.51-0.67 (m, 2H), 0.27-0.44 (m, 2H) | 632.13 | −48.08 (c 0.5, DCM) | | Crystallization from MeOH 64% yield | |

Example 47

(S)-3,5-Dichloro-4-(2-(3-(cyclopropylmethoxy)-4-(difluoromethoxy)-phenyl)-2-(2-(54N-(2-morpholinoethyl)methylsulfonamido)methyl)-1,3-dioxoisoindolin-2-yl)acetoxy)ethyl)pyridine 1-oxide (Compound 258)

Scheme 47.

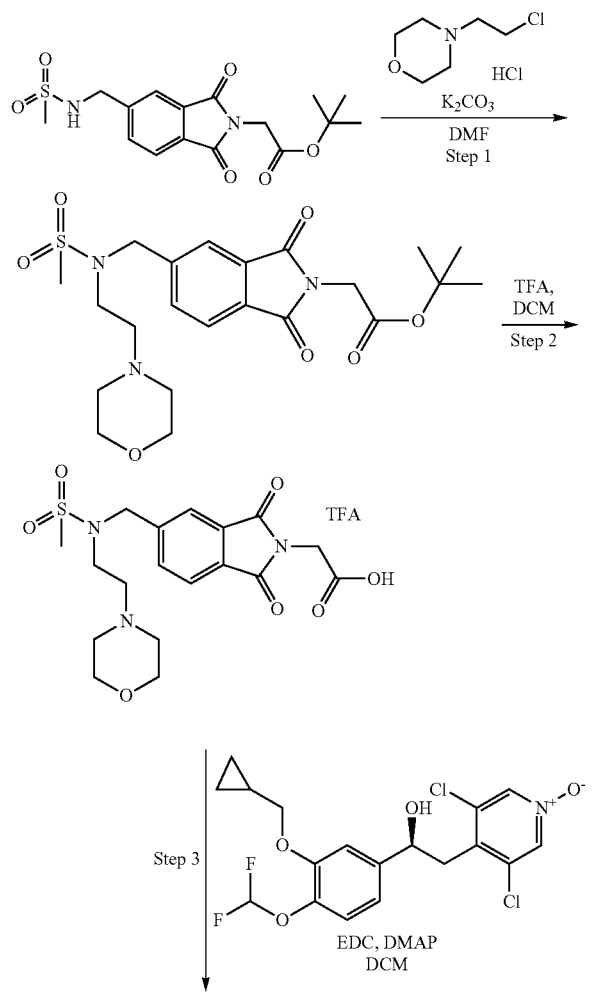

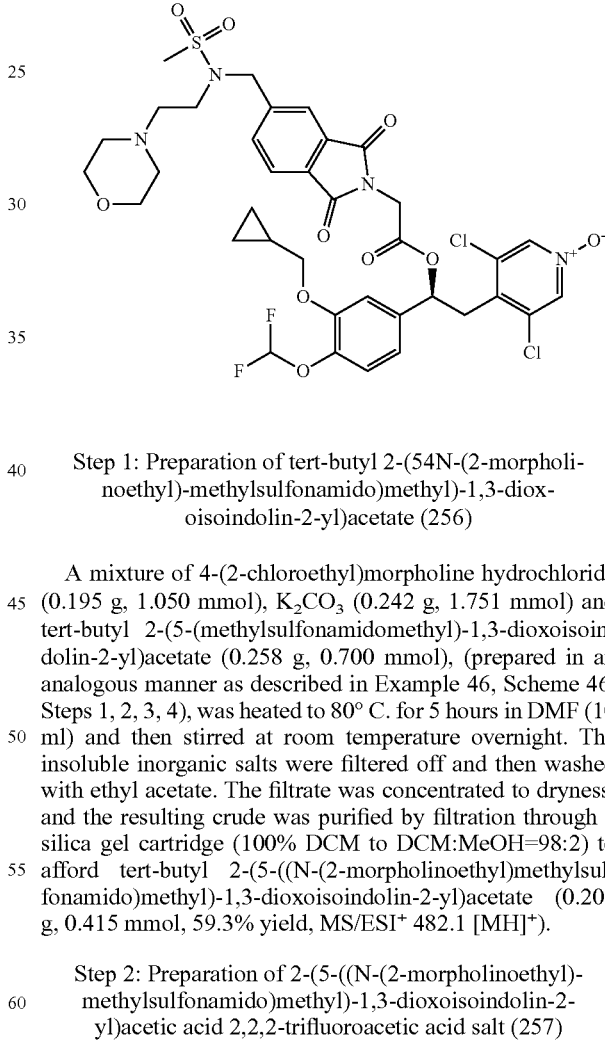

Step 1: Preparation of tert-butyl 2-(54N-(2-morpholinoethyl)-methylsulfonamido)methyl)-1,3-dioxoisoindolin-2-yl)acetate (256)

A mixture of 4-(2-chloroethyl)morpholine hydrochloride (0.195 g, 1.050 mmol), K₂CO₃ (0.242 g, 1.751 mmol) and tert-butyl 2-(5-(methylsulfonamidomethyl)-1,3-dioxoisoindolin-2-yl)acetate (0.258 g, 0.700 mmol), (prepared in an analogous manner as described in Example 46, Scheme 46, Steps 1, 2, 3, 4), was heated to 80° C. for 5 hours in DMF (10 ml) and then stirred at room temperature overnight. The insoluble inorganic salts were filtered off and then washed with ethyl acetate. The filtrate was concentrated to dryness, and the resulting crude was purified by filtration through a silica gel cartridge (100% DCM to DCM:MeOH=98:2) to afford tert-butyl 2-(5-((N-(2-morpholinoethyl)methylsulfonamido)methyl)-1,3-dioxoisoindolin-2-yl)acetate (0.200 g, 0.415 mmol, 59.3% yield, MS/ESI+ 482.1 [MH]+).

Step 2: Preparation of 2-(5-((N-(2-morpholinoethyl)-methylsulfonamido)methyl)-1,3-dioxoisoindolin-2-yl)acetic acid 2,2,2-trifluoroacetic acid salt (257)

To a solution of tert-butyl 2-(54N-(2-morpholinoethyl)methylsulfonamido)-methyl)-1,3-dioxoisoindolin-2-yl)acetate (0.200 g, 0.415 mmol) in DCM (10 ml), TFA (0.320 ml, 4.15 mmol) was added drop wise at 0° C. The reaction was allowed to warm to room temperature and stirred for 2 hours. Additional TFA (1.280 ml, 16.62 mmol) was added in two portions over 24 hours cooling at 0° C. and stirring at room temperature. The volatiles were removed under vacuum affording 2-(5-((N-(2-morpholinoethyl)-methylsulfonamido)methyl)-1,3-dioxoisoindolin-2-yl)acetic acid 2,2,2-trifluoroacetic acid salt (0.224 g, 0.415 mmol, 100% yield, MS/ESI$^+$ 426.0 [MH]$^+$).

Step 3: Preparation of (S)-3,5-dichloro-4-(2-(3-(cyclopropylmethoxy)-4-(difluoromethoxy)phenyl)-2-(2-(54N-(2-morpholinoethyl)-methylsulfonamido)-methyl)-1,3-dioxoisoindolin-2-yl)acetoxy)ethyl) pyridine 1-oxide (258)

A mixture of (S)-3,5-dichloro-4-(2-(3-(cyclopropylmethoxy)-4-(difluoromethoxy)phenyl)-2-hydroxyethyl)pyridine 1-oxide (0.174 g, 0.415 mmol), 2-(5-((N-(2-morpholinoethyl)methylsulfonamido)methyl)-1,3-dioxoisoindolin-2-yl)acetic acid 2,2,2 trifluoroacetic acid salt (0.224 g, 0.415 mmol), EDC (0.239 g, 1.246 mmol), and DMAP (0.101 g, 0.830 mmol) in DCM (10 ml) was stirred at room temperature for 3 hours. The mixture was diluted with DCM and washed with 0.5N HCl, aqueous 5% NaHCO$_3$ and brine; the organic phase was dried over sodium sulfate; and the solvent removed under vacuum. The crude was purified by filtration through a silica cartridge (DCM:MeOH=98:2); a further purification by flash chromatography on silica gel column (DCM:MeOH=99=1) was performed to afford S)-3,5-dichloro-4-(2-(3-(cyclopropylmethoxy)-4-(difluoromethoxy)phenyl)-2-(2-(5-((N-(2-morpholinoethyl)methylsulfonamido)methyl)-1,3-dioxoisoindolin-2-yl)acetoxy)ethyl)pyridine 1-oxide (0.125 g, 0.151 mmol, 36.4% yield, MS/ESI$^+$ 827.03 [MH]$^+$, [$\alpha_D$]=−28.63, c=0.8, DCM). $^1$H NMR (300 MHz, DMSO-d$_6$) δ ppm 8.44 (s, 2H), 7.70-8.09 (m, 3H), 7.19 (d, 1H), 7.03-7.13 (m, 1H), 6.96 (dd, 1H), 7.08 (t, 1H), 6.02 (dd, 1H), 4.59 (s, 2H), 4.21-4.52 (m, 2H), 3.75-4.03 (m, 2H), 3.44-3.54 (m, 4H), 3.30-3.44 (m, 3H), 3.17-3.23 (m, 1H), 3.12 (s, 3H), 2.37 (t, 2H), 2.16-2.32 (m, 4H), 1.13-1.33 (m, 1H), 0.48-0.72 (m, 2H), 0.16-0.48 (m, 2H)

Example 48

3,5-Dichloro-4-((2S)-2-(4-(difluoromethoxy)-3-(tetrahydrofuran-3-yloxy)phenyl)-2-(2-(1,3-dioxoisoindolin-2-yl)acetoxy)ethyl)pyridine 1-oxide (Compound 261)

Scheme 48.
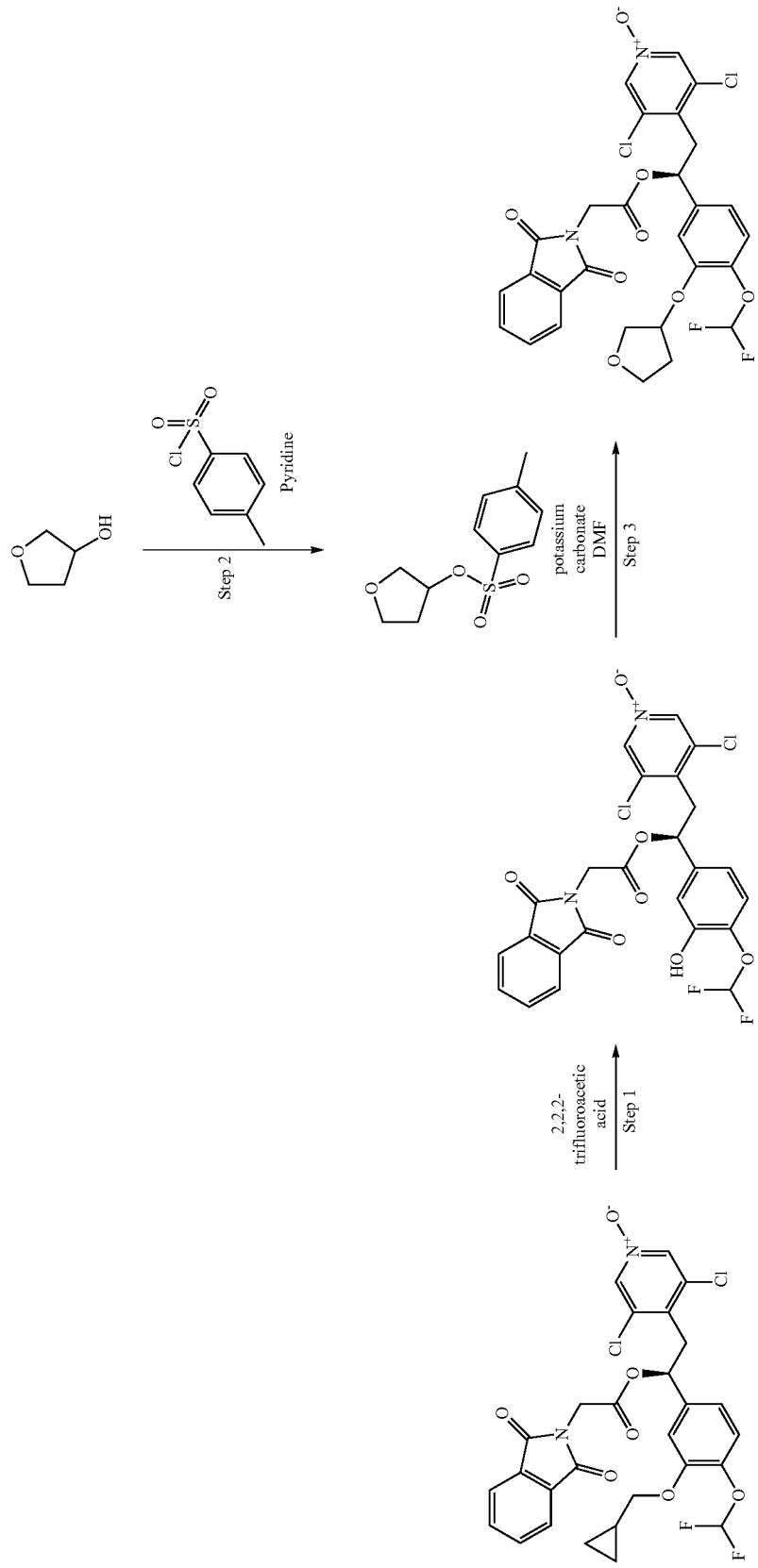

Step 1: Preparation of (S)-3,5-dichloro-4-(2-(4-(difluoromethoxy)-3-hydroxyphenyl)-2-(2-(1,3-dioxoisoindolin-2-yl)acetoxy)ethyl)pyridine 1-oxide (259)

A solution of (S)-3,5-dichloro-4-(2-(3-(cyclopropylmethoxy)-4-(difluoromethoxy)phenyl)-2-(2-(1,3-dioxoisoindolin-2-yl)acetoxy)ethyl)pyridine 1-oxide (500 mg, 0.823 mmol) (prepared in analogous manner as described in Example 4, Scheme 4) in 2,2,2-trifluoroacetic acid (7.5 ml, 0.823 mmol) was stirred at RT for 8 hours. Then the solvent was evaporated under vacuum, and the residue was taken up several times with AcOEt/Et$_{2O}$ and evaporated under reduced pressure to afford 302 mg of the title compound (66% yield).

Step 2: Preparation of tetrahydrofuran-3-yl 4-methylbenzenesulfonate (260)

To a solution of tetrahydrofuran-3-ol (500 mg, 5.68 mmol) in Py (5 ml), 4-methylbenzene-1-sulfonyl chloride (1623 mg, 8.51 mmol) was added, and the mixture and stirred at Rt for 1 hour. The mixture was poured into HCl 1M and extracted with AcOEt (2×). The organic phase was dried over Na2SO4 and evaporated under reduced pressure to give 350 mg of the title compound (26% yield).

Step 3: Preparation of 3,5-dichloro-4-((2S)-2-(4-(difluoromethoxy)-3-(tetrahydrofuran-3-yloxy)phenyl)-2-(2-(1,3-dioxoisoindolin-2-yl)acetoxy)-ethyl)pyridine 1-oxide (261)

To a solution of (S)-3,5-dichloro-4-(2-(4-(difluoromethoxy)-3-hydroxyphenyl)-2-(2-(1,3-dioxoisoindolin-2-yl)acetoxy)ethyl)pyridine 1-oxide (155 mg, 0.280 mmol) in DMF (3.8 ml), potassium carbonate (46.5 mg, 0.336 mmol) was added, and the mixture stirred at RT for 30 minutes. Tetrahydrofuran-3-yl 4-methylbenzenesulfonate (224 mg, 0.924 mmol) was added, and the mixture stirred at RT overnight. Water was added, and the aqueous phase extracted with AcOEt (2×). The organic phase was washed with brine, dried and evaporated under reduced pressure. The crude was purified through preparative HPLC (Method 2) to give 17 mg of title compound (yield 10%). $^1$H NMR (400 MHz, DMSO-d$_6$) δ ppm 8.45 (s, 2H), 7.92 (d, J=4.41 Hz, 4H), 7.18-7.27 (m, 1H), 7.05 (m, 2H), 6.98 (d, J=7.94 Hz, 1H), 6.02 (dd, J=8.38, 4.85 Hz, 1H), 5.12 (m, 1H), 4.30-4.58 (m, 2H), 3.62-4.06 (m, 4H), 3.14-3.43 (m, 2H), 2.20 (ddd, J=13.56, 6.73, 6.62 Hz, 1H), 1.86-2.05 (m, 1H). MS/ESI$^+$ [M+H]$^+$=622.7

Example 49

(S)-3,5-Dichloro-4-(2-(3-(cyclopropylmethoxy)-4-(difluoromethoxy)-phenyl)-2-(2-(1,3-dioxo-3,4-dihydroisoquinolin-2(1H)-yl)acetoxy)ethyl)pyridine 1-oxide (263)

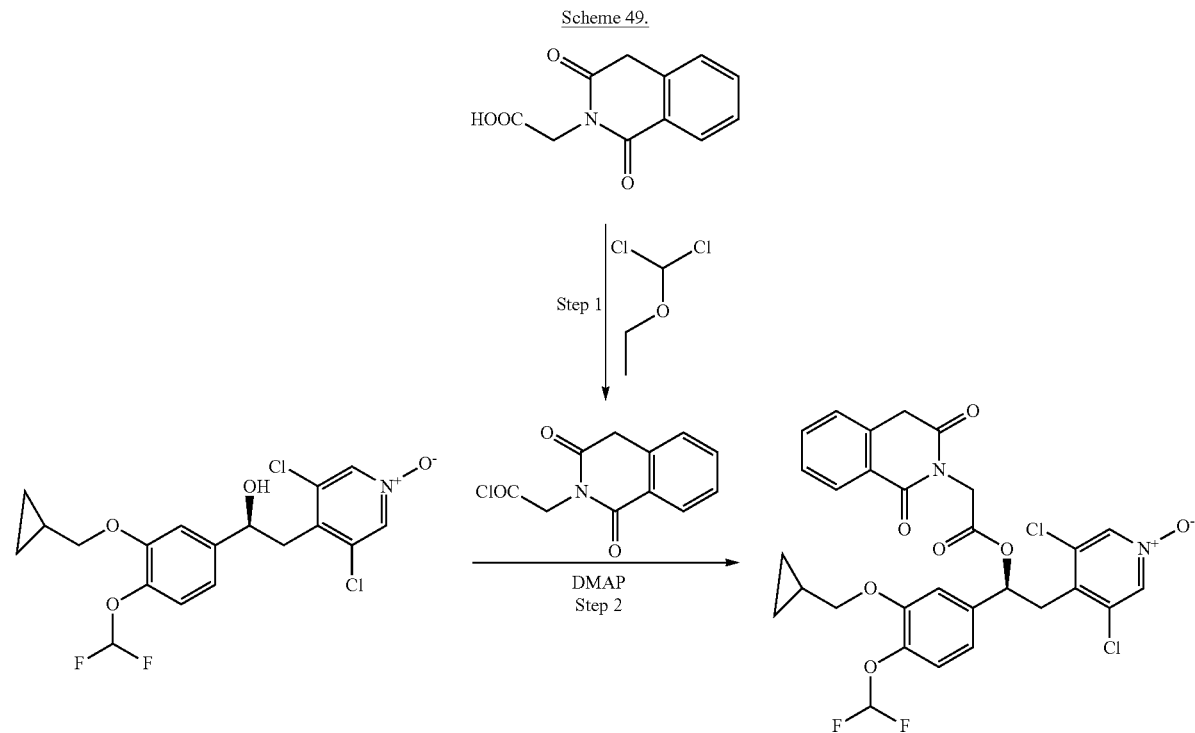

Scheme 49.

Step 1. Preparation of (2-(1,3-dioxo-3,4-dihydroisoquinolin-2(1H)-yl)acetyl chloride (262)

To a solution of 2-(1,3-dioxo-3,4-dihydroisoquinolin-2(1H)-yl)acetic acid (150 mg, 0.684 mmol) in CHCl3 (3 ml), (dichloromethoxy)ethane (1 ml, 0.684 mmol) was added, and the mixture refluxed for 3 hours. The solvent was evaporated under reduced pressure, the crude taken up with CHCl$_3$, and the solvent evaporated again to give the title compound (163 mg, quantitative yield).

Step 2. Preparation of (S)-3,5-dichloro-4-(2-(3-(cyclopropylmethoxy)-4-(difluoromethoxy)phenyl)-2-(2-(1,3-dioxo-3,4-dihydroisoquinolin-2(1H)-yl)acetoxy)ethyl)pyridine 1-oxide (263)

(S)-3,5-dichloro-4-(2-(3-(cyclopropylmethoxy)-4-(difluoromethoxy)phenyl)-2-(2-(5-nitro-1,3-dioxoisoindolin-2-yl)acetoxy)ethyl)pyridine 1-oxide (40 mg, 0.062 mmol) was dissolved in DCM (2 ml), and added with 2-(1,3-dioxo-3,4-dihydroisoquinolin-2(1H)-yl)acetyl chloride (163 mg, 0.686 mmol) and DMAP (84 mg, 0.686 mmol). The reaction was stirred at RT overnight and quenched by addition of HCl. The solution extracted with DCM and washed with $NaHCO_3$ sat. sol., then dried over $Na_2SO_4$ and the solvent removed under reduced pressure. The crude was purified by preparative HPLC (Method 2) to yield the titled compound (30.0 mg, 52% yield).). $^1H$ NMR (400 MHz, acetone) ppm 8.19 (s, 2H), 8.09-8.15 (m, 1H), 7.67-7.79 (m, 1H), 7.44-7.61 (m, 2H), 7.15-7.24 (m, 2H), 7.01-7.09 (m, 1H), 6.94 (t, J=75.00 Hz, 1H), 6.01-6.25 (m, 1H), 4.68 (s, 2H), 4.24 (s, 2H), 4.03 (dd, J=6.84, 2.87 Hz, 2H), 3.42-3.60 (m, 1H), 3.20-3.38 (m, 1H), 1.24-1.46 (m, 1H), 0.65 (dd, J=8.16, 1.54 Hz, 2H), 0.43 (d, J=5.73 Hz, 2H); MS/ESI$^+$ 621.3 [MH]$^+$ Pharmacological Activity of the Compounds of the Invention Example 50

In Vitro Determination of PDE4 Inhibitory Activity in the Cell Free Assay

PDE4 activity was determined in U937 human monocytic supernatants cells lysate. Cells were cultured, harvested and supernatant fraction prepared essentially as described in Torphy T J et al., *J. Pharmacol. Exp. Ther.*, 1992; 263:1195-1205, which is incorporated herein by reference in its entirety. U937 cells (Cell Bank, Interlab Cell Line Collection, ICLC HTL94002) were grown at 37° C., 5% $CO_2$ in RPMI 1640 with GlutaMAX™-I medium supplemented with 10% fetal bovine serum and 100 µg/ml Pen-strep (Gibco).

Cells were harvested and washed twice by centrifugation (150×g, 8 minutes) in cold PBS. Washed cells were resuspended in cold Krebs-Ringer-Henseleit buffer at a final concentration 20×10$^6$ cells/ml and sonicated. After centrifugation at 15000×g for 20 minutes, the supernatants were pooled, divided in aliquots and stored at −80° C.

PDE4 activity was determined in cells supernatants by assaying cAMP disappearance from the incubation mixtures. The concentration of the test compounds ranged between 10$^{-12}$ M and 10$^{-6}$ M. Reactions were stopped by enzyme heat inactivation (2.5 minutes at 100° C.), and residual cAMP content was determined using the 'LANCE cAMP Assay' from PerkinElmer following the providers instructions. The results of the tested compounds, representatives of the invention, expressed as mean±standard deviation of the nM concentration of the test compound producing 50% inhibition of cAMP disappearance (IC$_{50}$) are shown in the following Table:

| Compound | PDE4 inhibition |
|---|---|
| 102, 17, 35, 169, 170, 14, 18, 258, 162, 20, 167, 84, 16, 76, 112, 68, 99, 230, 39, 37, 26, 28, 243, 93, 142, 261, 24, 186, 27, 183, 156, 233, 77, 190, 61, 191, 138, 255, 214, 151, 213, | ++++ |
| 215, 192, 131, 208, 217, 227, 202, 185, 216, 184, 194, 236, 237, 197, 199, 248, 201, 200, 198, 254 | |
| 45, 25, 30, 19, 263, 54, 42, 64, 173, 11, 117, 176, 57, 69, 22, 38, 59, 15, 60, 58, 240, 53, 40, 14, 29, 48, 189, 49, 194, 195, 196, 126, 182, 205 | +++ |

In the table above, PDE4 binding potencies (IC$_{50}$ values) are indicated as follows: >10 nM, '+'; 10-1 nM, '++'; 1-0.1 nM, '+++'; and <0.1 nM, '++++'.

Percentage of inhibition of PDE4 activity was calculated, assuming cAMP disappearance in the absence of inhibitors as 100% and cAMP disappearance in heat inactivated samples as 0%.

Example 51

In Vitro Determination of PDE4 Inhibitory Activity in the Peripheral Blood Mononuclear Cells (PBMCs) Assay The assay, which is based on the known inhibitory activity exerted by PDE4 inhibitors on the lipopolyshaccarides (LPS)-induced tumour necrosis factor-alpha (TNF-α release in peripheral blood mononuclear cells (PBMCs), was performed according to a method previously described (Hatzelmann A et al., *J. Pharmacol. Exp. Ther.*, 2001; 297:267-279; and Draheim R et al., *J. Pharmacol. Exp. Ther.*, 2004; 308: 555-563, both of which are incorporated herein by reference in their entireties. Cryopreserved human PBMCs, (100 µl/well) were incubated in 96-well plates (10$^5$ cells/well), for 30 minutes, in the presence or absence (50 microl) of the test compounds whose concentrations ranged from 10$^{-12}$ M to 10$^{-6}$ M or from 10$^{-13}$ M to 10$^{-7}$ M. Subsequently, LPS (3 ng/ml) was added. After 18 hours of incubation at 37° C. in a humidified incubator under an atmosphere of 95% air and 5% $CO_2$, culture medium was collected and TNF-α measured by ELISA.

The results of the tested compounds, representatives of the invention, expressed as mean±95% confidence limits of the molar concentration of the test compound producing 50% inhibition of LPS-induced TNF-α release (IC$_{50}$) are shown in the following Table:

| Compound | PDE4 inhibition |
|---|---|
| 213, 102, 17, 12, 106, 45, 25, 169, 170, 14, 18, 258, 162, 20, 19, 167, 84, 42, 64, 173, 76, 117, 57, 112, 68, 230, 38, 39, 37, 15, 240, 243, 261, 183, 191, 214, 213, 215, 182, 105, 30, 186, 156, 190 | +++ |
| 9, 10, 35, 263, 54, 176, 31, 99, 32, 22, 60, 40, 93, 142, 143, 233, 61, 194, 131 | ++ |
| 26, 29, 189 | + |

In the table above, PDE4 binding potencies (IC$_{50}$ values) are indicated as follows: >10 nM, '+'; 10-1 nM, '++'; and <1 nM, '+++'.

The effects of the tested compounds were calculated as percentage of inhibition of TNF-α release, assuming LPS-induced TNF-α production in the absence of inhibitor compound as 100% and basal TNF-α production of PBMCs in the absence of LPS as 0%.

Example 52

In Vitro Determination of Intrinsic Clearance in Human Hepatic Microsomes

Method a.

Test compounds in duplicate at the final concentration of 1 µM are dissolved in DMSO (DMSO final concentration 0.5% v/v) and pre-incubated for 10 minutes at 37° C. in potassium phosphate buffer pH 7.4, 3 mM MgCl$_2$, with liver microsomes at the final concentration of 0.5 mg/ml. After the pre-incubation period, reactions are started by adding the cofactors mixture (NADP, Glc6P, Glc6P-DH); samples are taken at time 0, 5, 10, 15, 20 and 30 minutes, added to acetonitrile to stop reaction and centrifuged. The supernatants are analysed and quantified by LC-MS/MS.

A control sample without cofactors is always added in order to check the stability of test compounds in the matrix. 7-Ethoxycoumarin is added as reference standard. A fixed concentration of verapamil is added in every sample as internal standard for LC-MS/MS. Zero-time incubation is used as 100% value. Percent loss of substrate in incubation is determined to estimate in-vitro half life and in-vitro intrinsic clearance of compounds. The rate constant, k (min$^{-1}$) derived for the exponential decay equation (peak area vs time) is used to calculate the rate of intrinsic clearance (CLi) of the compounds using the following equation:

$$\text{CLi (mL/min/g liver)} = k \times V \times y$$

where:
k is calculated from the exponential fitting decay of the area values
V=incubation volume (mL)/mg protein
y=microsomal protein yield=52.5 mg/g liver Method b.

Test compounds are incubated, in duplicate, at the concentration of 1 µM with liver microsomes (0.8 mg protein/mL) in KHB buffer (pH 7.4) at 37° C. in the presence of 1 mM NADPH. At different time points (0, 5, 10, 20, 30 and 60 minutes), 50 µL aliquots of the incubates are taken, added with 80 µL of ice-cold acetonitrile and 204 of 1 µM warfarin in acetonitrile (injection check) to stop the reaction and samples centrifuged. The supernatant is analysed by LC-MS/MS for unchanged compounds.

Test compounds are incubated with liver microsomes in KHB buffer in the absence of NADPH for 0 and 60 minutes, as control. Midazolam at the concentration of 1 µM, is incubated with microsomes as positive control for phase I activity of microsomes. Control samples are processed as test compounds samples. The intrinsic clearance is determined using the half-life approach. The half-life is calculated from the relationship:

$$\text{Half-life (min)} = \frac{\text{LN}(2)}{-\text{SLOPE}} = \frac{0.693}{-\text{SLOPE}}$$

The slope refers to the curve obtained by plotting the natural logarithmic (LN) value of peak area of the compound remaining against the time and is calculated by linear regression analysis.

Results are reported as half-life in minutes and as in vitro intrinsic clearance values expressed in µL/min/mg protein (for incubation with microsomes) and scaled intrinsic clearance values as mL/min/kg.

Some of the representative compounds of the invention (i.e. Compounds 105, 102, 17, 12, 35, 45, 25, 14, 18, 258, 162, 30, 19, 167, 76, 176, 69, 38, 39, 37, 240, 243, 40, 142, 143, 261, 24, 186, 183, 156, 189, 190, 215, 192, 217, 216, 184, 200), when tested according to the protocol reported, showed an intrinsic Clearance >15 mL/min/g.

Compounds of the invention are endowed with high or moderate intrinsic metabolic clearance.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:
1. A compound of formula (I):

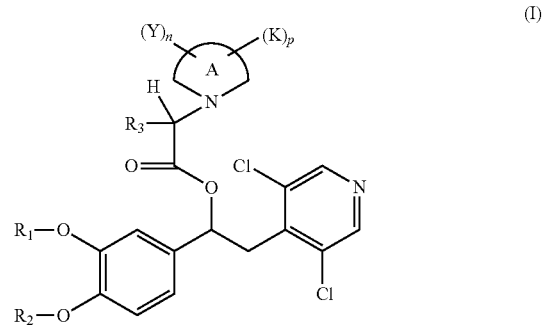

wherein:
R$_1$ and R$_2$, which can be the same or different, are each independently:
(C$_1$-C$_6$) alkyl, optionally substituted by (C$_3$-C$_7$) cycloalkyl;
(C$_1$-C$_6$) haloalkyl;
(C$_3$-C$_7$) cycloalkyl; or
(C$_3$-C$_7$) heterocycloalkyl;
R$_3$ is hydrogen, (C$_1$-C$_6$) alkyl, or (C$_1$-C$_3$) alkylthio(C$_1$-C$_6$) alkyl;
A is a partially unsaturated or unsaturated bicyclic ring system consisting of two fused monocyclic ring systems B and C as represented below:

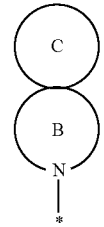

wherein ring B contains a nitrogen atom which represents the point of attachment for ring A to the rest of the molecule through a —(CHR$_3$)— group and wherein ring B and C may optionally contain further heteroatoms;

p is an integer from zero to 3;
Y is an oxo group;
n is an integer from zero to 3;
K is:
  ($C_1$-$C_6$) alkyl, optionally substituted by one or more ($C_3$-$C_7$) cycloalkyl groups;
  ($C_3$-$C_7$) heterocycloalkyl($C_1$-$C_4$) alkyl;
  ($C_3$-$C_7$) heterocycloalkyl, optionally substituted by one or more ($C_1$-$C_6$) alkyl groups;
  ($C_1$-$C_4$) haloalkyl;
  a group —$OR_4$ wherein $R_4$ is:
    H; or
    ($C_1$-$C_{10}$) alkyl, optionally substituted by ($C_3$-$C_7$) cycloalkyl or heteroaryl;
  halogen;
  —CN;
  —$NO_2$;
  $NR_5R_6$ wherein $R_5$ and $R_6$, which can be the same or different, are each independently:
    H;
    a group —OH;
    $NR_7R_8$($C_1$-$C_4$)alkyl wherein $R_7$ and $R_8$, which can be the same or different, are each independently: H; ($C_1$-$C_6$) alkyl, optionally substituted with ($C_1$-$C_6$) alkoxyl; or $NR_9R_{10}$($C_1$-$C_6$)alkyl wherein $R_9$ and $R_{10}$, which can be the same or different, are H or ($C_1$-$C_6$) alkyl; or they form with the nitrogen atom to which they are linked a ($C_3$-$C_7$) heterocycloalkyl ring optionally substituted by ($C_1$-$C_6$)alkyl or a group ($C_1$-$C_6$) alkylcarbonyl;
    ($C_1$-$C_6$) alkyl, optionally substituted by ($C_1$-$C_6$) alkoxyl or heteroaryl, ($C_3$-$C_7$) heterocycloalkylcarbonyl, heteroarylcarbonyl, all of them being optionally further substituted by one or more groups ($C_1$-$C_6$) alkyl, ($C_1$-$C_6$) haloalkyl or ($C_1$-$C_6$) alkoxyl, which may be the same or different and are independently selected;
    a group —$SO_2R_{11}$, wherein $R_{11}$ is ($C_1$-$C_6$) alkyl; or
    a group —$C(O)R_{12}$, wherein $R_{12}$ is ($C_1$-$C_6$) alkyl optionally substituted by ($C_1$-$C_6$) alkoxyl;
  $NR_{13}R_{14}$($C_1$-$C_4$)alkyl; wherein $R_{13}$ and $R_{14}$, which can be the same or different, are each independently:
    —$SO_2$($C_1$-$C_6$) alkyl, H, ($C_1$-$C_6$) alkyl, or ($C_3$-$C_7$)heterocycloalkyl($C_1$-$C_4$) alkyl; or
    —$SO_2NR_{15}R_{16}$, wherein $R_{15}$ and $R_{16}$, which can be the same or different, are each independently H or ($C_1$-$C_6$) alkyl;
  wherein groups $R_4$ to $R_{16}$ may have the same or different meanings at each occurrence, if present in more than one group;
  or a pyridine N-oxide or a pharmaceutically acceptable salt thereof;
  and wherein the compound of formula (I) is not 3,5-dichloro-4-(2-(3-(cyclopropylmethoxy)-4-(difluoromethoxy)phenyl)-2-(2-(1,3-dimethyl-2,6-dioxo-2,3-dihydro-1H-purin-7(6H)-yl)acetoxy)ethyl) pyridine or the pyridine N-oxide thereof.

2. A compound, pyridine N-oxide, or pharmaceutically acceptable salt according to claim 1, wherein $R_2$ is ($C_1$-$C_6$) haloalkyl and $R_1$ is ($C_1$-$C_6$) alkyl which is substituted by ($C_3$-$C_7$) cycloalkyl.

3. A compound, pyridine N-oxide, or pharmaceutically acceptable salt according to claim 1, wherein $R_3$ is hydrogen or methyl.

4. A compound, pyridine N-oxide, or pharmaceutically acceptable salt according to claim 1, wherein ring C is a monocyclic aryl or monocyclic heteroaryl ring system, ring B is a 5 or 6 membered heterocycloalkyl group, zero Y groups are connected to ring C, n groups Y are connected to ring B and n is an integer ranging from 1 to 3.

5. A compound, pyridine N-oxide, or pharmaceutically acceptable salt according to claim 1, which is a pyridine N-oxide.

6. A compound, pyridine N-oxide, or pharmaceutically acceptable salt according to claim 1, which has the absolute configuration at carbon (1) shown below:

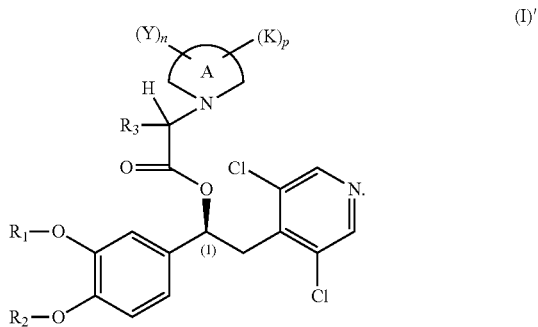

7. A compound, pyridine N-oxide, or pharmaceutically acceptable salt according to claim 1, which is a compound selected from the group consisting of:
  (S)-3,5-dichloro-4-(2-(3-(cyclopropylmethoxy)-4-(difluoromethoxy)phenyl)-2-(2-(6,7-dimethoxy-3,4-dihydroisoquinolin-2(1H)-yl)acetoxy)ethyl)pyridine 1-oxide;
  (S)-3,5-dichloro-4-(2-(3-(cyclopropylmethoxy)-4-(difluoromethoxy)phenyl)-2-(2-(1,3-dioxoisoindolin-2-yl)acetoxy)ethyl)pyridine 1-oxide;
  (S)-3,5-dichloro-4-(2-(3-(cyclopropylmethoxy)-4-(difluoromethoxy)phenyl)-2-(2-(5-(N-(2-morpholinoethyl)methylsulfonamido)-1,3-dioxoisoindolin-2-yl)acetoxy)ethyl) pyridine 1-oxide;
  (S)-3,5-dichloro-4-(2-(3-(cyclopropylmethoxy)-4-(difluoromethoxy)phenyl)-2-(2-(2,4-dioxo-1,2-dihydroquinazolin-3(4H)-yl)acetoxy)ethyl)pyridine 1-oxide;
  (S)-3,5-dichloro-4-(2-(3-(cyclopropylmethoxy)-4-(difluoromethoxy)phenyl)-2-(2-(5-(methylsulfonamido)-1,3-dioxoisoindolin-2-yl)acetoxy)ethyl)pyridine 1-oxide;
  (S)-3,5-dichloro-4-(2-(3-(cyclopropylmethoxy)-4-(difluoromethoxy)phenyl)-2-(2-(4-(2-methoxyacetamido)-1,3-dioxoisoindolin-2-yl)acetoxy)ethyl)pyridine 1-oxide;
  (S)-3,5-dichloro-4-(2-(3-(cyclopropylmethoxy)-4-(difluoromethoxy)phenyl)-2-(2-(5-(methylsulfonamido)-1H-indol-1-yl)acetoxy)ethyl)pyridine 1-oxide;
  (S)-3,5-dichloro-4-(2-(3-(cyclopropylmethoxy)-4-(difluoromethoxy)phenyl)-2-(2-(5-(N-(2-morpholinoethyl)methylsulfonamido)-2,3-dioxoindolin-1-yl)acetoxy)ethyl) pyridine 1-oxide;
  3,5-dichloro-4-((2S)-2-(4-(difluoromethoxy)-3-(tetrahydrofuran-3-yloxy)phenyl)-2-(2-(1,3-dioxoisoindolin-2-yl)acetoxy)ethyl)pyridine 1-oxide;
  (S)-3,5-dichloro-4-(2-(3-(cyclopropylmethoxy)-4-(difluoromethoxy)phenyl)-2-(2-(1,3-dioxo-5-(N-(pyridin-3-ylmethyl)methylsulfonamido)isoindolin-2-yl)acetoxy)ethyl)-pyridine 1-oxide;
  (S)-3,5-dichloro-4-(2-(3-(cyclopropylmethoxy)-4-(difluoromethoxy)phenyl)-2-(2-(1,3-dioxo-5-(N-(2-(pyrrolidin-1-yl)ethyl)methylsulfonamido)isoindolin-2-yl)acetoxy)-ethyl)pyridine 1-oxide;

(S)-3,5-dichloro-4-(2-(3-(cyclopropylmethoxy)-4-(difluoromethoxy)phenyl)-2-(2-(5,6-dimethoxy-1,3-dioxoisoindolin-2-yl)acetoxy)ethyl)pyridine 1-oxide;

(S)-3,5-dichloro-4-(2-(3-(cyclopropylmethoxy)-4-(difluoromethoxy)phenyl)-2-(2-(1,3-dioxo-5-(N-(pyridin-2-ylmethyl)methylsulfonamido)isoindolin-2-yl)acetoxy)ethyl)-pyridine 1-oxide;

(S)-3,5-dichloro-4-(2-(3-(cyclopropylmethoxy)-4-(difluoromethoxy)phenyl)-2-(2-(1,1-dioxido-3-oxobenzo[d]isothiazol-2(3H)-yl)acetoxy)ethyl)pyridine 1-oxide;

or a pharmaceutically acceptable salt of said compound.

8. A combination, comprising a compound, pyridine N-oxide, or pharmaceutically acceptable salt according to claim 1 and a second pharmaceutically active component selected from the group consisting of a beta2-agonist, a corticosteroid, and an antimuscarinic agent.

9. A pharmaceutical composition, comprising a compound, pyridine N-oxide, or pharmaceutically acceptable salt according to claim 1 and one or more pharmaceutically acceptable carriers and/or excipients.

10. A pharmaceutical composition, comprising a combination according to claim 8 and one or more pharmaceutically acceptable carriers and/or excipients.

11. A method for the prevention and/or treatment of a disease of a respiratory tract characterized by airway obstruction, said method comprising administering to a patient in need thereof a therapeutically effective amount of a compound, pyridine N-oxide, or pharmaceutically acceptable salt according to claim 1.

12. A method according to claim 11, wherein said disease of a respiratory tract characterized by airway obstruction is asthma or COPD.

13. A method for the prevention and/or treatment of allergic rhinitis, said method comprising administering to a patient in need thereof a therapeutically effective amount of a compound, pyridine N-oxide, or pharmaceutically acceptable salt according to claim 1.

14. A method for the prevention and/or treatment of atopic dermatitis, said method comprising administering to a patient in need thereof a therapeutically effective amount of a compound, pyridine N-oxide, or pharmaceutically acceptable salt according to claim 1.

15. A kit, comprising a pharmaceutical composition according to claim 9 and a device which may be a single- or multi-dose dry powder inhaler, a metered dose inhaler, or a soft mist nebulizer.

16. A pyridine N-oxide of a compound of formula (I):

wherein:

$R_1$ and $R_2$, which can be the same or different, are each independently:
- $(C_1-C_6)$ alkyl, optionally substituted by $(C_3-C_7)$ cycloalkyl;
- $(C_1-C_6)$ haloalkyl;
- $(C_3-C_7)$ cycloalkyl; or
- $(C_3-C_7)$ heterocycloalkyl;

$R_3$ is hydrogen, $(C_1-C_6)$ alkyl, or $(C_1-C_3)$ alkylthio$(C_1-C_6)$ alkyl;

A is a partially unsaturated or unsaturated bicyclic ring system consisting of two fused monocyclic ring systems B and C as represented below:

wherein ring B contains a nitrogen atom which represents the point of attachment for ring A to the rest of the molecule through a —(CHR$_3$)— group and wherein ring B is a 5 or 6 membered heterocycloalkyl group, ring C is a monocyclic aryl or monocyclic heteroaryl ring system, zero Y groups are connected to ring C, n groups Y are connected to ring B and n is an integer ranging from 1 to 3;

p is an integer from zero to 3;

Y is an oxo group;

n is an integer from zero to 3;

K is:
- $(C_1-C_6)$ alkyl, optionally substituted by one or more $(C_3-C_7)$ cycloalkyl groups;
- $(C_3-C_7)$ heterocycloalkyl$(C_1-C_4)$ alkyl;
- $(C_3-C_7)$ heterocycloalkyl, optionally substituted by one or more $(C_1-C_6)$ alkyl groups;
- $(C_1-C_4)$ haloalkyl;
- a group —OR$_4$ wherein R$_4$ is:
  - H; or
  - $(C_1-C_{10})$ alkyl, optionally substituted by $(C_3-C_7)$ cycloalkyl or heteroaryl;
- halogen;
- —CN;
- —NO$_2$;
- NR$_5$R$_6$ wherein R$_5$ and R$_6$, which can be the same or different, are each independently:
  - H;
  - a group —OH;
  - NR$_7$R$_8$(C$_1$-C$_4$)alkyl wherein R$_7$ and R$_8$, which can be the same or different, are each independently: H; $(C_1-C_6)$ alkyl, optionally substituted with $(C_1-C_6)$ alkoxyl; or NR$_9$R$_{10}$(C$_1$-C$_6$)alkyl wherein R$_9$ and R$_{10}$, which can be the same or different, are H or $(C_1-C_6)$ alkyl; or they form with the nitrogen atom to which they are linked a $(C_3-C_7)$ heterocycloalkyl ring optionally substituted by $(C_1-C_6)$alkyl or a group $(C_1-C_6)$ alkylcarbonyl;
  - $(C_1-C_6)$ alkyl, optionally substituted by $(C_1-C_6)$ alkoxyl or heteroaryl, $(C_3-C_7)$ heterocycloalkylcarbonyl, heteroarylcarbonyl, all of them being optionally further substituted by one or more groups $(C_1-C_6)$ alkyl, $(C_1-C_6)$ haloalkyl or $(C_1-C_6)$ alkoxyl, which may be the same or different and are independently selected;

a group —SO$_2$R$_{11}$, wherein R$_{11}$ is (C$_1$-C$_6$) alkyl; or
a group —C(O)R$_{12}$, wherein R$_{12}$ is (C$_1$-C$_6$) alkyl optionally substituted by (C$_1$-C$_6$) alkoxyl;
NR$_{13}$R$_{14}$(C$_1$-C$_4$)alkyl; wherein R$_{13}$ and R$_{14}$, which can be the same or different, are each independently: —SO$_2$(C$_1$-C$_6$) alkyl, H, (C$_1$-C$_6$) alkyl, or (C$_3$-C$_7$) heterocycloalkyl (C$_1$-C$_4$) alkyl; or
—SO$_2$NR$_{15}$R$_{16}$ wherein R$_{15}$ and R$_{16}$, which can be the same or different, are each independently H or (C$_1$-C$_6$) alkyl;
wherein groups R$_4$ to R$_{16}$ may have the same or different meanings at each occurrence, if present in more than one group;
or a pharmaceutically acceptable salt thereof.

17. A pyridine N-oxide or pharmaceutically acceptable salt according to claim 16, wherein R$_2$ is (C$_1$-C$_6$) haloalkyl and R$_1$ is (C$_1$-C$_6$) alkyl which is substituted by (C$_3$-C$_7$) cycloalkyl.

18. A pyridine N-oxide or pharmaceutically acceptable salt according to claim 16, wherein R$_3$ is hydrogen or methyl.

19. A pyridine N-oxide or pharmaceutically acceptable salt according to claim 16, which has the absolute configuration at carbon (1) shown below:

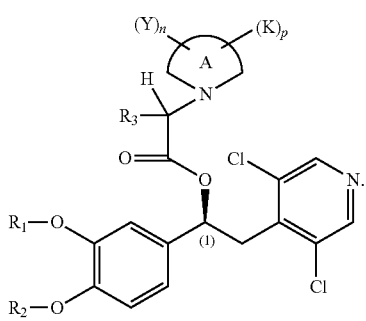

20. A pyridine N-oxide or pharmaceutically acceptable salt according to claim 16, which is a compound selected from the group consisting of:
   (S)-3,5-dichloro-4-(2-(3-(cyclopropylmethoxy)-4-(difluoromethoxy)phenyl)-2-(2-(1,3-dioxoisoindolin-2-yl)acetoxy)ethyl)pyridine 1-oxide;
   (S)-3,5-dichloro-4-(2-(3-(cyclopropylmethoxy)-4-(difluoromethoxy)phenyl)-2-(2-(5-(N-(2-morpholinoethyl)methylsulfonamido)-1,3-dioxoisoindolin-2-yl)acetoxy)ethyl) pyridine 1-oxide;
   (S)-3,5-dichloro-4-(2-(3-(cyclopropylmethoxy)-4-(difluoromethoxy)phenyl)-2-(2-(2,4-dioxo-1,2-dihydroquinazolin-3(4H)-yl)acetoxy)ethyl)pyridine 1-oxide;
   (S)-3,5-dichloro-4-(2-(3-(cyclopropylmethoxy)-4-(difluoromethoxy)phenyl)-2-(2-(5-(methylsulfonamido)-1,3-dioxoisoindolin-2-yl)acetoxy)ethyl)pyridine 1-oxide;
   (S)-3,5-dichloro-4-(2-(3-(cyclopropylmethoxy)-4-(difluoromethoxy)phenyl)-2-(2-(4-(2-methoxyacetamido)-1,3-dioxoisoindolin-2-yl)acetoxy)ethyl)pyridine 1-oxide;
   (S)-3,5-dichloro-4-(2-(3-(cyclopropylmethoxy)-4-(difluoromethoxy)phenyl)-2-(2-(5-(N-(2-morpholinoethyl)methylsulfonamido)-2,3-dioxoindolin-1-yl)acetoxy)ethyl) pyridine 1-oxide;
   3,5-dichloro-4-((2S)-2-(4-(difluoromethoxy)-3-(tetrahydrofuran-3-yloxy)phenyl)-2-(2-(1,3-dioxoisoindolin-2-yl)acetoxy)ethyl)pyridine 1-oxide;
   (S)-3,5-dichloro-4-(2-(3-(cyclopropylmethoxy)-4-(difluoromethoxy)phenyl)-2-(2-(1,3-dioxo-5-(N-(pyridin-3-ylmethyl)methylsulfonamido)isoindolin-2-yl)acetoxy)ethyl)-pyridine 1-oxide;
   (S)-3,5-dichloro-4-(2-(3-(cyclopropylmethoxy)-4-(difluoromethoxy)phenyl)-2-(2-(1,3-dioxo-5-(N-(2-(pyrrolidin-1-yl)ethyl)methylsulfonamido)isoindolin-2-yl)acetoxy)-ethyl)pyridine 1-oxide;
   (S)-3,5-dichloro-4-(2-(3-(cyclopropylmethoxy)-4-(difluoromethoxy)phenyl)-2-(2-(5,6-dimethoxy-1,3-dioxoisoindolin-2-yl)acetoxy)ethyl)pyridine 1-oxide;
   (S)-3,5-dichloro-4-(2-(3-(cyclopropylmethoxy)-4-(difluoromethoxy)phenyl)-2-(2-(1,3-dioxo-5-(N-(pyridin-2-ylmethyl)methylsulfonamido)isoindolin-2-yl)acetoxy)ethyl)-pyridine 1-oxide;
   (S)-3,5-dichloro-4-(2-(3-(cyclopropylmethoxy)-4-(difluoromethoxy)phenyl)-2-(2-(1,1-dioxido-3-oxobenzo[d]isothiazol-2(3H)-yl)acetoxy)ethyl)pyridine 1-oxide;
   or a pharmaceutically acceptable salt of said compound.

21. A combination, comprising a pyridine N-oxide or pharmaceutically acceptable salt according to claim 16 and a second pharmaceutically active component selected from the group consisting of a beta2-agonist, a corticosteroid, and an antimuscarinic agent.

22. A pharmaceutical composition, comprising a pyridine N-oxide, or pharmaceutically acceptable salt according to claim 16 and one or more pharmaceutically acceptable carriers and/or excipients.

23. A method for the treatment of a disease of a respiratory tract characterized by airway obstruction, said method comprising administering to a patient in need thereof a therapeutically effective amount of a pyridine N-oxide or pharmaceutically acceptable salt according to claim 16.

24. A method according to claim 11, wherein said disease of a respiratory tract characterized by airway obstruction is asthma or COPD.

25. A method for the treatment of allergic rhinitis, said method comprising administering to a patient in need thereof a therapeutically effective amount of a pyridine N-oxide or pharmaceutically acceptable salt according to claim 16.

26. A method for the prevention and/or treatment of atopic dermatitis, said method comprising administering to a patient in need thereof a therapeutically effective amount of a pyridine N-oxide or pharmaceutically acceptable salt according to claim 16.

27. A kit, comprising a pharmaceutical composition according to claim 9 and a device which may be a single- or multi-dose dry powder inhaler, a metered dose inhaler, or a soft mist nebulizer.

* * * * *